United States Patent
Babich et al.

(10) Patent No.: US 9,458,118 B2
(45) Date of Patent: Oct. 4, 2016

(54) SODIUM CHANNEL MODULATORS FOR THE TREATMENT OF PAIN AND DIABETES

(71) Applicant: CHROMOCELL CORPORATION, North Brunswick, NJ (US)

(72) Inventors: Olga Babich, Cranford, NJ (US); Tina Garyantes, Warren, NJ (US); Robert Z. Luo, New City, NY (US); David J. Palling, Glen Ridge, NJ (US); Srinivasan P. Venkatachalan, Monmouth Junction, NJ (US); Yanlin Wang-Fischer, Hillsborough, NJ (US)

(73) Assignee: Chromocell Corporation, North Brunswick, NJ (US)

(*) Notice: Subject to any disclaimer, the term of this patent is extended or adjusted under 35 U.S.C. 154(b) by 0 days.

(21) Appl. No.: 14/994,846

(22) Filed: Jan. 13, 2016

(65) Prior Publication Data

US 2016/0130239 A1  May 12, 2016

Related U.S. Application Data

(63) Continuation of application No. PCT/US2014/054764, filed on Sep. 9, 2014.

(60) Provisional application No. 61/876,046, filed on Sep. 10, 2013.

(51) Int. Cl.
| | |
|---|---|
| A01N 43/78 | (2006.01) |
| A61K 31/425 | (2006.01) |
| C07D 277/00 | (2006.01) |
| C07D 277/52 | (2006.01) |
| C07D 417/12 | (2006.01) |
| C07D 487/04 | (2006.01) |
| C07D 285/08 | (2006.01) |

(52) U.S. Cl.
CPC .......... *C07D 277/52* (2013.01); *C07D 285/08* (2013.01); *C07D 417/12* (2013.01); *C07D 487/04* (2013.01)

(58) Field of Classification Search
USPC .......................................... 514/370; 548/194
See application file for complete search history.

(56) References Cited

U.S. PATENT DOCUMENTS

| | | | |
|---|---|---|---|
| 5,624,931 | A | 4/1997 | Oku et al. |
| 7,230,020 | B2 | 6/2007 | Vicker et al. |
| 7,384,967 | B2 | 6/2008 | Polisetti et al. |
| 8,153,814 | B2 | 4/2012 | Beaudoin et al. |
| 8,410,054 | B2 | 4/2013 | Macdonald et al. |
| 8,476,434 | B2 | 7/2013 | Geuns-Meyer et al. |
| 8,541,588 | B2 | 9/2013 | Beaudoin et al. |
| 8,895,608 | B2 | 11/2014 | Iadonato et al. |
| 8,907,101 | B2 | 12/2014 | Beaudoin et al. |
| 2004/0127508 | A1 | 7/2004 | Gerlach et al. |
| 2006/0009453 | A1 | 1/2006 | Geuns-Meyer et al. |
| 2007/0037796 | A1 | 2/2007 | Barda et al. |
| 2008/0312235 | A1 | 12/2008 | Lane et al. |
| 2009/0023740 | A1 | 1/2009 | Fulp et al. |
| 2010/0197655 | A1 | 8/2010 | Beaudoin et al. |
| 2010/0249206 | A1 | 9/2010 | Larsen et al. |
| 2010/0267782 | A1 | 10/2010 | Beaudoin et al. |
| 2012/0010207 | A1 | 1/2012 | Bell et al. |
| 2012/0101105 | A1 | 4/2012 | Inoue et al. |
| 2012/0149679 | A1 | 6/2012 | Beaudoin et al. |
| 2013/0109667 | A1 | 5/2013 | Markworth et al. |
| 2013/0338111 | A1 | 12/2013 | Beaudoin et al. |
| 2014/0221286 | A1 | 8/2014 | Belardinelli et al. |

FOREIGN PATENT DOCUMENTS

| | | |
|---|---|---|
| WO | WO 2006/046916 | 5/2006 |
| WO | WO 2010/079443 | 7/2010 |
| WO | WO 2012/004706 | 1/2012 |
| WO | WO 2012/004714 A2 | 1/2012 |
| WO | WO 2012/004743 A2 | 1/2012 |
| WO | WO 2012/099983 | 7/2012 |
| WO | WO 2013/025883 | 2/2013 |
| WO | WO 2013/043925 | 3/2013 |

(Continued)

OTHER PUBLICATIONS

Supplemental Partial European Search Report, Jun. 22, 2016, Application No. 14767550.8, European Patent Office.
U.S. Appl. No. 14/776,016, filed Sep. 14, 2015, Babich et al, unpublished.
International Search Report and Written Opinion of International Patent Application No. PCT/US2014/054764 dated Nov. 13, 2014.
International Search Report and Written Opinion of International Patent Application No. PCT/US2014/025809 dated Jul. 7, 2014.
International Search Report of International Patent Application No. PCT/US2015/48927 dated Dec. 8, 2015.

(Continued)

*Primary Examiner* — Marcos Sznaidman
(74) *Attorney, Agent, or Firm* — Jones Day

(57) ABSTRACT

Provided herein are sodium channel modulating Compounds, in particular NaV1.7 modulating compounds of Formula I or compounds of Formula I':

Formula (I)/Formula (I')

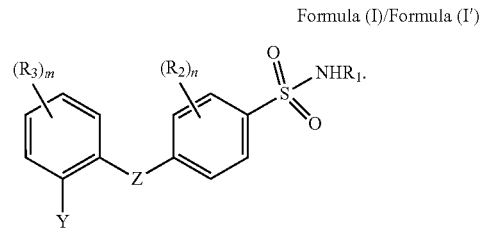

Figure 1:
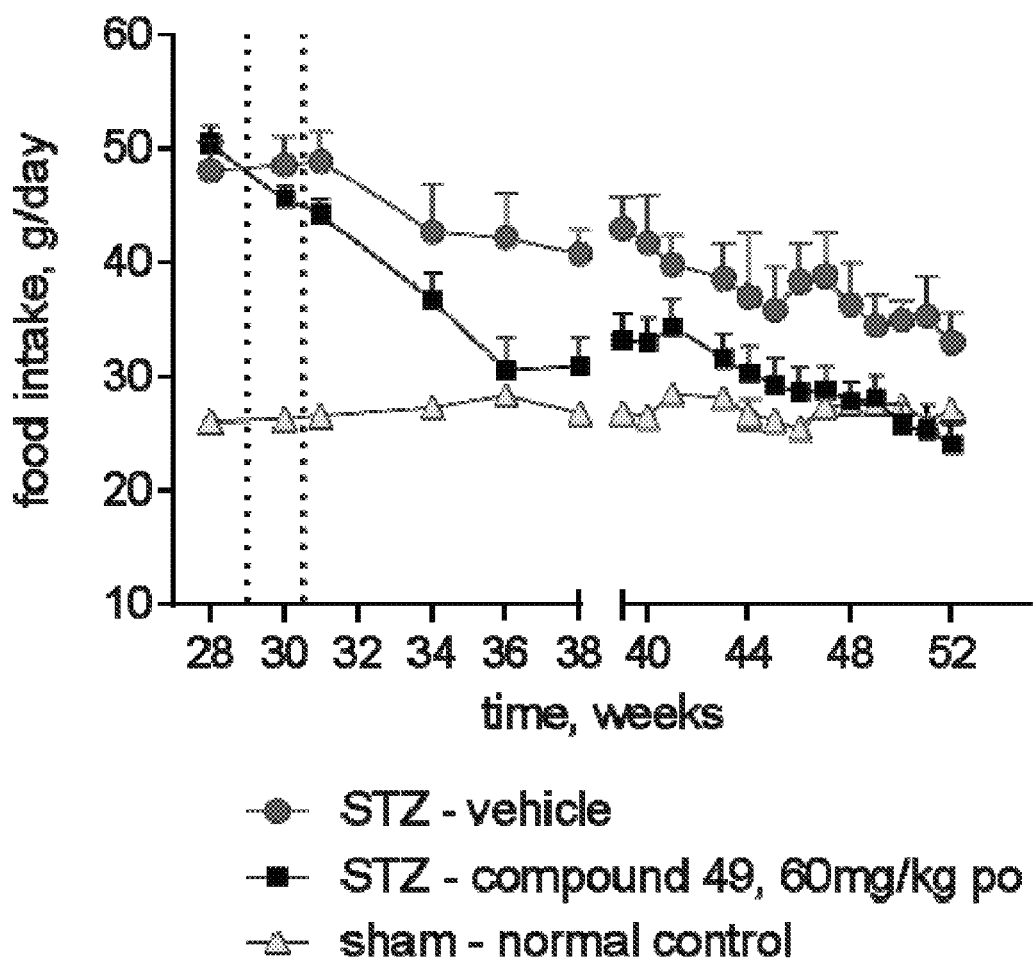

In particular, provided herein are processes for the preparation of, intermediates used in the preparation of, pharmaceutical compositions comprising, and therapeutic methods comprising administering such compounds. In particular, provided herein are compounds for the treatment of pain and diabetes.

18 Claims, 3 Drawing Sheets

(56) References Cited

FOREIGN PATENT DOCUMENTS

| WO | WO 2013/064984 | 5/2013 |
| WO | WO 2014/078479 | 5/2014 |
| WO | WO 2014/151472 | 9/2014 |
| WO | WO 2015/035223 | 3/2015 |
| WO | WO 2015/038533 | 3/2015 |
| WO | PCT/US2015/048927 | 9/2015 |

OTHER PUBLICATIONS

Bagal et al., 2014, "Recent progress in sodium channel modulators for pain", Biorgan. Med. Chem. Lett., 24(16):3690-3699.

Minett et al., 2012, "Distinct Nav1.7 dependent pain sensations require different sets of sensory and sympathetic neurons", Nature Communications, 3:791.

McCormack et al., 2013, "Voltage sensor interaction site for selective small molecule inhibitors of voltage-gated sodium channels", PNAS, 110(29):E2724-32.

Norinder et al., 2013, "QSAR investigation of NaV1.7 active compounds using the SVM/Signature approach and the Bioclipse Modeling platform", Biorg. Med. Chem. Lett., 23(1):261-263.

Shields et al., 2012, "Sodium channel $Na_v1.7$ is essential for lowering heat pain threshold after burn injury", J. of Neuroscience, 32(32): 10819-10832.

U.S. Appl. No. 15/021,153, filed Mar. 10, 2016, Chromocell Corporation, Unpublished.

Written Opinion of International Patent Application No. PCT/US2015/48927 dated Dec. 8, 2015.

Cox et al., "An SCN9A channelopathy causes congenital inability to experience pain", Nature, Dec. 14, 2006;444(7121): 894-98.

SODIUM CHANNEL MODULATORS FOR THE TREATMENT OF PAIN AND DIABETES

This application is a Continuation of International Patent Application No. PCT/US2014/054764, filed Sep. 9, 2014, which claims the benefit of U.S. provisional application No. 61/876,046 filed Sep. 10, 2013, which is incorporated by reference herein in its entirety.

1 FIELD

Provided herein are sodium channel modulating compounds, in particular NaV1.7 modulating compounds. In particular, provided herein are processes for the preparation of, intermediates used in the preparation of, pharmaceutical compositions comprising, and therapeutic methods comprising administering compounds. In particular, provided herein are compounds for the treatment or prevention of pain. Further provided herein are compounds for the treatment or prevention of diabetes.

2 BACKGROUND

Voltage-gated ion channels play a critical role in the electrical activity of neuronal and muscle cells. Large families of voltage-gated ion channels (e.g., sodium channels) have been identified. These ion channels have been the target of significant pharmacologic study, due to their potential role in a variety of pathological conditions.

Pain

Biophysical and pharmacological studies have identified the sodium channel isoforms NaV1.3, NaV1.7, NaV1.8, and NaV1.9 as particularly important in the pathophysiology of pain, in particular neuropathic pain. Recently, gain-of-function mutations in SCN9A, the gene which encodes NaV1.7, have been linked to two human-inherited pain syndromes, inherited erythromelalgia and paroxysmal extreme pain disorder, while loss-of-function mutations in SCN9A have been linked to complete insensitivity to pain. Dib-Hajj et al, *Pain Medicine* 10(7):1260-1269 (2009) (abstract). Pain conditions affect approximately 100 million U.S. adults at a cost of $560-635 billion annually in direct medical treatment costs and lost productivity. Relieving Pain in America, *National Academies Press*, Washington, D.C. (2011), page 2. Unfortunately, current treatment options typically provide only partial pain relief, and are limited by inconvenient dosing and by side effects, such as somnolence, ataxia, edema, gastrointestinal discomfort and respiratory depression. Therefore, novel compounds are desirable to address the shortcomings of presently available treatment options.

Prediabetes and Diabetes

Prediabetes and diabetes describe a group of metabolic diseases with high blood sugar levels over longer periods of time. Diabetes can result from insufficient production of the peptide hormone insulin. In other cases, diabetes can result from insulin resistance, i.e., an inability of cells to respond properly to insulin. If the blood sugar levels are higher than normal, but not high enough for a diagnosis of diabetes, the subject is prediabetic. There are three main types of diabetes: First, Type 1 results from the body's failure to produce sufficient levels of insulin. Second, Type 2 results from insulin resistance. Third, Gestational diabetes occurs when pregnant women without a previous history of diabetes develop a high blood glucose level. Another type of diabetes is latent autoimmune diabetes in adults (LADA). LADA is the most common term describing patients with a type 2 diabetic phenotype combined with islet antibodies and slowly progressive cell failure.

Type 2 diabetes, for example, is a serious and prevalent disease. Approximately 25.8 million people in the United States alone suffer from diabetes, whereby type 2 diabetes accounts for about 90-95% of all diagnosed diabetes cases. U.S. Patent Application Publication No. 2014/0228353 A1 at paragraph [0002]. The number of Americans with diabetes has more than tripled from 1980 to 2008. Id. Diabetes is also increasingly prevalent in other parts of the world, such as in certain Asian countries. Id. Rapid lifestyle and economic changes in, e.g., India and China, have led to a more sedentary lifestyle and poorer diet among the overall population, causing diabetes to become a major health concern. Id. There remains a continued need for novel and improved therapies that address this growing health concern.

3 SUMMARY

Provided herein are compounds of Formula (I),

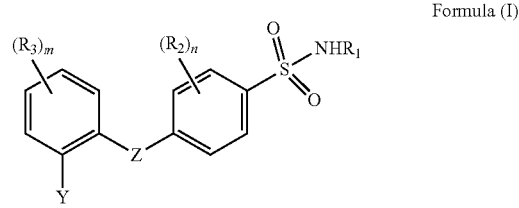

Formula (I)

or a pharmaceutically acceptable salt, or a stereoisomeric or tautomeric form thereof, wherein:

Z is —O— or —S—;

Y is —X—C(=O)NR$_4$R$_5$, —(CH$_2$)$_3$—NR$_9$R$_{10}$, or 4,5,6,7-tetrahydropyrazolo[1,5-c]pyrimidine-(2-yl or 3-yl);

X is (C$_6$-C$_{10}$)aryl or 5- or 6-membered heteroaryl;

R$_1$ is a partially unsaturated or aromatic 5- or 6-membered heterocycle;

R$_2$ is independently at each occurrence —F, —Cl, —Br, —CH$_3$ or —CN;

R$_3$ is independently at each occurrence —H, —F, —Cl, —Br, —CF$_3$, —OCF$_3$, —CN, (C$_1$-C$_{12}$)alkyl, or (C$_1$-C$_{12}$)alkoxy;

R$_4$ and R$_5$ are each independently H, (C$_1$-C$_9$)alkyl, (C$_4$-C$_{12}$) cycloalkyl, or R$_4$ and R$_5$ together form a 5- to 7-membered heterocycloalkyl ring; with the proviso that:

R$_4$ and R$_5$ are not both H; and at least one of R$_4$ and R$_5$ independently or said heterocycloalkyl ring formed by R$_4$ and R$_5$ together is substituted with 1 or 2 substituents selected from the group consisting of —CO$_2$H, —CO$_2$R$_6$, —CN, —OH, —CONR$_7$R$_8$, and —NR$_7$R$_8$; wherein:

R$_6$ is (C$_1$-C$_{12}$)alkyl;

R$_7$ and R$_8$ are each independently H, (C$_1$-C$_{12}$)alkyl, or R$_7$ and R$_8$ together form a 4- to 7-membered heterocycloalkyl ring;

R$_9$ is (C$_1$-C$_6$)alkyl, (C$_3$-C$_8$)cycloalkyl, pyrazolyl or pyridinyl; wherein R$_9$ is optionally further substituted with 1 or 2 substituents selected from the group consisting of —COOH, —COOR$_{11}$, —CONR$_{11}$R$_{12}$, —SO$_2$R$_{11}$, —SO$_2$NR$_{11}$R$_{12}$, —OH, —CN, —OR$_{11}$, and —NR$_{11}$R$_{12}$; wherein R$_{11}$ and R$_{12}$ may form a 6 membered heterocycloalkyl ring R$_{10}$ is R$_{11}$, —COR$_{11}$, —COOR$_{11}$, 5-methyl-2-oxo-1,3-dioxol-4-yl,

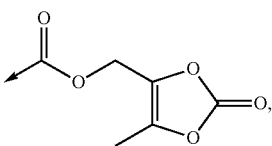

—COO—CH(CH$_3$)OCOCH(CH$_3$)$_2$; or R$_9$ and R$_{10}$ together form a piperazinone or a 4- to 8-membered heterocycloalkyl ring, wherein said heterocycloalkyl ring is substituted with 1 or 2 substituents selected from the group consisting of —COOH, —COOR$_{11}$, —CH$_2$—COOR$_{11}$, —OH, —CN, and (C$_1$-C$_8$)alkoxy;

R$_{11}$ and R$_{12}$ are independently H or (C$_1$-C$_6$)alkyl, optionally substituted with 4- to 8-membered heterocycloalkyl ring; and m and n are each independently 1, 2, 3, or 4.

In a certain embodiment, the compounds of Formula (I')

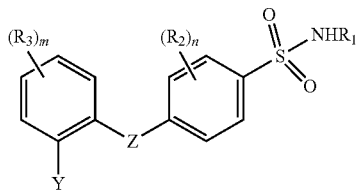

Formula (I')

are those wherein

R$_{10}$ is R$_{11}$, (C$_3$-C$_6$)alkynyl, (C$_3$-C$_6$)alkenyl, —COR$_{11}$, —COOR$_{11}$, —SO$_2$R$_{11}$, 5-methyl-2-oxo-1,3-dioxol-4-yl,

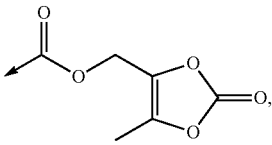

—COO—CH(CH$_3$)OCOCH(CH$_3$)$_2$; or R$_9$ and R$_{10}$ together form a piperazinone or a 4- to 8-membered heterocycloalkyl ring, wherein said heterocycloalkyl ring is substituted with 1 or 2 substituents selected from the group consisting of —COOH, —COOR$_{11}$, —CH$_2$—COOR$_{11}$, —OH, —NH$_2$, —CN, and (C$_1$-C$_8$)alkoxy; or R$_9$ and R$_{10}$ together form a unsubstituted 4- to 8-membered heterocycloalkyl ring, wherein said heterocycloalkyl ring is fused with a 5-membered heteroaryl; and wherein all other substituents are as defined above.

In a certain embodiment, the compounds of Formula (I) or Formula (I') are those wherein Y is —(CH$_2$)$_3$—NR$_9$R$_{10}$.

In a particular embodiment, the compounds of Formula (I) or Formula (I') are those wherein R$_1$ is an aromatic 5- or 6-membered heterocycle, with 1-3 heteroatoms independently selected from the group consisting of N, O, and S.

In a particular embodiment, the compounds of Formula (I) or Formula (I') are those wherein R$_1$ is pyridyl or pyrimidinyl.

In a particular embodiment, the compounds of Formula (I) or Formula (I') are those wherein R$_1$ is an aromatic 5-membered heterocycle with 1 or 2 nitrogen atoms and optionally 1 or 2 sulphur atoms. In a particular embodiment, the compounds of Formula (I) or Formula (I') are those wherein R$_1$ is thiazolyl, isothiazolyl, or thiadiazolyl. In a particular embodiment, the compounds of Formula (I) or Formula (I') are those wherein R$_1$ is thiazolyl. In a particular embodiment, the compounds of Formula (I) or Formula (I') are those wherein R$_1$ is 1,2,4-thiadiazol-5-yl. In a particular embodiment, the compounds of Formula (I) or Formula (I') are those wherein R$_1$ is thiadiazol-4-yl.

In a particular embodiment, the compounds of Formula (I) or Formula (I') are those wherein R$_2$ is independently at each occurrence —F or —Cl.

In a particular embodiment, the compounds of Formula (I) or Formula (I') are those wherein n is 1, 2, or 3. In a particular embodiment, the compounds of Formula (I) or Formula (I') are those wherein n is 2.

In a particular embodiment, the compounds of Formula (I) or Formula (I') are those wherein Z is —O—.

In a particular embodiment, the compounds of Formula (I) or Formula (I') are those wherein R$_3$ is independently at each occurrence —H, —F, —Cl, or —Br. In a particular embodiment, the compounds of Formula (I) or Formula (I') are those wherein R$_3$ is —H or —Cl. In a particular embodiment, the compounds of Formula (I) or Formula (I') are those wherein R$_3$ is —Cl.

In a particular embodiment, the compounds of Formula (I) or Formula (I') are those wherein m is 1, 2, or 3. In a particular embodiment, the compounds of Formula (I) or Formula (I') are those wherein m is 1.

In a particular embodiment, the compounds of Formula (I) or Formula (I') are those wherein R$_9$ is (C$_1$-C$_6$)alkyl; wherein R$_9$ is optionally further substituted with 1 or 2 substituents selected from the group consisting of —COOH, —COOMe, —CONH$_2$, and —NH$_2$. In a particular embodiment, the compounds of Formula (I) or Formula (I') are those wherein R$_9$ is methyl or ethyl. In a particular embodiment, the compounds of Formula (I) or Formula (I') are those wherein R$_9$ is further substituted with —COOH.

In a particular embodiment, the compounds of Formula (I) or Formula (I') are those wherein R$_{10}$ is H and R$_9$ is (C$_1$-C$_6$)alkyl; wherein R$_9$ is further substituted with —CONR$_{11}$R$_{12}$, and wherein R$_{11}$ and R$_{12}$ are independently H or (C$_1$-C$_6$)alkyl. In a particular embodiment, the compounds of Formula (I) or Formula (I') are those wherein R$_9$ is further substituted with —CONH$_2$. In a particular embodiment, the compounds of Formula (I) or Formula (I') are those wherein R$_9$ is methyl and wherein R$_9$ is further substituted with —CONH$_2$.

In a particular embodiment, the compounds of Formula (I) or Formula (I') are those wherein R$_{10}$ is —H, —COMe, —COOEt. In a particular embodiment, the compounds of Formula (I) or Formula (I') are those wherein R$_{10}$ is —H or —COMe. In a particular embodiment, the compounds of Formula (I) or Formula (I') are those wherein R$_{10}$ is —H.

In a particular embodiment, the compounds of Formula (I) or Formula (I') are those wherein R$_9$ and R$_{10}$ together form a 4 to 8 membered heterocycloalkyl ring, wherein said heterocycloalkyl ring is substituted with 1 or 2 groups selected from the group consisting of —COOH, —COOMe, —COOEt, —CH$_2$—COOH, and —NH$_2$. In a particular embodiment, the compounds of Formula (I) or Formula (I') are those wherein R$_9$ and R$_{10}$ together form a 4 to 8 membered heterocycloalkyl ring, wherein said heterocycloalkyl ring is substituted with 1 or 2 groups selected from the group consisting of —COOH, —CH$_2$—COOH, and —NH$_2$.

In a particular embodiment, the compounds of Formula (I) or Formula (I') are those wherein R$_9$ and R$_{10}$ together form a piperidine substituted with 1 or 2 groups selected from the group consisting of —COOH, —COOMe, —COOEt, —CH$_2$—COOH, —CH$_2$—COOMe, —CH$_2$—COOEt, and —NH$_2$. In a particular embodiment, the compounds of Formula (I) or Formula (I') are those wherein R$_9$ and R$_{10}$ together form a piperidine substituted with 1 or 2 groups selected from the group consisting of —COOH, —CH$_2$—COOH, and —NH$_2$.

In a certain embodiment, the compounds of Formula (I) or Formula (I') are those wherein Y is —X—C(=O)NR$_4$R$_5$.

In a particular embodiment, the compounds of Formula (I) or Formula (I') are those wherein R$_1$ is an aromatic 5- or 6-membered heterocycle, with 1-3 heteroatoms independently selected from the group consisting of N, O, and S.

In a particular embodiment, the compounds of Formula (I) or Formula (I') are those wherein R$_1$ is pyridyl or pyrimidinyl.

In a particular embodiment, the compounds of Formula (I) or Formula (I') are those wherein R$_1$ is an aromatic 5-membered heterocycle with 1 or 2 nitrogen atoms and optionally 1 or 2 sulphur atoms. In a particular embodiment, the compounds of Formula (I) or Formula (I') are those wherein R$_1$ is thiazolyl, isothiazolyl, or thiadiazolyl. In a particular embodiment, the compounds of Formula (I) or Formula (I') are those wherein R$_1$ is thiazolyl. In a particular embodiment, the compounds of Formula (I) or Formula (I') are those wherein R$_1$ is 1,2,4-thiadiazol-5-yl.

In a particular embodiment, the compounds of Formula (I) or Formula (I') are those wherein R$_2$ is independently at each occurrence —F or —Cl.

In a particular embodiment, the compounds of Formula (I) or Formula (I') are those wherein n is 1, 2, or 3. In a particular embodiment, the compounds of Formula (I) or Formula (I') are those wherein n is 2.

In a particular embodiment, the compounds of Formula (I) or Formula (I') are those wherein Z is —O—.

In a particular embodiment, the compounds of Formula (I) or Formula (I') are those wherein R$_3$ is independently at each occurrence —H, —F, —Cl, or —Br. In a particular embodiment, the compounds of Formula (I) or Formula (I') are those wherein R$_3$ is —H or —Cl. In a particular embodiment, the compounds of Formula (I) or Formula (I') are those wherein R$_3$ is —Cl.

In a particular embodiment, the compounds of Formula (I) or Formula (I') are those wherein m is 1, 2, or 3. In a particular embodiment, the compounds of Formula (I) or Formula (I') are those wherein m is 1.

In a particular embodiment, the compounds of Formula (I) or Formula (I') are those wherein X is 5- or 6-membered heteroaryl. In a particular embodiment, the compounds of Formula (I) or Formula (I') are those wherein X is pyridyl or pyrimidinyl. In a particular embodiment, the compounds of Formula (I) or Formula (I') are those wherein X is pyridyl.

In a particular embodiment, the compounds of Formula (I) or Formula (I') are those wherein R$_4$ is H and R$_5$ is (C$_1$-C$_9$)alkyl.

In a particular embodiment, the compounds of Formula (I) or Formula (I') are those wherein R$_5$ is methyl or ethyl, substituted with 1 or 2 substituents selected from the group consisting of —CO$_2$H, —CO$_2$R$_6$, and —CONR$_7$R$_8$.

In a particular embodiment, the compounds of Formula (I) or Formula (I') are those wherein R$_6$ is (C$_1$-C$_6$)alkyl.

In a particular embodiment, the compounds of Formula (I) or Formula (I') are those wherein R$_5$ is methyl or ethyl, substituted with —CO$_2$H.

In a certain embodiment, the compounds of Formula (I) or Formula (I') are those wherein Y is 4,5,6,7-tetrahydropyrazolo[1,5-a]pyrimidine-(2-yl or 3-yl). In a particular embodiment, the compounds of Formula (I) or Formula (I') are those wherein Y is 4,5,6,7-tetrahydropyrazolo[1,5-a]pyrimidine-3-yl.

In a particular embodiment, the compounds of Formula (I) or Formula (I') are those wherein R$_1$ is an aromatic 5- or 6-membered heterocycle, with 1-3 heteroatoms independently selected from the group consisting of N, O, and S.

In a particular embodiment, the compounds of Formula (I) or Formula (I') are those wherein R$_1$ is pyridyl or pyrimidinyl.

In a particular embodiment, the compounds of Formula (I) or Formula (I') are those wherein R$_1$ is an aromatic 5-membered heterocycle with 1 or 2 nitrogen atoms and optionally 1 or 2 sulphur atoms. In a particular embodiment, the compounds of Formula (I) or Formula (I') are those wherein R$_1$ is thiazolyl, isothiazolyl, or thiadiazolyl. In a particular embodiment, the compounds of Formula (I) or Formula (I') are those wherein R$_1$ is thiazolyl. In a particular embodiment, the compounds of Formula (I) or Formula (I') are those wherein R$_1$ is 1,2,4-thiadiazol-5-yl.

In a particular embodiment, the compounds of Formula (I) or Formula (I') are those wherein R$_2$ is independently at each occurrence —F or —Cl.

In a particular embodiment, the compounds of Formula (I) or Formula (I') are those wherein n is 1, 2, or 3. In a particular embodiment, the compounds of Formula (I) or Formula (I') are those wherein n is 2.

In a particular embodiment, the compounds of Formula (I) or Formula (I') are those wherein Z is —O—.

In a particular embodiment, the compounds of Formula (I) or Formula (I') are those wherein R$_3$ is independently at each occurrence —H, —F, —Cl, or —Br. In a particular embodiment, the compounds of Formula (I) or Formula (I') are those wherein R$_3$ is —H or —Cl. In a particular embodiment, the compounds of Formula (I) or Formula (I') are those wherein R$_3$ is —Cl.

In a particular embodiment, the compounds of Formula (I) or Formula (I') are those wherein m is 1, 2, or 3. In a particular embodiment, the compounds of Formula (I) or Formula (I') are those wherein m is 1.

In a certain embodiment, the compounds of Formula (I) or Formula (I') are those wherein the compound is 3-(4-(2-(4-(N-(1,2,4-thiadiazol-5-yl)sulfamoyl)-2-chloro-5-fluorophenoxy)-5-chlorophenyl)picolinamido)propanoic acid, 2-(4-(2-(4-(N-(1,2,4-thiadiazol-5-yl)sulfamoyl)-2-chloro-5-fluorophenoxy)-5-chlorophenyl)picolinamido)acetic acid, 5-(4-(2-(4-(N-(1,2,4-thiadiazol-5-yl)sulfamoyl)-2-chloro-5-fluorophenoxy)-5-chlorophenyl)picolinamido)pentanoic acid, 4-(4-(2-(4-(N-(1,2,4-thiadiazol-5-yl)sulfamoyl)-2-chloro-5-fluorophenoxy)-5-chlorophenyl)picolinamido)butanoic acid, 2-(4-(2-(4-(N-(1,2,4-thiadiazol-5-yl)sulfamoyl)-2-chloro-5-fluorophenoxy)-5-chlorophenyl)picolinamido)propanoic acid, (R)-2-(4-(2-(4-(N-(1,2,4-thiadiazol-5-yl)sulfamoyl)-2-chloro-5-fluorophenoxy)-5-chlorophenyl)picolinamido) propanoic acid, 2-(6-(2-(4-(N-(1,2,4-thiadiazol-5-yl)sulfamoyl)-2-chloro-5-fluorophenoxy)-5-chlorophenyl)picolinamido)acetic acid, (S)-2-(4-(2-(4-(N-(1,2,4-thiadiazol-5-yl)sulfamoyl)-2-chloro-5-fluorophenoxy)-5-chlorophenyl)picolinamido) propanoic acid, 3-(4-(2-(4-(N-(1,2,4-thiadiazol-5-yl)sulfamoyl)-2-cyanophenoxy)-5-chlorophenyl)picolinamido)propanoic acid, 3-(4-(2-(4-(N-(1,2,4-thiadiazol-5-yl)sulfamoyl)-2,5-difluorophenoxy)-5-chlorophenyl)picolinamido)propanoic acid,
2-((3-(5-chloro-2-(2-chloro-5-fluoro-4-(N-(thiazol-4-yl)sulfamoyl)phenoxy)phenyl)propyl)amino)acetic acid,
3-((3-(2-(4-(N-(1,2,4-thiadiazol-5-yl)sulfamoyl)-2-chloro-5-fluorophenoxy)-5-chlorophenyl)propyl)amino)propanoic acid,
2-((3-(5-chloro-2-(2-chloro-5-fluoro-4-(N-(thiazol-2-yl)sulfamoyl)phenoxy)phenyl)propyl)amino)acetic acid,
1-(3-(5-chloro-2-(2-chloro-5-fluoro-4-(N-(thiazol-4-yl)sulfamoyl)phenoxy)phenyl)propyl)piperidine-4-carboxylic acid,
3-((3-(5-chloro-2-(2-chloro-5-fluoro-4-(N-(thiazol-4-yl)sulfamoyl)phenoxy)phenyl)propyl)amino)propanoic acid,
4-amino-1-(3-(5-chloro-2-(2-chloro-5-fluoro-4-(N-(thiazol-4-yl)sulfamoyl)phenoxy)phenyl)propyl)piperidine-4-carboxylic acid,
2-amino-4-((3-(5-chloro-2-(2-chloro-5-fluoro-4-(N-(thiazol-4-yl)sulfamoyl)phenoxy)phenyl)propyl)amino)butanoic acid,
2-((3-(5-chloro-2-(2,5-difluoro-4-(N-(thiazol-2-yl)sulfamoyl)phenoxy)phenyl)propyl)amino)acetic acid,
1-(3-(5-chloro-2-(2-chloro-5-fluoro-4-(N-(thiazol-4-yl)sulfamoyl)phenoxy)phenyl)propyl)piperidine-3-carboxylic acid,
2-((3-(2-(4-(N-(1,2,4-thiadiazol-5-yl)sulfamoyl)-2-chloro-5-fluorophenoxy)phenyl)propyl)amino)acetic acid,
2-((3-(5-chloro-2-(2,5-difluoro-4-(N-(thiazol-4-yl)sulfamoyl)phenoxy)phenyl)propyl)amino)acetic acid,
3-((3-(5-chloro-2-(2,5-difluoro-4-(N-(thiazol-4-yl)sulfamoyl)phenoxy)phenyl)propyl)amino)propanoic acid,
3-((3-(5-chloro-2-(2-cyano-4-(N-(thiazol-4-yl)sulfamoyl)phenoxy)phenyl)propyl)amino)propanoic acid,
methyl 2-((3-(5-chloro-2-(2-chloro-5-fluoro-4-(N-(thiazol-4-yl)sulfamoyl)phenoxy)phenyl)propyl)amino)acetate,
3-((3-(2-(2-chloro-5-fluoro-4-(N-(thiazol-4-yl)sulfamoyl)phenoxy)-5-fluorophenyl)propyl)amino)propanoic acid,
3-((3-(5-chloro-2-(2-chloro-5-fluoro-4-(N-(thiazol-4-yl)sulfamoyl)phenoxy)phenyl)propyl)amino)propanamide,
2-(N-(3-(5-chloro-2-(2-chloro-5-fluoro-4-(N-(thiazol-4-yl)sulfamoyl)phenoxy)phenyl)propyl)acetamido)acetic acid,
2-(1-(3-(2-(4-(N-(1,2,4-thiadiazol-5-yl)sulfamoyl)-2-chloro-5-fluorophenoxy)-5-chlorophenyl)propyl)piperidin-4-yl)acetic acid,
3-((3-(5-chloro-2-(2-chloro-5-fluoro-4-(N-(thiazol-2-yl)sulfamoyl)phenoxy)phenyl)propyl)amino)propanoic acid,
2-((3-(5-chloro-2-(2-chloro-5-fluoro-4-(N-(thiazol-4-yl)sulfamoyl)phenoxy)phenyl)propyl)amino)-N-methylacetamide,
5-chloro-4-(4-chloro-2-(3-((2-(methylsulfonyl)ethyl)amino)propyl)phenoxy)-2-fluoro-N-(thiazol-4-yl)benzenesulfonamide,
1-(3-(2-(4-(N-(1,2,4-thiadiazol-5-yl)sulfamoyl)-2-chloro-5-fluorophenoxy)-5-chlorophenyl)propyl)piperidine-4-carboxylic acid,
5-chloro-4-(4-chloro-2-(4,5,6,7-tetrahydropyrazolo[1,5-a]pyrimidin-3-yl)phenoxy)-2-fluoro-N-(thiazol-4-yl)benzenesulfonamide,
2-((3-(5-chloro-2-(2-chloro-5-fluoro-4-(N-(thiazol-2-yl)sulfamoyl)phenoxy)phenyl)propyl)(ethoxycarbonyl)amino)acetic acid,
ethyl 2-((3-(5-chloro-2-(2-chloro-5-fluoro-4-(N-(thiazol-2-yl)sulfamoyl)phenoxy)phenyl)propyl)amino)acetate, or
4-(2-(3-((1H-pyrazol-4-yl)amino)propyl)-4-chlorophenoxy)-5-chloro-2-fluoro-N-(thiazol-2-yl)benzenesulfonamide;

or a pharmaceutically acceptable salt, or a stereoisomeric or tautomeric form thereof.

In a certain embodiment, the compounds of Formula (I) or Formula (I') are those wherein the compound is
3-((3-(5-chloro-2-(2,5-difluoro-4-(N-(thiazol-2-yl)sulfamoyl)phenoxy)phenyl)propyl)amino)propanoic acid,
5-chloro-4-(4-chloro-2-(3-((2-(methylsulfonyl)ethyl)amino)propyl)phenoxy)-2-fluoro-N-(thiazol-4-yl)benzenesulfonamide,
4-(2-(3-((1H-pyrazol-3-yl)amino)propyl)-4-chlorophenoxy)-5-chloro-2-fluoro-N-(thiazol-4-yl)benzenesulfonamide,
2-((3-(5-chloro-2-(2-chloro-5-fluoro-4-(N-(thiazol-4-yl)sulfamoyl)phenoxy)phenyl)propyl)amino)-N-methylacetamide,
2-((3-(5-chloro-2-(2-chloro-5-fluoro-4-(N-(thiazol-4-yl)sulfamoyl)phenoxy)phenyl)propyl)(methyl)amino)acetic acid,
5-chloro-4-(4-chloro-2-(3-(6,7-dihydro-1H-pyrazolo[4,3-c]pyridin-5(4H)-yl)propyl)phenoxy)-2-fluoro-N-(thiazol-4-yl)benzenesulfonamide,
2-((3-(5-chloro-2-(2-chloro-5-fluoro-4-(N-(thiazol-4-yl)sulfamoyl)phenoxy)phenyl)propyl)amino)acetamide,
isopentyl 2-((3-(5-chloro-2-(2-chloro-5-fluoro-4-(N-(thiazol-2-yl)sulfamoyl)phenoxy)phenyl)propyl)amino)acetate,
isopropyl 2-((3-(5-chloro-2-(2-chloro-5-fluoro-4-(N-(thiazol-2-yl)sulfamoyl)phenoxy)phenyl)propyl)amino)acetate,
methyl 2-((3-(5-chloro-2-(2-chloro-5-fluoro-4-(N-(thiazol-4-yl)sulfamoyl)phenoxy)phenyl)propyl)(methyl)amino)acetate,
2-((3-(5-chloro-2-(2-chloro-5-fluoro-4-(N-(thiazol-2-yl)sulfamoyl)phenoxy)phenyl)propyl)((pentyloxy)carbonyl)amino)acetic acid,
2-((3-(5-chloro-2-(2-chloro-5-fluoro-4-(N-(thiazol-2-yl)sulfamoyl)phenoxy)phenyl)propyl)(prop-2-yn-1-yl)amino)acetic acid,
5-chloro-4-(4-chloro-2-(3-(5,6-dihydroimidazo[1,2-a]pyrazin-7(8H)-yl)propyl)phenoxy)-2-fluoro-N-(thiazol-4-yl)benzenesulfonamide,
5-chloro-2-fluoro-4-(2-(4,5,6,7-tetrahydropyrazolo[1,5-a]pyrimidin-3-yl)phenoxy)-N-(thiazol-2-yl)benzenesulfonamide,
5-chloro-4-(4-chloro-2-(4,5,6,7-tetrahydropyrazolo[1,5-a]pyrimidin-3-yl)phenoxy)-2-fluoro-N-(thiazol-2-yl)benzenesulfonamide,
5-chloro-2-fluoro-4-(2-(4,5,6,7-tetrahydropyrazolo[1,5-a]pyrimidin-3-yl)phenoxy)-N-(thiazol-4-yl)benzenesulfonamide,
5-chloro-4-(4-chloro-2-(3-((2-(methylsulfonyl)ethyl)amino)propyl)phenoxy)-2-fluoro-N-(thiazol-2-yl)benzenesulfonamide,
2-((3-(2-(2-chloro-5-fluoro-4-(N-(thiazol-4-yl)sulfamoyl)phenoxy)phenyl)propyl)amino)acetamide,
2-((3-(5-chloro-2-(2-chloro-5-fluoro-4-(N-(thiazol-4-yl)sulfamoyl)phenoxy)phenyl)propyl)(prop-2-yn-1-yl)amino)acetic acid,
2-(allyl(3-(5-chloro-2-(2-chloro-5-fluoro-4-(N-(thiazol-2-yl)sulfamoyl)phenoxy)phenyl)propyl)amino)acetic acid,
2-((3-(5-chloro-2-(2-chloro-5-fluoro-4-(N-(thiazol-2-yl)sulfamoyl)phenoxy)phenyl)propyl)amino)acetamide,
2-(but-2-yn-1-yl(3-(5-chloro-2-(2-chloro-5-fluoro-4-(N-(thiazol-2-yl)sulfamoyl)phenoxy)phenyl)propyl)amino)acetic acid, 2-((3-(5-chloro-2-(2-chloro-5-fluoro-4-(N-(thiazol-2-yl)sulfamoyl)phenoxy)phenyl)propyl)(propyl)amino)acetic acid,
3-((3-(5-chloro-2-(2-chloro-5-fluoro-4-(N-(thiazol-2-yl)sulfamoyl)phenoxy)phenyl)propyl)(prop-2-yn-1-yl)amino)propanoic acid,
2-((3-(5-chloro-2-(2,5-difluoro-4-(N-(thiazol-2-yl)sulfamoyl)phenoxy)phenyl)propyl)(prop-2-yn-1-yl)amino)acetic acid,
ethyl 2-((3-(5-chloro-2-(2-chloro-5-fluoro-4-(N-(thiazol-2-yl)sulfamoyl)phenoxy)phenyl)propyl)(methyl)amino)acetate, or
2-((3-(5-chloro-2-(2,5-difluoro-4-(N-(thiazol-4-yl)sulfamoyl)phenoxy)phenyl)propyl)amino)acetamid;
or a pharmaceutically acceptable salt, or a stereoisomeric or tautomeric form thereof.

In a particular embodiment, the compounds of Formula (I) or Formula (I') are those wherein the compound is
2-(4-(2-(4-(N-(1,2,4-thiadiazol-5-yl)sulfamoyl)-2-chloro-5-fluorophenoxy)-5-chlorophenyl)picolinamido)acetic acid,
3-(4-(2-(4-(N-(1,2,4-thiadiazol-5-yl)sulfamoyl)-2-chloro-5-fluorophenoxy)-5-chlorophenyl)picolinamido)propanoic acid,
2-(4-(2-(4-(N-(1,2,4-thiadiazol-5-yl)sulfamoyl)-2-chloro-5-fluorophenoxy)-5-chlorophenyl)picolinamido)propanoic acid, or
3-((3-(2-(4-(N-(1,2,4-thiadiazol-5-yl)sulfamoyl)-2-chloro-5-fluorophenoxy)-5-chlorophenyl)propyl)amino)propanoic acid;
or a pharmaceutically acceptable salt, or a stereoisomeric or tautomeric form thereof.

In a particular embodiment, the compounds of Formula (I) or Formula (I') are those wherein the compound is
2-((3-(5-chloro-2-(2-chloro-5-fluoro-4-(N-(thiazol-4-yl)sulfamoyl)phenoxy)phenyl)propyl)amino)acetamide,
2-((3-(5-chloro-2-(2-chloro-5-fluoro-4-(N-(thiazol-2-yl)sulfamoyl)phenoxy)phenyl)propyl)((pentyloxy)carbonyl)amino)acetic acid, or
2-((3-(5-chloro-2-(2-chloro-5-fluoro-4-(N-(thiazol-2-yl)sulfamoyl)phenoxy)phenyl)propyl)(prop-2-yn-1-yl)amino)acetic acid;
or a pharmaceutically acceptable salt, or a stereoisomeric or tautomeric form thereof.

In a particular embodiment, the compounds of Formula (I) or Formula (I') are those wherein the compound is
3-((3-(5-chloro-2-(2-chloro-5-fluoro-4-(N-(thiazol-4-yl)sulfamoyl)phenoxy)phenyl)propyl)amino)propanoic acid,
2-((3-(5-chloro-2-(2-chloro-5-fluoro-4-(N-(thiazol-4-yl)sulfamoyl)phenoxy)phenyl)propyl)amino)acetamide,
2-((3-(5-chloro-2-(2-chloro-5-fluoro-4-(N-(thiazol-2-yl)sulfamoyl)phenoxy)phenyl)propyl)(prop-2-yn-1-yl)amino)acetic acid,
2-((3-(5-chloro-2-(2-chloro-5-fluoro-4-(N-(thiazol-4-yl)sulfamoyl)phenoxy)phenyl)propyl)(prop-2-yn-1-yl)amino)acetic acid,
2-((3-(5-chloro-2-(2-chloro-5-fluoro-4-(N-(thiazol-4-yl)sulfamoyl)phenoxy)phenyl)propyl)amino)acetamide,
2-((3-(5-chloro-2-(2-chloro-5-fluoro-4-(N-(thiazol-2-yl)sulfamoyl)phenoxy)phenyl)propyl)(propyl)amino)acetic acid,
2-((3-(5-chloro-2-(2,5-difluoro-4-(N-(thiazol-2-yl)sulfamoyl)phenoxy)phenyl)propyl)(prop-2-yn-1-yl)amino)acetic acid, or
2-((3-(5-chloro-2-(2,5-difluoro-4-(N-(thiazol-4-yl)sulfamoyl)phenoxy)phenyl)propyl)amino)acetamide;
or a pharmaceutically acceptable salt, or a stereoisomeric or tautomeric form thereof.

Provided herein are methods for treating neuropathic pain, comprising administering to a subject in need thereof a therapeutically effective amount of a compound of Formula (I) or Formula (I'), or a pharmaceutically acceptable salt, solvate or tautomeric form thereof.

Provided herein are methods for treating pain comprising use of a compound of Formula (I) or Formula (I'), as a voltage-gated sodium channel inhibitor. In a particular embodiment, the methods are those, wherein the pain is neuropathic, nociceptive or inflammatory pain. In a particular embodiment, the methods are those, wherein the voltage-gated sodium channel is NaV1.7.

Provided herein are pharmaceutical compositions comprising a compound of Formula (I) or Formula (I') and a pharmaceutically acceptable carrier. In a particular embodiment, the pharmaceutical compositions are those, wherein the composition is suitable for topical, oral, subcutaneous, or intravenous administration.

Provided herein are methods for prevention or treatment of pain in a subject, wherein the method comprises administering to the subject in need of such prevention or treatment a therapeutically effective amount of a compound of Formula (I) or Formula (I'). In a particular embodiment, the methods are those, wherein the therapeutically effective amount is effective to alleviate pain in a subject, wherein the compound of Formula (I) or Formula (I') shows a reduction in pain response in the Formalin Assay (in phase 1 or phase 2, or both) (see Section 5.1.2) at a dose between 0.1 mg/kg and 1,000 mg/kg, at a dose between 0.5 mg/kg and 100 mg/kg, at a dose between 1 mg/kg to 50 mg/kg, or at a dose of 5 mg/kg. In certain embodiments, a compound of Formula (I) or Formula (I') provided herein shows a reduction in pain response in the Formalin Assay (in phase 1 or phase 2, or both) by at least 10%, 20%, 30%, 40%, 50%, 60%, 70%, 80%, 90%, 95%, 98%, 99%, or 100%, or by ranges between any of the recited percentages (e.g., 10-20%, 10-30%, 10-40%, 20-30%, or 20-40%) relative to a vehicle control. In a particular embodiment, the methods are those, wherein the pain is nociceptive pain, such as that resulting from physical trauma (e.g., a cut or contusion of the skin including surgery or dental pain; or a chemical or thermal burn), osteoarthritis, rheumatoid arthritis or tendonitis; myofascial pain; neuropathic pain, such as that associated with stroke, diabetic neuropathy, luetic neuropathy, postherpetic neuralgia, trigeminal neuralgia, fibromyalgia, or painful neuropathy induced iatrogenically by drugs; or mixed pain (e.g., pain with both nociceptive and neuropathic components); visceral pain; headache pain (e.g., migraine headache pain); complex regional pain syndrome ("CRPS"); CRPS type I; CRPS type II; reflex sympathetic dystrophy ("RSD"); reflex neurovascular dystrophy; reflex dystrophy; sympathetically maintained pain syndrome; causalgia; Sudeck atrophy of bone; algoneurodystrophy; shoulder hand syndrome; post-traumatic dystrophy; autonomic dysfunction; autoimmune-related pain; inflammation-related pain; cancer-related pain; phantom limb pain; chronic fatigue syndrome; post-operative pain; spinal cord injury pain; central post-stroke pain; radiculopathy; sensitivity to temperature, light touch or color change to the skin (allodynia); pain from hyperthermic or hypothermic conditions; and other painful conditions (e.g., diabetic neuropathy, luetic neuropathy, postherpetic neuralgia, trigeminal neuralgia); chronic pain; acute pain; pain from neuromas, pain or itch associated with channelopathies such as small fiber neuralgia, inherited erythromelalgia ("IEM"), or Raynodes; or itch from various origins such as allergic itch.

Provided herein are methods modulating the activity of a voltage-gated sodium channel, wherein the method comprises contacting a cell that expresses the voltage-gated sodium channel with a compound of Formula (I) or Formula (I'). In a particular embodiment, the methods are those, wherein the voltage-gated sodium channel is NaV1.7. In a particular embodiment, the methods are those, wherein the method results in inhibition of the voltage-gated sodium channel.

Provided herein are methods for treating or preventing prediabetes, comprising administering to a subject in need thereof a therapeutically effective amount of a compound of Formula (I) or Formula (I'), or a pharmaceutically acceptable salt, solvate or tautomeric form thereof.

Provided herein are methods for treating or preventing diabetes, comprising administering to a subject in need thereof a therapeutically effective amount of a compound of Formula (I) or Formula (I'), or a pharmaceutically acceptable salt, solvate or tautomeric form thereof.

Also provided herein are methods for lowering blood or plasma glucose in a subject in need thereof, comprising administering to the subject a therapeutically effective amount of a compound of Formula (I) or Formula (I'), or a pharmaceutically acceptable salt, solvate or tautomeric form thereof.

Further provided herein are methods for lowering blood or plasma glycated hemoglobin in a subject in need thereof, comprising administering to the subject a therapeutically effective amount of a compound of Formula (I) or Formula (I'), or a pharmaceutically acceptable salt, solvate or tautomeric form thereof.

In one embodiment, the subject has prediabetes.

In another embodiment, the subject has diabetes. In certain embodiments, diabetes is gestational diabetes, type-1 diabetes, type-2 diabetes, or latent autoimmune diabetes of adults.

4 DETAILED DESCRIPTION

4.1 Definitions

A "Compound" or "Compounds" as used herein comprise a compound of Formula (I), a compound of Formula (I'), a compound of Formula (Ia), a compound of Formula (I'a), a compound of Formula (Ib), a compound of Formula (Ic), a compound of Formula (Id), a compound listed in Table 1, a compound listed in Table 2, or a compound listed in Table 3.

A "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Others are well known in the art, see for example, *Remington's Pharmaceutical Sciences,* 18th eds., Mack Publishing, Easton Pa. (1990) or *Remington: The Science and Practice of Pharmacy,* 19th eds., Mack Publishing, Easton Pa. (1995).

A "stereoisomer" or "stereoisomeric form" refers to one stereoisomer of a Compound that is substantially free of other stereoisomers of that Compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Compounds can have chiral centers and can occur as racemates, individual enantiomers or diastereomers, and mixtures thereof. All such isomeric forms are included within the embodiments disclosed herein, including mixtures thereof. The use of stereomerically pure forms of such Compounds, as well as the use of mixtures of those forms, are encompassed by the embodiments disclosed herein. For example, mixtures comprising equal or unequal amounts of the enantiomers of a particular Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, NY, 1962); and Wilen, S. H., Tables of *Resolving Agents and Optical Resolutions* p. 268 (E. L. Eliel, Ed., Univ. of Notre Dame Press, Notre Dame, Ind., 1972).

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

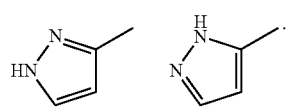

As readily understood by one skilled in the art, a wide variety of functional groups and other structures may exhibit tautomerism and all tautomers of the Compounds provided herein are within the scope of the present disclosure.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include, but are not limited to, phenyl, naphthyl and the like.

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Examples include, but are not limited to, groups such as pyrrolyl, pyrazolyl, imidazolyl, triazolyl, tetrazolyl, oxazolyl, isoxazolyl, thiazolyl, isothiazolyl, thiadiazolyl (e.g., 1,2,4-thiadiazolyl), pyrrolyl, pyridyl, pyridazinyl, pyrimidinyl, pyrazinyl, thiophenyl, benzothiophenyl, furanyl, benzofuranyl, indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl, pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinazolinyl, and quinoxalinyl groups.

A "partially unsaturated or aromatic heterocycle" is a partially unsaturated or aromatic ring system having one to four heteroatoms as ring atoms in a heteroaromatic ring system, wherein the remainder of the atoms are carbon atoms. If the "partially unsaturated or aromatic heterocycle" is an aromatic heterocycle, then the aromatic heterocycle is a "heteroaryl" as defined above. In one embodiment, the partially unsaturated or aromatic heterocycle is a partially unsaturated or aromatic 5- or 6-membered heterocycle. Examples of partially unsaturated heterocycles include, but are not limited to, groups such as 2,5-dihydro-1H-pyrrolyl, 2,5-dihydrofuranyl, 2,5-dihydrothiophenyl, 4,5-dihydrooxazolyl, 4,5-dihydrothiazolyl, 4,5-dihydro-1H-imidazolyl, 4,5-dihydro-1H-1,2,3-triazolyl, 1,2,5,6-tetrahydropyridinyl, and 1,4,5,6-tetrahydropyrimidinyl groups.

A "heterocycloalkyl" group is a non-aromatic cycloalkyl in which one to four of the ring carbon atoms are independently replaced with a heteroatom from the group consisting of O, S and N. Examples of a heterocycloalkyl group include, but are not limited to, morpholinyl, pyrrolidinyl, piperazinyl, (1,4)-dioxanyl, and (1,3)-dioxolanyl. Heterocycloalkyls can also be bonded at any ring atom (i.e., at any carbon atom or heteroatom of the heterocyclic ring). In one embodiment, the heterocycloalkyl is a 5- or 6-membered or 4- to 8-membered heterocycloalkyl.

An "alkyl" group is a saturated straight chain or branched non-cyclic hydrocarbon having, for example, from 1 to 12 carbon atoms, 1 to 9 carbon atoms, 1 to 6 carbon atoms, 1 to 4 carbon atoms, or 2 to 6 carbon atoms. Representative alkyl groups include -methyl, -ethyl, -n-propyl, -n-butyl, -n-pentyl and -n-hexyl; while branched alkyls include -isopropyl, -sec-butyl, -iso-butyl, -tert-butyl, -iso-pentyl, 2-methylpentyl, 3-methylpentyl, 4-methylpentyl, 2,3-dimethylbutyl and the like.

An "alkenyl" group is a partially unsaturated straight chain or branched non-cyclic hydrocarbon having, for example, from 3 to 6 carbon atoms, 3 to 4 carbon atoms, or 3 carbon atoms. Representative alkenyl groups include allyl, propenyl and the like.

An "alkynyl" group is a partially unsaturated straight chain or branched non-cyclic hydrocarbon having, for example, from 3 to 6 carbon atoms, 4 to 6 carbon atoms, or 3 carbon atoms. Representative alkynyl groups include propynyl, butynyl and the like.

A "cycloalkyl" group is a saturated cyclic alkyl group of from 3 to 12 carbon atoms having a single cyclic ring or multiple condensed or bridged rings. In some embodiments, the cycloalkyl group has 4 to 12 ring members, whereas in other embodiments the number of ring carbon atoms ranges, for example, from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, and the like, or multiple or bridged ring structures such as adamantyl and the like.

A "subject in need thereof" refers to a mammal (e.g., human, dog, horse, or cat) in need of treatment with any method provided herein. In one embodiment the subject is a patient.

An "adult" refers to a human over the age of 30.

4.2 Brief Description of the Drawings

FIG. 1 shows the change in food intake measured in the rat streptozotocin-induced model for diabetes. The change in food intake is shown for a diabetic vehicle group, a diabetic test compound treatment group, and a sham group. The diabetic test compound treatment group received a 60 mg/kg/day dose of compound 49 for 9 days. The beginning and the end of the treatment period is marked by a dotted line.

Figure 2:
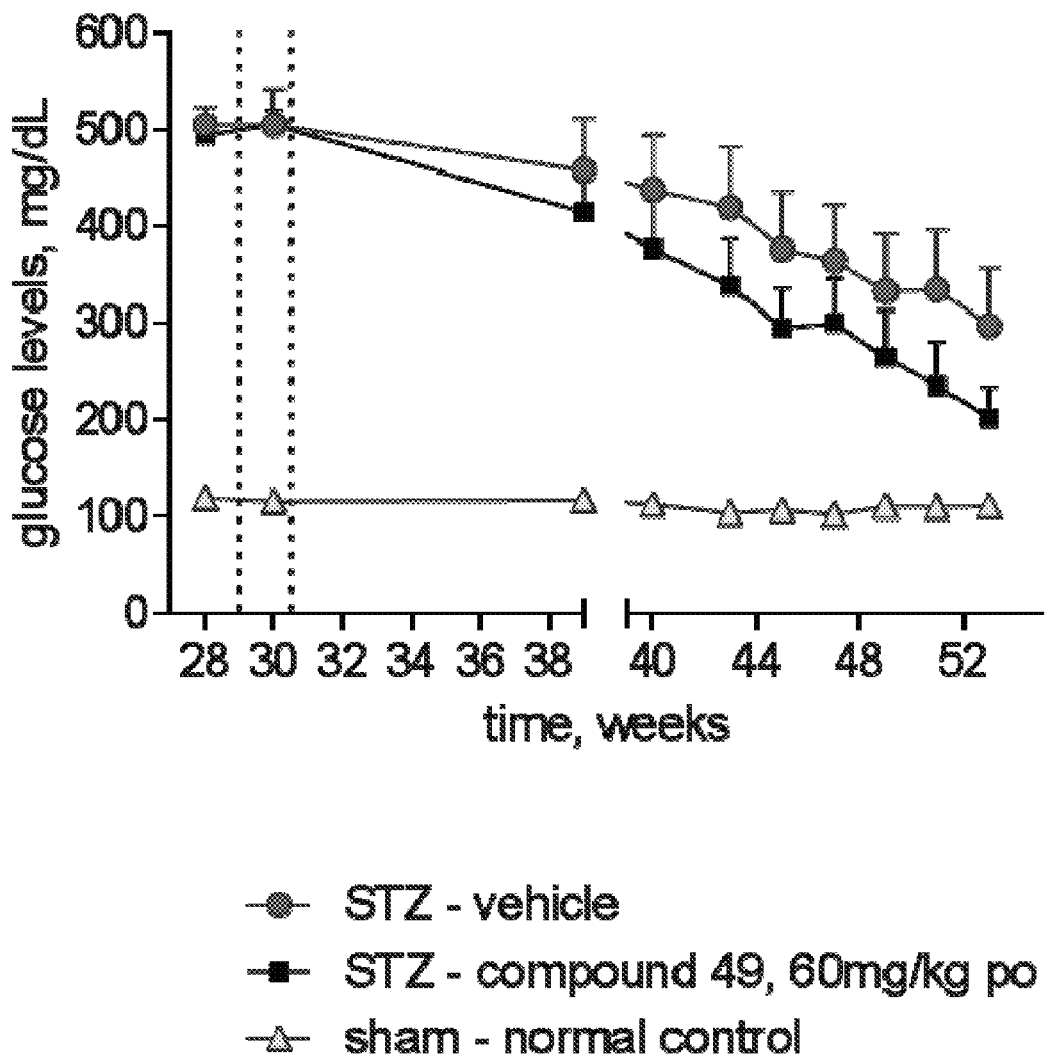

FIG. 2 shows the change in glucose level measured in the rat streptozotocin-induced model for diabetes. The change in glucose levels is shown for a diabetic vehicle group, a diabetic test compound treatment group, and a sham group. The diabetic test compound treatment group received a 60 mg/kg/day dose of compound 49 for 9 days. The beginning and the end of the treatment period is marked by a dotted line.

Figure 3:
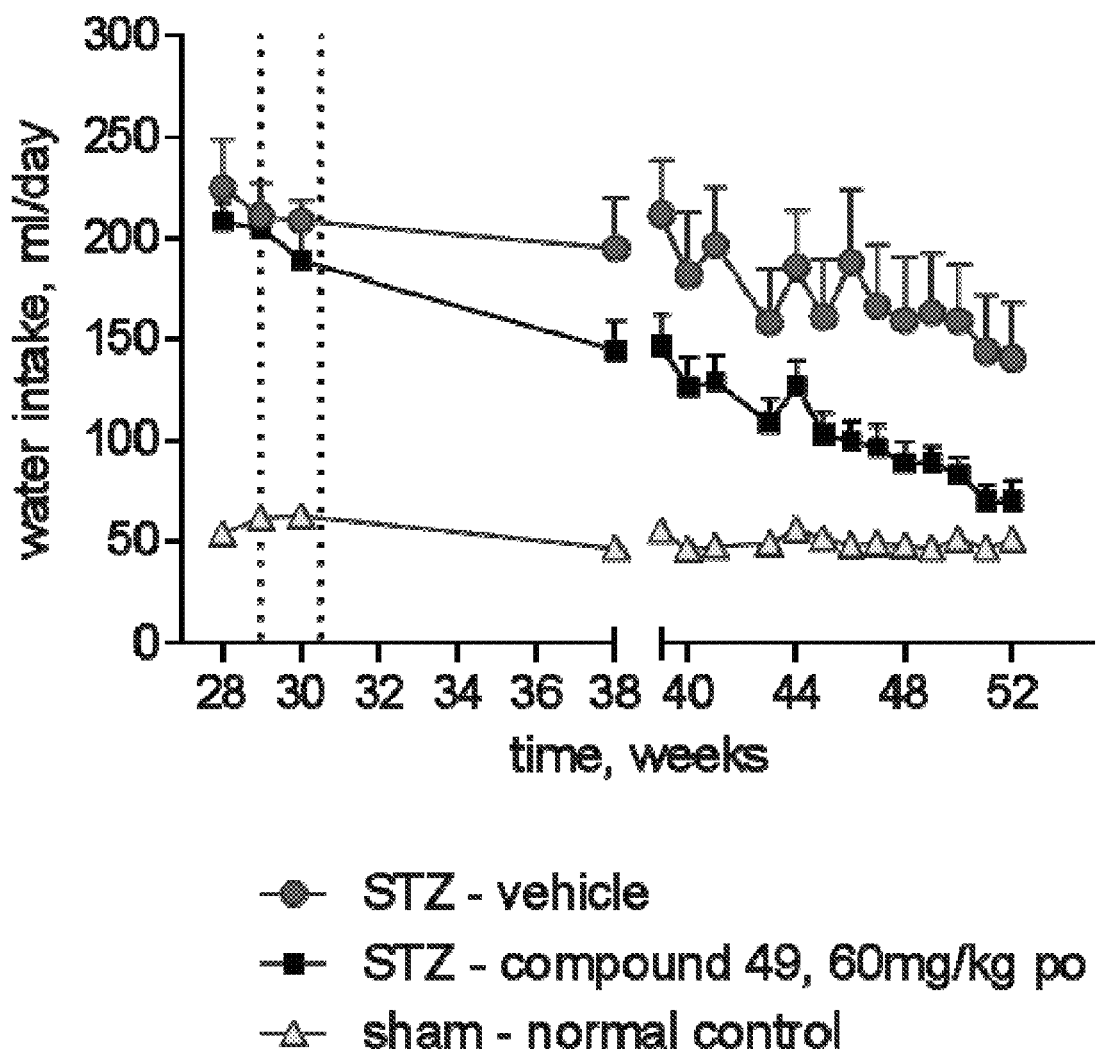

FIG. 3 shows the change in water intake measured in the rat streptozotocin-induced model for diabetes. The change in water intake is shown for a diabetic vehicle group, a diabetic test compound treatment group, and a sham group. The diabetic test compound treatment group received a 60 mg/kg/day dose of compound 49 for 9 days. The beginning and the end of the treatment period is marked by a dotted line.

4.3 Compounds

Provided herein are compounds of Formula (I),

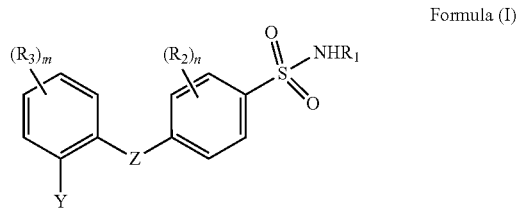

Formula (I)

or a pharmaceutically acceptable salt, or a stereoisomeric or tautomeric form thereof, wherein:

Z is —O— or —S—;

Y is —X—C(=O)NR$_4$R$_5$, —(CH$_2$)$_3$—NR$_9$R$_{10}$, or 4,5,6,7-tetrahydropyrazolo[1,5-a]pyrimidine-(2-yl or 3-yl);

X is (C$_6$-C$_{10}$)aryl or 5- or 6-membered heteroaryl;

$R_1$ is a partially unsaturated or aromatic 5- or 6-membered heterocycle;

$R_2$ is independently at each occurrence —F, —Cl, —Br, —CH$_3$ or —CN;

$R_3$ is independently at each occurrence —H, —F, —Cl, —Br, —CF$_3$, —OCF$_3$, —CN, (C$_1$-C$_{12}$)alkyl, or (C$_1$-C$_{12}$)alkoxy;

$R_4$ and $R_5$ are each independently H, (C$_1$-C$_9$)alkyl, (C$_4$-C$_{12}$)cycloalkyl, or $R_4$ and $R_5$ together form a 5- to 7-membered heterocycloalkyl ring; with the proviso that:

$R_4$ and $R_5$ are not both H; and at least one of $R_4$ and $R_5$ independently or said heterocycloalkyl ring formed by $R_4$ and $R_5$ together is substituted with 1 or 2 substituents selected from the group consisting of —CO$_2$H, —CO$_2$R$_6$, —CN, —OH, —CONR$_7$R$_8$, and —NR$_7$R$_8$; wherein:

$R_6$ is (C$_1$-C$_{12}$)alkyl;

$R_7$ and $R_8$ are each independently H, (C$_1$-C$_{12}$)alkyl, or $R_7$ and $R_8$ together form a 4- to 7-membered heterocycloalkyl ring;

$R_9$ is (C$_1$-C$_6$)alkyl, (C$_3$-C$_8$)cycloalkyl, pyrazolyl or pyridinyl; wherein $R_9$ is optionally further substituted with 1 or 2 substituents selected from the group consisting of —COOH, —COOR$_{11}$, —CONR$_{11}$R$_{12}$, —SO$_2$NR$_{11}$R$_{12}$, —OH, —CN, and —NR$_{11}$R$_{12}$; wherein $R_{11}$ and $R_{12}$ may form a 6 membered heterocycloalkyl ring $R_{10}$ is $R_{11}$, —COR$_{11}$, —COOR$_{11}$, 5-methyl-2-oxo-1,3-dioxol-4-yl,

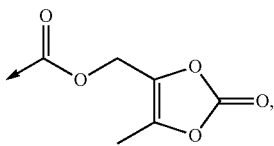

—COO—CH(CH$_3$)OCOCH(CH$_3$)$_2$; or $R_9$ and $R_{10}$ together form a piperazinone or a 4- to 8-membered heterocycloalkyl ring, wherein said heterocycloalkyl ring is substituted with 1 or 2 substituents selected from the group consisting of —COOH, —COOR$_{11}$, —CH$_2$—COOR$_{11}$, —OH, —CN, and (C$_1$-C$_8$)alkoxy;

$R_{11}$ and $R_{12}$ are independently H or (C$_1$-C$_6$)alkyl, optionally substituted with 4- to 8-membered heterocycloalkyl ring; and m and n are each independently 1, 2, 3, or 4.

In a certain embodiment, the compounds of Formula (I')

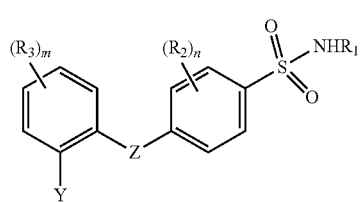

Formula (I')

are those wherein $R_{10}$ is $R_{11}$, (C$_3$-C$_6$)alkynyl, (C$_3$-C$_6$)alkenyl, —COR$_{11}$, —COOR$_{11}$, —SO$_2$R$_{11}$, 5-methyl-2-oxo-1,3-dioxol-4-yl,

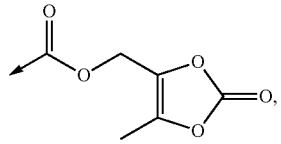

—COO—CH(CH$_3$)OCOCH(CH$_3$)$_2$; or $R_9$ and $R_{10}$ together form a piperazinone or a 4- to 8-membered heterocycloalkyl ring, wherein said heterocycloalkyl ring is substituted with 1 or 2 substituents selected from the group consisting of COOH, —COOR$_{11}$, —CH$_2$—COOR$_{11}$, —OH, —NH$_2$, —CN, and (C$_1$-C$_8$)alkoxy; or $R_9$ and $R_{10}$ together form a unsubstituted 4- to 8-membered heterocycloalkyl ring, wherein said heterocycloalkyl ring is fused with a 5-membered heteroaryl; and wherein all other substituents are as defined above.

In a certain embodiment, the compounds of Formula (I) or Formula (I') are those wherein Y is —(CH$_2$)$_3$—NR$_9$R$_{10}$.

In a particular embodiment, the compounds of Formula (I) or Formula (I') are those wherein $R_1$ is an aromatic 5- or 6-membered heterocycle, with 1-3 heteroatoms independently selected from the group consisting of N, O, and S.

In a particular embodiment, the compounds of Formula (I) or Formula (I') are those wherein $R_1$ is pyridyl or pyrimidinyl.

In a particular embodiment, the compounds of Formula (I) or Formula (I') are those wherein $R_1$ is an aromatic 5-membered heterocycle with 1 or 2 nitrogen atoms and optionally 1 or 2 sulphur atoms. In a particular embodiment, the compounds of Formula (I) or Formula (I') are those wherein $R_1$ is thiazolyl, isothiazolyl, or thiadiazolyl. In a particular embodiment, the compounds of Formula (I) or Formula (I') are those wherein $R_1$ is thiazolyl. In a particular embodiment, the compounds of Formula (I) or Formula (I') are those wherein $R_1$ is 1,2,4-thiadiazol-5-yl. In a particular embodiment, the compounds of Formula (I) or Formula (I') are those wherein $R_1$ is thiadiazol-4-yl.

In a particular embodiment, the compounds of Formula (I) or Formula (I') are those wherein $R_2$ is independently at each occurrence —F or —Cl.

In a particular embodiment, the compounds of Formula (I) or Formula (I') are those wherein n is 1, 2, or 3. In a particular embodiment, the compounds of Formula (I) or Formula (I') are those wherein n is 2.

In a particular embodiment, the compounds of Formula (I) or Formula (I') are those wherein Z is —O—.

In a particular embodiment, the compounds of Formula (I) or Formula (I') are those wherein $R_3$ is independently at each occurrence —H, —F, —Cl, or —Br. In a particular embodiment, the compounds of Formula (I) or Formula (I') are those wherein $R_3$ is —H or —Cl. In a particular embodiment, the compounds of Formula (I) or Formula (I') are those wherein $R_3$ is —Cl.

In a particular embodiment, the compounds of Formula (I) or Formula (I') are those wherein m is 1, 2, or 3. In a particular embodiment, the compounds of Formula (I) or Formula (I') are those wherein m is 1.

In a particular embodiment, the compounds of Formula (I) or Formula (I') are those wherein $R_9$ is (C$_1$-C$_6$)alkyl; wherein $R_9$ is optionally further substituted with 1 or 2 substituents selected from the group consisting of —COOH, —COOMe, —CONH$_2$, and —NH$_2$. In a particular embodiment, the compounds of Formula (I) or Formula (I') are those wherein $R_9$ is methyl or ethyl. In a particular embodiment, the compounds of Formula (I) or Formula (I') are those wherein $R_9$ is further substituted with —COOH.

In a particular embodiment, the compounds of Formula (I) or Formula (I') are those wherein $R_{10}$ is H and $R_9$ is $(C_1-C_6)$alkyl; wherein $R_9$ is further substituted with —CONR$_{11}$R$_{12}$, and wherein $R_{11}$ and $R_{12}$ are independently H or $(C_1-C_6)$alkyl. In a particular embodiment, the compounds of Formula (I) or Formula (I') are those wherein $R_9$ is further substituted with —CONH$_2$. In a particular embodiment, the compounds of Formula (I) or Formula (I') are those wherein $R_9$ is methyl and wherein $R_9$ is further substituted with —CONH$_2$.

In a particular embodiment, the compounds of Formula (I) or Formula (I') are those wherein $R_{10}$ is —H, —COMe, —COOEt. In a particular embodiment, the compounds of Formula (I) or Formula (I') are those wherein $R_{10}$ is —H or —COMe. In a particular embodiment, the compounds of Formula (I) or Formula (I') are those wherein $R_{10}$ is —H.

In a particular embodiment, the compounds of Formula (I) or Formula (I') are those wherein $R_9$ and $R_{10}$ together form a 4 to 8 membered heterocycloalkyl ring, wherein said heterocycloalkyl ring is substituted with 1 or 2 groups selected from the group consisting of —COOH, —COOMe, —COOEt, —CH$_2$—COOH, and —NH$_2$. In a particular embodiment, the compounds of Formula (I) are those wherein $R_9$ and $R_{10}$ together form a 4 to 8 membered heterocycloalkyl ring, wherein said heterocycloalkyl ring is substituted with 1 or 2 groups selected from the group consisting of —COOH, —CH$_2$—COOH, and —NH$_2$.

In a particular embodiment, the compounds of Formula (I) or Formula (I') are those wherein $R_9$ and $R_{10}$ together form a piperidine substituted with 1 or 2 groups selected from the group consisting of —COOH, —COOMe, —COOEt, —CH$_2$—COOH, —CH$_2$—COOMe, —CH$_2$—COOEt, and —NH$_2$. In a particular embodiment, the compounds of Formula (I) or Formula (I') are those wherein $R_9$ and $R_{10}$ together form a piperidine substituted with 1 or 2 groups selected from the group consisting of —COOH, —CH$_2$—COOH, and —NH$_2$.

In a certain embodiment, the compounds of Formula (I) or Formula (I') are those wherein Y is —X—C(=O)NR$_4$R$_5$.

In a particular embodiment, the compounds of Formula (I) or Formula (I') are those wherein $R_1$ is an aromatic 5- or 6-membered heterocycle, with 1-3 heteroatoms independently selected from the group consisting of N, O, and S.

In a particular embodiment, the compounds of Formula (I) or Formula (I') are those wherein $R_1$ is pyridyl or pyrimidinyl.

In a particular embodiment, the compounds of Formula (I) or Formula (I') are those wherein $R_1$ is an aromatic 5-membered heterocycle with 1 or 2 nitrogen atoms and optionally 1 or 2 sulphur atoms. In a particular embodiment, the compounds of Formula (I) or Formula (I') are those wherein $R_1$ is thiazolyl, isothiazolyl, or thiadiazolyl. In a particular embodiment, the compounds of Formula (I) or Formula (I') are those wherein $R_1$ is thiazolyl. In a particular embodiment, the compounds of Formula (I) or Formula (I') are those wherein $R_1$ is 1,2,4-thiadiazol-5-yl.

In a particular embodiment, the compounds of Formula (I) or Formula (I') are those wherein $R_2$ is independently at each occurrence —F or —Cl.

In a particular embodiment, the compounds of Formula (I) or Formula (I') are those wherein n is 1, 2, or 3. In a particular embodiment, the compounds of Formula (I) or Formula (I') are those wherein n is 2.

In a particular embodiment, the compounds of Formula (I) or Formula (I') are those wherein Z is —O—.

In a particular embodiment, the compounds of Formula (I) or Formula (I') are those wherein $R_3$ is independently at each occurrence —H, —F, —Cl, or —Br. In a particular embodiment, the compounds of Formula (I) or Formula (I') are those wherein $R_3$ is —H or —Cl. In a particular embodiment, the compounds of Formula (I) or Formula (I') are those wherein $R_3$ is —Cl.

In a particular embodiment, the compounds of Formula (I) or Formula (I') are those wherein m is 1, 2, or 3. In a particular embodiment, the compounds of Formula (I) or Formula (I') are those wherein m is 1.

In a particular embodiment, the compounds of Formula (I) or Formula (I') are those wherein X is 5- or 6-membered heteroaryl. In a particular embodiment, the compounds of Formula (I) or Formula (I') are those wherein X is pyridyl or pyrimidinyl. In a particular embodiment, the compounds of Formula (I) or Formula (I') are those wherein X is pyridyl.

In a particular embodiment, the compounds of Formula (I) or Formula (I') are those wherein $R_4$ is H and $R_5$ is $(C_1-C_9)$alkyl.

In a particular embodiment, the compounds of Formula (I) or Formula (I') are those wherein $R_5$ is methyl or ethyl, substituted with 1 or 2 substituents selected from the group consisting of —CO$_2$H, —CO$_2$R$_6$, and —CONR$_7$R$_8$.

In a particular embodiment, the compounds of Formula (I) or Formula (I') are those wherein $R_6$ is $(C_1-C_6)$alkyl.

In a particular embodiment, the compounds of Formula (I) or Formula (I') are those wherein $R_5$ is methyl or ethyl, substituted with —CO$_2$H.

In a certain embodiment, the compounds of Formula (I) or Formula (I') are those wherein Y is 4,5,6,7-tetrahydropyrazolo[1,5-c]pyrimidine-(2-yl or 3-yl). In a particular embodiment, the compounds of Formula (I) or Formula (I') are those wherein Y is 4,5,6,7-tetrahydropyrazolo[1,5-a]pyrimidine-3-yl.

In a particular embodiment, the compounds of Formula (I) or Formula (I') are those wherein $R_1$ is an aromatic 5- or 6-membered heterocycle, with 1-3 heteroatoms independently selected from the group consisting of N, O, and S.

In a particular embodiment, the compounds of Formula (I) or Formula (I') are those wherein $R_1$ is pyridyl or pyrimidinyl.

In a particular embodiment, the compounds of Formula (I) or Formula (I') are those wherein $R_1$ is an aromatic 5-membered heterocycle with 1 or 2 nitrogen atoms and optionally 1 or 2 sulphur atoms. In a particular embodiment, the compounds of Formula (I) or Formula (I') are those wherein $R_1$ is thiazolyl, isothiazolyl, or thiadiazolyl. In a particular embodiment, the compounds of Formula (I) or Formula (I') are those wherein $R_1$ is thiazolyl. In a particular embodiment, the compounds of Formula (I) or Formula (I') are those wherein $R_1$ is 1,2,4-thiadiazol-5-yl.

In a particular embodiment, the compounds of Formula (I) or Formula (I') are those wherein $R_2$ is independently at each occurrence —F or —Cl.

In a particular embodiment, the compounds of Formula (I) or Formula (I') are those wherein n is 1, 2, or 3. In a particular embodiment, the compounds of Formula (I) or Formula (I') are those wherein n is 2.

In a particular embodiment, the compounds of Formula (I) or Formula (I') are those wherein Z is —O—.

In a particular embodiment, the compounds of Formula (I) or Formula (I') are those wherein $R_3$ is independently at each occurrence —H, —F, —Cl, or —Br. In a particular embodiment, the compounds of Formula (I) or Formula (I') are those wherein $R_3$ is —H or —Cl. In a particular embodiment, the compounds of Formula (I) or Formula (I') are those wherein $R_3$ is —Cl.

In a particular embodiment, the compounds of Formula (I) or Formula (I') are those wherein m is 1, 2, or 3. In a particular embodiment, the compounds of Formula (I) or Formula (I') are those wherein m is 1.

In a certain embodiment, the compounds of Formula (I) or Formula (I') are those wherein the compound is selected from the group consisting of the compounds in Table 1 or a pharmaceutically acceptable salt, or a stereoisomeric or tautomeric form thereof.

TABLE 1

| Compound | Compound structure | Chemical name* |
|---|---|---|
| 1 | 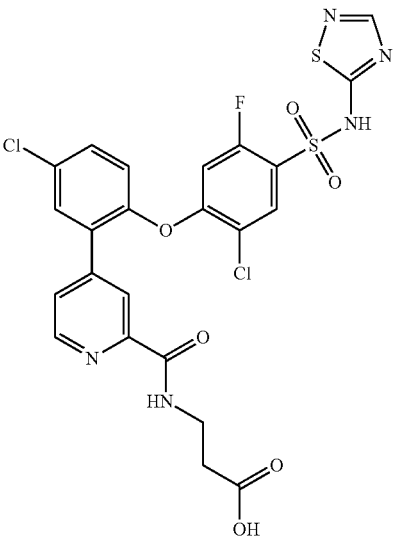 [SMILES: O=C(O)CCNC(=O)c1cc(-c2cc(Cl)ccc2Oc2cc(F)c(S(=O)(=O)Nc3ncns3)cc2Cl)ccn1] | 3-(4-(2-(4-(N-(1,2,4-thiadiazol-5-yl)sulfamoyl)-2-chloro-5-fluorophenoxy)-5-chlorophenyl)picolinamido)propanoic acid |
| 2 | 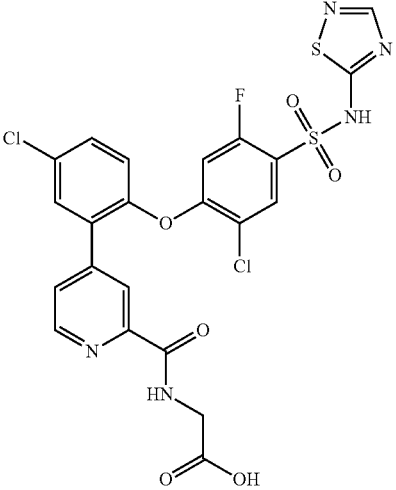 [SMILES: O=C(O)CNC(=O)c1cc(-c2cc(Cl)ccc2Oc2cc(F)c(S(=O)(=O)Nc3ncns3)cc2Cl)ccn1] | 2-(4-(2-(4-(N-(1,2,4-thiadiazol-5-yl)sulfamoyl)-2-chloro-5-fluorophenoxy)-5-chlorophenyl)picolinamido)acetic acid |

TABLE 1-continued
| Compound | Compound structure | Chemical name* |
|---|---|---|
| 3 | 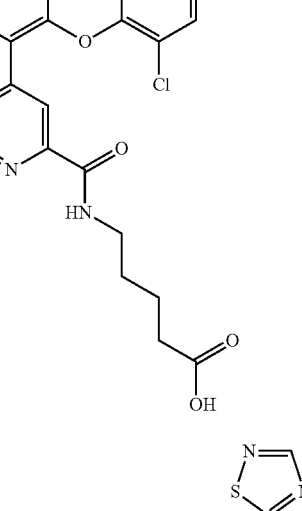 | 5-(4-(2-(4-(N-(1,2,4-thiadiazol-5-yl)sulfamoyl)-2-chloro-5-fluorophenoxy)-5-chlorophenyl)picolinamido)pentanoic acid |
| 4 | 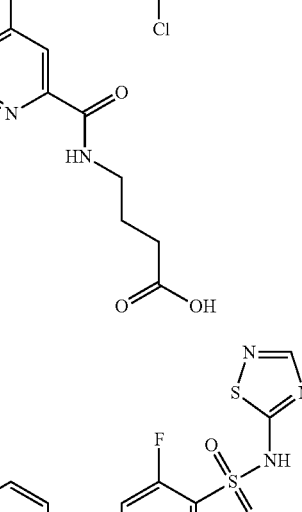 | 4-(4-(2-(4-(N-(1,2,4-thiadiazol-5-yl)sulfamoyl)-2-chloro-5-fluorophenoxy)-5-chlorophenyl)picolinamido)butanoic acid |
| 5 | 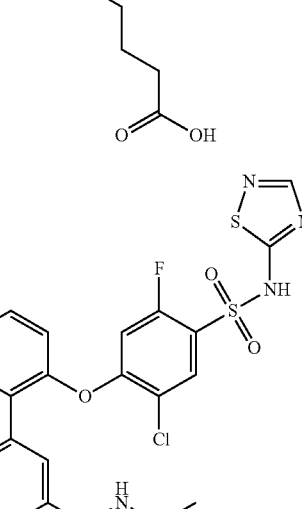 | 2-(4-(2-(4-(N-1,2,4-thiadiazol-5-yl)sulfamoyl)-2-chloro-5-fluorophenoxy)-5-chlorophenyl)picolinamido)propanoic acid |

TABLE 1-continued
| Compound | Compound structure | Chemical name* |
|---|---|---|
| 6 | 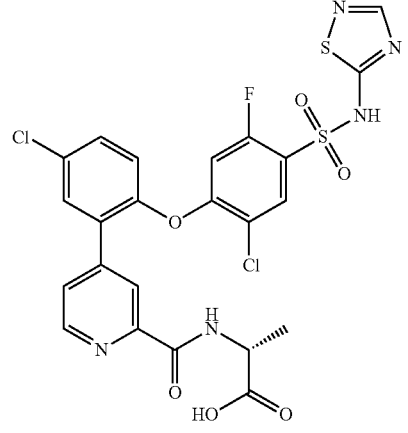 [SMILES: C[C@@H](NC(=O)c1cc(-c2cc(Cl)ccc2Oc2cc(F)c(S(=O)(=O)Nc3ncns3)cc2Cl)ccn1)C(=O)O] | (R)-2-(4-(2-(4-(N-(1,2,4-thiadiazol-5-yl)sulfamoyl)-2-chloro-5-fluorophenoxy)-5-chlorophenyl)picolinamido)propanoic acid |
| 7 | 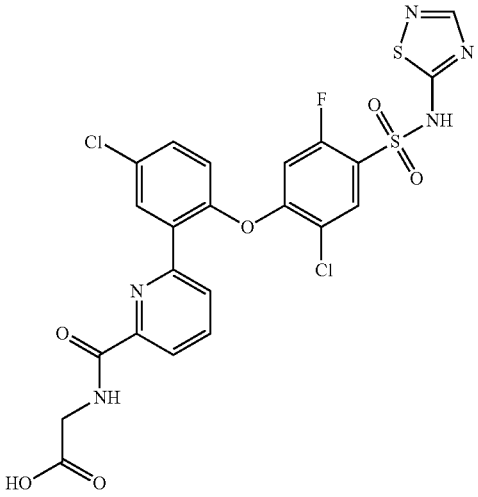 [SMILES: O=C(O)CNC(=O)c1cccc(-c2cc(Cl)ccc2Oc2cc(F)c(S(=O)(=O)Nc3ncns3)cc2Cl)n1] | 2-(6-(2-(4-(N-(1,2,4-thiadiazol-5-yl)sulfamoyl)-2-chloro-5-fluorophenoxy)-5-chlorophenyl)picolinamido)acetic acid |
| 8 | 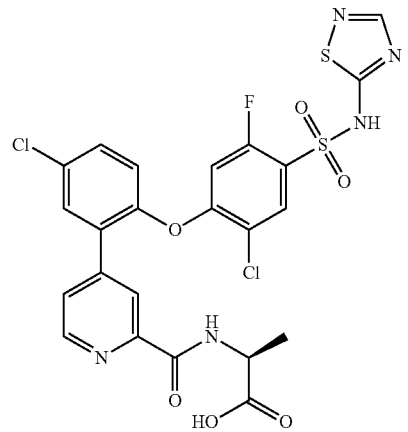 [SMILES: C[C@H](NC(=O)c1cc(-c2cc(Cl)ccc2Oc2cc(F)c(S(=O)(=O)Nc3ncns3)cc2Cl)ccn1)C(=O)O] | (S)-2-(4-(2-(4-(N-(1,2,4-thiadiazol-5-yl)sulfamoyl)-2-chloro-5-fluorophenoxy)-5-chlorophenyl)picolinamido)propanoic acid |

TABLE 1-continued

| Compound | Compound structure | Chemical name* |
|---|---|---|
| 9 | 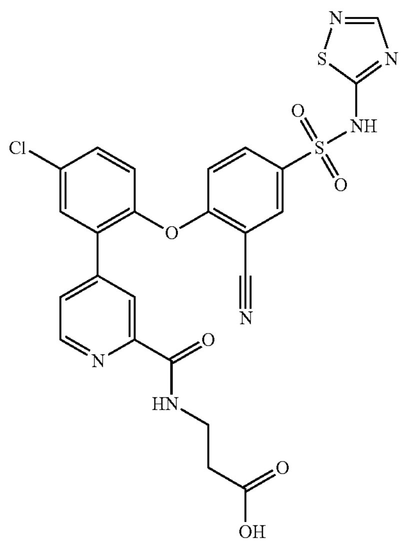 [SMILES: N#Cc1cc(S(=O)(=O)Nc2ncns2)ccc1Oc1ccc(Cl)cc1-c1ccnc(C(=O)NCCC(=O)O)c1] | 3-(4-(2-(4-(N-(1,2,4-thiadiazol-5-yl)sulfamoyl)-2-cyanophenoxy)-5-chlorophenyl)picolinamido)propanoic acid |
| 10 | 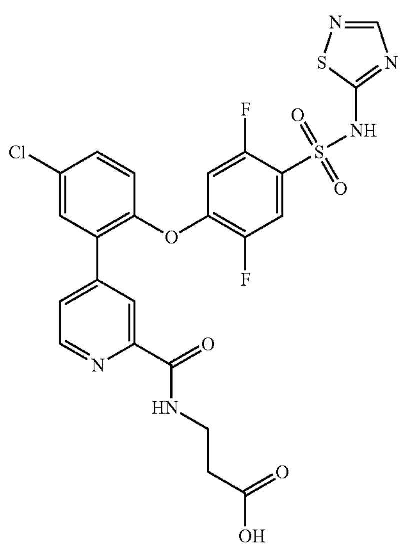 | 3-(4-(2-(4-(N-(1,2,4-thiadiazol-5-yl)sulfamoyl-2,5-difluorophenoxy)-5-chlorophenyl)picolinamido)propanoic acid |
| 11 | 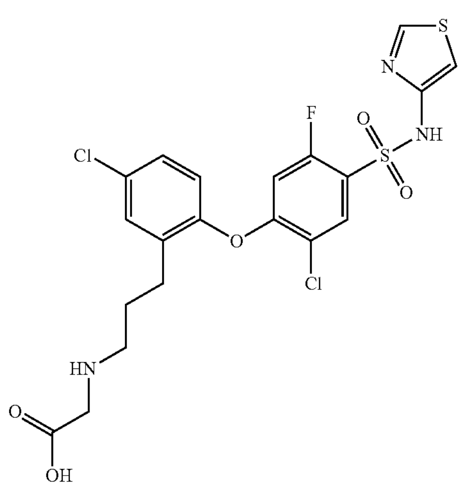 [SMILES: O=C(O)CNCCCc1cc(Cl)ccc1Oc1cc(F)c(S(=O)(=O)Nc2cscn2)cc1Cl] | 2-((3-(5-chloro-2-(2-chloro-5-fluoro-4-(N-(thiazol-4-yl)sulfamoyl)phenoxy)phenyl)propyl)amino)acetic acid |

TABLE 1-continued
| Compound | Compound structure | Chemical name* |
|---|---|---|
| 12 | 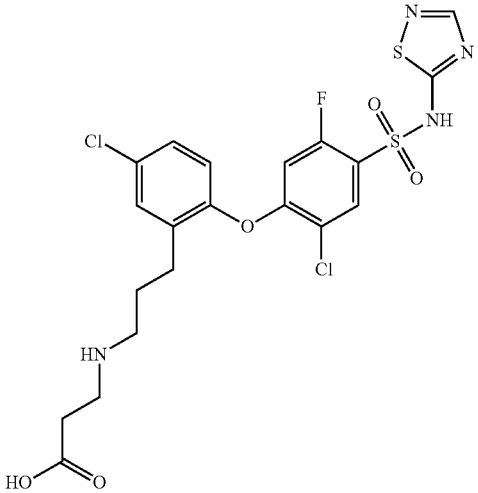 [SMILES: O=C(O)CCNCCCc1cc(Cl)ccc1Oc1cc(F)c(S(=O)(=O)Nc2ncns2)cc1Cl] | 3-((3-(2-(4-(N-(1,2,4-thiadiazol-5-yl)sulfamoyl)-2-chloro-5-fluorophenoxy)-5-chlorophenyl)propyl)amino)propanoic acid |
| 13 | 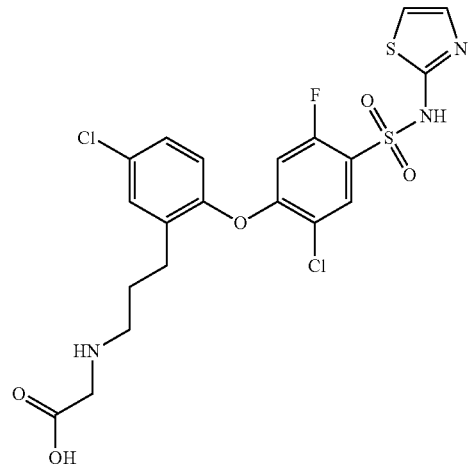 | 2-((3-(5-chloro-2-(2-chloro-5-fluoro-4-(N-(thiazol-2-yl)sulfamoyl)phenoxy)phenyl)propyl)amino)acetic acid |
| 14 | 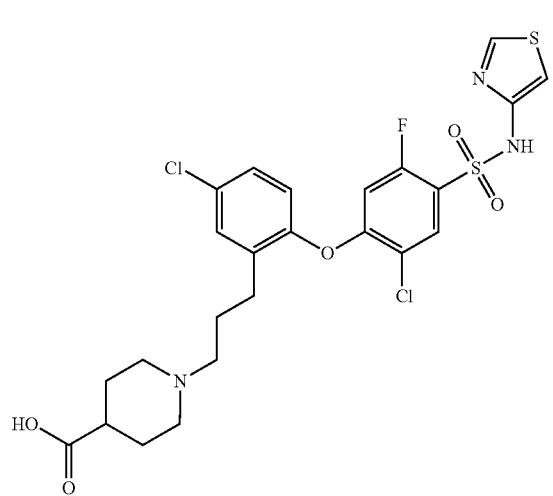 [SMILES: O=C(O)C1CCN(CCCc2cc(Cl)ccc2Oc2cc(F)c(S(=O)(=O)Nc3cscn3)cc2Cl)CC1] | 1-(3-(5-chloro-2-(2-chloro-5-fluoro-4-(N-(thiazol-4-yl)sulfamoyl)phenoxy)phenyl)propyl)piperidine-4-carboxylic acid |

TABLE 1-continued
| Compound | Compound structure | Chemical name* |
|---|---|---|
| 15 | 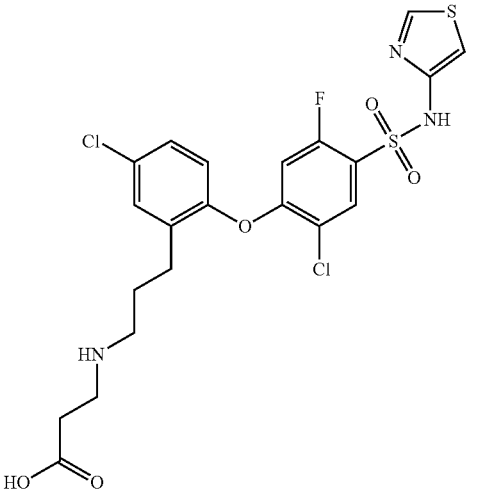 [SMILES: O=C(O)CCNCCCc1cc(Cl)ccc1Oc1cc(F)c(S(=O)(=O)Nc2cscn2)cc1Cl] | 3-((3-(5-chloro-2-(2-chloro-5-fluoro-4-(N-(thiazol-4-yl)sulfamoyl)phenoxy)phenyl)propyl)amino)propanoic acid |
| 16 | 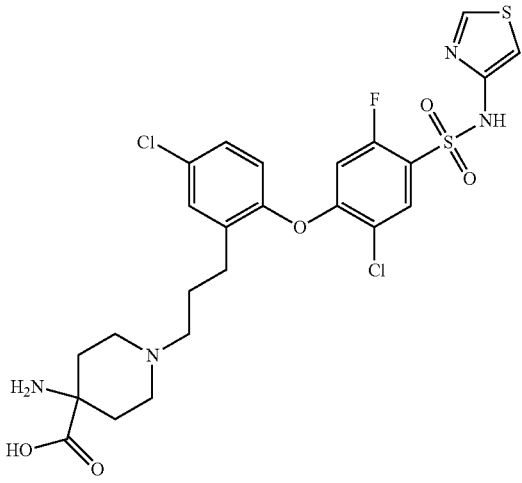 [SMILES: NC1(C(=O)O)CCN(CCCc2cc(Cl)ccc2Oc2cc(F)c(S(=O)(=O)Nc3cscn3)cc2Cl)CC1] | 4-amino-1-(3-(5-chloro-2-(2-chloro-5-fluoro-4-(N-(thiazol-4-yl)sulfamoyl)phenoxy)phenyl)propyl)piperidine-4-carboxylic acid |
| 17 | 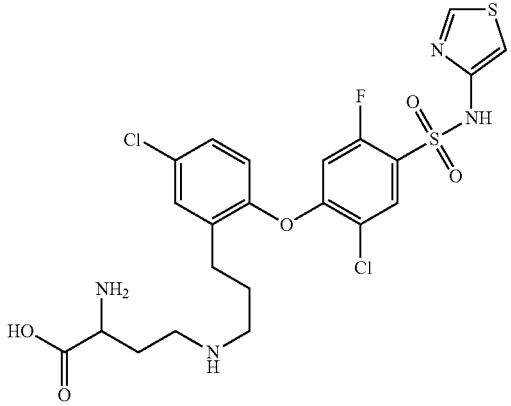 [SMILES: NC(CCNCCCc1cc(Cl)ccc1Oc1cc(F)c(S(=O)(=O)Nc2cscn2)cc1Cl)C(=O)O] | 2-amino-4-((3-(5-chloro-2-(2-chloro-5-fluoro-4-(N-thiazol-4-yl)sulfamoyl)phenoxy)phenyl)propyl)amino)butanoic acid |

TABLE 1-continued
| Compound | Compound structure | Chemical name* |
|---|---|---|
| 18 | 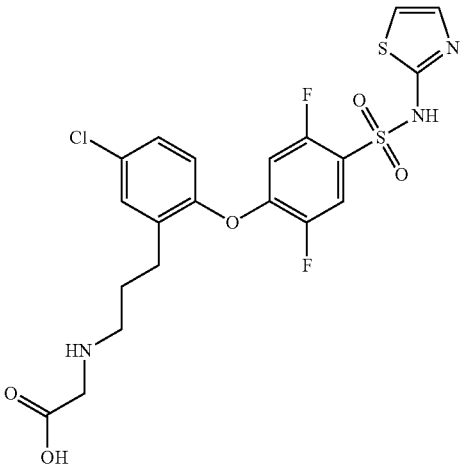 [SMILES: O=C(O)CNCCCc1cc(Cl)ccc1Oc1cc(F)c(S(=O)(=O)Nc2nccs2)cc1F] | 2-((3-(5-chloro-2-(2,5-difluoro-4-(N-(thiazol-2-yl)sulfamoyl)phenoxy)phenyl)propyl)amino)acetic acid |
| 19 | 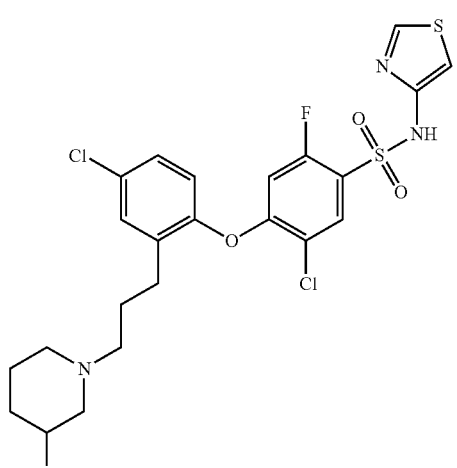 | 1-(3-(5-chloro-2-(2-chloro-5-fluoro-4-(N-(thiazol-4-yl)sulfamoyl)phenoxy)phenyl)propyl)piperidine-3-carboxylic acid |
| 20 | 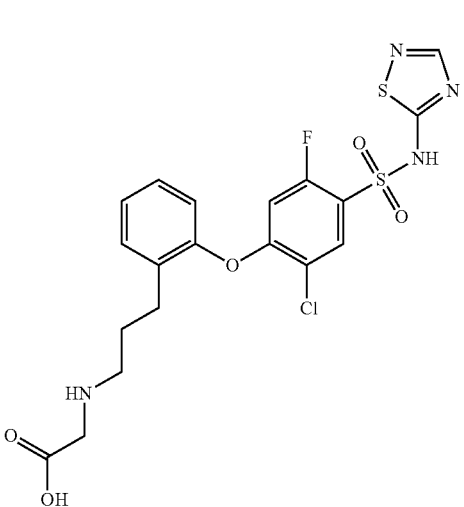 [SMILES: O=C(O)CNCCCc1ccccc1Oc1cc(F)c(S(=O)(=O)Nc2ncns2)cc1Cl] | 2-((3-(2-(4-(N-(1,2,4-thiadiazol-5-yl)sulfamoyl)-2-chloro-5-fluorophenoxy)phenyl)propyl)amino)acetic acid |

TABLE 1-continued

| Compound | Compound structure | Chemical name* |
|---|---|---|
| 21 | 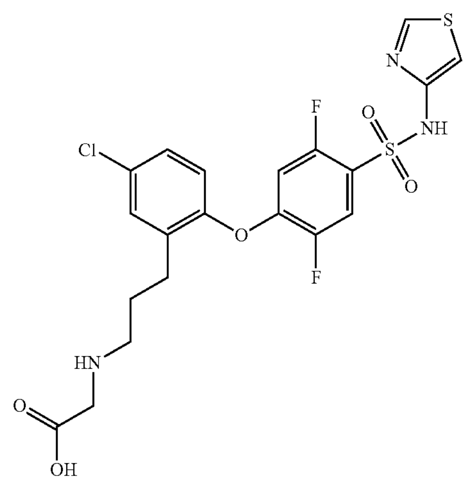 [SMILES: O=C(O)CNCCCc1cc(Cl)ccc1Oc1cc(F)c(S(=O)(=O)Nc2cscn2)cc1F] | 2-((3-(5-chloro-2-(2,5-difluoro-4-(N-(thiazol-4-yl)sulfamoyl)phenoxy)phenyl)propyl)amino)acetic acid |
| 22 | 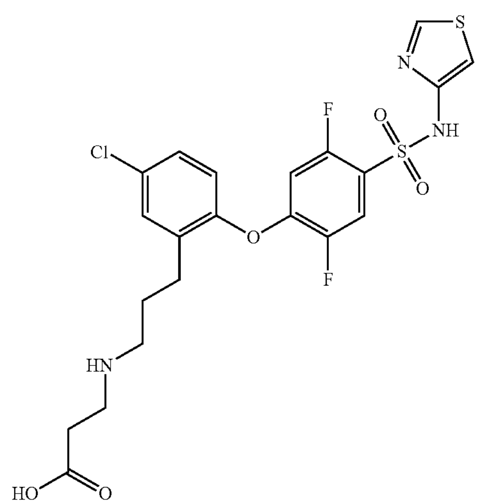 [SMILES: O=C(O)CCNCCCc1cc(Cl)ccc1Oc1cc(F)c(S(=O)(=O)Nc2cscn2)cc1F] | 3-((3-(5-chloro-2-(2,5-difluoro-4-(N-(thiazol-4-yl)sulfamoyl)phenoxy)phenyl)propyl)amino)propanoic acid |
| 23 | 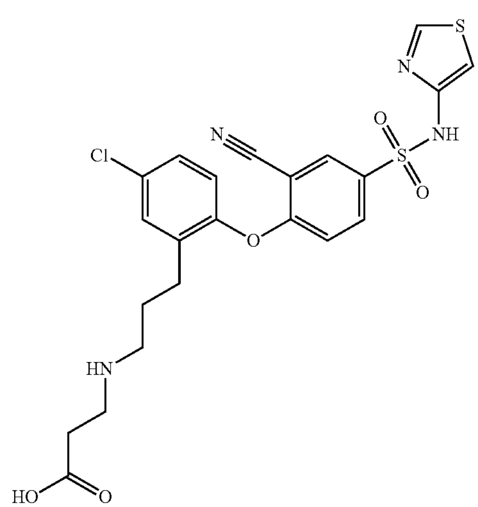 [SMILES: N#Cc1cc(S(=O)(=O)Nc2cscn2)ccc1Oc1ccc(Cl)cc1CCCNCCC(=O)O] | 3-((3-(5-chloro-2-(2-cyano-4-(N-(thiazol-4-yl)sulfamoyl)phenoxy)phenyl)propyl)amino)propanoic acid |

TABLE 1-continued

| Compound | Compound structure | Chemical name* |
|---|---|---|
| 24 | 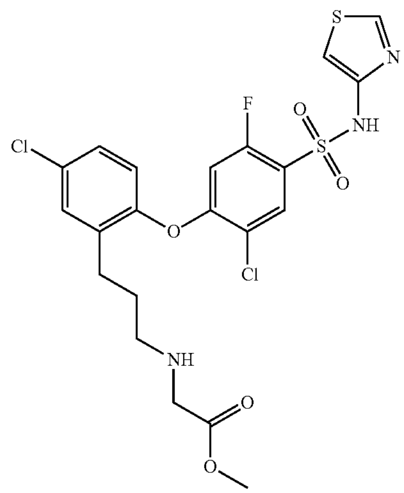 [SMILES: COC(=O)CNCCCc1cc(Cl)ccc1Oc1cc(F)c(S(=O)(=O)Nc2cscn2)cc1Cl] | methyl 2-((3-(5-chloro-2-(2-chloro-5-fluoro-4-(N-(thiazol-4-yl)sulfamoyl)phenoxy)phenyl)propyl)amino)acetate |
| 25 | 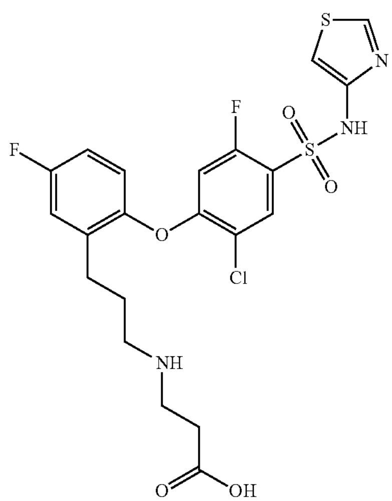 [SMILES: O=C(O)CCNCCCc1cc(F)ccc1Oc1cc(F)c(S(=O)(=O)Nc2cscn2)cc1Cl] | 3-((3-(2-(2-chloro-5-fluoro-4-(N-(thiazol-4-yl)sulfamoyl)phenoxy)-5-fluorophenyl)propyl)amino)propanoic acid |
| 26 | 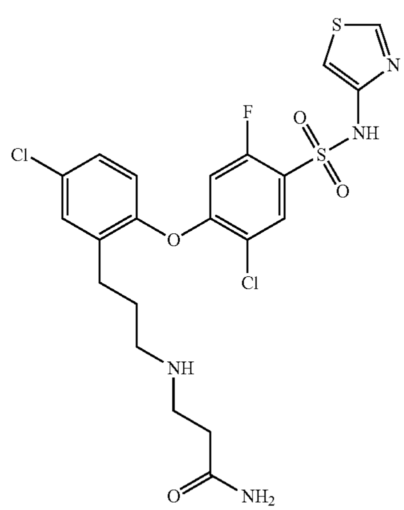 [SMILES: NC(=O)CCNCCCc1cc(Cl)ccc1Oc1cc(F)c(S(=O)(=O)Nc2cscn2)cc1Cl] | 3-((3-(5-chloro-2-(2-chloro-5-fluoro-4-(N-(thiazol-4-yl)sulfamoyl)phenoxy)phenyl)propyl)amino)propanamide |

TABLE 1-continued

| Compound | Compound structure | Chemical name* |
|---|---|---|
| 27 | 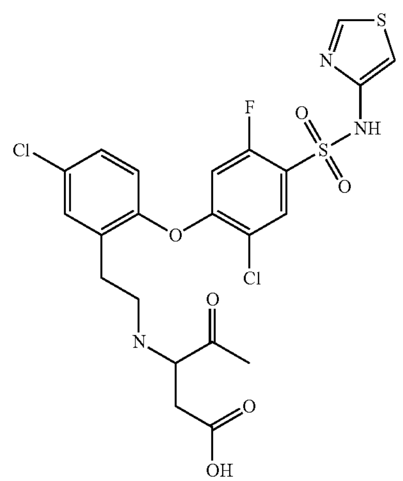 [SMILES: CC(=O)C(CC(=O)O)NCCc1cc(Cl)ccc1Oc1cc(F)c(S(=O)(=O)Nc2cscn2)cc1Cl] | 2-(N-(3-(5-chloro-2-(2-chloro-5-fluoro-4-(N-(thiazol-4-yl)sulfamoyl)phenoxy)phenyl)propyl)acetamido)acetic acid |
| 28 | 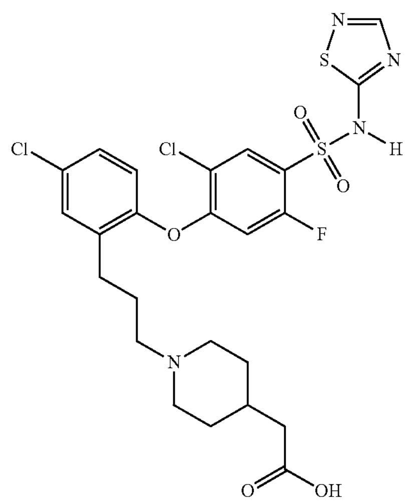 [SMILES: O=C(O)CC1CCN(CCCc2cc(Cl)ccc2Oc2cc(F)c(S(=O)(=O)Nc3ncns3)cc2Cl)CC1] | 2-(1-(3-(2-(4-(N-(1,2,4-thiadiazol-5-yl)sulfamoyl)-2-chloro-5-fluorophenoxy)-5-chlorophenyl)propyl)piperidin-4-yl)acetic acid |
| 29 | 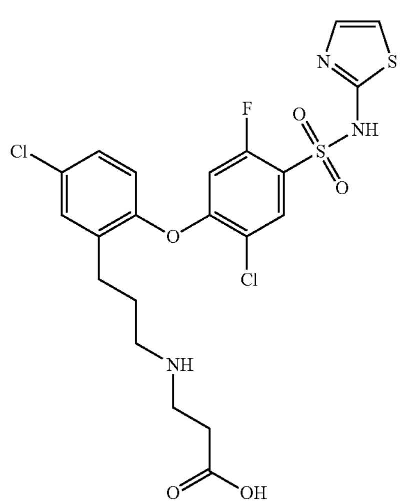 [SMILES: O=C(O)CCNCCCc1cc(Cl)ccc1Oc1cc(F)c(S(=O)(=O)Nc2nccs2)cc1Cl] | 3-((3-(5-chloro-2-(2-chloro-5-fluoro-4-(N-(thiazol-2-yl)sulfamoyl)phenoxy)phenyl)propyl)amino)propanoic acid |

TABLE 1-continued

| Compound | Compound structure | Chemical name* |
|---|---|---|
| 30 | 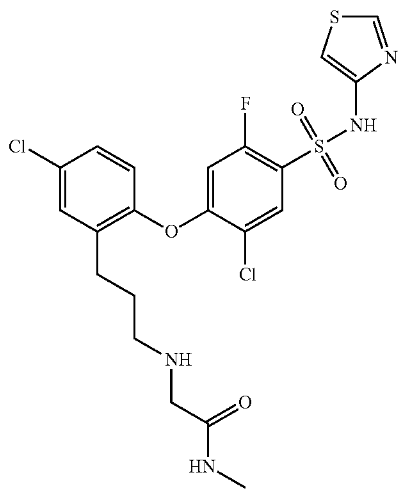 [SMILES: CNC(=O)CNCCCc1cc(Cl)ccc1Oc1cc(F)c(S(=O)(=O)Nc2cscn2)cc1Cl] | 2-((3-(5-chloro-2-(2-chloro-5-fluoro-4-(N-(thiazol-4-yl)sulfamoyl)phenoxy)phenyl)propyl)amino)-N-methylacetamide |
| 31 | 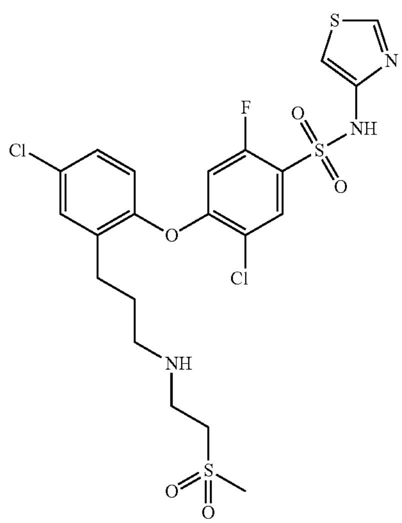 [SMILES: CS(=O)(=O)CCNCCCc1cc(Cl)ccc1Oc1cc(F)c(S(=O)(=O)Nc2cscn2)cc1Cl] | 5-chloro-4-(4-chloro-2-(3-((2-(methylsulfonyl)ethyl)amino)propyl)phenoxy)-2-fluoro-N-(thiazol-4-yl)benzenesulfonamide |
| 32 | 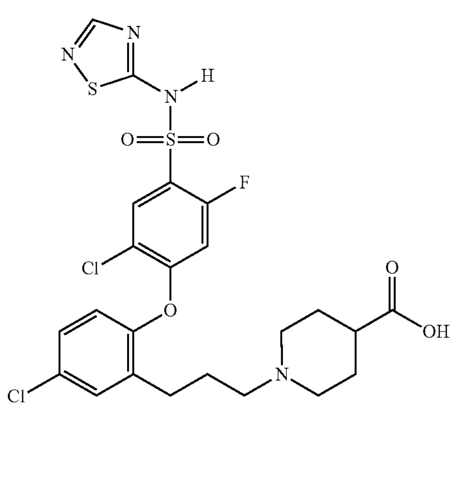 [SMILES: O=C(O)C1CCN(CCCc2cc(Cl)ccc2Oc2cc(F)c(S(=O)(=O)Nc3ncns3)cc2Cl)CC1] | 1-(3-(2-(4-(N-(1,2,4-thiadiazol-5-yl)sulfamoyl)-2-chloro-5-fluorophenoxy)-5-chlorophenyl)propyl)piperidine-4-carboxylic acid |

TABLE 1-continued

| Compound | Compound structure | Chemical name* |
|---|---|---|
| 33 | 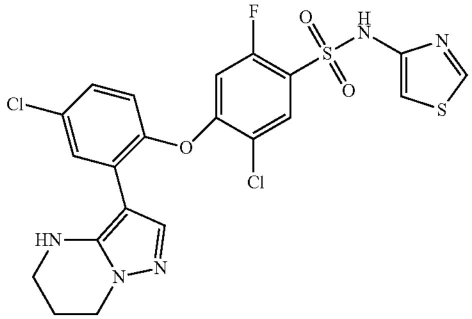 [SMILES: O=S(=O)(Nc1cscn1)c1cc(Cl)c(Oc2ccc(Cl)cc2-c2cnn3c2NCCC3)cc1F] | 5-chloro-4-(4-chloro-2-(4,5,6,7-tetrahydropyrazolo[1,5-a]pyrimidin-3-yl)phenoxy)-2-fluoro-N-(thiazol-4-yl)benzenesulfonamide |

*Chemical Names automatically generated with ChemDraw Ultra, Version 12.0.

In a certain embodiment, the compounds of Formula (I) or Formula (I') are those wherein the compound is selected from the group consisting of the compounds in Table 2 or a pharmaceutically acceptable salt, or a stereoisomeric or tautomeric form thereof.

TABLE 2

| Prophetic Compound | Compound structure | Chemical name* |
|---|---|---|
| 36 | 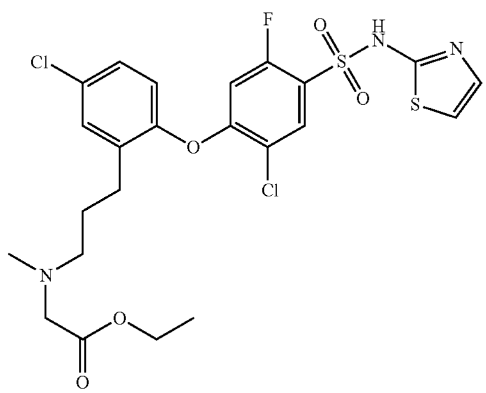 [SMILES: CCOC(=O)CN(C)CCCc1cc(Cl)ccc1Oc1cc(F)c(S(=O)(=O)Nc2nccs2)cc1Cl] | ethyl 2-((3-(5-chloro-2-(2-chloro-5-fluoro-4-(N-(thiazol-2-yl)sulfamoyl)phenoxy)phenyl)propyl)(methyl)amino)acetate |
| 37 | 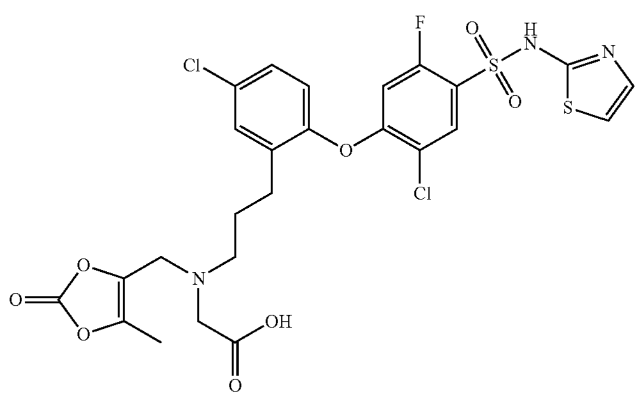 [SMILES: Cc1oc(=O)oc1CN(CCCc1cc(Cl)ccc1Oc1cc(F)c(S(=O)(=O)Nc2nccs2)cc1Cl)CC(=O)O] | 2-((3-(5-chloro-2-(2-chloro-5-fluoro-4-(N-(thiazol-2-yl)sulfamoyl)phenoxy)phenyl)propyl)((5-methyl-2-oxo-1,3-dioxol-4-yl)methyl)amino)acetic acid |

TABLE 2-continued

| Prophetic Compound | Compound structure | Chemical name* |
|---|---|---|
| 38 | 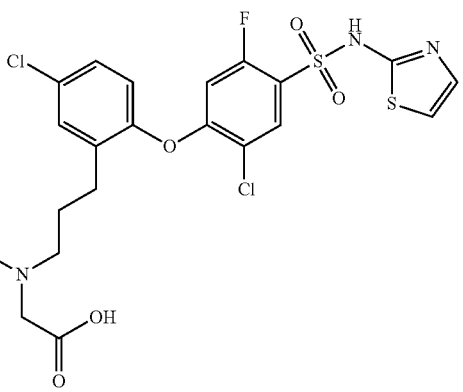 | 2-((3-(5-chloro-2-(2-chloro-5-fluoro-4-(N-(thiazol-2-yl)sulfamoyl)phenoxy)phenyl)propyl)((1-(isobutyryloxy)ethoxy)carbonyl)amino)acetic acid |
| 39 | 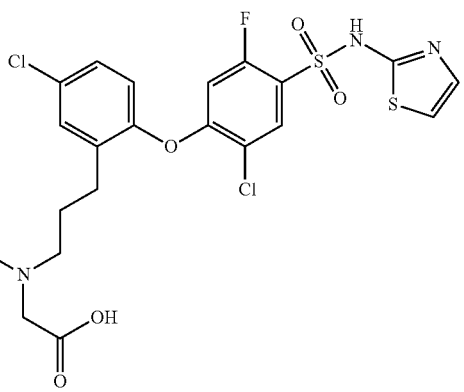 | 2-((3-(5-chloro-2-(2-chloro-5-fluoro-4-(N-(thiazol-2-yl)sulfamoyl)phenoxy)phenyl)propyl)(((5-methyl-2-oxo-1,3-dioxol-4-yl)methoxy)carbonyl)amino)acetic acid |
| 40 | 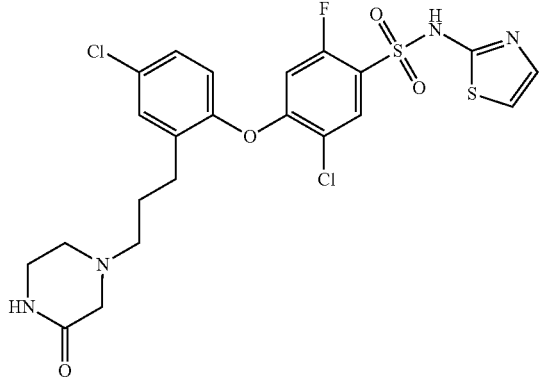 [SMILES: O=C1CN(CCCc2cc(Cl)ccc2Oc2cc(F)c(S(=O)(=O)Nc3nccs3)cc2Cl)CCN1] | 5-chloro-4-(4-chloro-2-(3-(3-oxopiperazin-1-yl)propyl)phenoxy)-2-fluoro-N-(thiazol-2-yl)benzenesulfonamide |

TABLE 2-continued

| Prophetic Compound | Compound structure | Chemical name* |
|---|---|---|
| 41 | 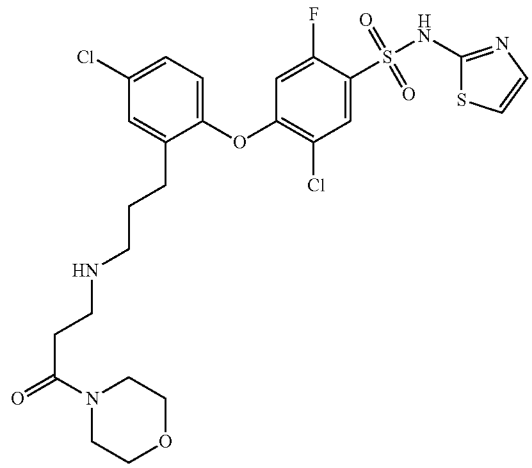 [SMILES: O=C(CCNCCCc1cc(Cl)ccc1Oc1cc(F)c(S(=O)(=O)Nc2nccs2)cc1Cl)N1CCOCC1] | 5-chloro-4-(4-chloro-2-(3-((3-morpholino-3-oxopropyl)amino)propyl)phenoxy)-2-fluoro-N-(thiazol-2-yl)benzenesulfonamide |

*Chemical Names automatically generated with ChemDraw Ultra, Version 12.0.

In a certain embodiment, the compounds of Formula (I) or Formula (I') are those wherein the compound is selected from the group consisting of the compounds in Table 3 or a pharmaceutically acceptable salt, or a stereoisomeric or tautomeric form thereof.

TABLE 3

| Compound | Compound structure | Chemical name* |
|---|---|---|
| 34 | 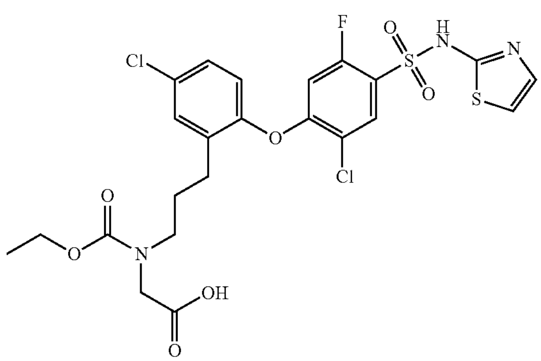 [SMILES: CCOC(=O)N(CCCc1cc(Cl)ccc1Oc1cc(F)c(S(=O)(=O)Nc2nccs2)cc1Cl)CC(=O)O] | 2-((3-(5-chloro-2-(2-chloro-5-fluoro-4-(N-(thiazol-2-yl)sulfamoyl)phenoxy)phenyl)propyl)(ethoxycarbonyl)amino)acetic acid |
| 35 | 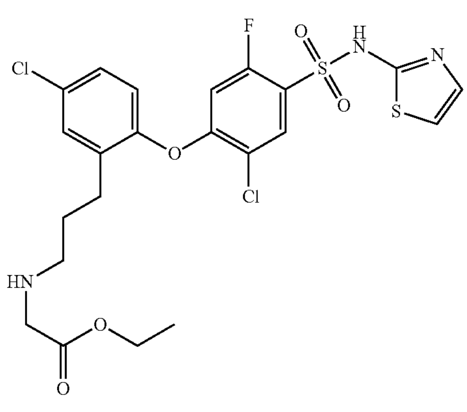 [SMILES: CCOC(=O)CNCCCc1cc(Cl)ccc1Oc1cc(F)c(S(=O)(=O)Nc2nccs2)cc1Cl] | ethyl 2-((3-(5-chloro-2-(2-chloro-5-fluoro-4-(N-(thiazol-2-yl)sulfamoyl)phenoxy)phenyl)propyl)amino)acetate |

TABLE 3-continued
| Compound | Compound structure | Chemical name* |
|---|---|---|
| 42 | 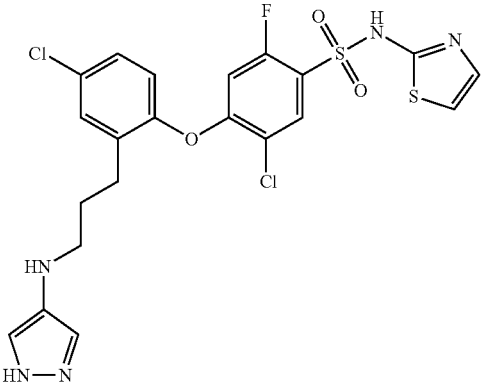 [SMILES: O=S(=O)(Nc1nccs1)c1cc(Cl)c(Oc2ccc(Cl)cc2CCCNc2cn[nH]c2)cc1F] | 4-(2-(3-((1H-pyrazol-4-yl)amino)propyl)-4-chlorophenoxy)-5-chloro-2-fluoro-N-(thiazol-2-yl)benzenesulfonamide |
| 43 | 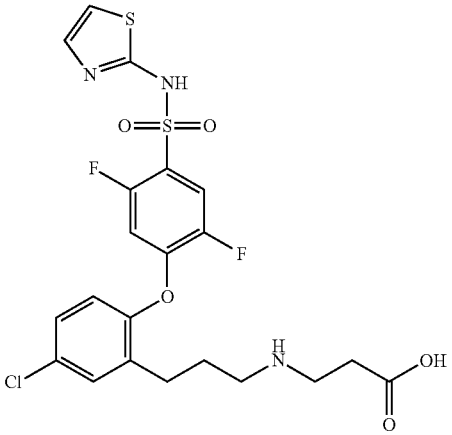 [SMILES: O=C(O)CCNCCCc1cc(Cl)ccc1Oc1cc(F)c(S(=O)(=O)Nc2nccs2)cc1F] | 3-((3-(5-chloro-2-(2,5-difluoro-4-(N-(thiazol-2-yl)sulfamoyl)phenoxy)phenyl)propyl)amino)propanoic acid |
| 44 | 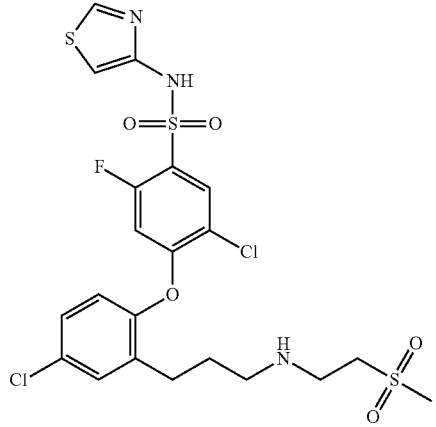 [SMILES: CS(=O)(=O)CCNCCCc1cc(Cl)ccc1Oc1cc(F)c(S(=O)(=O)Nc2cscn2)cc1Cl] | 5-chloro-4-(4-chloro-2-(3-((2-(methylsulfonyl)ethyl)amino)propyl)phenoxy)-2-fluoro-N-(thiazol-4-yl)benzenesulfonamide |

TABLE 3-continued
| Compound | Compound structure | Chemical name* |
|---|---|---|
| 45 | 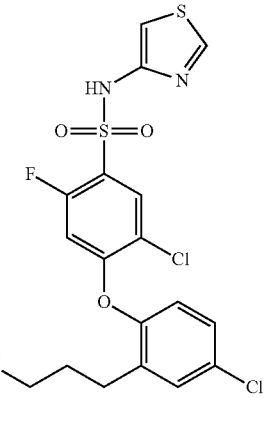 | 4-(2-(3-((1H-pyrazol-3-yl)amino)propyl)-4-chlorophenoxy)-5-chloro-2-fluoro-N-(thiazol-4-yl)benzenesulfonamide |
| 46 | 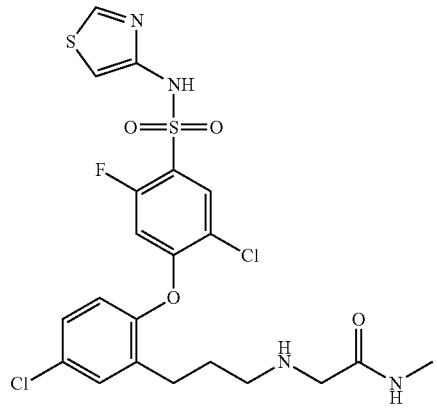 [SMILES: CNC(=O)CNCCCc1cc(Cl)ccc1Oc1cc(F)c(S(=O)(=O)Nc2cscn2)cc1Cl] | 2-((3-(5-chloro-2-(2-chloro-5-fluoro-4-(N-(thiazol-4-yl)sulfamoyl)phenoxy)phenyl)propyl)amino)-N-methylacetamide |
| 47 | 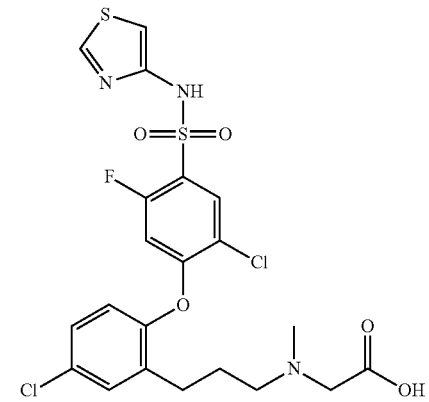 [SMILES: CN(CCCc1cc(Cl)ccc1Oc1cc(F)c(S(=O)(=O)Nc2cscn2)cc1Cl)CC(=O)O] | 2-((3-(5-chloro-2-(2-chloro-5-fluoro-4-(N-(thiazol-4-yl)sulfamoyl)phenoxy)phenyl)propyl)(methyl)amino)acetic acid |

TABLE 3-continued

| Compound | Compound structure | Chemical name* |
|---|---|---|
| 48 | 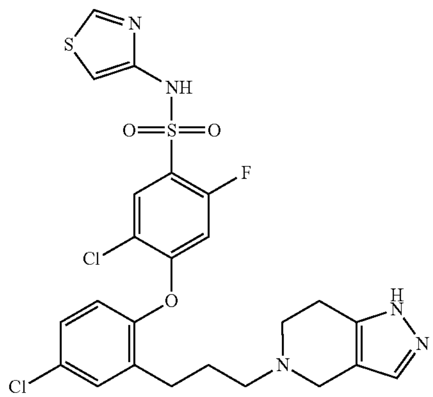 [SMILES: O=S(=O)(Nc1cscn1)c1cc(Cl)c(Oc2ccc(Cl)cc2CCCN2CCc3[nH]ncc3C2)cc1F] | 5-chloro-4-(4-chloro-2-(3-(6,7-dihydro-1H-pyrazolo[4,3-c]pyridin-5(4H)-yl)propyl)phenoxy)-2-fluoro-N-(thiazol-4-yl)benzenesulfonamide |
| 49 | 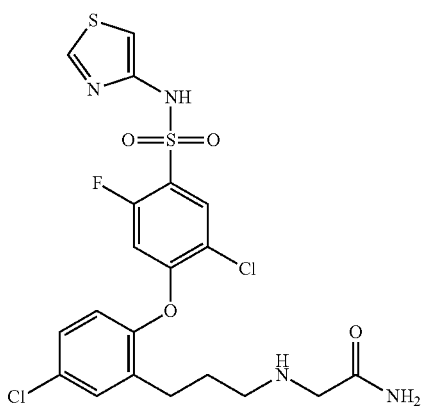 | 2-((3-(5-chloro-2-(2-chloro-5-fluoro-4-(N-(thiazol-4-yl)sulfamoyl)phenoxy)phenyl)propyl)amino)acetamide |
| 50 | 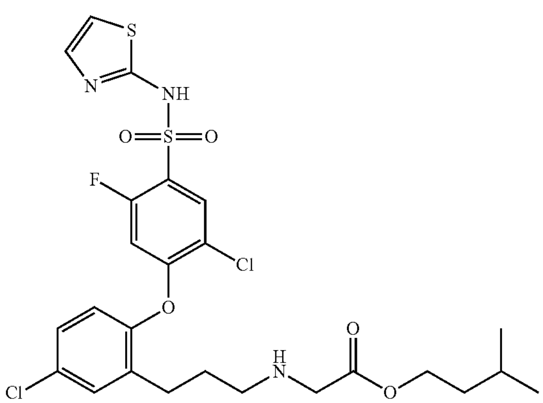 [SMILES: CC(C)CCOC(=O)CNCCCc1cc(Cl)ccc1Oc1cc(F)c(S(=O)(=O)Nc2nccs2)cc1Cl] | isopentyl 2-((3-(5-chloro-2-(2-chloro-5-fluoro-4-(N-(thiazol-2-yl)sulfamoyl)phenoxy)phenyl)propyl)amino)acetate |
| 51 | 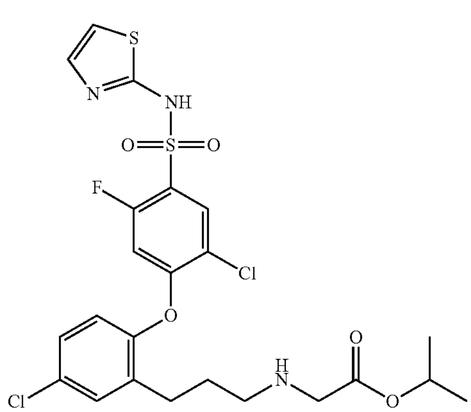 [SMILES: CC(C)OC(=O)CNCCCc1cc(Cl)ccc1Oc1cc(F)c(S(=O)(=O)Nc2nccs2)cc1Cl] | isopropyl 2-((3-(5-chloro-2-(2-chloro-5-fluoro-4-(N-(thiazol-2-yl)sulfamoyl)phenoxy)phenyl)propyl)amino)acetate |

TABLE 3-continued
| Compound | Compound structure | Chemical name* |
|---|---|---|
| 52 | 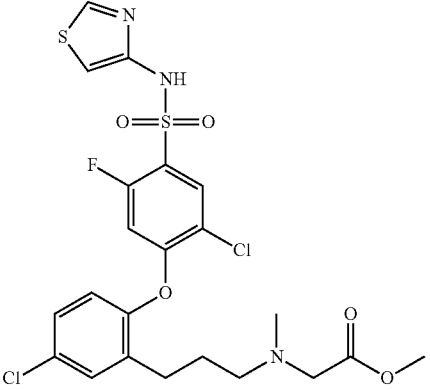 [SMILES: COC(=O)CN(C)CCCc1cc(Cl)ccc1Oc1cc(F)c(S(=O)(=O)Nc2cscn2)cc1Cl] | methyl 2-((3-(5-chloro-2-(2-chloro-5-fluoro-4-(N-(thiazol-4-yl)sulfamoyl)phenoxy)phenyl)propyl)(methyl)amino)acetate |
| 53 | 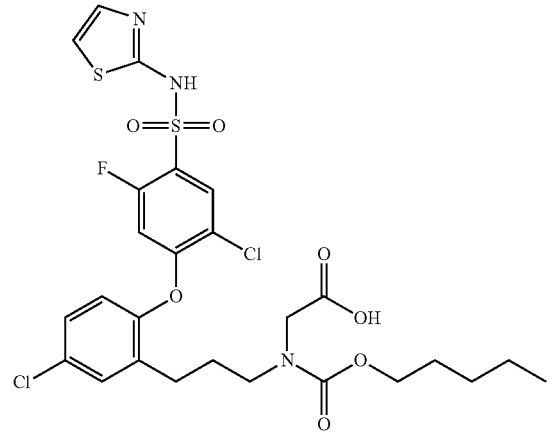 [SMILES: CCCCCOC(=O)N(CCCc1cc(Cl)ccc1Oc1cc(F)c(S(=O)(=O)Nc2nccs2)cc1Cl)CC(=O)O] | 2-((3-(5-chloro-2-(2-chloro-5-fluoro-4-(N-(thiazol-2-yl)sulfamoyl)phenoxy)phenyl)propyl)((pentyloxy)carbonyl)amino)acetic acid |
| 54 | 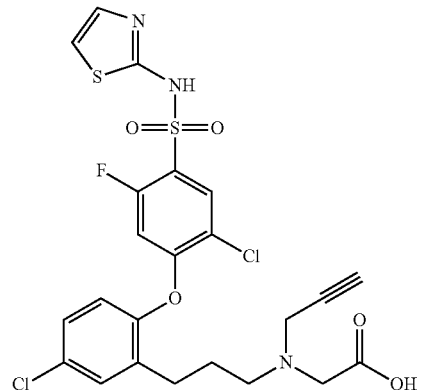 [SMILES: C#CCN(CCCc1cc(Cl)ccc1Oc1cc(F)c(S(=O)(=O)Nc2nccs2)cc1Cl)CC(=O)O] | 2-((3-(5-chloro-2-(2-chloro-5-fluoro-4-(N-(thiazol-2-yl)sulfamoyl)phenoxy)phenyl)propyl)(prop-2-yn-1-yl)amino)acetic acid |

TABLE 3-continued

| Compound | Compound structure | Chemical name* |
|---|---|---|
| 55 | 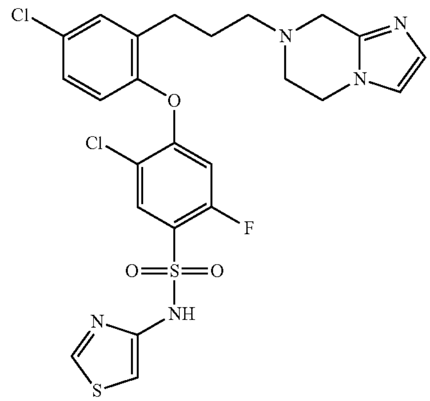 [SMILES: O=S(=O)(Nc1cscn1)c1cc(Cl)c(Oc2ccc(Cl)cc2CCCN2CCn3ccnc3C2)cc1F] | 5-chloro-4-(4-chloro-2-(3-(5,6-dihydroimidazo[1,2-a]pyrazin-7(8H)-yl)propyl)phenoxy)-2-fluoro-N-(thiazol-4-yl)benzenesulfonamide |
| 56 | 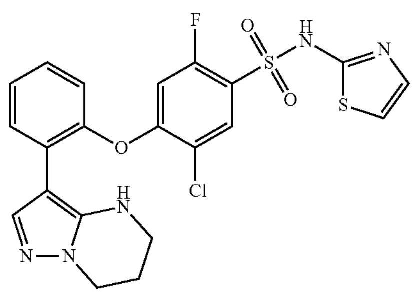 [SMILES: O=S(=O)(Nc1nccs1)c1cc(Cl)c(Oc2ccccc2-c2cnn3c2NCCC3)cc1F] | 5-chloro-2-fluoro-4-(2-(4,5,6,7-tetrahydropyrazolo[1,5-a]pyrimidin-3-yl)phenoxy)-N-(thiazol-2-yl)benzenesulfonamide |
| 57 | 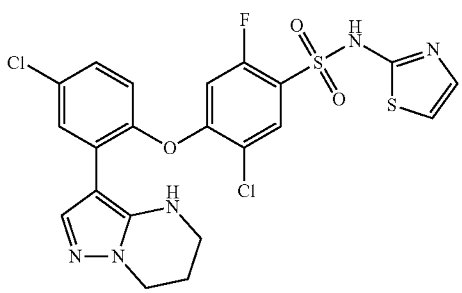 [SMILES: O=S(=O)(Nc1nccs1)c1cc(Cl)c(Oc2ccc(Cl)cc2-c2cnn3c2NCCC3)cc1F] | 5-chloro-4-(4-chloro-2-(4,5,6,7-tetrahydropyrazolo[1,5-a]pyrimidin-3-yl)phenoxy)-2-fluoro-N-(thiazol-2-yl)benzenesulfonamide |
| 58 | 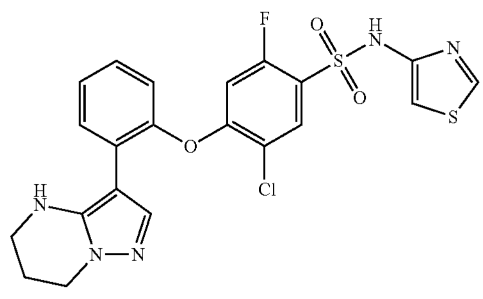 [SMILES: O=S(=O)(Nc1cscn1)c1cc(Cl)c(Oc2ccccc2-c2cnn3c2NCCC3)cc1F] | 5-chloro-2-fluoro-4-(2-(4,5,6,7-tetrahydropyrazolo[1,5-a]pyrimidin-3-yl)phenoxy)-N-(thiazol-4-yl)benzenesulfonamide |

TABLE 3-continued

| Compound | Compound structure | Chemical name* |
|---|---|---|
| 59 | 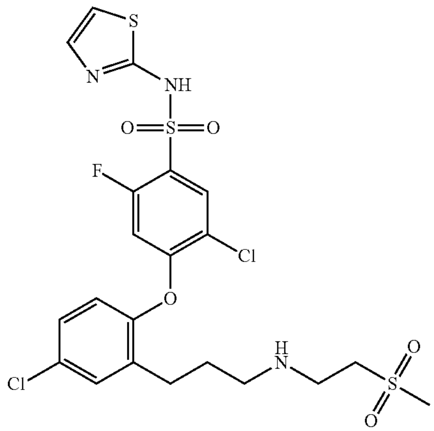 [SMILES: CS(=O)(=O)CCNCCCc1cc(Cl)ccc1Oc1cc(F)c(S(=O)(=O)Nc2nccs2)cc1Cl] | 5-chloro-4-(4-chloro-2-(3-((2-(methylsulfonyl)ethyl)amino)propyl)phenoxy)-2-fluoro-N-(thiazol-2-yl)benzenesulfonamide |
| 60 | 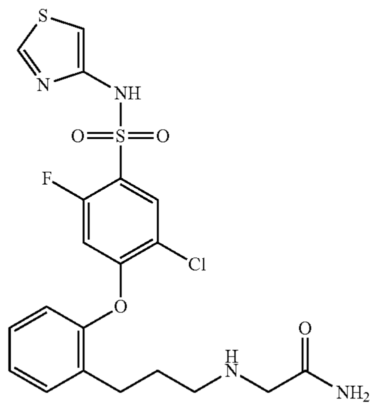 [SMILES: NC(=O)CNCCCc1ccccc1Oc1cc(F)c(S(=O)(=O)Nc2cscn2)cc1Cl] | 2-((3-(2-(2-chloro-5-fluoro-4-(N-(thiazol-4-yl)sulfamoyl)phenoxy)phenyl)propyl)amino)acetamide |
| 61 | 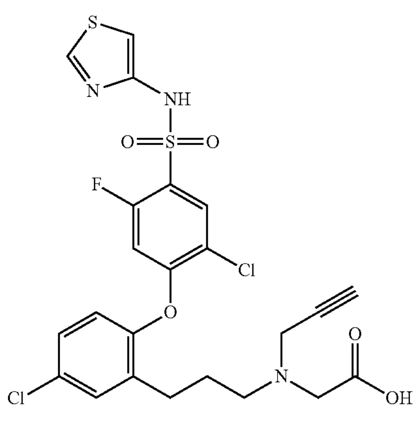 [SMILES: C#CCN(CCCc1cc(Cl)ccc1Oc1cc(F)c(S(=O)(=O)Nc2cscn2)cc1Cl)CC(=O)O] | 2-((3-(5-chloro-2-(2-chloro-5-fluoro-4-(N-(thiazol-4-yl)sulfamoyl)phenoxy)phenyl)propyl)(prop-2-yn-1-yl)amino)acetic acid |

TABLE 3-continued

| Compound | Compound structure | Chemical name* |
|---|---|---|
| 62 | 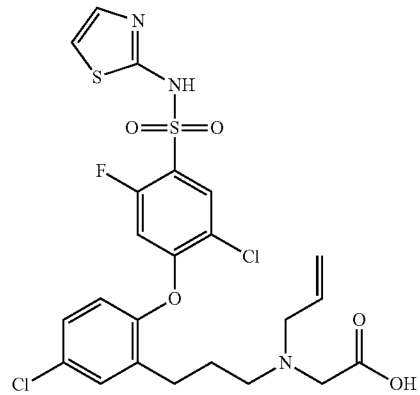 [SMILES: C=CCN(CCCc1cc(Cl)ccc1Oc1cc(F)c(S(=O)(=O)Nc2nccs2)cc1Cl)CC(=O)O] | 2-(allyl(3-(5-chloro-2-(2-chloro-5-fluoro-4-(N-(thiazol-2-yl)sulfamoyl)phenoxy)phenyl)propyl)amino)acetic acid |
| 63 | 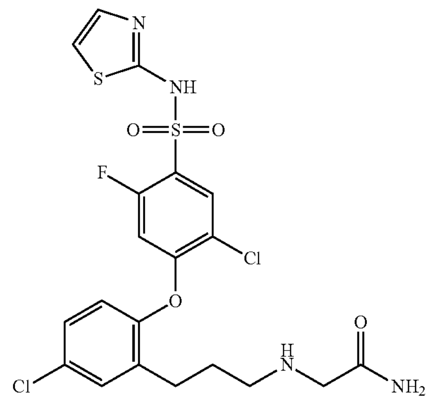 [SMILES: NC(=O)CNCCCc1cc(Cl)ccc1Oc1cc(F)c(S(=O)(=O)Nc2nccs2)cc1Cl] | 2-((3-(5-chloro-2-(2-chloro-5-fluoro-4-(N-(thiazol-2-yl)sulfamoyl)phenoxy)phenyl)propyl)amino)acetamide |
| 64 | 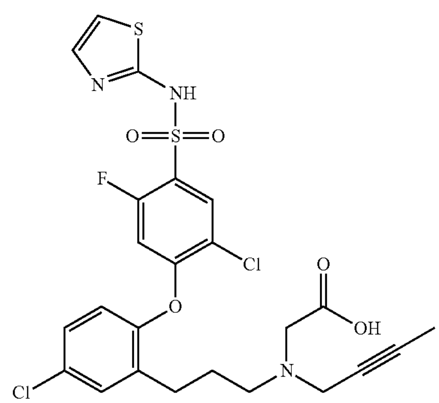 [SMILES: CC#CCN(CCCc1cc(Cl)ccc1Oc1cc(F)c(S(=O)(=O)Nc2nccs2)cc1Cl)CC(=O)O] | 2-(but-2-yn-1-yl(3-(5-chloro-2-(2-chloro-5-fluoro-4-(N-(thiazol-2-yl)sulfamoyl)phenoxy)phenyl)propyl)amino)acetic acid |
| 65 | 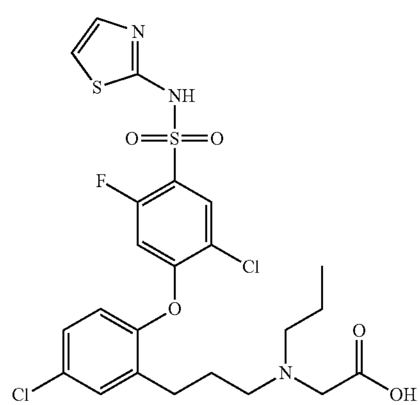 [SMILES: CCCN(CCCc1cc(Cl)ccc1Oc1cc(F)c(S(=O)(=O)Nc2nccs2)cc1Cl)CC(=O)O] | 2-((3-(5-chloro-2-(2-chloro-5-fluoro-4-(N-(thiazol-2-yl)sulfamoyl)phenoxy)phenyl)propyl)(propyl)amino)acetic acid |

TABLE 3-continued

| Compound | Compound structure | Chemical name* |
|---|---|---|
| 66 | 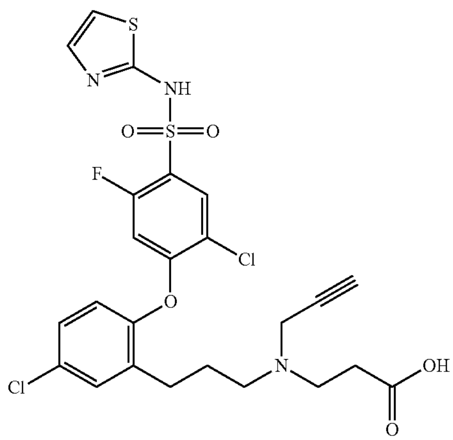 [SMILES: C#CCN(CCCc1cc(Cl)ccc1Oc1cc(F)c(S(=O)(=O)Nc2nccs2)cc1Cl)CCC(=O)O] | 3-((3-(5-chloro-2-(2-chloro-5-fluoro-4-(N-(thiazol-2-yl)sulfamoyl)phenoxy)phenyl)propyl)(prop-2-yn-1-yl)amino)propanoic acid |
| 67 | 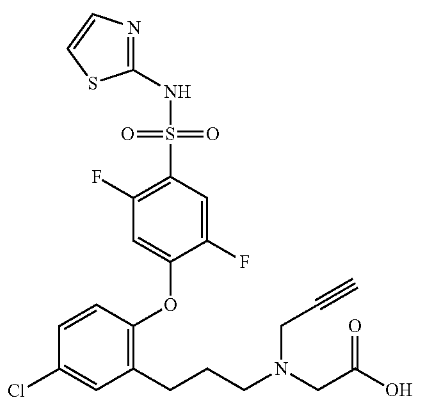 [SMILES: C#CCN(CCCc1cc(Cl)ccc1Oc1cc(F)c(S(=O)(=O)Nc2nccs2)cc1F)CC(=O)O] | 2-((3-(5-chloro-2-(2,5-difluoro-4-(N-(thiazol-2-yl)sulfamoyl)phenoxy)phenyl)propyl)(prop-2-yn-1-yl)amino)acetic acid |
| 68 | 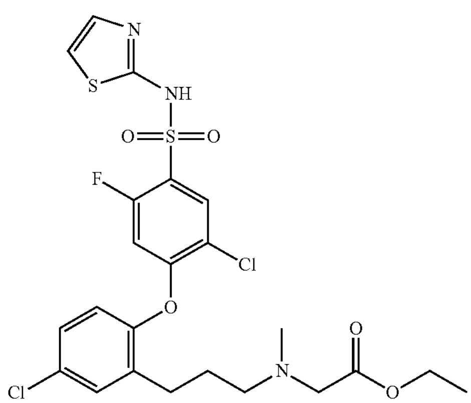 [SMILES: CCOC(=O)CN(C)CCCc1cc(Cl)ccc1Oc1cc(F)c(S(=O)(=O)Nc2nccs2)cc1Cl] | ethyl 2-((3-(5-chloro-2-(2-chloro-5-fluoro-4-(N-(thiazol-2-yl)sulfamoyl)phenoxy)phenyl)propyl)(methyl)amino)acetate |

TABLE 3-continued

| Compound | Compound structure | Chemical name* |
|---|---|---|
| 69 | (structure) | 2-((3-(5-chloro-2-(2,5-difluoro-4-(N-(thiazol-4-yl)sulfamoyl)phenoxy)phenyl)propyl)amino)acetamide |

*Chemical Names automatically generated with ChemDraw Ultra, Version 12.0.

For the proposes of this disclosure, Table 1, Table 2, and Table 3 serve to define that a particular structure is associated with a particular name. Whenever a particular name is recited in this disclosure or the claims, the chemical structure associated with that particular name shall be the structure identified in Table 1, Table 2, or Table 3.

In a particular embodiment, the compounds of Formula (I) or Formula (I') are those wherein the compound is 2-(4-(2-(4-(N-(1,2,4-thiadiazol-5-yl)sulfamoyl)-2-chloro-5-fluorophenoxy)-5-chlorophenyl)picolinamido)acetic acid, 3-(4-(2-(4-(N-(1,2,4-thiadiazol-5-yl)sulfamoyl)-2-chloro-5-fluorophenoxy)-5-chlorophenyl)picolinamido)propanoic acid, 2-(4-(2-(4-(N-(1,2,4-thiadiazol-5-yl)sulfamoyl)-2-chloro-5-fluorophenoxy)-5-chlorophenyl)picolinamido)propanoic acid, or 3-((3-(2-(4-(N-(1,2,4-thiadiazol-5-yl)sulfamoyl)-2-chloro-5-fluorophenoxy)-5-chlorophenyl)propyl)amino)propanoic acid;

or a pharmaceutically acceptable salt, or a stereoisomeric or tautomeric form thereof.

In a particular embodiment, the compounds of Formula (I) or Formula (I') are those wherein the compound is 2-((3-(5-chloro-2-(2-chloro-5-fluoro-4-(N-(thiazol-4-yl)sulfamoyl)phenoxy)phenyl)propyl)amino)acetamide, 2-((3-(5-chloro-2-(2-chloro-5-fluoro-4-(N-(thiazol-2-yl)sulfamoyl)phenoxy)phenyl)propyl)((pentyloxy)carbonyl)amino)acetic acid, or 2-((3-(5-chloro-2-(2-chloro-5-fluoro-4-(N-(thiazol-2-yl)sulfamoyl)phenoxy)phenyl)propyl)(prop-2-yn-1-yl)amino)acetic acid;

or a pharmaceutically acceptable salt, or a stereoisomeric or tautomeric form thereof.

In a particular embodiment, the compounds of Formula (I) or Formula (I') are those wherein the compound is 3-((3-(5-chloro-2-(2-chloro-5-fluoro-4-(N-(thiazol-4-yl)sulfamoyl)phenoxy)phenyl)propyl)amino)propanoic acid, 2-((3-(5-chloro-2-(2-chloro-5-fluoro-4-(N-(thiazol-4-yl)sulfamoyl)phenoxy)phenyl)propyl)amino)acetamide, 2-((3-(5-chloro-2-(2-chloro-5-fluoro-4-(N-(thiazol-2-yl)sulfamoyl)phenoxy)phenyl)propyl)(prop-2-yn-1-yl)amino)acetic acid, 2-((3-(5-chloro-2-(2-chloro-5-fluoro-4-(N-(thiazol-4-yl)sulfamoyl)phenoxy)phenyl)propyl)(prop-2-yn-1-yl)amino)acetic acid, 2-((3-(5-chloro-2-(2-chloro-5-fluoro-4-(N-(thiazol-2-yl)sulfamoyl)phenoxy)phenyl)propyl)amino)acetamide, 2-((3-(5-chloro-2-(2-chloro-5-fluoro-4-(N-(thiazol-2-yl)sulfamoyl)phenoxy)phenyl)propyl)(propyl)amino)acetic acid, 2-((3-(5-chloro-2-(2,5-difluoro-4-(N-(thiazol-2-yl)sulfamoyl)phenoxy)phenyl)propyl)(prop-2-yn-1-yl)amino)acetic acid, or 2-((3-(5-chloro-2-(2,5-difluoro-4-(N-(thiazol-4-yl)sulfamoyl)phenoxy)phenyl)propyl)amino)acetamide;

or a pharmaceutically acceptable salt, or a stereoisomeric or tautomeric form thereof.

Further provided herein are compounds of Formula (Ia),

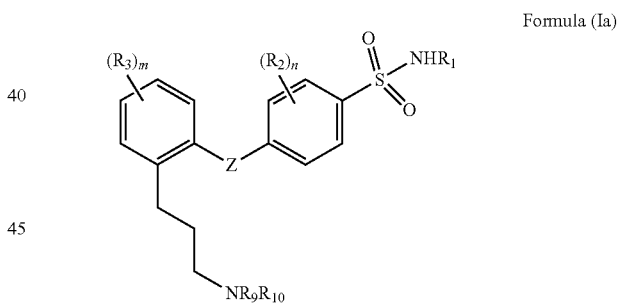

Formula (Ia)

or a pharmaceutically acceptable salt, or a stereoisomeric or tautomeric form thereof, wherein:

Z is —O— or —S—;

$R_1$ is a partially unsaturated or aromatic 5- or 6-membered heterocycle;

$R_2$ is independently at each occurrence —F, —Cl, —Br, —$CH_3$ or —CN;

$R_3$ is independently at each occurrence —H, —F, —Cl, —Br, —$CF_3$, —$OCF_3$, —CN, ($C_1$-$C_{12}$)alkyl, or ($C_1$-$C_{12}$)alkoxy;

$R_9$ is ($C_1$-$C_6$)alkyl, ($C_3$-$C_8$)cycloalkyl, pyrazolyl or pyridinyl; wherein $R_9$ is optionally further substituted with 1 or 2 substituents selected from the group consisting of —COOH, —$COOR_{11}$, —$CONR_{11}R_{12}$, —$SO_2NR_{11}R_{12}$, —OH, —CN, —$OR_{11}$, and —$NR_{11}R_{12}$; wherein $R_{11}$ and $R_{12}$ may form a 6 membered heterocycloalkyl ring $R_{10}$ is $R_{11}$, —$COR_{11}$, —$COOR_{11}$, 5-methyl-2-oxo-1,3-dioxol-4-yl,

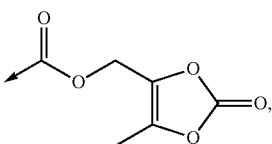

—COO—CH(CH$_3$)OCOCH(CH$_3$)$_2$; or R$_9$ and R$_{10}$ together form a piperazinone or a 4- to 8-membered heterocycloalkyl ring, wherein said heterocycloalkyl ring is substituted with 1 or 2 substituents selected from the group consisting of —COOH, —COOR$_{11}$, —CH$_2$—COOR$_{11}$, —OH, —CN, and (C$_1$-C$_8$)alkoxy;

R$_{11}$ and R$_{12}$ are independently H or (C$_1$-C$_6$)alkyl, optionally substituted with 4- to 8-membered heterocycloalkyl ring; and m and n are each independently 1, 2, 3, or 4.

In a certain embodiment, the compounds of Formula (I'a)

Formula (I'a)

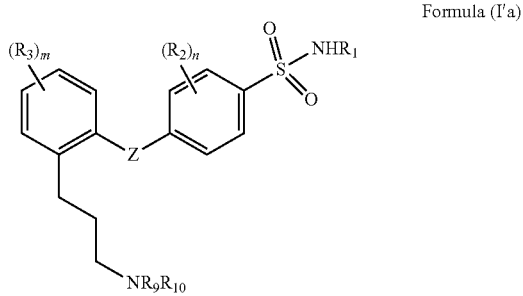

are those wherein

R$_{10}$ is R$_{11}$, (C$_3$-C$_6$)alkynyl, (C$_3$-C$_6$)alkenyl, —COR$_{11}$, —COOR$_{11}$, —SO$_2$R$_{11}$, 5-methyl-2-oxo-1,3-dioxol-4-yl,

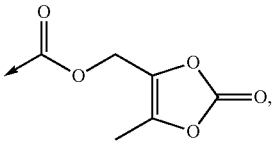

—COO—CH(CH$_3$)OCOCH(CH$_3$)$_2$; or R$_9$ and R$_{10}$ together form a piperazinone or a 4- to 8-membered heterocycloalkyl ring, wherein said heterocycloalkyl ring is substituted with 1 or 2 substituents selected from the group consisting of —COOH, —COOR$_{11}$, —CH$_2$—COOR$_{11}$, —OH, —NH$_2$, —CN, and (C$_1$-C$_8$)alkoxy; or R$_9$ and R$_{10}$ together form a unsubstituted 4- to 8-membered heterocycloalkyl ring, wherein said heterocycloalkyl ring is fused with a 5-membered heteroaryl; and wherein all other substituents are as defined above.

In a particular embodiment, the compounds of Formula (Ia) or Formula (I'a) are those wherein R$_1$ is an aromatic 5- or 6-membered heterocycle, with 1-3 heteroatoms independently selected from the group consisting of N, O, and S.

In a particular embodiment, the compounds of Formula (Ia) or Formula (I'a) are those wherein R$_1$ is pyridyl or pyrimidinyl.

In a particular embodiment, the compounds of Formula (Ia) or Formula (I'a) are those wherein R$_1$ is an aromatic 5-membered heterocycle with 1 or 2 nitrogen atoms and optionally 1 or 2 sulphur atoms. In a particular embodiment, the compounds of Formula (Ia) or Formula (I'a) are those wherein R$_1$ is thiazolyl, isothiazolyl, or thiadiazolyl. In a particular embodiment, the compounds of Formula (Ia) or Formula (I'a) are those wherein R$_1$ is thiazolyl. In a particular embodiment, the compounds of Formula (Ia) or Formula (I'a) are those wherein R$_1$ is 1,2,4-thiadiazol-5-yl. In a particular embodiment, the compounds of Formula (Ia) or Formula (I'a) are those wherein R$_1$ is thiadiazol-4-yl.

In a particular embodiment, the compounds of Formula (Ia) or Formula (I'a) are those wherein R$_2$ is independently at each occurrence —F or —Cl.

In a particular embodiment, the compounds of Formula (Ia) or Formula (I'a) are those wherein n is 1, 2, or 3. In a particular embodiment, the compounds of Formula (Ia) or Formula (I'a) are those wherein n is 2.

In a particular embodiment, the compounds of Formula (Ia) or Formula (I'a) are those wherein Z is —O—.

In a particular embodiment, the compounds of Formula (Ia) or Formula (I'a) are those wherein R$_3$ is independently at each occurrence —H, —F, —Cl, or —Br. In a particular embodiment, the compounds of Formula (Ia) or Formula (I'a) are those wherein R$_3$ is —H or —Cl. In a particular embodiment, the compounds of Formula (Ia) or Formula (I'a) are those wherein R$_3$ 1 S—Cl.

In a particular embodiment, the compounds of Formula (Ia) or Formula (I'a) are those wherein m is 1, 2, or 3. In a particular embodiment, the compounds of Formula (Ia) or Formula (I'a) are those wherein m is 1.

In a particular embodiment, the compounds of Formula (Ia) or Formula (I'a) are those wherein R$_9$ is (C$_1$-C$_6$)alkyl; wherein R$_9$ is optionally further substituted with 1 or 2 substituents selected from the group consisting of —COOH, —COOMe, —CONH$_2$, and —NH$_2$. In a particular embodiment, the compounds of Formula (Ia) or Formula (I'a) are those wherein R$_9$ is methyl or ethyl. In a particular embodiment, the compounds of Formula (Ia) or Formula (I'a) are those wherein R$_9$ is further substituted with —COOH.

In a particular embodiment, the compounds of Formula (Ia) or Formula (I'a) are those wherein R$_{10}$ is H and R$_9$ is (C$_1$-C$_6$)alkyl; wherein R$_9$ is further substituted with —CONR$_{11}$R$_{12}$, and wherein R$_{11}$ and R$_{12}$ are independently H or (C$_1$-C$_6$)alkyl. In a particular embodiment, the compounds of Formula (Ia) or Formula (I'a) are those wherein R$_9$ is further substituted with —CONH$_2$. In a particular embodiment, the compounds of Formula (Ia) or Formula (I'a) are those wherein R$_9$ is methyl and wherein R$_9$ is further substituted with —CONH$_2$.

In a particular embodiment, the compounds of Formula (Ia) or Formula (I'a) are those wherein R$_{10}$ is —H, —COMe, —COOEt. In a particular embodiment, the compounds of Formula (Ia) or Formula (I'a) are those wherein R$_{10}$ is —H or —COMe. In a particular embodiment, the compounds of Formula (Ia) or Formula (I'a) are those wherein R$_{10}$ is —H.

In a particular embodiment, the compounds of Formula (Ia) or Formula (I'a) are those wherein R$_9$ and R$_{10}$ together form a 4 to 8 membered heterocycloalkyl ring, wherein said heterocycloalkyl ring is substituted with 1 or 2 groups selected from the group consisting of —COOH, —COOMe, —COOEt, —CH$_2$—COOH, and —NH$_2$. In a particular embodiment, the compounds of Formula (I) are those wherein R$_9$ and R$_{10}$ together form a 4 to 8 membered heterocycloalkyl ring, wherein said heterocycloalkyl ring is substituted with 1 or 2 groups selected from the group consisting of —COOH, —CH$_2$—COOH, and —NH$_2$.

In a particular embodiment, the compounds of Formula (Ia) or Formula (I'a) are those wherein R$_9$ and R$_{10}$ together form a piperidine substituted with 1 or 2 groups selected from the group consisting of —COOH, —COOMe, —COOEt, —CH$_2$—COOH, —CH$_2$—COOMe, —CH$_2$—COOEt, and —NH$_2$. In a particular embodiment, the compounds of Formula (Ia) or Formula (I'a) are those wherein R$_9$ and R$_{10}$ together form a piperidine substituted with 1 or 2 groups selected from the group consisting of —COOH, —CH$_2$—COOH, and —NH$_2$.

In a particular embodiment, the compounds of Formula (Ia) or Formula (I'a) are selected from the group consisting of 2-((3-(5-chloro-2-(2-chloro-5-fluoro-4-(N-(thiazol-4-yl)sulfamoyl)phenoxy)phenyl)propyl)amino)acetic acid,
3-((3-(2-(4-(N-(1,2,4-thiadiazol-5-yl)sulfamoyl)-2-chloro-5-fluorophenoxy)-5-chlorophenyl)propyl)amino)propanoic acid,
2-((3-(5-chloro-2-(2-chloro-5-fluoro-4-(N-(thiazol-2-yl)sulfamoyl)phenoxy)phenyl)propyl)amino)acetic acid,
1-(3-(5-chloro-2-(2-chloro-5-fluoro-4-(N-(thiazol-4-yl)sulfamoyl)phenoxy)phenyl)propyl)piperidine-4-carboxylic acid,
3-((3-(5-chloro-2-(2-chloro-5-fluoro-4-(N-(thiazol-4-yl)sulfamoyl)phenoxy)phenyl)propyl)amino)propanoic acid,
4-amino-1-(3-(5-chloro-2-(2-chloro-5-fluoro-4-(N-(thiazol-4-yl)sulfamoyl)phenoxy)phenyl)propyl)piperidine-4-carboxylic acid,
2-amino-4-((3-(5-chloro-2-(2-chloro-5-fluoro-4-(N-(thiazol-4-yl)sulfamoyl)phenoxy)phenyl)propyl)amino)butanoic acid,
2-((3-(5-chloro-2-(2,5-difluoro-4-(N-(thiazol-2-yl)sulfamoyl)phenoxy)phenyl)propyl)amino)acetic acid,
1-(3-(5-chloro-2-(2-chloro-5-fluoro-4-(N-(thiazol-4-yl)sulfamoyl)phenoxy)phenyl)propyl)piperidine-3-carboxylic acid,
2-((3-(2-(4-(N-(1,2,4-thiadiazol-5-yl)sulfamoyl)-2-chloro-5-fluorophenoxy)phenyl)propyl)amino)acetic acid,
2-((3-(5-chloro-2-(2,5-difluoro-4-(N-(thiazol-4-yl)sulfamoyl)phenoxy)phenyl)propyl)amino)acetic acid,
3-((3-(5-chloro-2-(2,5-difluoro-4-(N-(thiazol-4-yl)sulfamoyl)phenoxy)phenyl)propyl)amino)propanoic acid,
3-((3-(5-chloro-2-(2-cyano-4-(N-(thiazol-4-yl)sulfamoyl)phenoxy)phenyl)propyl)amino)propanoic acid,
methyl 2-((3-(5-chloro-2-(2-chloro-5-fluoro-4-(N-(thiazol-4-yl)sulfamoyl)phenoxy)phenyl)propyl)amino)acetate,
3-((3-(2-(2-chloro-5-fluoro-4-(N-(thiazol-4-yl)sulfamoyl)phenoxy)-5-fluorophenyl)propyl)amino)propanoic acid,
3-((3-(5-chloro-2-(2-chloro-5-fluoro-4-(N-(thiazol-4-yl)sulfamoyl)phenoxy)phenyl)propyl)amino)propanamide,
2-(N-(3-(5-chloro-2-(2-chloro-5-fluoro-4-(N-(thiazol-4-yl)sulfamoyl)phenoxy)phenyl)propyl)acetamido)acetic acid,
2-(1-(3-(2-(4-(N-(1,2,4-thiadiazol-5-yl)sulfamoyl)-2-chloro-5-fluorophenoxy)-5-chlorophenyl)propyl)piperidin-4-yl)acetic acid,
3-((3-(5-chloro-2-(2-chloro-5-fluoro-4-(N-(thiazol-2-yl)sulfamoyl)phenoxy)phenyl)propyl)amino)propanoic acid,
2-((3-(5-chloro-2-(2-chloro-5-fluoro-4-(N-(thiazol-4-yl)sulfamoyl)phenoxy)phenyl)propyl)amino)-N-methylacetamide,
5-chloro-4-(4-chloro-2-(3-((2-(methylsulfonyl)ethyl)amino)propyl)phenoxy)-2-fluoro-N-(thiazol-4-yl)benzenesulfonamide,
1-(3-(2-(4-(N-(1,2,4-thiadiazol-5-yl)sulfamoyl)-2-chloro-5-fluorophenoxy)-5-chlorophenyl)propyl)piperidine-4-carboxylic acid,
2-((3-(5-chloro-2-(2-chloro-5-fluoro-4-(N-(thiazol-2-yl)sulfamoyl)phenoxy)phenyl)propyl)(ethoxycarbonyl)amino)acetic acid,
ethyl 2-((3-(5-chloro-2-(2-chloro-5-fluoro-4-(N-(thiazol-2-yl)sulfamoyl)phenoxy)phenyl)propyl)amino)acetate, and
4-(2-(3-((1H-pyrazol-4-yl)amino)propyl)-4-chlorophenoxy)-5-chloro-2-fluoro-N-(thiazol-2-yl)benzenesulfonamide;

or a pharmaceutically acceptable salt, or a stereoisomeric or tautomeric form thereof.

In a particular embodiment, the compounds of Formula (Ia) or Formula (I'a) are selected from the group comprising ethyl 2-((3-(5-chloro-2-(2-chloro-5-fluoro-4-(N-(thiazol-2-yl)sulfamoyl)phenoxy)phenyl)propyl)(methyl)amino)acetate,
2-((3-(5-chloro-2-(2-chloro-5-fluoro-4-(N-(thiazol-2-yl)sulfamoyl)phenoxy)phenyl)propyl)((5-methyl-2-oxo-1,3-dioxol-4-yl)methyl)amino)acetic acid,
2-((3-(5-chloro-2-(2-chloro-5-fluoro-4-(N-(thiazol-2-yl)sulfamoyl)phenoxy)phenyl)propyl)((1-(isobutyryloxy)ethoxy)carbonyl)amino)acetic acid,
2-((3-(5-chloro-2-(2-chloro-5-fluoro-4-(N-(thiazol-2-yl)sulfamoyl)phenoxy)phenyl)propyl)(((5-methyl-2-oxo-1,3-dioxol-4-yl)methoxy)carbonyl)amino)acetic acid,
5-chloro-4-(4-chloro-2-(3-(3-oxopiperazin-1-yl)propyl)phenoxy)-2-fluoro-N-(thiazol-2-yl)benzenesulfonamide, and
5-chloro-4-(4-chloro-2-(3-((3-morpholino-3-oxopropyl)amino)propyl)phenoxy)-2-fluoro-N-(thiazol-2-yl)benzenesulfonamide;

or a pharmaceutically acceptable salt, or a stereoisomeric or tautomeric form thereof.

In a particular embodiment, the compounds of Formula (Ia) or Formula (I'a) are selected from the group comprising 3-((3-(5-chloro-2-(2,5-difluoro-4-(N-(thiazol-2-yl)sulfamoyl)phenoxy)phenyl)propyl)amino)propanoic acid,
5-chloro-4-(4-chloro-2-(3-((2-(methylsulfonyl)ethyl)amino)propyl)phenoxy)-2-fluoro-N-(thiazol-4-yl)benzenesulfonamide,
4-(2-(3-((1H-pyrazol-3-yl)amino)propyl)-4-chlorophenoxy)-5-chloro-2-fluoro-N-(thiazol-4-yl)benzenesulfonamide,
2-((3-(5-chloro-2-(2-chloro-5-fluoro-4-(N-(thiazol-4-yl)sulfamoyl)phenoxy)phenyl)propyl)amino)-N-methylacetamide,
2-((3-(5-chloro-2-(2-chloro-5-fluoro-4-(N-(thiazol-4-yl)sulfamoyl)phenoxy)phenyl)propyl)(methyl)amino)acetic acid,
5-chloro-4-(4-chloro-2-(3-(6,7-dihydro-1H-pyrazolo[4,3-c]pyridin-5(4H)-yl)propyl)phenoxy)-2-fluoro-N-(thiazol-4-yl)benzenesulfonamide,
2-((3-(5-chloro-2-(2-chloro-5-fluoro-4-(N-(thiazol-4-yl)sulfamoyl)phenoxy)phenyl)propyl)amino)acetamide,
isopentyl 2-((3-(5-chloro-2-(2-chloro-5-fluoro-4-(N-(thiazol-2-yl)sulfamoyl)phenoxy)phenyl)propyl)amino)acetate,
isopropyl 2-((3-(5-chloro-2-(2-chloro-5-fluoro-4-(N-(thiazol-2-yl)sulfamoyl)phenoxy)phenyl)propyl)amino)acetate,
methyl 2-((3-(5-chloro-2-(2-chloro-5-fluoro-4-(N-(thiazol-4-yl)sulfamoyl)phenoxy)phenyl)propyl)(methyl)amino)acetate,
2-((3-(5-chloro-2-(2-chloro-5-fluoro-4-(N-(thiazol-2-yl)sulfamoyl)phenoxy)phenyl)propyl)((pentyloxy)carbonyl)amino)acetic acid,
2-((3-(5-chloro-2-(2-chloro-5-fluoro-4-(N-(thiazol-2-yl)sulfamoyl)phenoxy)phenyl)propyl)(prop-2-yn-1-yl)amino)acetic acid,
5-chloro-4-(4-chloro-2-(3-(5,6-dihydroimidazo[1,2-a]pyrazin-7(8H)-yl)propyl)phenoxy)-2-fluoro-N-(thiazol-4-yl)benzenesulfonamide, 5-chloro-4-(4-chloro-2-(3-((2-(methylsulfonyl)ethyl)amino) propyl)phenoxy)-2-fluoro-N-(thiazol-2-yl)benzenesulfonamide, 2-((3-(2-(2-chloro-5-fluoro-4-(N-(thiazol-4-yl)sulfamoyl) phenoxy)phenyl)propyl)amino)acetamide, 2-((3-(5-chloro-2-(2-chloro-5-fluoro-4-(N-(thiazol-4-yl)sulfamoyl)phenoxy)phenyl)propyl)(prop-2-yn-1-yl)amino) acetic acid, 2-(allyl(3-(5-chloro-2-(2-chloro-5-fluoro-4-(N-(thiazol-2-yl)sulfamoyl)phenoxy)phenyl)propyl)amino)acetic acid, 2-((3-(5-chloro-2-(2-chloro-5-fluoro-4-(N-(thiazol-2-yl)sulfamoyl)phenoxy)phenyl)propyl)amino)acetamide, 2-(but-2-yn-1-yl(3-(5-chloro-2-(2-chloro-5-fluoro-4-(N-(thiazol-2-yl)sulfamoyl)phenoxy)phenyl)propyl)amino) acetic acid, 2-((3-(5-chloro-2-(2-chloro-5-fluoro-4-(N-(thiazol-2-yl)sulfamoyl)phenoxy)phenyl)propyl)(propyl)amino)acetic acid, 3-((3-(5-chloro-2-(2-chloro-5-fluoro-4-(N-(thiazol-2-yl)sulfamoyl)phenoxy)phenyl)propyl)(prop-2-yn-1-yl)amino) propanoic acid, 2-((3-(5-chloro-2-(2,5-difluoro-4-(N-(thiazol-2-yl)sulfamoyl)phenoxy)phenyl)propyl)(prop-2-yn-1-yl)amino) acetic acid, ethyl 2-((3-(5-chloro-2-(2-chloro-5-fluoro-4-(N-(thiazol-2-yl)sulfamoyl)phenoxy)phenyl)propyl)(methyl)amino)acetate, and 2-((3-(5-chloro-2-(2,5-difluoro-4-(N-(thiazol-4-yl)sulfamoyl)phenoxy)phenyl)propyl)amino)acetamide;

or a pharmaceutically acceptable salt, or a stereoisomeric or tautomeric form thereof.

Provided herein are compounds of Formula (Ib),

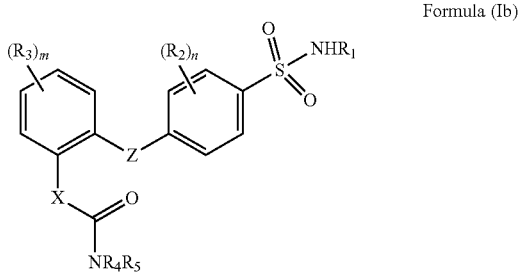

Formula (Ib)

or a pharmaceutically acceptable salt, or a stereoisomeric or tautomeric form thereof, wherein:

Z is —O— or —S—;

X is $(C_6-C_{10})$aryl or 5- or 6-membered heteroaryl;

$R_1$ is a partially unsaturated or aromatic 5- or 6-membered heterocycle;

$R_2$ is independently at each occurrence —F, —Cl, —Br, —CH$_3$ or —CN;

$R_3$ is independently at each occurrence —H, —F, —Cl, —Br, —CF$_3$, —OCF$_3$, —CN, $(C_1-C_{12})$alkyl, or $(C_1-C_{12})$ alkoxy;

$R_4$ and $R_5$ are each independently H, $(C_1-C_9)$alkyl, $(C_4-C_{12})$ cycloalkyl, or $R_4$ and $R_5$ together form a 5- to 7-membered heterocycloalkyl ring; with the proviso that:

$R_4$ and $R_5$ are not both H; and at least one of $R_4$ and $R_5$ independently or said heterocycloalkyl ring formed by $R_4$ and $R_5$ together is substituted with 1 or 2 substituents selected from the group consisting of —CO$_2$H, —CO$_2$R$_6$, —CN, —OH, —CONR$_7$R$_8$, and —NR$_7$R$_8$; wherein:

$R_6$ is $(C_1-C_{12})$alkyl;

$R_7$ and $R_8$ are each independently H, $(C_1-C_{12})$alkyl, or $R_7$ and $R_8$ together form a 4- to 7-membered heterocycloalkyl ring; and m and n are each independently 1, 2, 3, or 4.

In a particular embodiment, the compounds of Formula (Ib) are those wherein $R_1$ is an aromatic 5- or 6-membered heterocycle, with 1-3 heteroatoms independently selected from the group consisting of N, O, and S.

In a particular embodiment, the compounds of Formula (Ib) are those wherein $R_1$ is pyridyl or pyrimidinyl.

In a particular embodiment, the compounds of Formula (Ib) are those wherein $R_1$ is an aromatic 5-membered heterocycle with 1 or 2 nitrogen atoms and optionally 1 or 2 sulphur atoms. In a particular embodiment, the compounds of Formula (Ib) are those wherein $R_1$ is thiazolyl, isothiazolyl, or thiadiazolyl. In a particular embodiment, the compounds of Formula (Ib) are those wherein $R_1$ is thiazolyl. In a particular embodiment, the compounds of Formula (Ib) are those wherein $R_1$ is 1,2,4-thiadiazol-5-yl.

In a particular embodiment, the compounds of Formula (Ib) are those wherein $R_2$ is independently at each occurrence —F or —Cl.

In a particular embodiment, the compounds of Formula (Ib) are those wherein n is 1, 2, or 3. In a particular embodiment, the compounds of Formula (Ib) are those wherein n is 2.

In a particular embodiment, the compounds of Formula (Ib) are those wherein Z is —O—.

In a particular embodiment, the compounds of Formula (Ib) are those wherein $R_3$ is independently at each occurrence —H, —F, —Cl, or —Br. In a particular embodiment, the compounds of Formula (Ib) are those wherein $R_3$ is —H or —Cl. In a particular embodiment, the compounds of Formula (Ib) are those wherein $R_3$ is —Cl.

In a particular embodiment, the compounds of Formula (Ib) are those wherein m is 1, 2, or 3. In a particular embodiment, the compounds of Formula (Ib) are those wherein m is 1.

In a particular embodiment, the compounds of Formula (Ib) are those wherein X is 5- or 6-membered heteroaryl. In a particular embodiment, the compounds of Formula (Ib) are those wherein X is pyridyl or pyrimidinyl. In a particular embodiment, the compounds of Formula (Ib) are those wherein X is pyridyl.

In a particular embodiment, the compounds of Formula (Ib) are those wherein $R_4$ is H and $R_5$ is $(C_1-C_9)$alkyl.

In a particular embodiment, the compounds of Formula (Ib) are those wherein $R_5$ is methyl or ethyl, substituted with 1 or 2 substituents selected from the group consisting of —CO$_2$H, —CO$_2$R$_6$, and —CONR$_7$R$_8$.

In a particular embodiment, the compounds of Formula (Ib) are those wherein $R_6$ is $(C_1-C_6)$alkyl.

In a particular embodiment, the compounds of Formula (Ib) are those wherein $R_5$ is methyl or ethyl, substituted with —CO$_2$H.

Provided herein are compounds of Formula (Ic),

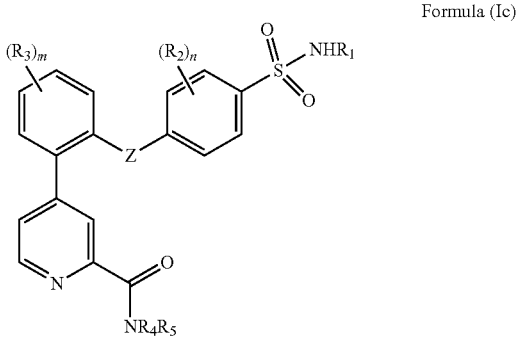

Formula (Ic)

or a pharmaceutically acceptable salt, or a stereoisomeric or tautomeric form thereof, wherein:

Z is —O— or —S—;

$R_1$ is a partially unsaturated or aromatic 5- or 6-membered heterocycle;

$R_2$ is independently at each occurrence —F, —Br, —$CH_3$ or —CN;

$R_3$ is independently at each occurrence —H, —F, —Br, —$CF_3$, —$OCF_3$, —CN, ($C_1$-$C_{12}$)alkyl, or ($C_1$-$C_{12}$) alkoxy;

$R_4$ and $R_5$ are each independently H, ($C_1$-$C_9$)alkyl, ($C_4$-$C_{12}$) cycloalkyl, or $R_4$ and $R_5$ together form a 5- to 7-membered heterocycloalkyl ring; with the proviso that:

$R_4$ and $R_5$ are not both H; and at least one of $R_4$ and $R_5$ independently or said heterocycloalkyl ring formed by $R_4$ and $R_5$ together is substituted with 1 or 2 substituents selected from the group consisting of —$CO_2H$, —$CO_2R_6$, —CN, —OH, —$CONR_7R_8$, and —$NR_7R_8$; wherein:

$R_6$ is ($C_1$-$C_{12}$)alkyl;

$R_7$ and $R_8$ are each independently H, or $R_7$ and $R_8$ together form a 4- to 7-membered heterocycloalkyl ring; and m and n are each independently 1, 2, 3, or 4.

In a particular embodiment, the compounds of Formula (Ic) are those wherein $R_1$ is an aromatic 5- or 6-membered heterocycle, with 1-3 heteroatoms independently selected from the group consisting of N, O, and S.

In a particular embodiment, the compounds of Formula (Ic) are those wherein $R_1$ is pyridyl or pyrimidinyl.

In a particular embodiment, the compounds of Formula (Ic) are those wherein $R_1$ is an aromatic 5-membered heterocycle with 1 or 2 nitrogen atoms and optionally 1 or 2 sulphur atoms. In a particular embodiment, the compounds of Formula (Ic) are those wherein $R_1$ is thiazolyl, isothiazolyl, or thiadiazolyl. In a particular embodiment, the compounds of Formula (Ic) are those wherein $R_1$ is thiazolyl. In a particular embodiment, the compounds of Formula (Ic) are those wherein $R_1$ is 1,2,4-thiadiazol-5-yl.

In a particular embodiment, the compounds of Formula (Ic) are those wherein $R_2$ is independently at each occurrence —F or —Cl.

In a particular embodiment, the compounds of Formula (Ic) are those wherein n is 1, 2, or 3. In a particular embodiment, the compounds of Formula (Ic) are those wherein n is 2.

In a particular embodiment, the compounds of Formula (Ic) are those wherein Z is —O—.

In a particular embodiment, the compounds of Formula (Ic) are those wherein $R_3$ is independently at each occurrence —H, —F, —Cl, or —Br. In a particular embodiment, the compounds of Formula (I) are those wherein $R_3$ is —H or —Cl. In a particular embodiment, the compounds of Formula (Ic) are those wherein $R_3$ is —Cl.

In a particular embodiment, the compounds of Formula (Ic) are those wherein m is 1, 2, or 3. In a particular embodiment, the compounds of Formula (Ic) are those wherein m is 1.

In a particular embodiment, the compounds of Formula (Ic) are those wherein X is 5- or 6-membered heteroaryl. In a particular embodiment, the compounds of Formula (Ic) are those wherein X is pyridyl or pyrimidinyl. In a particular embodiment, the compounds of Formula (Ic) are those wherein X is pyridyl.

In a particular embodiment, the compounds of Formula (Ic) are those wherein $R_4$ is H and $R_5$ is ($C_1$-$C_9$)alkyl.

In a particular embodiment, the compounds of Formula (Ic) are those wherein $R_5$ is methyl or ethyl, substituted with 1 or 2 substituents selected from the group consisting of —$CO_2H$, —$CO_2R_6$, and —$CONR_7R_8$.

In a particular embodiment, the compounds of Formula (Ic) are those wherein $R_6$ is ($C_1$-$C_6$)alkyl.

In a particular embodiment, the compounds of Formula (Ic) are those wherein $R_5$ is methyl or ethyl, substituted with —$CO_2H$.

In a particular embodiment, the compounds of Formula (Ic) are selected from the group consisting of 3-(4-(2-(4-(N-(1,2,4-thiadiazol-5-yl)sulfamoyl)-2-chloro-5-fluorophenoxy)-5-chlorophenyl)picolinamido)propanoic acid, 2-(4-(2-(4-(N-(1,2,4-thiadiazol-5-yl)sulfamoyl)-2-chloro-5-fluorophenoxy)-5-chlorophenyl)picolinamido)acetic acid, 5-(4-(2-(4-(N-(1,2,4-thiadiazol-5-yl)sulfamoyl)-2-chloro-5-fluorophenoxy)-5-chlorophenyl)picolinamido)pentanoic acid, 4-(4-(2-(4-(N-(1,2,4-thiadiazol-5-yl)sulfamoyl)-2-chloro-5-fluorophenoxy)-5-chlorophenyl)picolinamido)butanoic acid, 2-(4-(2-(4-(N-(1,2,4-thiadiazol-5-yl)sulfamoyl)-2-chloro-5-fluorophenoxy)-5-chlorophenyl)picolinamido)propanoic acid, (R)-2-(4-(2-(4-(N-(1,2,4-thiadiazol-5-yl)sulfamoyl)-2-chloro-5-fluorophenoxy)-5-chlorophenyl)picolinamido) propanoic acid, (S)-2-(4-(2-(4-(N-(1,2,4-thiadiazol-5-yl)sulfamoyl)-2-chloro-5-fluorophenoxy)-5-chlorophenyl)picolinamido) propanoic acid, 3-(4-(2-(4-(N-(1,2,4-thiadiazol-5-yl)sulfamoyl)-2-cyano-phenoxy)-5-chlorophenyl)picolinamido)propanoic acid, and 3-(4-(2-(4-(N-(1,2,4-thiadiazol-5-yl)sulfamoyl)-2,5-difluorophenoxy)-5-chlorophenyl)picolinamido)propanoic acid; or a pharmaceutically acceptable salt, or a stereoisomeric or tautomeric form thereof.

Provided herein are compounds of Formula (Id),

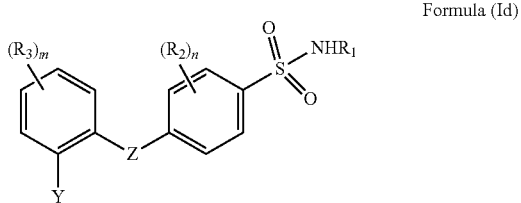

Formula (Id)

Y = 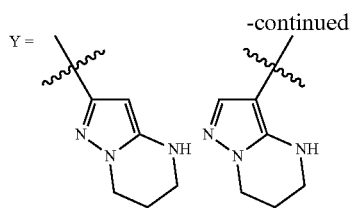

or a pharmaceutically acceptable salt, or a stereoisomeric or tautomeric form thereof, wherein:
Y is 4,5,6,7-tetrahydropyrazolo[1,5-c]pyrimidine-(2-yl or 3-yl);
Z is —O— or —S—;
$R_1$ is a partially unsaturated or aromatic 5- or 6-membered heterocycle;
$R_2$ is independently at each occurrence —F, —Cl, —Br, —CH$_3$ or —CN;
$R_3$ is independently at each occurrence —H, —F, —Cl, —Br, —CF$_3$, —OCF$_3$, —CN, (C$_1$-C$_{12}$)alkyl, or (C$_1$-C$_{12}$) alkoxy; and
m and n are each independently 1, 2, 3, or 4.

In a certain embodiment, the compounds of Formula (Id) are those wherein Y is 4,5,6,7-tetrahydropyrazolo[1,5-a]pyrimidine-(2-yl or 3-yl). In a particular embodiment, the compounds of Formula (Id) are those wherein Y is 4,5,6,7-tetrahydropyrazolo[1,5-a]pyrimidine-3-yl.

In a particular embodiment, the compounds of Formula (Id) are those wherein $R_1$ is an aromatic 5- or 6-membered heterocycle, with 1-3 heteroatoms independently selected from the group consisting of N, O, and S.

In a particular embodiment, the compounds of Formula (Id) are those wherein $R_1$ is pyridyl or pyrimidinyl.

In a particular embodiment, the compounds of Formula (Id) are those wherein $R_1$ is an aromatic 5-membered heterocycle with 1 or 2 nitrogen atoms and optionally 1 or 2 sulphur atoms. In a particular embodiment, the compounds of Formula (Id) are those wherein $R_1$ is thiazolyl, isothiazolyl, or thiadiazolyl. In a particular embodiment, the compounds of Formula (Id) are those wherein $R_1$ is thiazolyl. In a particular embodiment, the compounds of Formula (Id) are those wherein $R_1$ is 1,2,4-thiadiazol-5-yl.

In a particular embodiment, the compounds of Formula (Id) are those wherein $R_2$ is independently at each occurrence —F or —Cl.

In a particular embodiment, the compounds of Formula (Id) are those wherein n is 1, 2, or 3. In a particular embodiment, the compounds of Formula (Id) are those wherein n is 2.

In a particular embodiment, the compounds of Formula (Id) are those wherein Z is —O—.

In a particular embodiment, the compounds of Formula (Id) are those wherein $R_3$ is independently at each occurrence —H, —F, —Cl, or —Br. In a particular embodiment, the compounds of Formula (Id) are those wherein $R_3$ is —H or —Cl. In a particular embodiment, the compounds of Formula (Id) are those wherein $R_3$ is —Cl.

In a particular embodiment, the compounds of Formula (Id) are those wherein m is 1, 2, or 3. In a particular embodiment, the compounds of Formula (Id) are those wherein m is 1.

In a particular embodiment, the compound of Formula (Id) is
5-chloro-4-(4-chloro-2-(4, 5, 6,7-tetrahydropyrazolo[1,5-a]pyrimidin-3-yl)phenoxy)-2-fluoro-N-(thiazol-4-yl)benzenesulfonamide, or a pharmaceutically acceptable salt, or a stereoisomeric or tautomeric form thereof.

In a particular embodiment, the compound of Formula (Id) is
5-chloro-2-fluoro-4-(2-(4,5,6,7-tetrahydropyrazolo[1,5-a]pyrimidin-3-yl)phenoxy)-N-(thiazol-2-yl)benzenesulfonamide,
5-chloro-4-(4-chloro-2-(4, 5, 6,7-tetrahydropyrazolo[1,5-a]pyrimidin-3-yl)phenoxy)-2-fluoro-N-(thiazol-2-yl)benzenesulfonamide, or
5-chloro-2-fluoro-4-(2-(4,5,6,7-tetrahydropyrazolo[1,5-a]pyrimidin-3-yl)phenoxy)-N-(thiazol-4-yl)benzenesulfonamide;
or a pharmaceutically acceptable salt, or a stereoisomeric or tautomeric form thereof.

It should also be noted the Compounds provided herein can contain unnatural proportions of atomic isotopes at one or more of the atoms. For example, the Compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched Compound. The term "isotopically enriched" refers to an atom having an isotopic composition other than the natural isotopic composition of that atom. "Isotopically enriched" may also refer to a Compound containing at least one atom having an isotopic composition other than the natural isotopic composition of that atom. The term "isotopic composition" refers to the amount of each isotope present for a given atom. Radiolabeled and isotopically enriched Compounds are useful as therapeutic agents, e.g., cancer and inflammation therapeutic agents; research reagents, e.g., binding assay reagents; and diagnostic agents, e.g., in vivo imaging agents. All isotopic variations of the Compounds as described herein, whether radioactive or not, are intended to be encompassed within the scope of the embodiments provided herein. In some embodiments, there are provided isotopologues of the Compounds, for example, the isotopologues are deuterium, carbon-13, or nitrogen-15 enriched Compounds.

In certain embodiments, a Compound provided herein modulates the activity of a sodium ion channel, such as a voltage-gated sodium ion channel. In more specific embodiments, such a voltage-gated sodium ion channel is NaV1.7 (whose alpha subunit is encoded by the human gene SCN9A).

In certain embodiments, a Compound provided herein reduces the sodium ion flux through NaV1.7 by at least 10%, 20%, 30%, 40%, 50%, 60%, 70%, 80%, 90%, 95%, 98%, 99%, or 100%, or by ranges between any of the recited percentages (e.g., 10-20%, 10-30%, 10-40%, 20-30%, or 20-40%) relative to the activated channel in the absence of the Compound.

In certain embodiments, a Compound provided herein, desensitizes the response of NaV1.7 to the change in membrane potential such that the channel requires at least 10%, 20%, 30%, 40%, 50%, 60%, 70%, 80%, 90%, or 100%, or ranges between any of the recited percentages (e.g., 10-20%, 10-30%, 10-40%, 20-30%, or 20-40%) higher change in membrane potential to be activated relative to the channel in the absence of the Compound.

In certain embodiments, a Compound provided herein, affects a voltage-gated sodium ion channel, e.g., NaV1.7, in one or more of the following states: resting (closed), activated (open), or inactivated (closed). In certain embodiments, a Compound provided herein, affects activation, inactivation, or deinactivation of a voltage-gated sodium ion channel, e.g., NaV1.7.

In certain embodiments, a Compound provided herein, modulates NaV1.7 specifically, i.e., the compound modulates NaV1.7 to at least 10%, 20%, 30%, 40%, 50%, 60%, 70%, 80%, 90%, 100%, 250%, 500%, 750%, or 1000% higher degree than another voltage-gated sodium ion channel (such as NaV1.1, NaV1.2, NaV1.3, NaV1.4, NaV1.5, NaV1.6, NaV1.8, and/or NaV1.9), or to a higher degree between any of the recited percentages (e.g., 10-20%, 10-30%, 10-40%, 20-30%, or 20-40%) than another voltage-gated sodium channel.

In certain embodiments, a Compound provided herein binds to NaV1.7 with at least 5-fold, 10-fold, 50-fold, 100-fold, 500-fold, or 1000-fold higher affinity than it binds to either one of or all of NaV1.1, NaV1.2, NaV1.3, NaV1.4, NaV1.5, NaV1.6, NaV1.8, and NaV1.9. In certain embodiments, a Compound provided herein binds to the inactivated (closed) state of NaV1.7 with at least 5-fold, 10-fold, 50-fold, 100-fold, 500-fold, or 1000-fold higher affinity than to any other state of NaV1.7, i.e., deactivated (closed) and activated (open).

Any assay known to the skilled artisan can be used to test the effect of a compound provided herein on a voltage-gated sodium ion channel. In certain embodiments, a cell culture assay is used, wherein the voltage-gated sodium ion channel is recombinantly expressed in the cultured cells. In certain more specific embodiments, the alpha subunit of the voltage-gated sodium ion channel is expressed but no accessory proteins are recombinantly expressed in the same cell. In a specific embodiment, SCN9A and SCN9B1 and SCN9B2 are co-expressed in the same cell. In other embodiments, the alpha subunit of the voltage-gated sodium ion channel is expressed and at least one accessory protein (e.g., a beta-subunit) is co-expressed in the same cell.

In certain embodiments, an FDSS membrane potential assay can be used to test the activity of the voltage-gated sodium ion channel (see the Section entitled "FDSS Membrane Potential In-Vitro Assay" below). In other embodiments, the current through a voltage-gated sodium ion channel is tested using the patch clamp method (see the Section entitled "Patchliner Electrophysiological In-Vitro Assay" below)

4.4 Methods for Making Compounds

A compound of Formula (Ia) or a compound of Formula (I'a) can be synthesized according to synthetic Scheme 1. An $R_3$ substituted 2-hydroxybenzaldehyde or 2-mercaptobenzaldehyde is reacted under Horner-Wadsworth-Emmons ("HWE") conditions with formylmethylene-triphenylphosphorane to give an α,β-unsaturated aldehyde, Intermediate A. Intermediate A is reacted with $HNR_9R_{10}$ under reductive amination conditions using, for example, sodium borohydride, to give Intermediate B. Intermediate B is then reduced to give Intermediate C using, for example, hydrogen in the presence of metal catalyst, such as palladium on carbon. Intermediate C is reacted with a fluoro-substituted phenylsulfonamide, wherein the sulfonamide nitrogen is optionally protected by a group ("PG"), such as tert-butoxycarbonyl ("BOC") or 2,4-dimethoxybenzyl, in presence of a base, such as potassium carbonate, to give Intermediate D. Deprotection of the sulfonamide group of Intermediate D by using, for example, hydrochloric acid, gives a compound of Formula (Ia) or a compound of Formula (I'a).

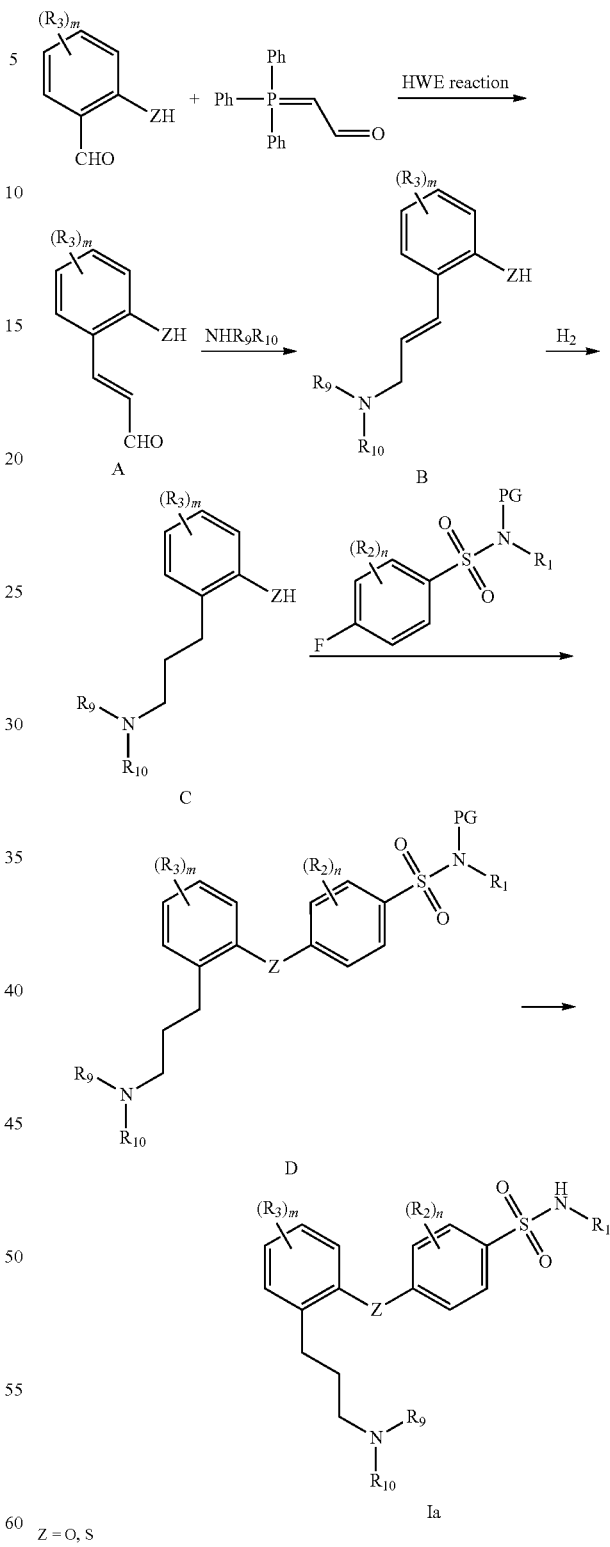

A compound of Formula (Ib) can be prepared according to synthetic Scheme 2. A Suzuki coupling between an $R_3$ substituted 2-hydroxy-boronic acid or 2-mercapto-boronic acid and derivative of X, wherein X is, for example, a $(C_6-C_{10})$aryl or 5- or 6-membered heteroaryl, such as a 4-halo-picolinonitrile or a 4-halo-picolinic ester (e.g., a methyl picolinate), wherein the halo substituent is, for example, a chloro or bromo substituent, provides Intermediate E. Intermediate E is reacted with a base, such as potassium hydroxide, to give Intermediate F. Intermediate F is reacted with NHR$_4$R$_5$ to form the amide Intermediate G using, for example, 1-ethyl-3-(3-dimethylaminopropyl)carbodiimide ("EDC") and 1-hydroxy-1H-benzotriazole ("HOBt"). Intermediate G is reacted with a fluoro-substituted phenylsulfonamide, wherein the sulfonamide nitrogen is optionally protected by a group, such as BOC or 2,4-dimethoxybenzyl, in presence of a base, such as potassium carbonate, to give Intermediate H. Deprotection of the sulfonamide group of Intermediate H by using, for example, hydrochloric acid, gives a compound of Formula (Ib).

A compound of Formula (Ic) can be prepared according to synthetic Scheme 3. A Suzuki coupling between an R$_3$ substituted 2-hydroxy-boronic acid or 2-mercapto-boronic acid and pyridine derivative, such as a 4-halo-picolinonitrile or a 4-halo-picolinic ester (e.g., a methyl picolinate), wherein the halo substituent is, for example, a chloro or bromo substituent, provides Intermediate I. Intermediate I is reacted with a base, such as potassium hydroxide, to give Intermediate J. Intermediate J is reacted with NHR$_4$R$_5$ to form the amide Intermediate K using, for example, EDC and HOBt. Intermediate K is reacted with a fluoro-substituted phenylsulfonamide, wherein the sulfonamide nitrogen is optionally protected by a group, such as BOC or 2,4-dimethoxybenzyl, in presence of a base, such as potassium carbonate, to give Intermediate L. Deprotection of the sulfonamide group of Intermediate L by using, for example, hydrochloric acid, gives a compound of Formula (Ic).

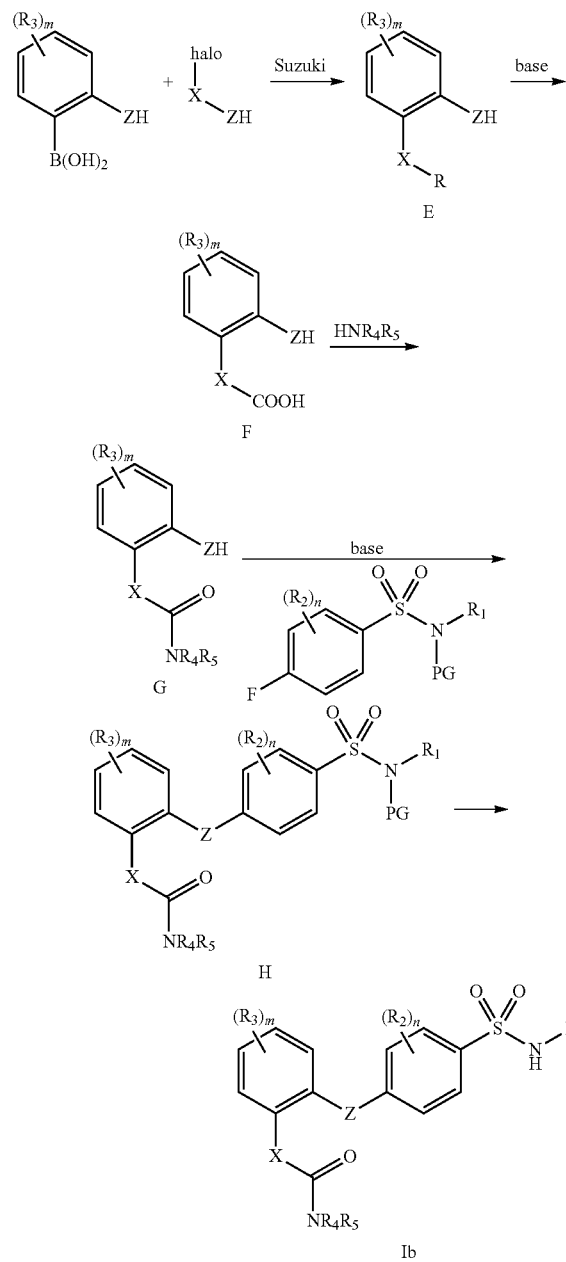

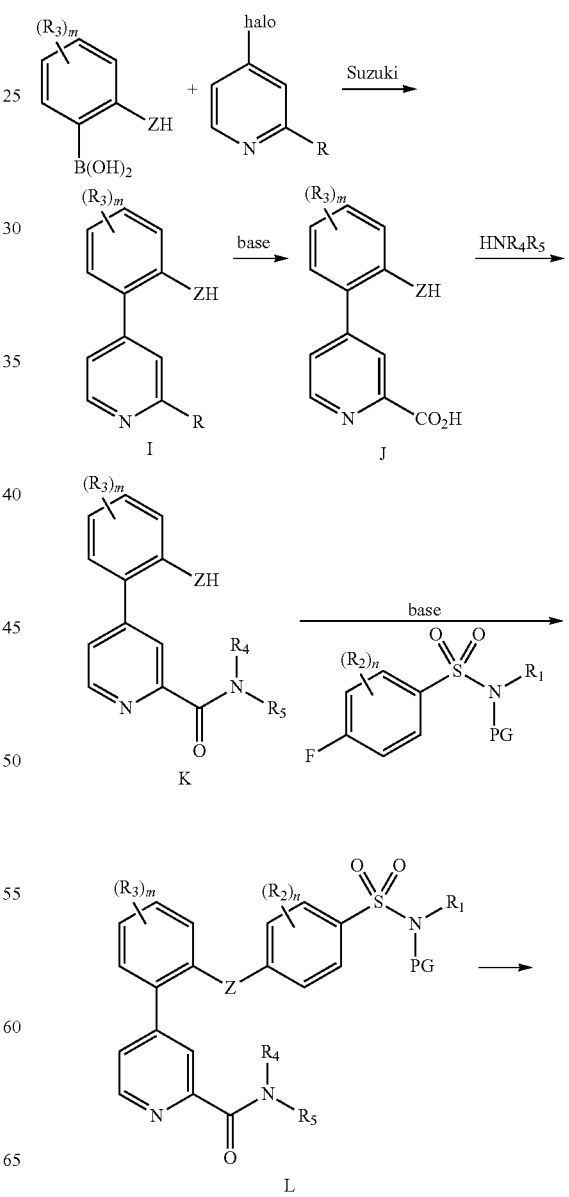

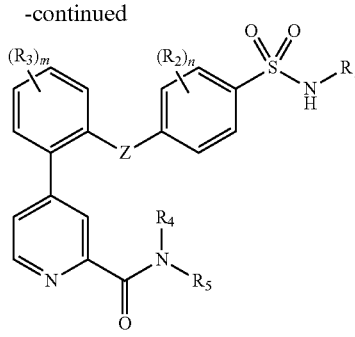

Ic

Z = O, S

R = CN, CO₂Me

A compound of Formula (Id) can be prepared according to synthetic Scheme 4. Phenylacetonitrile derivative M with a protected hydroxy or thiol group, such as a methyl protected hydroxy group, i.e., a —OMe group, is formylated by using, for example, Na/ethyl formate or NaOEt/ethyl formate to give Intermediate N. Intermediate N is reacted with hydrazine to provide Intermediate O. Intermediate O is reacted with dihaloalkanes, such as 1,3-dibromopropane, under basic conditions, for example, in presence of NaH or Cs₂CO₃, to give Intermediate P. Intermediate P, after deprotection of the phenol or thiol, for example, by reacting a methyl protected hydroxy group with BBr₃, can undergo same synthetic sequence as described Scheme 1, Scheme 2, or Scheme 3 to give compound S, which is a compound of Formula (Id). Furthermore, Intermediate W, which is deprotected and subjected to the procedures described and referred to in this paragraph to give compounds of Formula (Id), can be obtained as follows: Intermediate T is reacted under Suzuki conditions in presence of a base and a palladium catalyst with Intermediate U or U', wherein R of Intermediate U or U' is a nitro group or a suitably protected amino group, to give Intermediate V. Intermediate V is subjected to conditions, which reduce the nitro group to an amino group or deprotect the nitrogen to release an amino group, such as zinc in acetic acid or hydrogen and Raney-Nickel, to give Intermediate W.

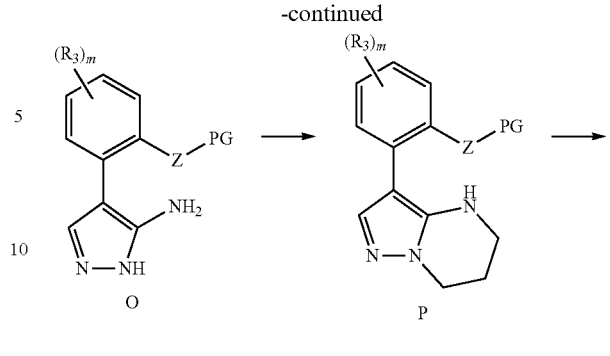

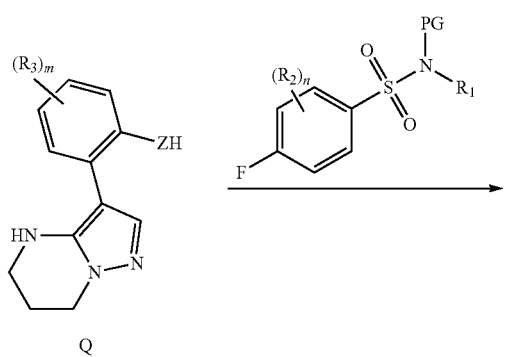

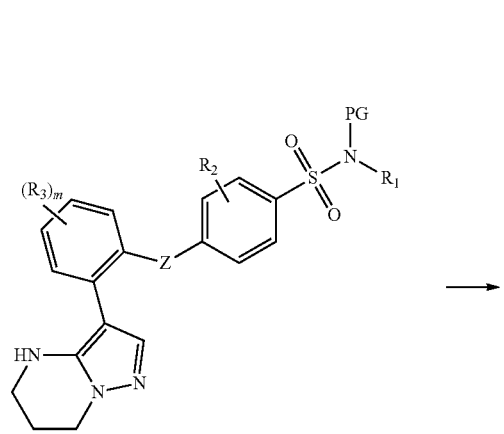

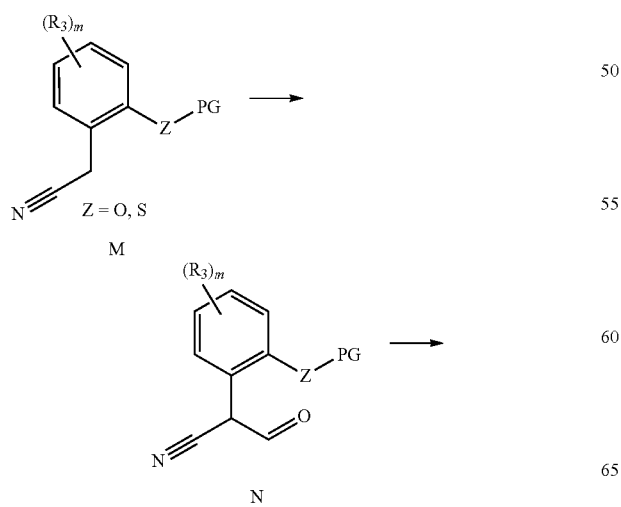

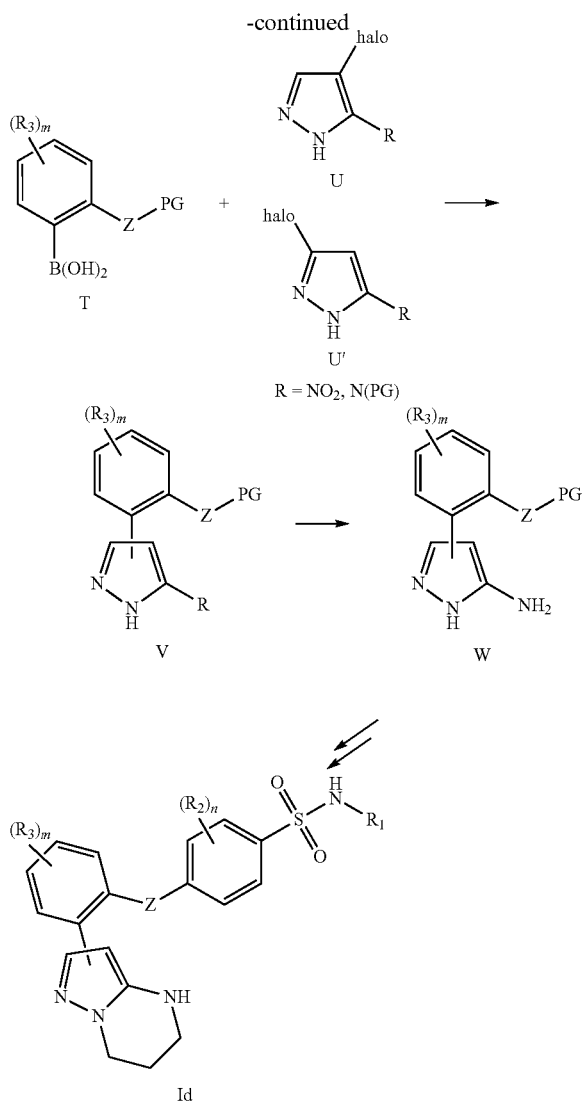

4.5 Methods of Use

4.5.1 Pain

Provided herein are methods for the treatment or prevention of pain in a subject in need thereof, wherein the methods comprise administering to the subject in need of such treatment or prevention a Compound provided herein (i.e., a compound of Formula (I), a compound of Formula (I'), a compound of Formula (Ia), a compound of Formula (I'a), a compound of Formula (Ib), a compound of Formula (Ic), a compound of Formula (Id), a compound listed in Table 1, Table 2, or Table 3), or a pharmaceutically acceptable salt, solvate or tautomeric form thereof.

Provided herein are methods for delaying the onset of pain in a subject in need thereof, wherein the methods comprise administering to the subject in need of such treatment or prevention a Compound provided herein, or a pharmaceutically acceptable salt, solvate or tautomeric form thereof.

In one embodiment, the onset of pain is delayed for 10 min, 30 min, 60 min, 2 h, 5 h, 10 h, 24 h, 2 days, 5 days, 10 days, 20 days, 1 month, 3 months, 5 months, 6 months, 1 year or for the duration of treatment and beyond. In one embodiment, none of the Compounds provided herein are administered to the subject during the period of delay.

Provided herein are methods for managing pain, or reducing the frequency of recurring pain, comprising administering to a subject in need thereof a therapeutically effective amount of a Compound, or a pharmaceutically acceptable salt, solvate or tautomeric form thereof.

Provided herein are methods for treating neuropathic pain, comprising administering to a subject in need thereof a therapeutically effective amount of a Compound, or a pharmaceutically acceptable salt, solvate or tautomeric form thereof.

Provided herein are methods for treating pain comprising use of a Compound, as a voltage-gated sodium channel inhibitor. In a particular embodiment, the methods are those, wherein the pain is neuropathic, nociceptive or inflammatory pain. In a particular embodiment, the methods are those, wherein the voltage-gated sodium channel is NaV1.7.

Provided herein are methods for treating or preventing a NaV1.7-dysfunction-associated disorder, comprising administering to a subject in need thereof a therapeutically effective amount of a Compound, or a pharmaceutically acceptable salt, solvate or tautomeric form thereof.

Provided herein are methods for prevention or treatment of pain in a subject, wherein the method comprises administering to the subject in need of such prevention or treatment a therapeutically effective amount of a Compound or a pharmaceutically acceptable salt, solvate or tautomeric form thereof. In a particular embodiment, the methods are those, wherein the therapeutically effective amount of a Compound or a pharmaceutically acceptable salt, solvate or tautomeric form thereof, is effective to alleviate pain in a subject, wherein the Compound shows a reduction in pain response in the Formalin Assay (in phase 1 or phase 2, or both) (see Section 5.1.2) at a dose between 0.1 mg/kg and 1,000 mg/kg, at a dose between 0.5 mg/kg and 100 mg/kg, at a dose between 1 mg/kg to 50 mg/kg, or at a dose of 5 mg/kg. In certain embodiments, a Compound or a pharmaceutically acceptable salt, solvate or tautomeric form thereof, provided herein shows a reduction in pain response in the Formalin Assay (in phase 1 or phase 2, or both) by at least 10%, 20%, 30%, 40%, 50%, 60%, 70%, 80%, 90%, 95%, 98%, 99%, or 100%, or by ranges between any of the recited percentages (e.g., 10-20%, 10-30%, 10-40%, 20-30%, or 20-40%) relative to a vehicle control. In a particular embodiment, the methods are those, wherein the pain is nociceptive pain, such as that resulting from physical trauma (e.g., a cut or contusion of the skin including surgery or dental pain; or a chemical or thermal burn), osteoarthritis, rheumatoid arthritis or tendonitis; myofascial pain; neuropathic pain, such as that associated with stroke, diabetic neuropathy, luetic neuropathy, postherpetic neuralgia, trigeminal neuralgia, fibromyalgia, or painful neuropathy induced iatrogenically by drugs; or mixed pain (e.g., pain with both nociceptive and neuropathic components); visceral pain; headache pain (e.g., migraine headache pain); CRPS; CRPS type I; CRPS type II; RSD; reflex neurovascular dystrophy; reflex dystrophy; sympathetically maintained pain syndrome; causalgia; Sudeck atrophy of bone; algoneurodystrophy; shoulder hand syndrome; post-traumatic dystrophy; autonomic dysfunction; autoimmune-related pain; inflammation-related pain; cancer-related pain; phantom limb pain; chronic fatigue syndrome; post-operative pain; spinal cord injury pain; central post-stroke pain; radiculopathy; sensitivity to temperature, light touch or color change to the skin (allodynia); pain from hyperthermic or hypothermic conditions; and other painful conditions (e.g., diabetic neuropathy, luetic neuropathy, postherpetic neuralgia, trigeminal neuralgia); chronic pain; acute pain, pain from neuromas, pain or itch associated with channelopathies such as small fiber neuralgia, IEM or Raynodes; or itch from various origins such as allergic itch.

In a particular embodiment, the methods are those that, treat, ameliorate, diminish and/or cure syndromes and diseases associated with, or potentially associated with sodium gated channel dysfunction, and related sensory and/or autonomic nervous system disorders such as inherited erythromyalgias, small fiber neuropathies, Raynaud's phenomenon, CRPS; CRPS type I; CRPS type II; RSD; reflex neurovascular dystrophy; reflex dystrophy, causalgia, migraine; shoulder hand syndrome, sensitivity to temperature, light touch or color change to the skin, hyperthermic or hypothermic conditions, hyperhidrosis, orthostatic hypotension, vasovagal syndromes and other autonomic disorders.

Provided herein are methods modulating the activity of a voltage-gated sodium channel, wherein the method comprises contacting a cell that expresses the voltage-gated sodium channel with a Compound or a pharmaceutically acceptable salt, solvate or tautomeric form thereof. In a particular embodiment, the methods are those, wherein the voltage-gated sodium channel is NaV1.7. In a particular embodiment, the methods are those, wherein the method results in inhibition of the voltage-gated sodium channel.

In certain embodiments, a Compound provided herein, is administered to a patient population with a gain of function mutation in a gene encoding the alpha subunit of a voltage gated sodium ion channel, such as NaV1.7.

In certain embodiments, a Compound provided herein is administered to a patient population diagnosed with erythromelalgia, primary erythromelalgia, paroxysmal extreme pain disorder (PEPD), or NaV1.7-associated fibromyalgia.

In certain embodiments, provided herein is a method for the treatment or prevention of pain in a patient wherein the method comprises administering to the patient a pharmaceutically effective amount of a Compound provided herein wherein the administering step results in a reduction or prevention of pain sensation and wherein the administering step results in at most 1%, 2%, 3%, 4%, 5%, 6%, 7%, 8%, 9%, 10%, 15%, 20%, 25%, 30%, 35%, 40%, 45%, at most 50% or no reduction in sensation of non-noxious tactile mechanical stimuli. In certain specific embodiments, the degree of sensation of non-noxious tactile mechanical stimuli is measured using the von Frey assay.

In certain embodiments, provided herein is a method for the treatment or prevention of pain in a patient wherein the method comprises administering to the patient a pharmaceutically effective amount of a Compound provided herein wherein the administering step results in a reduction or prevention of pain sensation and wherein the administering step results in at most 1%, 2%, 3%, 4%, 5%, 6%, 7%, 8%, 9%, 10%, 15%, 20%, 25%, 30%, 35%, 40%, 45%, at most 50% or no reduction in locomotor function. In certain specific embodiments, the degree of locomotor function is measured using the Foot Fault test.

In certain embodiments, provided herein is a method for the treatment or prevention of allodynia in a patient wherein the method comprises administering to the patient a pharmaceutically effective amount of a Compound provided herein wherein the administering step results in a reduction or prevention of pain sensation and wherein the administering step results in at most 1%, 2%, 3%, 4%, 5%, 6%, 7%, 8%, 9%, 10%, 15%, 20%, 25%, 30%, 35%, 40%, 45%, at most 50% or no reduction in locomotor function. In certain specific embodiments, the allodynia is caused by heat injury or other tissue damage.

In certain embodiments, provided herein is a method for the treatment or prevention of pain caused by tissue damage in a patient wherein the method comprises administering to the patient a pharmaceutically effective amount of a Compound provided herein wherein the administering step results in an enrichment of the administered Compound at the site of the tissue injury by at least 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100% of the concentration in the rest of the patient.

In certain embodiments, the Compounds provided herein for the use in the methods described herein are Compounds that show a reduction/inhibition of pain response in the formalin test (see Section 5.1.2), phase 1, of at least about 1%, 2%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 100%, or any range resulting from a combination of any two of the foregoing percentages, for example at least about 10% to about 20%, and at least about 15% to about 80%.

In certain embodiments, the Compounds provided herein for the use in the methods described herein are Compounds that show a reduction/inhibition of pain response in the formalin test (see Section 5.1.2), phase 2, of at least about 1%, 2%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 100%, or any range resulting from a combination of any two of the foregoing percentages, for example at least about 10% to about 20%, and at least about 15% to about 80%.

In certain embodiments, the Compounds provided herein for the use in the methods described herein are Compounds that show a recovery in the plantar test using a suitable animal model, such as the Partial Sciatic Nerve Ligation ("PSNL") Model or the Streptozotocin ("STZ")-Induced Model of Diabetic Neuropathy (see Section 5.1.2), of at least about 1%, 2%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 100%, or any range resulting from a combination of any two of the foregoing percentages, for example at least about 10% to about 20%, and at least about 15% to about 80%.

In certain embodiments, the Compounds provided herein for the use in the methods described herein are Compounds that show a recovery in the paw pressure test using a suitable animal model, such as the Partial Sciatic Nerve Ligation ("PSNL") Model or the Streptozotocin ("STZ")-Induced Model of Diabetic Neuropathy (see Section 5.1.2), of at least about 1%, 2%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 100%, or any range resulting from a combination of any two of the foregoing percentages, for example at least about 10% to about 20%, and at least about 15% to about 80%.

In certain embodiments, the Compounds provided herein for the use in the methods described herein are Compounds that show a recovery in the Von Frey Test (Tactile Allodynia) using a suitable animal model, such as the Partial Sciatic Nerve Ligation ("PSNL") Model or the Streptozotocin ("STZ")-Induced Model of Diabetic Neuropathy (see Section 5.1.2), of at least about 1%, 2%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 100%, or any range resulting from a combination of any two of the foregoing percentages, for example at least about 10% to about 20%, and at least about 15% to about 80%.

In certain embodiments, the Compounds provided herein for the use in the methods described herein are Compounds that show a recovery in the weight bearing test using a suitable animal model, such as the Partial Sciatic Nerve Ligation ("PSNL") Model or the Streptozotocin ("STZ")-Induced Model of Diabetic Neuropathy (see Section 5.1.2), of at least about 1%, 2%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 100%, or any range resulting from a combination of any two of the foregoing percentages, for example at least about 10% to about 20%, and at least about 15% to about 80%.

In certain embodiments, the Compounds provided herein for the use in the methods described herein are Compounds that show reduction in pain in the Writhing Model (Inflammatory Abdominal Pain) (see Section 5.1.2) of at least about 1%, 2%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 100%, or any range resulting from a combination of any two of the foregoing percentages, for example at least about 10% to about 20%, and at least about 15% to about 80%.

In certain embodiments, the Compounds provided herein for the use in the methods described herein are Compounds that show reduction in itching or scratching in the Itching/Puritis Model (see Section 5.1.2) of at least about 1%, 2%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 100%, or any range resulting from a combination of any two of the foregoing percentages, for example at least about 10% to about 20%, and at least about 15% to about 80%.

In certain embodiments, the Compounds provided herein for the use in the methods described herein are Compounds that show reduction of one or more of food intake, glucose level, and water intake in diabetic animals, wherein the diabetic animals are generated via suitable method know in the art, such as streptozotocin ("STZ") injection (see Section 5.1.2), of at least about 1%, 2%, 5%, 10%, 15%, 20%, 25%, 30%, 35%, 40%, 45%, 50%, 55%, 60%, 70%, 75%, 80%, 85%, 90%, 95%, 96%, 97%, 98%, 99%, 100%, or any range resulting from a combination of any two of the foregoing percentages, for example at least about 10% to about 20%, and at least about 15% to about 80% compared to a non-diabetic sham group of animals.

4.5.2 Diabetes, Lowering Blood or Plasma Glucose, and Lowering Blood or Plasma Glycated Hemoglobin Provided herein are methods for treating or preventing prediabetes, comprising administering to a subject in need thereof a therapeutically effective amount of a Compound provided herein (i.e., a compound of Formula (I), a compound of Formula (I'), a compound of Formula (Ia), a compound of Formula (I'a), a compound of Formula (Ib), a compound of Formula (Ic), a compound of Formula (Id), a compound listed in Table 1, Table 2, or Table 3), or a pharmaceutically acceptable salt, solvate or tautomeric form thereof.

Further provided herein are methods for treating or preventing diabetes in a subject in need thereof, comprising administering to the subject a therapeutically effective amount of a Compound, or a pharmaceutically acceptable salt, solvate or tautomeric form thereof.

Provided herein are methods for maintaining or lowering blood or plasma glucose in a subject in need thereof, comprising administering to the subject a therapeutically effective amount of a Compound, or a pharmaceutically acceptable salt, solvate or tautomeric form thereof.

Also provided herein are methods for maintaining or lowering blood or plasma glycated hemoglobin in a subject in need thereof, comprising administering to the subject a therapeutically effective amount of a Compound or a pharmaceutically acceptable salt, solvate or tautomeric form thereof.

In one embodiment, the subject has prediabetes.

In another embodiment, the subject has diabetes. In certain embodiments, diabetes is gestational diabetes, type-1 diabetes, type-2 diabetes, or latent autoimmune diabetes of adults. In one embodiment, diabetes is gestational diabetes. In one embodiment, diabetes is type-1 diabetes. In one embodiment, diabetes is type-2 diabetes. In one embodiment, type-2 diabetes is hyperinsulinemic Type 2 diabetes. In one embodiment, wherein diabetes is latent autoimmune diabetes of adults.

Blood or plasma glucose may be determined by any method known in the art, such as a commercially available blood glucose meter, a lancet device with lancets, or commercially available test strips.

Blood or plasma glycated hemoglobin may be determined by any method known in the art, such as the A1C test using, for example, the methods provided by the NGSP ("National Glycohemoglobin Standardization Program"). See http://www.ngsp.org/index.asp (last accessed Aug. 27, 2014) for further details.

In one embodiment, the methods of treating prediabetes or treating diabetes or lowering blood or plasma glucose lower the blood or plasma glucose in a subject in need thereof by at least about 5%, 10%, 15%, 20%, 25%, 30%, 35%, 40%, 45%, 50%, 55%, 60%, 65%, 70%, 75%, 80%, 85%, or 90%, or any range resulting from a combination of any two of the foregoing percentages, for example, at least about 5% to about 10% or at least about 15% to about 50%, relative to the blood or plasma glucose prior to the administration of a Compound provided herein. In one embodiment, the blood or plasma glucose continues to lower or remains at a reduced level relative to the blood or plasma glucose prior to the administration of a Compound provided herein after administration of the Compound has stopped. In a specific embodiment, the blood or plasma glycated hemoglobin continues to lower or remains at the reduced level for at least about 5 days, 10 days, 15 days, 20 days, 1 month, 3 months, 6 months, 1 year, 2 years, 3 years, or 5 years, after an administration period of at least about 1 day, 5 days, 10 days, 15 days, 20 days, 1 month, 3 months, 6 months, or 1 year.

In one embodiment, the methods of treating prediabetes or treating diabetes or lowering blood or plasma glycated hemoglobin lower the blood or plasma glycated hemoglobin in a subject in need thereof by at least about 5%, 10%, 15%, 20%, 25%, 30%, 35%, 40%, 45%, 50%, 55%, 60%, 65%, 70%, 75%, 80%, 85%, or 90%, or any range resulting from a combination of any two of the foregoing percentages, for example, at least about 5% to about 10% or at least about 15% to about 50%, relative to the blood or plasma glycated hemoglobin prior to the administration of a Compound provided herein. In one embodiment, the blood or plasma glycated hemoglobin continues to lower or remains at a reduced level relative to the blood or plasma glycated hemoglobin prior to the administration of a Compound provided herein after administration of the Compound has stopped. In a specific embodiment, the blood or plasma glycated hemoglobin continues to lower or remains at the reduced level for at least about 5 days, 10 days, 15 days, 20 days, 1 month, 3 months, 6 months, 1 year, 2 years, 3 years, or 5 years, after an administration period of at least about 1 day, 5 days, 10 days, 15 days, 20 days, 1 month, 3 months, 6 months, or 1 year.

The diagnosis and classification of diabetes mellitus is described by the American Diabetes Association in *Diabetes Care* 37, Supplement 1, S67-S90 (2014) ("ADA 2014"). Erratum to "Diagnosis and Classification of Diabetes Mellitus," *Diabetes Care* 37, Supplement 1: S81-S90 (2014) published in *Diabetes Care* 37, 887 (2014).

4.5.2.1 Diagnosis of Diabetes

In one embodiment, a subject is in need of: treatment for diabetes; or maintaining or lowering blood or plasma glucose; or maintaining or lowering blood or plasma glycated hemoglobin, if the subject shows:
(1) A1C equal or greater than about 6.5%. The test should be performed in a laboratory using a method that is NGSP ("National Glycohemoglobin Standardization Program") certified and standardized to the DCCT ("Diabetes Control and Complications Trial" assay.*
OR
(2) FPG ("fasting plasma glucose") equal or greater than about 126 mg/dL (7.0 mmol/L). Fasting is defined as no substantial caloric intake for about at least 8 hours.*
OR
(3) Two-hour plasma glucose equal or greater than about 200 mg/dL (11.1 mmol/L) during an OGTT ("oral glucose tolerance test"). The test should be performed as described by the World Health Organization, using a glucose load containing the equivalent of about 75 g anhydrous glucose dissolved in water.*
OR
(4) In a patient with classic symptoms of hyperglycemia or hyperglycemic crisis, a random plasma glucose equal or greater than about 200 mg/dL (11.1 mmol/L).

* In the absence of unequivocal hyperglycemia, criteria 1-3 should be confirmed by repeat testing.

A1C (also known as, inter alia, hemoglobin A1c, HbA1c, glycohemoglobin, glycated hemoglobin, or glycosylated hemoglobin) is a widely used marker of chronic glycemia, reflecting average blood glucose levels over a 2- to 3-month period of time. The test plays a critical role in the management of subjects with diabetes, since it correlates well with both microvascular and, to a lesser extent, macrovascular complications and is widely used as the standard biomarker for the adequacy of glycemic management. ADA 2014 at S87, left column.

FPG test checks the subject's fasting blood glucose levels. Fasting means not eating or drinking (except water) for at least 8 hours before the test. In one embodiment, the FPG test is run in the morning, before the subject had breakfast.

In the OGTT, which is the most commonly performed version of the glucose tolerance test, a standard dose of glucose is orally administered to a subject and blood samples taken afterward (about 2 hours later) to determine how quickly glucose is cleared from the blood. A random plasma glucose test is a measure of how much glucose a subject has circulating in the blood. "Random" means that the subject has blood drawn at any time. Whether the subject has fasted or recently eaten will not affect the test.

Further, in connection with Item (4) above, the symptoms of hyperglycemia or hyperglycemic crisis include, but are not limited to: frequent urination, increased thirst, blurred vision, fatigue, headache, fruity-smelling breath, nausea and vomiting, shortness of breath, dry mouth, weakness, confusion, coma, and abdominal pain.

In one embodiment, the methods of treating diabetes, or maintaining or lowering blood or plasma glucose, or maintaining or lowering blood or plasma glycated hemoglobin, maintain the A1C level in a subject in need thereof or lower the A1C level in a subject in need thereof by at least about 5%, 10%, 15%, 20%, 25%, 30%, 35%, 40%, 45%, 50%, 55%, 60%, 65%, 70%, 75%, 80%, 85%, or 90%, or any range resulting from a combination of any two of the foregoing percentages, for example, at least about 5% to about 10% or at least about 15% to about 50%, relative to the A1C level prior to the administration of a Compound provided herein. In a particular embodiment, the methods of treating diabetes, or lowering blood or plasma glucose, or lowering blood or plasma glycated hemoglobin lower the A1C level to at least about 14%, 13%, 12%, 11%, 10%, 9%, 8%, 7%, 6.5%, 6.2%, 6.0%, 5.7%, 5.5%, 5.2%, 5.0%, 4.7%, 4.5%, 4.2%, 4.0%, 3.7%, 3.5%, 3.2%, or 3.0%, or to at least a range formed by any two of the foregoing percentages, for example, to at least about 4.5% to about 6%, or to at least about 5.7% to 6.4%.

In one embodiment, the methods of treating diabetes, or maintaining or lowering blood or plasma glucose, or maintaining or lowering blood or plasma glycated hemoglobin maintain the FPG level in a subject in need thereof or lower the FPG level in a subject in need thereof by at least about 5%, 10%, 15%, 20%, 25%, 30%, 35%, 40%, 45%, 50%, 55%, 60%, 65%, 70%, 75%, 80%, 85%, or 90%, or any range resulting from a combination of any two of the foregoing percentages, for example, at least about 5% to about 10% or at least about 15% to about 50%, relative to the FPG level prior to the administration of a Compound provided herein. In a particular embodiment, the methods of treating diabetes, or lowering blood or plasma glucose, or lowering blood or plasma glycated hemoglobin lower the FPG level to at least about 150 mg/dL, 145 mg/dL, 140 mg/dL, 135 mg/dL, 130 mg/dL, 126 mg/dL, 125 mg/dL, 120 mg/dL, 115 mg/dL, 110 mg/dL, 105 mg/dL, 100 mg/dL, 99 mg/dL, 95 mg/dL, 90 mg/dL, 85 mg/dL, 80 mg/dL, 75 mg/dL, 70 mg/dL, or 60 mg/dL, or to at least a range formed by any two of the foregoing percentages, for example, to at least about 70 mg/dL to about 99 mg/dL, or to at least about 100 mg/dL to about 125 mg/dL.

In one embodiment, the methods of treating diabetes, or maintaining or lowering blood or plasma glucose, or maintaining or lowering blood or plasma glycated hemoglobin maintain the two-hour plasma glucose during an OGTT in a subject in need thereof or lower the two-hour plasma glucose during an OGTT in a subject in need thereof by at least about 5%, 10%, 15%, 20%, 25%, 30%, 35%, 40%, 45%, 50%, 55%, 60%, 65%, 70%, 75%, 80%, 85%, or 90%, or any range resulting from a combination of any two of the foregoing percentages, for example, at least about 5% to about 10% or at least about 15% to about 50%, relative to the two-hour plasma glucose during an OGTT prior to the administration of a Compound provided herein. In a particular embodiment, the methods of treating diabetes or lowering blood or plasma glucose or lowering blood or plasma glycated hemoglobin lower the two-hour plasma glucose during an OGTT using a glucose load of, for example, 75 g of anhydrous glucose dissolved in water, to at least about 300 mg/dL, 270 mg/dL, 250 mg/dL, 220 mg/dL, 200 mg/dL, 199 mg/dL, 190 mg/dL, 180 mg/dL, 170 mg/dL, 160 mg/dL, 150 mg/dL, 140 mg/dL, 139 mg/dL, 130 mg/dL, 120 mg/dL, 110 mg/dL, or 100 mg/dL, or to at least a range formed by any two of the foregoing percentages, for example, to at least about 199 mg/dL to about 140 mg/dL.

In one embodiment, the methods of treating diabetes, or lowering blood or plasma glucose, or lowering blood or plasma glycated hemoglobin lower the A1C level or the FPG level or the A1C, or any combination thereof, in a subject in need thereof such that the subject is no longer diagnosed as having diabetes in view of the criteria discussed in this Section.

4.5.2.2 Diagnosis of Prediabetes

In one embodiment, a subject is in need of: treatment for prediabetes; or maintaining or lowering blood or plasma glucose; or maintaining or lowering blood or plasma glycated hemoglobin, if the subject shows:
(1) FPG ("fasting plasma glucose") of about 100 mg/dL (5.6 mmol/L) to about 125 mg/dL (6.9 mmol/L) (IFG ("impaired fasting glucose"))
OR
(2) 2-h PG ("plasma glucose") in the 75-g OGTT ("oral glucose tolerance test") of about 140 mg/dL (7.8 mmol/L) to about 199 mg/dL (11.0 mmol/L) (IGT ("impaired glucose tolerance"))
OR
(3) A1C of about 5.7 to about 6.4%

For all three tests, risk is continuous, extending below the lower limit of the range and becoming disproportionately greater at higher ends of the range.

FPG test checks the subject's fasting blood glucose levels. Fasting means not eating or drinking (except water) for at least 8 hours before the test. In the OGTT, which is the most commonly performed version of the glucose tolerance test, a standard dose of glucose is orally administered to a subject and blood samples taken afterward (about 2 hours later) to determine how quickly glucose is cleared from the blood. A1C (also known as, inter alia, hemoglobin A1c, HbA1c, A1C, glycohemoglobin, glycated hemoglobin, or glycosylated hemoglobin) is a widely used marker of chronic glycemia, reflecting average blood glucose levels over a 2- to 3-month period of time. ADA 2014 at S87, left column.

In one embodiment, the methods of treating prediabetes, or maintaining or lowering blood or plasma glucose, or maintaining or lowering blood or plasma glycated hemoglobin maintain the FPG level in a subject in need thereof or lower the FPG level in a subject in need thereof by at least about 5%, 10%, 15%, 20%, 25%, 30%, 35%, 40%, 45%, 50%, 55%, 60%, 65%, 70%, 75%, 80%, 85%, or 90%, or any range resulting from a combination of any two of the foregoing percentages, for example, at least about 5% to about 10% or at least about 15% to about 50%, relative to the FPG level prior to the administration of a Compound provided herein. In a particular embodiment, the methods of treating prediabetes or lowering blood or plasma glucose or lowering blood or plasma glycated hemoglobin lower the FPG level to at least about 125 mg/dL, 120 mg/dL, 115 mg/dL, 110 mg/dL, 105 mg/dL, 100 mg/dL, 99 mg/dL, 95 mg/dL, 90 mg/dL, 85 mg/dL, 80 mg/dL, 75 mg/dL, 70 mg/dL, or 60 mg/dL, or to at least a range formed by any two of the foregoing percentages, for example, to at least about 99 mg/dL to about 70 mg/dL.

In one embodiment, the methods of treating prediabetes, or maintaining or lowering blood or plasma glucose, or maintaining or lowering blood or plasma glycated hemoglobin maintain the two-hour plasma glucose during an OGTT in a subject in need thereof or lower the two-hour plasma glucose during an OGTT in a subject in need thereof by at least about 5%, 10%, 15%, 20%, 25%, 30%, 35%, 40%, 45%, 50%, 55%, 60%, 65%, 70%, 75%, 80%, 85%, or 90%, or any range resulting from a combination of any two of the foregoing percentages, for example, at least about 5% to about 10% or at least about 15% to about 50%, relative to the two-hour plasma glucose during an OGTT prior to the administration of a Compound provided herein. In a particular embodiment, the methods of treating prediabetes or lowering blood or plasma glucose or lowering blood or plasma glycated hemoglobin lower the two-hour plasma glucose during an OGTT using a glucose load of, for example, 75 g of anhydrous glucose dissolved in water, to at least about 199 mg/dL, 190 mg/dL, 180 mg/dL, 170 mg/dL, 160 mg/dL, 150 mg/dL, 140 mg/dL, 139 mg/dL, 130 mg/dL, 120 mg/dL, 110 mg/dL, or 100 mg/dL, or to at least a range formed by any two of the foregoing percentages, for example, to at least about 139 mg/dL to about 100 mg/dL.

In one embodiment, the methods of treating prediabetes, or maintaining or lowering blood or plasma glucose, or maintaining or lowering blood or plasma glycated hemoglobin maintain the A1C level in a subject in need thereof or lower the A1C level in a subject in need thereof by at least about 5%, 10%, 15%, 20%, 25%, 30%, 35%, 40%, 45%, 50%, 55%, 60%, 65%, 70%, 75%, 80%, 85%, or 90%, or any range resulting from a combination of any two of the foregoing percentages, for example, at least about 5% to about 10% or at least about 15% to about 50%, relative to the A1C level prior to the administration of a Compound provided herein. In a particular embodiment, the methods of treating prediabetes or lowering blood or plasma glucose or lowering blood or plasma glycated hemoglobin lower the A1C level to at least about 5.7%, 5.6%, 5.5%, 5.2%, 5.0%, 4.7%, 4.5%, 4.2%, 4.0%, 3.7%, 3.5%, 3.2%, or 3.0%, or to at least a range formed by any two of the foregoing percentages, for example, to at least about 5.6% to about 3.0%.

In one embodiment, the methods of treating prediabetes or lowering blood or plasma glucose or lowering blood or plasma glycated hemoglobin lower the FPG level or the plasma glucose level or the A1C, or any combination thereof, in a subject in need thereof such that the subject is no longer diagnosed as having prediabetes in view of the criteria discussed in this Section.

4.5.2.3 Diagnosis of Gestational Diabetes

In one embodiment, a subject is in need of: treatment for diabetes, wherein diabetes is gestational diabetes; or maintaining or lowering blood or plasma glucose; or maintaining or lowering blood or plasma glycated hemoglobin, if the subject shows:

One Step Method (IADPSG ("International Association of the Diabetes and Pregnancy Study Groups" Consensus):

Perform a 75 g OGTT, with plasma glucose measurement fasting and at about 1 h and at about 2 h, at about 24-28 weeks of gestation in women not previously diagnosed with overt diabetes. The OGTT should be performed in the morning after an overnight fast of at least about 8 h. The diagnosis of gestational diabetes is made when any of the following plasma glucose values are met:
(1) Fasting: equal or greater than about 92 mg/dL (5.1 mmol/L);
(2) 1 h: equal or greater than about 180 mg/dL (10.0 mmol/L); and
(3) 2 h: equal or greater than about 153 mg/dL (8.5 mmol/L).

Two Step Method (NIH ("National Institutes of Health") Consensus):

Perform an about 50 g GLT ("glucose load test," nonfasting), with plasma glucose measurement at about 1 h, at about 24-28 weeks of gestation in women not previously diagnosed with overt diabetes. If the plasma glucose level measured about 1 h after the load is equal or greater than 140 mg/dL (7.8 mmol/L), proceed to about 100 g OGTT (Step 2). The American College of Obstetricians and Gynecologists ("ACOG") recommends a lower threshold of about 135 mg/dL (7.5 mmol/L) in high-risk ethnic minorities with higher prevalence of gestational diabetes and some experts also recommend about 130 mg/dL (7.2 mmol/L). The about 100 g OGTT should be performed when the patient is fasting.

The diagnosis of gestational diabetes is made when at least two of the following four plasma glucose levels (measured fasting, about 1 h, about 2 h, about 3 h after the OGTT) are met or exceeded:

|  | Carpenter/Coustan* | or | NDDG ("National Diabetes Data Group")# |
| --- | --- | --- | --- |
| (1) Fasting | 95 mg/dL (5.3 mmol/L) |  | 105 mg/dL (5.8 mmol/L) |
| (2) 1 h | 180 mg/dL (10.0 mmol/L |  | 190 mg/dL (10.6 mmol/L) |
| (3) 2 h | 155 mg/dL (8.6 mmol/L) |  | 165 mg/dL (9.2 mmol/L) |
| (4) 3 h | 140 mg/dL (7.8 mmol/L) |  | 145 mg/dL (8.0 mmol/L) |

*Carpenter and Coustan, "Criteria for screening tests for gestational diabetes," *Am. J. Obstet. Gynecol*. 44: 768-773 (1982).
National Diabetes Data Group, "Classification and diagnosis of diabetes mellitus and other categories of glucose intolerance." *Diabetes* 28: 1039-1057 (1979).

In one embodiment, the methods of treating diabetes, wherein diabetes is gestational diabetes, or lowering blood or plasma glucose or lowering blood or plasma glycated hemoglobin lower the plasma glucose level such that the subject is no longer diagnosed as having gestational diabetes using the One Step Test or the Two Step Test, or both.

4.5.2.4 Diagnosis of Latent Autoimmune Diabetes in Adults

In one embodiment, a subject is in need of: treatment for diabetes, wherein diabetes is Latent Autoimmune Diabetes in Adults; or maintaining or lowering blood or plasma glucose; or maintaining or lowering blood or plasma glycated hemoglobin, if the subject shows at least two of the following characteristics:
  younger than age 50 at diabetes diagnosis
  normal weight (a body mass index less than 25)
  acute symptoms (such as extreme thirst, frequent urination, or unintentional weight loss) when diagnosed with diabetes
  a personal history of another autoimmune disease, such as autoimmune thyroid disease, rheumatoid arthritis, or celiac disease
  a family history of type 1 diabetes or other autoimmune diseases In another embodiment, a subject is in need of: treatment for diabetes, wherein diabetes is Latent Autoimmune Diabetes in Adults; or maintaining or lowering blood or plasma glucose; or maintaining or lowering blood or plasma glycated hemoglobin, if the subject shows elevated levels of pancreatic autoantibodies and has recently been diagnosed with diabetes, but does not require insulin. In a specific embodiment, the presence of antibodies is measured using a GAD ("Glutamic Acid Decarboxylase") Antibody Test. A GAD Antibody Test is a blood test, which measures whether the body of the subject is producing a type of antibody, which destroys its own GAD cells.

In one embodiment, the methods of treating diabetes, wherein diabetes is Latent Autoimmune Diabetes in Adults, or lowering blood or plasma glucose or lowering blood or plasma glycated hemoglobin lower the plasma glucose level such that the subject is no longer diagnosed as having Latent Autoimmune Diabetes.

4.5.2.5 Patient Populations

In one embodiment, the prediabetes or diabetes is caused by or accompanied by obesity. In a certain embodiment, an obese subject has a body mass index ("BMI") of at least about 30 kg/m². Diagnosis and Management of Obesity, American Academy of Family Physicians, 2013, available at http://www.aafp.org/dam/AAFP/documents/patient_care/fitness/obesity-diagnosis-management.pdf (last accessed Aug. 28, 2014). The BMI is calculated as follows:

$$BMI = (\text{weight in kg})/(\text{height of subject in meters})^2.$$

In one embodiment, the subject in need for treatment of prediabetes or diabetes or in need for maintaining or lowering blood or plasma glucose, or in need for maintaining or lowering glycated hemoglobin has not been previously treated for prediabetes or diabetes.

In one embodiment, the subject in need for treatment of prediabetes or diabetes or in need for maintaining or lowering blood or plasma glucose, or in need for maintaining or lowering glycated hemoglobin shows hypersensitivity and allergic reactions, including, but not limited to, anaphylaxis, to insulin medications, such as HUMALOG®.

In one embodiment, the subject in need for treatment of prediabetes or diabetes or in need for maintaining or lowering blood or plasma glucose, or in need for maintaining or lowering glycated hemoglobin is at risk for hypokalemia. All insulin products, such as HUMALOG®, cause a shift in potassium from the extracellular to intracellular space, possibly leading to hypokalemia. Untreated hypokalemia may cause, e.g., respiratory paralysis, ventricular arrhythmia, and death. Subjects at risk for hypokalemia are, e.g., subjects using potassium-lowering medications, subjects taking medications sensitive to serum potassium concentrations, and subjects receiving intravenously administered insulin.

In one embodiment, the subject in need for treatment of prediabetes or diabetes or in need for maintaining or lowering blood or plasma glucose, or in need for maintaining or lowering glycated hemoglobin is female. In one embodiment, the subject in need for treatment of prediabetes or diabetes or in need for maintaining or lowering blood or plasma glucose, or in need for maintaining or lowering glycated hemoglobin is pregnant. In one embodiment, the subject in need for treatment of prediabetes or diabetes or in need for maintaining or lowering blood or plasma glucose, or in need for maintaining or lowering glycated hemoglobin is male.

In one embodiment, the subject in need for treatment of prediabetes or diabetes or in need for maintaining or lowering blood or plasma glucose, or in need for maintaining or lowering glycated hemoglobin is at least about 10, 15, 20, 25, 30, 35, 40, 45, 50, 55, 60, 65, 70, 75, 80, 85, or 90 years old. In one embodiment, the subject in need for treatment of prediabetes or diabetes or in need for maintaining or lowering blood or plasma glucose, or in need for maintaining or lowering glycated hemoglobin is less than about 10, 15, 20, 25, 30, 35, 40, 45, 50, 55, 60, 65, 70, 75, 80, 85, or 90 years old. In a specific embodiment, the age of the subject described in this paragraph ranges from about 10, 15, 20, 25, 30, 35, 40, 45, 50, 55, 60, 65, 70, 75, 80, or 85, 90 years (the "First List") to about 10, 15, 20, 25, 30, 35, 40, 45, 50, 55, 60, 65, 70, 75, 80, 85, or 90 years (the "Second List"), e.g., 10-45 year, 30-90 years, or any age range resulting from a combination of a number of the First List with a number of the Second List, wherein the number of the Second List is greater than the number of the First List.

In one embodiment, the subject in need for treatment of prediabetes or diabetes or in need for maintaining or lowering blood or plasma glucose, or in need for maintaining or lowering glycated hemoglobin is a nursing subject. Sulfonylurea drugs stimulate the beta cells of the pancreas to release insulin. Some sulfonylurea drugs are known to be excreted in human milk. Because of the potential for hypoglycemia in nursing infants may exist, the use of sulfonylureas in nursing subjects should be avoided.

In one embodiment, the subject in need for treatment of prediabetes or diabetes or in need for maintaining or lowering blood or plasma glucose, or in need for maintaining or lowering glycated hemoglobin is a subject with New York Heart Association ("NYHA") Class III or IV heart failure. Doctors usually classify heart failure according to the severity of a subject's symptoms. The table below describes the most commonly used classification system, the NYHA Functional Classification. The system places patients in one of four categories based on how much they are limited during physical activity. Some diabetes medications, such as rosiglitazone (AVANDIA®) are contraindicated for subjects described in this paragraph.

| Class | Functional Capacity: How a patient with cardiac disease feels during physical activity |
|---|---|
| I | Patients with cardiac disease but resulting in no limitation of physical activity. Ordinary physical activity does not cause undue fatigue, palpitation, dyspnea or anginal pain. |
| II | Patients with cardiac disease resulting in slight limitation of physical activity. They are comfortable at rest. Ordinary physical activity results in fatigue, palpitation, dyspnea or anginal pain. |
| III | Patients with cardiac disease resulting in marked limitation of physical activity. They are comfortable at rest. Less than ordinary activity causes fatigue, palpitation, dyspnea or anginal pain. |
| IV | Patients with cardiac disease resulting in inability to carry on any physical activity without discomfort. Symptoms of heart failure or the anginal syndrome may be present even at rest. If any physical activity is undertaken, discomfort increases. | http://www.heart.org/HEARTORG/Conditions/HeartFailure/AboutHeartFailure/Classes-of-Heart-Failure_UCM_306328_Article.jsp (last accessed Aug. 28, 2014).

In one embodiment, the subject in need for treatment of prediabetes or diabetes or in need for maintaining or lowering blood or plasma glucose, or in need for maintaining or lowering glycated hemoglobin is a subject with a hypersensitivity reaction to dipeptidyl peptidase-4 ("DPP-4") inhibitors, such as sitagliptin (JANUVIA®). These reactions include, but are not limited to, anaphylaxis, angioedema, and exfoliative skin conditions, such as Stevens-Johnson syndrome.

In one embodiment, the subject in need for treatment of prediabetes or diabetes or in need for maintaining or lowering blood or plasma glucose, or in need for maintaining or lowering glycated hemoglobin is a subject with normal kidney function (glomerular filtration rate ("GFR") above about 90 mL/min/1.73 m$^2$ and no proteinuria), with chronic kidney disease (Stage 1) (GFR above about 90 mL/min/1.73 m$^2$ with evidence of kidney damage), with chronic kidney disease (Stage 2) (mild, GFR of about 60 to about 89 mL/min/1.73 m$^2$ with evidence of kidney damage), with chronic kidney disease (Stage 3) (moderate, GFR of about 30 to about 59 mL/min/1.73 m$^2$), with chronic kidney disease (Stage 4) (severe, GFR of about 15 to about 29 mL/min/1.73 m$^2$), or with chronic kidney disease (Stage 5) (kidney failure, GFR less than about 15 mL/min/1.73 m$^2$, wherein the subject may or may not require dialysis).

4.6 Pharmaceutical Compositions and Routes of Administration

Provided herein are pharmaceutical compositions comprising a Compound provided herein and a pharmaceutically acceptable carrier. In a particular embodiment, the pharmaceutical compositions are those, wherein the composition is suitable for topical, oral, subcutaneous, or intravenous administration.

Provided herein are compositions comprising an effective amount of a Compound and compositions comprising an effective amount of a Compound and a pharmaceutically acceptable carrier or vehicle. In some embodiments, the pharmaceutical composition described herein are suitable for oral, parenteral, mucosal, transdermal or topical administration.

The Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Compound in the pharmaceutical composition may be at a level that will exercise the desired effect; for example, about 0.1 mg/kg to about 1000 mg/kg or about 0.5 mg/kg to about 100 mg/kg of a patient's body weight in unit dosage for both oral and parenteral administration.

The dose of a Compound to be administered to a patient is rather widely variable and can be the judgment of a health-care practitioner. In general, the Compounds can be administered one to four times a day in a dose of about 0.1 mg/kg of a patient's body weight to about 1000 mg/kg of a patient's body weight in a patient, but the above dosage may be properly varied depending on the age, body weight and medical condition of the patient and the type of administration. In one embodiment, the dose is about 0.05 mg/kg of a patient's body weight to about 500 mg/kg of a patient's body weight, 0.05 mg/kg of a patient's body weight to about 100 mg/kg of a patient's body weight, about 0.5 mg/kg of a patient's body weight to about 100 mg/kg of a patient's body weight, about 0.1 mg/kg of a patient's body weight to about 50 mg/kg of a patient's body weight or about 0.1 mg/kg of a patient's body weight to about 25 mg/kg of a patient's body weight. In one embodiment, one dose is given per day. In another embodiment, two doses are given per day. In any given case, the amount of the Compound administered will depend on such factors as the solubility of the active component, the formulation used and the route of administration.

In another embodiment, provided herein are methods for the treatment of pain, prediabetes, and diabetes; and methods of maintaining or lowering blood or plasma glucose, and maintaining or lowering glycated hemoglobin; comprising the administration of about 7.5 mg/day to about 75 g/day, about 3.75 mg/day to about 37.5 g/day, about 3.75 mg/day to about 7.5 g/day, about 37.5 mg/day to about 7.5 g/day, about 7.5 mg/day to about 3.75 g/day, about 3.75 mg/day to about 1.875 g/day, about 3.75 mg/day to about 1,000 mg/day, about 3.75 mg/day to about 800 mg/day, about 3.75 mg/day to about 500 mg/day, about 3.75 mg/day to about 300 mg/day, or about 3.75 mg/day to about 150 mg/day of a Compound to a patient in need thereof. In a particular embodiment, the methods disclosed herein comprise the administration of 1 mg/day, 5 mg/day, 10 mg/day, 15 mg/day, 20 mg/day, 30 mg/day, 40 mg/day, 45 mg/day, 50 mg/day, 60 mg/day, 75 mg/day, 100 mg/day, 125 mg/day, 150 mg/day, 200 mg/day, 250 mg/day, 300 mg/day, 400 mg/day, 600 mg/day, 800 mg/day, 1,000 mg/day, 1,500 mg/day, 2,000 mg/day, 2,500 mg/day, 5,000 mg/day, or 7,500 mg/day of a Compound to a in need thereof.

In another embodiment, provided herein are unit dosage formulations that comprise between about 7.5 mg to about 75 g, about 3.75 mg to about 37.5 g, about 3.75 mg to about 7.5 g, about 37.5 mg to about 7.5 g, about 7.5 mg to about 3.75 g, about 3.75 mg to about 1.875 g, about 3.75 mg to about 1,000 mg, about 3.75 mg to about 800 mg, about 3.75 mg to about 500 mg, about 3.75 mg to about 300 mg, or about 3.75 mg to about 150 mg of a Compound.

In a particular embodiment, provided herein are unit dosage formulation comprising about 1 mg, 5 mg, 10 mg, 15 mg, 20 mg, 30 mg, 40 mg, 45 mg, 50 mg, 60 mg, 75 mg, 100 mg, 125 mg, 150 mg, 200 mg, 250 mg, 300 mg, 400 mg, 600 mg, 800 mg 1,000 mg, 1,500 mg, 2,000 mg, 2,500 mg, 5,000 mg, or 7,500 mg of a Compound.

In another embodiment, provided herein are unit dosage formulations that comprise a Compound dosage that achieves a target plasma concentration of the Compound in a patient or an animal model. In a particular embodiment, provided herein are unit dosage formulations that achieves a plasma concentration of the Compound ranging from approximately 0.001 µg/mL to approximately 100 mg/mL, approximately 0.01 µg/mL to approximately 100 mg/mL, approximately 0.01 µg/mL to approximately 10 mg/mL, approximately 0.1 µg/mL to approximately 10 mg/mL, approximately 0.1 µg/mL to approximately 500 µg/mL, approximately 0.1 µg/mL to approximately 500 µg/mL, approximately 0.1 µg/mL to approximately 100 µg/mL, or approximately 0.5 µg/mL to approximately 10 µg/mL in a patient or an animal model. To achieve such plasma concentrations, a Compound or a pharmaceutical composition thereof may be administered at doses that vary from 0.001 µg to 100,000 mg, depending upon the route of administration. In certain embodiments, subsequent doses of a Compound may be adjusted accordingly based on the plasma concentrations of the Compound achieved with initial doses of the Compound or pharmaceutical composition thereof administered to the subject.

A Compound can be administered once, twice, three, four or more times daily.

A Compound can be administered orally for reasons of convenience. In one embodiment, when administered orally, a Compound is administered with a meal and water. In another embodiment, the Compound is dispersed in water or juice (e.g., apple juice or orange juice) and administered orally as a suspension. In another embodiment, when administered orally, a Compound is administered in a fasted state.

The Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Compound without an additional carrier, excipient or vehicle.

In another embodiment, provided herein are compositions comprising an effective amount of a Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts. In general, all of the compositions are prepared according to known methods in pharmaceutical chemistry. Capsules can be prepared by mixing a Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Compound can be delayed or prolonged by proper formulation. For example, a slowly soluble pellet of the Compound can be prepared and incorporated in a tablet or capsule, or as a slow-release implantable device. The technique also includes making pellets of several different dissolution rates and filling capsules with a mixture of the pellets. Tablets, capsules, or pellets can be coated with a film that resists dissolution for a predictable period of time (the coating may comprise, for example, polymethylacrylates or ethyl cellulose). Even the parenteral preparations can be made long-acting, by dissolving or suspending the Compound in oily or emulsified vehicles that allow it to disperse slowly in the serum.

5 EXAMPLES

5.1 Biological Examples

5.1.1 In Vitro Assays

Recombinant NaV Cell Lines

In vitro assays were performed in recombinant cell line that stably express a heterotrimeric protein of interest from an introduced nucleic acid encoding the alpha subunit (hNav1.7, SCN9A), the beta subunit (SCNB1) and the beta subunit (SCNB2). The cell line was engineered using Human Embryonic Kidney 293 cells as host background. Additional cell lines stably expressing recombinant Nav1.7 or Nav1.5 alpha subunit alone or in combination with various beta subunits can also be used in in-vitro assays.

To generate cells and cell lines provided herein, one can use, for example, the technology described in U.S. Pat. No. 6,692,965 and WO/2005/079462. Both of these documents are incorporated herein by reference in their entirety. This technology provides real-time assessment of millions of cells such that any desired number of clones (from hundreds to thousands of clones) expressing the desired gene(s) can be selected. Using cell sorting techniques, such as flow cytometric cell sorting (e.g., with a FACS machine) or magnetic cell sorting (e.g., with a MACS machine), one cell per well is automatically deposited with high statistical confidence in a culture vessel (such as a 96 well culture plate). The speed and automation of the technology allows multigene recombinant cell lines to be readily isolated.

FDSS Membrane Potential In-Vitro Assay

Cells stably expressing hNaV1.7α, β1 and β2 subunits were maintained under standard cell culture conditions in Dulbecco's Modified Eagles medium supplemented with 10% fetal bovine serum, glutamine and HEPES. On the day before assay, the cells were harvested from stock plates using cell dissociation reagent, e.g., trypsin, CDB (GIBCO) or cell-stripper (Mediatech), and plated at 10,000-25,000 cells per well in 384 well plates in growth media. The assay plates were maintained in a 37° C. cell culture incubator under 5% $CO_2$ for 22-48 hours. The media was then removed from the assay plates and membrane potential fluorescent dye diluted in load buffer (137 mM NaCl, 5 mM KCl, 1.25 mM $CaCl_2$, 25 mM HEPES, 10 mM glucose) was added.

Membrane Potential Dye(s):

Blue membrane potential dye (Molecular Devices Inc.), or membrane potential-sensitive dye, HLB021-152 (AnaSpec) were combined with a fluorescence quencher, e.g., Dipicrylamine (DPA), Acid Violet 17 (AV 17), Diazine Black (DB), HLB30818, FD and C Black Shade, Trypan Blue, Bromophenol Blue, HLB30701, HLB30702, HLB30703, Nitrazine Yellow, Nitro Red, DABCYL (Molecular Probes), FD and C Red NO. 40, QSY (Molecular Probes), metal ion quenchers (e.g., $Co^{2+}$, $Ni^{2+}$, $Cu^{2+}$), and iodide ions.

The cells were incubated with the membrane potential dye for 45-60 mins at 37° C. The dye-loaded assay plates were then placed in the high-throughput fluorescent plate reader (Hamamatsu FDSS). The kinetic read was started with assay plate imaging every second. After 10 s, the assay buffer alone, or test compound diluted in the assay buffer, were added to the cells ($1^{st}$ addition step) and the kinetic read continued every 2 s for 2 mins total after which cells were stimulated with veratridine and scorpion venom ($2^{nd}$ addition step) diluted in assay buffer to evaluate the effects of the test compounds.

Veratridine and scorpion venom proteins modulate the activity of voltage-gated sodium channels through a combination of mechanisms, including an alteration of the inactivation kinetics. The resulting activation of sodium channels in stable NaV1.7-expressing cells changes cell membrane potential and the fluorescent signal increases as a result of depolarization.

Control response elicited by veratridine and scorpion venom with buffer only (without test compounds added) was taken as the maximal response. Assay results are expressed in relative fluorescence units (RFU) and can be determined by using the maximum signal during the $2^{nd}$ addition/stimulation step or by computing the difference of maximum and minimum signal during the $2^{nd}$ addition/stimulation step. The signal inhibition was estimated for each test compound concentration in triplicate. The data were analyzed using GraphPad Prism software to determine the 1050 value for the test compound.

Veratridine and scorpion venom from Leiurus quinquestriatus quinquestriatus can be purchased from Sigma-Aldrich (St Louis, Mo.). Stock solutions were prepared as 10 mM (veratridine) in DMSO and as 1 mg/ml (scorpion venom) in de-ionised water. The sodium channels agonists were diluted in assay buffer to a 4× concentration with final concentration being 2-25 μM for veratridine and 2-20 μg/ml for scorpion venom.

Test compounds were prepared as 2-10 mM stock in DMSO. The stock solutions were further diluted in DMSO in serial dilution steps and then transferred to assay buffer as 4× of the final assay concentrations. Test compounds were added during the first addition (pre-stimulation) step in the kinetic read. All test compound concentrations were evaluated in triplicate.

Compounds 1, 2, 3, 12, 13, 16, 26, and 32 showed NaV1.7 IC50 values less than 0.13 μM; Compounds 4, 5, 6, 7, 8, 9, 10, 15, 18, 20, and 28 showed NaV1.7 IC50 values between 0.13 and 1.0 µM; Compounds 14, 17, 19, 21, 22, and 23 showed NaV1.7 IC50 values greater than 1.0 µM and less than 20.0 µM.

Compound 54 showed NaV1.7 IC50 value of less than 0.1 µM. Compounds 35, 43, 46, 49, 55, 57, and 59 showed NaV1.7 IC50 values between 0.104 and 0.5 µM. Compounds 34, 48, 49, 50, 51, 56 and 68 showed NaV1.7 IC50 values of greater than 0.5 µM and equal or less than 1.0 Compounds 42, 45, 47, 52, and 58 showed NaV1.7 IC50 values of greater than 1.0 µM and less than 20.0 µM Patchliner Electrophysiological In-Vitro Assay The recording of sodium current from stable HEK293 cell lines expressing NaV1.7 or NaV1.5 was done on a Patchliner® instrument, Nanion Technologies. The Patchliner® is a fully automated bench-top patch clamp platform and can record simultaneously from up to eight single cells with GΩ seals.

For patch-clamp experiments, cells were grown under standard culturing conditions in Dulbecco's Modified Eagles medium supplemented with 10% fetal bovine serum, glutamine and HEPES. Cells were harvested and kept in suspension for up to 4 hours with no significant change in quality or ability to patch. Whole cell patch clamp recordings were conducted according to Nanion's standard procedure for the Patchliner®. Experiments were conducted at room temperature.

Voltage protocols were designed to establish: 1) peak current amplitude ($I_{max}$), 2) test potential ($V_{max}$) and 3) half-inactivation potential ($V_{1/2}$) for each of the eight individual cells. To determine $V_{1/2}$, a standard steady-state inactivation protocol was executed using a series of fifteen 500 ms depolarizing pre-pulses in 10 mV increments (starting at −130 mV) and immediately followed by a 10 ms test pulse to $V_{max}$. To estimate test compound affinity to the inactivated state of sodium channel ($K_i$), the holding potential for each cell was set automatically to the $V_{1/2}$ calculated from a steady-state inactivation data. The current was activated with the following voltage protocol: holding at $V_{1/2}$ for 2-5 seconds, return to the −120 mV for 5-10 ms to relieve fast inactivation, stepping to test potential ($V_{max}$) for 10-20 ms. This voltage protocol was repeated every 10 seconds to establish the baseline with 2-3 buffer additions followed by the test compound addition. The dose-dependent inhibition was analyzed using Nanion's Data Analysis Package.

Compounds 1, 2, 5, 6, 8, 11, 12, 13, 15, 16, 20, 24, 26, 28, 29 and 32 showed NaV1.7 IC50 values less than 0.1 µM; Compounds 14, 17, 18, 19, 21, 22, 23, 25 and 33 showed NaV1.7 IC50 value between 0.1 and 1.0 µM.

Compounds 44, 49, 53, 54, 60, 61, 62, 63, 64, 65, 66, 67, and 69 showed NaV1.7 IC50 values of less than 0.1 µM. Compound 34 and 52 showed an NaV1.7 IC50 value of greater than 0.1 µM and equal or less than 0.5 µM. Compounds 47 and 58 showed NaV1.7 IC50 values of greater than 1.0 µM and less than 10.0 µM. Compounds 44, 49, 56, and 58 showed a NaV1.5 IC50 greater than 10.0 µM (IC50 as measured in the Patchliner Electrophysiological Assay as described in this Section 5.1.1.

In-Vitro Cytochrome P450 (CYP450) Inhibition Assay

We evaluated interaction of drug candidates with cytochrome P450 enzymes which are a major determinant of drug clearance via oxidative metabolism using a high throughput compatible, fluorescence based CYP450 screening assay (Vivid® CYP450, Invitrogen) according to manufacturer's directions.

In brief, test compounds at four different concentrations (µM—6.0, 2.0, 0.7, 0.2), a positive control (Ketoconazole) and a solvent control were incubated at room temperature in unique wells of a 96-well microtiter plate with CYP3A4 enzyme complex for 20 minutes. A pre-read fluorescence (Ex—485 nm/Em—530 nm) was measured at the start of the incubation using a Tecan Safire[2] microplate reader-monochromator to determine background fluorescence. At the end of the incubation period, enzyme substrate and co-enzyme were added and the reaction was kinetically monitored for 1 hour by measuring fluorescence every minute. Effect of test compounds on inhibition of CYP3A4 metabolism of provided substrate was determined by calculating the ratio of the effective reaction rate in presence of test compound to that in the absence of inhibitor.

Compounds 9, 11, 13, 14, 15, 17, 18, 19, 21, and 22 showed 0-25% CYP3A4 inhibition at 6 µM test concentration; Compounds 5, 6, 8, 10 and 16 showed 25-50% CYP3A4 inhibition at 6 µM test concentration; Compounds 1, 2, 3, 4, 12, 20 and 32 showed 50-100% CYP3A4 inhibition at 6 µM test concentration.

5.1.2 In Vivo Assays

Formalin Test

The Formalin Test (pain behaviors) produces two phases of response, phase 1 (0 to 10 minutes post-formalin injection) is related to direct damage on nociceptors at the sensory nerve endings and mimics post-surgical pain and wound pain, while phase 2 (11 to 40 minutes post-formalin injection) is related to neuro-inflammation pain which mimics inflammatory arthritis (joint pain).

Each animal was acclimatized for 2-3 days prior to tests. Following acclimatization, a test compound, a positive control, such as mexiletine or lidocaine, which are well-known to inhibit pain, or a vehicle control, such as saline, was administered by intraperitoneal injection or oral gavage 15-20 minutes prior to administration of formalin. The time of administration of test compound was recorded. Formalin solution (1.25%) in PBS was injected subcutaneously (s.c.) in a volume of 50 µL into the dorsum of a hindpaw of each rat at time (T)=0 minutes. Each animal was then placed in a clear observation chamber. Observation was started at T=1 minute and continued to 60 minutes post-injection. The number of flinches (licking, biting, or shaking) per minute was recorded for each animal by an automated nociception analyzer (Yaksh et al. "An automated flinch detecting system for use in the formalin nociceptive bioassay," *J. Appl. Physiol.* 2001; 90:2386-2402). This was accomplished by measuring the movement of a small metal band (0.5 grams) that was placed on the ankle near the injected paw 15-30 minutes before administration of the test compound. Formalin was injected into the paw with the band and the animal was then placed without restraint inside the observation chamber over an electromagnetic detector system. The paw flinches were detected by the system and counted automatically using a computer. At the end of the test, a file was written that contains identifying information for each animal and the number of flinches per minute over time. The Foot fault test was conducted 75 minutes post-dosing. Other observations of changes in movement such as immobility and seizure were recorded during the whole study period. At the end of study, the animals were euthanized.

For each compound tested, the individual score was obtained by calculating the accumulated number of flinches from the formalin test. The reduction in pain response obtained for each compound was then expressed as a percentage of inhibition (% inhibition) over vehicle (control), calculated according to the formula:

% inhibition=[(test compound score−vehicle score)/ (vehicle score)]×100%.

Compounds 1, 2, 6, 8 and 12 showed reduction in pain response of 24-78% (formalin assay, phase 1) and 29-73% (formalin assay phase 2) relative to vehicle control at doses of 3 to 30 mg/kg via the intraperitoneal route.

Compound 1 showed reduction in pain response of 14% (formalin assay, phase 1) and 17% (formalin assay phase 2) relative to vehicle control at a dose of 75 mg/kg via the oral route.

Compound 12 showed reduction in pain response of 13-24% (formalin assay, phase 1) and 29-43% (formalin assay phase 2) relative to vehicle control at a dose of 150 μL of 1 or 2% w/v solution via the topical route.

Partial Sciatic Nerve Ligation (PSNL) and the Streptozotocin (STZ)-Induced Model of Diabetes The Partial Sciatic Nerve Ligation Model is associated with neuropathic pain such as spinal disc bulge. The Diabetes Model is associated with diabetic nerve damage, which is one of the severe complications in diabetic patients.

Method of Partial Sciatic Nerve Ligation (PSNL)

250-350 g male Sprague-Dawley rats from appropriate animal resources were anesthetized with 2.5% isoflurane. A hind leg was shaved, and the skin was sterilized with 0.5% iodine and 75% alcohol. All surgical instruments were sterilized before surgery and between animals. An incision (1 cm) was made at the middle of the thigh in parallel with the muscle and sciatic nerve distribution. The muscle was exposed and dissected at the joint of two muscles (biceps femoris) indicated by the light colored (white) fascia line. The sciatic nerve was just beneath the muscle and was hooked out using an 18-20 G feeding needle (90 degree curved); the sciatic nerve was flat on the feeding needle and approximately one-half the diameter of the nerve is tightly ligated with 7-0 silk suture. A response of the injured leg twitch indicates the success of ligation. After checking hemostasis, bupivicaine 0.1-0.2 ml (0.125%) was given at the incision area, the muscle and the adjacent fascia are closed with 5-0 absorbable sutures. The skin was sutured with absorbable suture and tissue glue. The control group using sham surgery animals (about 8-10 animals) underwent the same surgical procedure but with no nerve ligation. Animals were returned to their home cage after recovery from anesthesia.

The Streptozotocin (STZ)-Induced Model of Diabetic Neuropathy 250-350 g male Sprague-Dawley rats from appropriate animal resources were used. Type I diabetes was induced by a single injection, (intraperitoneally, intravenously or intramuscularly) of 50-100 mg/kg of streptozotocin (STZ, Sigma Chemicals, St. Louis, Mo. or VWR) freshly dissolved in sodium citrate (0.01 M, pH 4.5). Sham animals were given either saline or same vehicle injection. Following a wait time of about two days, inducement of diabetes was confirmed in STZ-injected rats by measuring the plasma glucose concentrations in blood samples from the tail vein after a fast of 6 hours. The glucose level was assayed using a mini glucose monitor (kit for AlphaTRAK 2 meter, available from Abbott Laboratories). Screening for hyperglycemia in STZ-injected animals was done, with only animals with a final blood glucose level ≥300 mg/dl being selected for the study. Glucose levels in the sham animals remained normal. Other parameters (water intake, food intake, and bodyweight) were monitored before the treatment with a test compound and after the cessation of the treatment.

The analgesic effect of the test compound was expressed as a percent recovery (% Recovery) relative to the sham control group baseline and calculated according to the formula:

% Recovery=100%−{[(sham mean-test compound mean)/(sham mean-vehicle mean)]×100%} wherein "sham mean" refers to average score in the sham-operated group; "test compound mean" refers to average score in the PSNL-group (animals with partial sciatic nerve ligation) or diabetic group (animals treated with STZ) treated with a test compound; "vehicle mean" refers to average score in the PSNL-group or diabetic group treated with vehicle only. The above formula was used to obtain data for the following in vivo behavioral tests.

The following behavioral tests were conducted (i.e., plantar test, paw pressure test, and von Frey test) started on day 3 and thereafter once weekly following surgery or use of a diabetic inducer. The test compound was tested starting at week 1 in the PSNL model and at week 5 in the diabetic neuropathy model to evaluate therapeutic effect on the established neuropathic chronic pain.

Prevention or Delay of the Development of Neuropathic Pain

A Compound provided herein is tested starting treatment with the Compound prior to PSNL surgery and/or immediately after the PSNL surgery and is continued on a daily oral dosing regimen for multiple days to evaluate prevention and/or delay in the development of neuropathic pain before the establishment of pain or after the cessation of dosing. To test if the Compound can prevent or delay the development of neuropathic pain in the PSNL model, the treatment with the Compound is started on day 1 (3-4 hours after PSNL surgery) and continued for two weeks until day 15. The pain response is evaluated using behavioral tests, e.g., von Frey test, plantar test, or the paw pressure test, all of which are described herein below, before the surgery and every three days following the surgery (e.g., on day 2, day 5, day 8 day 11 and day 14 after surgery) and compared to a sham group, a vehicle group and a Compound group in which the treatment with the Compound starts on day 7 after PSNL surgery and continues until day 15. The behavioral tests are conducted every three days after the cessation of dosing (e.g., on day 18, day 21, day 24 and day 27 after surgery).

Diabetic Neuropathy and Anti-Diabetic Effect after Chronic Dosing

A Compound provided herein is tested in the rat STZ model of diabetes by chronic administration of the Compound for at least 7 days to evaluate analgesic and antidiabetic effects of the Compound. The analgesic effect of the Compound can be evaluated using behavioral tests (e.g., von Frey test, plantar test, and paw pressure test described herein below). The anti-diabetic effect of the Compound can be evaluated based on the improvement in the glucose level, food intake, water intake in the compound treated group compared to the untreated vehicle group and the normal, non-diabetic sham control group.

Thermal Hyperalgesia (Plantar Test):

The plantar test quantitatively assesses the thermal threshold of the hindpaw.

Rats were placed on the glass surface of a thermal testing apparatus (Model 336, IITC/Life Science Instruments, Woodland Hills, Calif.) and were allowed to acclimate for 10 min before testing on the glass surface at room temperature. The animals were placed in chambers with the temperature of the glass surface maintained constant at 30-32° C. A mobile radiant heat source located under the glass is focused onto the hindpaw of each rat. The device was set at 55% (heating rate ~3° C. per sec) heating intensity with a cut-off at 10 sec. The paw withdrawal latency was recorded by a digital timer. The thermal threshold was determined as the mean withdrawal latency from two to three consecutive trials of both hindpaws. The cutoff of 10 s was used to prevent potential tissue damage.

Mechanical Hyperalgesia (Paw Pressure Test)

The paw pressure test assesses nociceptive mechanical thresholds, expressed in grams, and is measured with a Ugo Basile Analgesiometer (Varese, Italy).

The test was performed by applying a noxious (painful) pressure to the hindpaw. By pressing a pedal that activates a motor, the force was increased (32 g/s) on a linear scale. When the animal displayed pain by withdrawal of the paw or vocalization, the pedal was immediately released and the nociceptive pain threshold was read on a scale (a cutoff of 150 g was used to avoid tissue injury) (Courteix et al. Study of the sensitivity of the diabetes-induced pain model in rats to a range of analgesics. Pain 1994, May; 57(2):153-160.) Both hindpaws were used for assessment of mechanical hyperalgesia. At least two trials, separated by 10 min, were performed in each rat, and the mean value was used. A testing session for a particular rat began after 5 min of habituation or as soon as the rat stopped exploring and appeared acclimatized to the testing environment.

Tactile Allodynia (Von Frey Test)

The Von Frey test quantifies mechanical sensitivity of the hindpaw. The test utilizes a non-noxious stimulus and is therefore considered a measure of tactile allodynia.

Animals were placed under clear plastic boxes above a wire mesh floor, which allowed full access to the paws. Behavioral acclimation was allowed for at least 5 min. Mechanical paw withdrawal thresholds (PWTs) were measured with the up-down testing paradigm. Von Frey filaments in log increments of force (2.0, 4.0, 6.0, 8.0, 10.0, 15.0, 26, 60 g or size 4.31, 4.56, 4.74, 4.93, 5.07, 5.18, 5.46, 5.88) were applied for a duration of 2-3 s to the mid-plantar paw in neuropathic pain (e.g., PSNL or diabetic) animals. Application was to the central region of the plantar surface avoiding the foot pads. The 4.0-g stimulus was applied first Whenever a withdrawal response to a given probe occurred, the next smaller von Frey probe was applied. Whenever a negative response occurred, the next higher von Frey probe was applied. The test continued until (1) the responses of four more stimuli (total 3-5 trials) after the first change in response was obtained or (2) the upper/lower end of the von Frey hair was reached (bending). If the animal showed no response to any of the von Frey hairs, a value of 26 g, corresponding to the next log increment in potential von Frey filament, was assigned as the threshold. The testing was continued until the hair with the lowest force to induce a rapid flicking of paw was determined or when the cut off force of approximately 26 g was reached. This cut off force was used, because it represented approximately 10% of the animals' body weight and served to prevent rising of the entire limb due to the use of stiffer hairs, which would have changed the nature of the stimulus. The value of each hair was confirmed weekly by measuring the magnitude in grams exerted by the hair when applied to an electronic balance. The hair was applied only when the rat was stationary and standing on all four paws. A withdrawal response was considered valid only if the hind paw was completely removed from the platform. Although infrequent, if a rat walked immediately after application of a hair instead of simply lifting the paw, the hair was reapplied. On rare occasions, the hind paw only flinched after a single application; as the hind paw was not lifted from the platform, this was not considered a withdrawal response. A trial consisted of the application of a von Frey hair to the hind paw five times at 5 s intervals or as soon as the hind paw was placed appropriately on the platform. If withdrawal did not occur during five applications of a particular hair, the next larger hair in the series was applied in a similar manner. When the hind paw was withdrawn from a particular hair either four or five times out of the five applications, the value of that hair in grams was considered to be the withdrawal threshold. Once the threshold was determined for the left hind paw, the same testing procedure was repeated on the right hind paw after 5 min.

Weight Bearing (Spontaneous Pain)

Weight bearing test was conducted in the partial sciatic nerve ligation model described herein. Rats were tested for hypersensitivity and spontaneous pain in the weight-bearing test, using an Incapacitance tester (Linton Instruments, Norfolk, UK). The rat was placed into the plastic box of the device. The integrated paw pressure during this period (1-2 seconds) was displayed separately for the right and left leg. The ratio between the pressure of the right and left leg was calculated as left/right hind leg weight distribution ratio. The weight bearing assay was repeated 3 times in 5 minutes. The mean distribution ratio of 3 assays was calculated.

In the PSNL model, Compounds 1 and 2 showed recovery of 49-62% (paw pressure test), 59-73% (plantar test) and 50-66% (weight bearing) relative to vehicle control at a dose of 30 mg/kg via the intraperitoneal route. Compounds 1 and 2 gave no significant effect in the tactile allodynia test measured 30-60 minutes post dose.

In the PSNL model, compounds 49 and 54 showed recovery of 28-32% (paw pressure test), 54-63% (plantar test) and 40-65% (weight bearing) relative to vehicle control at dose 10 mg/kg via the oral route and 64-85% (paw pressure test), 81-90% (plantar test) and 64-75% (weight bearing) relative to vehicle control at dose 30 mg/kg via the oral route. There was no significant effect in the tactile allodynia test relative to vehicle control measured 30 minutes post dose. Up to 90% reversal of the tactile allodynia relative to vehicle control is normally expected at 2 hours post dose.

In the streptozotocin (STZ)-induced diabetic model, compounds 15 and 49 showed recovery of 66-68% (paw pressure test), 93-100% (plantar test) relative to vehicle control at dose 30 mg/kg via the intraperitoneal or oral route with no significant effect in the tactile allodynia test relative to vehicle control when measured 30 minutes post dose. Up to 90% reversal of the tactile allodynia relative to vehicle control is expected after 9 days of repeated dosing.

Writhing Model (Inflammatory Abdominal Pain)

The Acetic Acid Writhing Model is associated with visceral pain (abdominal pain, such as stomach pain, and pain caused by, for example, bile duct congestion and kidney stones). A writhing test assesses acute peritoneovisceral pain.

After acclimation of 2-3 days, a test compound, positive control or vehicle control was administered by intraperitoneal injection (i.p.) or by oral gavage 15-30 minutes prior to administration of acetic acid. The time of administration of test compound was recorded. For mice: Method A: 0.6% Acetic acid solution in saline was injected i.p. in a volume of 10 ml/kg; Method B: 1.2% Acetic acid solution in saline was injected i.p. in a volume of 5 ml/kg. For rats: 4% acetic acid in saline was injected i.p in a volume of 2 ml/kg at T=0 minutes. Each animal was placed in a clear plastic cage. At T=5 minutes, the number of writhing movements was counted over a 45 minute period. Alternatively, the writhing movements were counted over a 5-minute period and repeated every 5 minutes, starting at T=5 minutes over a 45-minute period.

For each compound tested, the individual score was obtained by calculating the accumulated writhing movements for the time period studied. The reduction in pain obtained for each compound was then expressed as a percentage of inhibition (% inhibition) over vehicle (control), calculated according to the formula:

$$\% \text{ inhibition} = [(\text{test compound score} - \text{vehicle score})/(\text{vehicle score})] \times 100\%.$$

wherein "test compound score" refers to group treated with test compound or substance; "vehicle score" refers to group treated with vehicle only.

Compound 2 tested in rats showed reduction in pain of 48-58% relative to vehicle control at doses of 10 to 30 mg/kg via the intraperitoneal route.

Compounds 49, 53, and 54 (Method B) showed reduction in pain of 25-35% at dose 10 mg/kg via the oral route (C57 mice). Compounds 2, 15, 49, 53 and 54 showed reduction in pain of 37-47% at dose 30 mg/kg via the oral route and 54-75% via the intraperitoneal route (C57 mice).

Itching/Pruritis Model

The itching or scratching behavior in animals studied can be used as a measure of pruritis.

Scratching is analyzed by counting the number of scratches from a video recording or live by direct visual observation, or by using an automated analyzer (purchased from University of California, San Diego, Calif.). Using an automated analyzer, itching is measured by measuring the movement of a small metal band (0.5 grams) that is placed on the ankle near the hind paw of the animal before injection of the pruritogenic agent. A pruritogenic agent such as histamine hydrochloride (5 mg/ml saline, 20 µl/mouse or 50 µl/rat) or serotonin hydrochloride (5 mg/ml saline, 20 µl/mouse, 50-µl/rat) is injected into the shaved scapular area of the animal to induce local skin pruritis.

The injection site is chosen so that it is only accessible by the hind paw with the metal band and when the animal scratches the area that is itchy using this hindpaw, a rhythmical scratching action, (distinct from that of grooming undertaken by the forelimbs) is recorded.

Following injection of the pruritogenic agent either intradermally (i.d.) or subcutaneously (s.c.), the animal is placed without restraint inside the observation chamber (typically 22×22×24 cm) over an electromagnetic detector system. The number of scratches on the injected scapular area are detected by the system and counted automatically using a computer for a period 45 min-60 min. During the test period, observations such as manually counting the number of scratches over time are also recorded and compared to the number recorded by the automated analyzer.

To measure the efficacy of test compounds as inhibitors of itch, a Compound provided herein is dissolved in an appropriate vehicle such as a mixture of PEG, Tween and water (typically 30% PEG/20% Tween/50% water) in concentrations of about 1-20% w/v, and about 100 µl is applied to the shaved circular area (approximately 20 mm in diameter), about 15 min-30 min before the injection of the pruritogenic agent. For an orally administered Compound, 10-30 mg/kg of the test compound is dissolved in a vehicle, such as water or PEG/water (typically 50% each of PEG/water) and administrated by oral gavage 30 min-45 min before injection of the pruritogenic agent. Instead of the Compound, positive a control, such as 20% Lanacane, as well as a negative control, such as saline or vehicle, are also separately administered and the results recorded.

For the in vivo models described above, the data obtained is analysed using the Student t-test, two-tailed distribution. All the data is presented as mean±S.E.M. ANOVA (analysis of variance between groups) is used as a method to analyze the overall effects of dose responses in the compounds tested. For the compounds which give a significant F value when tested, the Bonferonni test is subsequently applied.

Evaluation of Anti-Diabetic Effect in In Vivo Model of Diabetes

Diabetes mellitus was induced in rats as described in the section entitled "The Streptozotocin (STZ)-Induced Model of Diabetic Neuropathy" above.

The animals selected for the study showed stable signs of diabetic condition, e.g., hyperglycemia, increased water and food intake with no gain in bodyweight or loss of body weight. Only animals with a final (fasted 6 hrs from 8 am-2 pm) blood glucose level ≥300 mg/dl were included in the study, animals that showed no hyperglycemia (blood glucose level ≤300 mg/dl) were excluded from study. The baseline glucose levels, daily food and water intake and behavioral tests (von Frey, paw pressure and plantar tests) were measured for each animal once weekly for 28 weeks, and once every 2-4 weeks for an additional 28-30 weeks. At a selected week (started from week 6) for a compound test, diabetic rats were divided into two test groups: a vehicle control group and a test compound treated group (n=10 each group). A sham group (saline only without STZ i.p. injection, n=10) was added as a normal, non-diabetic control group. To minimize animal stress associated with repeated daily handling, the compound treated diabetic group of animals received the test compound at a daily dose of 60 mg/kg in their drinking water containing 2% PEG600 and 1% glycofurol (the test compound concentration in the drinking water was based on the individual animal's average daily water consumption as determined the pre-dosing period, which averaged 0.1-0.11 mg/ml). The vehicle control group received drinking water containing 2% PEG600 and 1% glycofurol without the test compound. The treatment continued for 9 days. On day 10 drinking water with test compound or vehicle (2% PEG600 and 1% glycofurol) was replaced with plain drinking water in all groups. The monitoring of glucose levels, food and water intake as well as behavior tests continued for additional 28-30 weeks. Chronic treatment with compound 49 at 60 mg/kg/day in drinking water resulted in a rapid and sustained improvement in mechanical (paw pressure test) and thermal pain (plantar test) with no tachyphylaxis. A gradual, significant reversal of up to 90% of mechanical allodynia (von Frey test) was achieved after 9 days of treatment. The paw pressure test and plantar test thresholds returned to the pretreatment baseline (measured on day 11, two days after compound withdrawal), while allodynia threshold (von Frey test) continued to measure significantly above the pretreatment level baseline for up to 5 days after compound withdrawal.

FIGS. 1-3 show food intake, glucose level, and water intake, respectively, for the vehicle control group, the test compound treated group (compound 49, 60 mg/kg/day), and the sham group. After the treatment with compound 49 stopped on day 9 (treatment period marked by dotted lines in each of FIGS. 1-3), the test compound treated group showed improvements in general appearance and/or health. In particular, FIGS. 1, 2, and 3 show that the food intake, glucose level, and water intake, all of which are manifestations of diabetes in the animal model, were significantly reduced compared to the vehicle control group. The significant reduction of food intake, glucose level, and water intake of the compound treated group compared to the vehicle control group continues through week 52. The sham group showed no significant change in food intake, glucose level, or water intake over the course of the experiment. Since the standard deviation in the sham groups are less than 5%, no error bars are shown.

5.2 Examples of NaV Modulators

5.2.1 General Methods

5.2.1.1 LCMS Method

Method-A

LC-MS was carried out on Acquity H-Class UPLC, PDA and SQ Detector. The column used was BEH C18 50×2.1 mm, 1.7 micron and column flow was 0.55 ml/min. Mobile phase were used (A) 0.1% Formic acid+5 mM Ammonium Acetate in water and (B) 0.1% Formic acid in Acetonitrile. The UV spectra were recorded at its lambda Max and Mass spectra were recorded using ESI technique. The following gradient is used to monitor reaction progress and analyze final products.

| Time (min) | % A | % B |
|---|---|---|
| 0.01 | 95 | 05 |
| 0.40 | 95 | 05 |
| 0.80 | 65 | 35 |
| 1.20 | 45 | 55 |
| 2.50 | 00 | 100 |
| 3.30 | 00 | 100 |
| 3.31 | 95 | 05 |
| 4.00 | 95 | 05 |

Method-B

LC-MS was carried out on Waters LC alliance 2995, PDA 2996 and SQ Detector. The column used was X-BRIDGE C18 150×4.6 mm×5 micron and column flow was 1.0 ml/min. Mobile phase were used (A) 0.1% Ammonia in water and (B) 0.1% Ammonia in Acetonitrile. The UV spectra were recorded at its lambda Max and Mass spectra were recorded using ESI technique. The following gradient is used to monitor reaction progress and analyze final products.

| Time (min) | % A | % B |
|---|---|---|
| 0.01 | 90 | 10 |
| 5.00 | 10 | 90 |
| 7.00 | 00 | 100 |
| 11.00 | 00 | 100 |
| 11.01 | 90 | 10 |
| 12.00 | 90 | 10 |

Method-C

LC-MS was carried out on Waters LC alliance 2995, PDA 2996 and SQ Detector. The column used was X-BRIDGE C18 150×4.6 mm×5 micron and column flow was 1.0 ml/min. Mobile phase were used (A) 0.1% Ammonia in water and (B) 0.1% Ammonia in Acetonitrile. The UV spectra were recorded at its lambda Max and Mass spectra were recorded using ESI technique. The following gradient is used to monitor reaction progress and analyze final products.

| Time (min) | % A | % B |
|---|---|---|
| 0.01 | 100 | 00 |
| 7.00 | 50 | 50 |
| 9.00 | 00 | 100 |
| 11.00 | 00 | 100 |
| 11.01 | 100 | 00 |
| 12.00 | 100 | 00 |

Method-D

LC-MS was carried out on Waters LC alliance 2995, PDA 2996 and SQ Detector. The column used was X-BRIDGE C18 150×4.6 mm×5 micron and column flow was 1.0 ml/min. Mobile phase were used (A) 20 mM Ammonium Acetate in water and (B) 100% Methanol. The UV spectra were recorded at its lambda Max and Mass spectra were recorded using ESI technique. The following gradient is used to monitor reaction progress and analyze final products.

| Time (min) | % A | % B |
|---|---|---|
| 0.01 | 90 | 10 |
| 5.00 | 10 | 90 |
| 7.00 | 00 | 100 |
| 11.00 | 00 | 100 |
| 11.01 | 90 | 10 |
| 12.00 | 90 | 10 |

5.2.1.2 HPLC Method

Method-A

HPLC was carried out on Waters e2695, PDA Detector. The column used was Phenomenex Gemini, C18 150×4.6 mm, 5 micron and column flow was 1.00 ml/min. Mobile phase were used (A) 0.1% Formic acid in water and (B) 0.1% Formic acid in Acetonitrile. The UV spectra were recorded at its lambda Max. The following gradient is used.

| Time (min) | % A | % B |
|---|---|---|
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

Method-B

HPLC was carried out on Waters e2695, PDA Detector. The column used was Phenomenex Gemini, C18 150×4.6 mm, 5 micron and column flow was 1.00 ml/min. Mobile phase were used (A) 0.1% Formic acid in water and (B) 0.1% Formic acid in Acetonitrile. The UV spectra were recorded at its lambda Max. The following gradient is used.

| Time (min) | % A | % B |
|---|---|---|
| 0.01 | 100 | 00 |
| 7.00 | 50 | 50 |
| 9.00 | 00 | 100 |
| 13.00 | 00 | 100 |
| 13.01 | 100 | 00 |
| 17.00 | 100 | 00 |

Method-C

HPLC was carried out on Waters e2695, PDA Detector. The column used was X-BRIDGE, C18 150×4.6 mm, 5 micron and column flow was 1.00 ml/min. Mobile phase were used (A) 0.1% Ammonia in water and (B) 0.1% Ammonia in Acetonitrile. The UV spectra were recorded at its lambda Max. The following gradient is used.

| Time (min) | % A | % B |
| --- | --- | --- |
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

Method-D

HPLC was carried out on Waters e2695, PDA Detector. The column used was X-BRIDGE, C18 150×4.6 mm, 5 micron and column flow was 1.00 ml/min. Mobile phase were used (A) 0.1% Ammonia in water and (B) 0.1% Ammonia in Acetonitrile. The UV spectra were recorded at its lambda Max. The following gradient is used.

| Time (min) | % A | % B |
| --- | --- | --- |
| 0.01 | 100 | 00 |
| 7.00 | 50 | 50 |
| 9.00 | 00 | 100 |
| 13.00 | 00 | 100 |
| 13.01 | 100 | 00 |
| 17.00 | 100 | 00 |

5.2.1.3 PREP HPLC Method

Method-A

PREP HPLC was carried out on Shimadzu UFLC, LC-20 AP, and UV Detector. The column used was Sunfire OBD, C18 250×19 mm, 5 micron and column flow was 18.00 ml/min. Mobile phase were used (A) 0.1% HCL in water and (B) 100% Acetonitrile. The UV spectra were recorded at its lambda Max. The following gradient was used.

| Time (min) | % A | % B |
| --- | --- | --- |
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

Method-B

PREP HPLC was carried out on Shimadzu UFLC, LC-20 AP, and UV Detector. The column used was Sunfire OBD, C18 250×19 mm, 5 micron and column flow was 18.00 ml/min. Mobile phase were used (A) 0.1% Formic acid in water and (B) 0.1% Formic acid in Acetonitrile. The UV spectra were recorded at its lambda Max. The following gradient was used.

| Time (min) | % A | % B |
| --- | --- | --- |
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

Method-C

PREP HPLC was carried out on Shimadzu UFLC, LC-20 AP, and UV Detector. The column used was X-BRIDGE, C18 250×19 mm, 5 micron and column flow was 18.00 ml/min. Mobile phase were used (A) 0.1% Ammonia in water and (B) 0.1% Ammonia in Acetonitrile. The UV spectra were recorded at its lambda Max. The following gradient was used.

| Time (min) | % A | % B |
| --- | --- | --- |
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

5.2.1.4 List of Abbreviations

Ac=Acetyl
EtOAc=ethyl acetate
Bn=Benzyl
Boc=tert-Butoxycarbonyl
Bzl=Benzyl
DBU=1,8-Diazabyciclo[5.4.0]undec-7-ene
DCC=1,3-Dicyclohexylcarbodiimide
DCM=Dichloromethane
DEAD=Diethyl azodicarboxylate
DIC=Diisopropylcarbodiimide
DIPEA=Diisopropylethylamine
D. M. water=demineralized water
DME=1,2-Dimethoxyethane
DMF=N,N-Dimethylformamide
DMSO=Dimethylsulphoxide
EDC=1-Ethyl-3-(3-dimethylaminopropy)carbodiimide hydrochloride
Et$_2$O=Diethyl ether
HOBt=1-Hydroxybenzotriazole
IPA=Isopropyl alcohol
KHMDS=Potassium bis(trimethylsilyl)amide
LAH=Lithium aluminium hydride
LDA=Lithium diisopropylamide
LHMDS=Lithium bis(trimethylsilyl)amide
MOM=Methoxymethyl
NaHMDS=Sodium bis(trimethylsilyl)amide
NBS=N-Bromosuccinimide
Ph=Phenyl
PMB=p-Methoxybenzyl
Py=Pyridine
TEA=Triethylamine
TFA=Trifluoroacetic acid
THF=Tetrahydrofurane
Tol=p-Toluoyl

5.2.2 Examples

Example 1

Synthesis of 3-(4-(2-(4-(N-1,2,4-thiadiazol-5-ylsulfamoyl)-2-chloro-5-fluorophenoxy)-5-chlorophenyl)picolinamido)propanoicacid

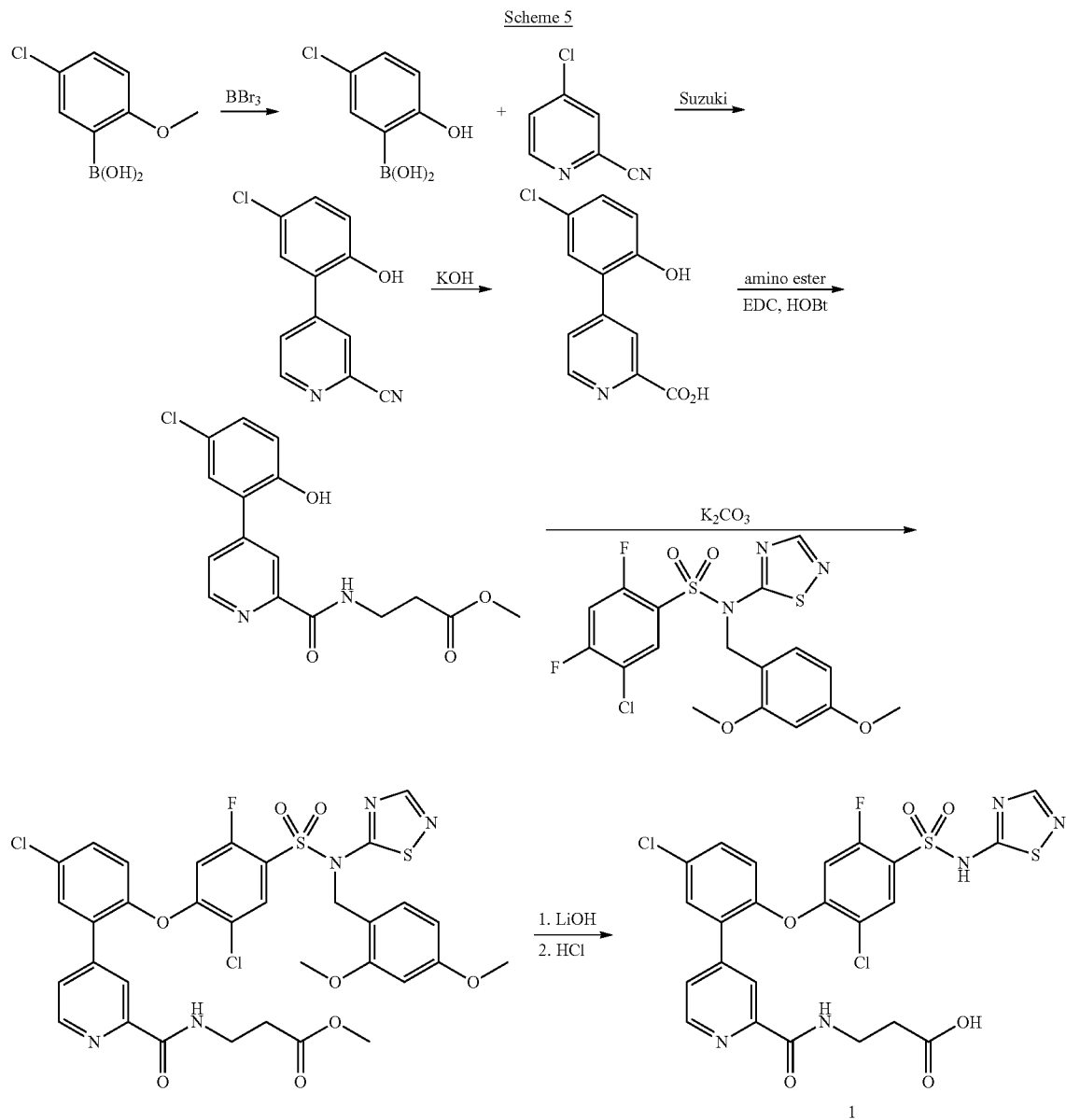

Step 1: Preparation of (5-chloro-2-hydroxyphenyl)boronic acid

A solution of 5-chloro-2-methoxyphenylboronic acid (10.0 g, 53.6 mmol) in dichloromethan (100 ml) was cooled to temperature between 5-10° C. To the above mixture, 100 ml 1M solution of borontribromide in DCM was added drop wise using a pressure equalizing dropping funnel, over a period of 30 minutes. The resulting reaction mixture was then stirred at room temperature for 30 minutes. After completion of reaction, the mixture was poured drop wise on to an ice cold saturated sodium bicarbonate solution (600 ml). The resulting mixture was allowed to stir at room temperature for 1 hr. The DCM layer was separated out and the aqueous layer thus collected was cooled to temperature between 10-15° C. 1N solution of dilute hydrochloric acid was then added to the above cooled aqueous layer and this resulted in precipitate formation. The solid was filtered off under vacuo and dried to afford 9 g (yield: 97%) of product. LC-MS: m/z=170.9 (M+H).

Step 2: Preparation of 4-(5-chloro-2-hydroxyphenyl)picolinonitrile

To a solution of 4-Chloropicolinonitrile (1.0 g, 7.2 mmol) in IPA:toluene (7 ml:7 ml) were sequentially added (5-chloro-2-hydroxyphenyl)boronic acid (1.49 g, 8.65 mmol) and potassium carbonate (3.99 g, 21.64 mmol) at room temperature. The resulting reaction mixture was degassed for 15 minutes by purging with nitrogen. Thereafter calculated quantity of Tetrakis (0.416 g, 0.36 mmol) was added to the reaction mixture and nitrogen purging was further continued for next 20 minutes. The resulting reaction mixture was then refluxed at 100° C. for 20 hours. After completion of the reaction, the mixture was concentrated under vacuo. To the resulting crude mass water (50 ml) was added and the mixture was extracted with ethyl acetate (3×25 ml). The combined organic extract was washed with water (20 ml), brine (20 ml), dried over sodium sulfate and concentrated under vacuo to get the desired crude product. The crude product was purified by column chromatography using normal phase silica gel. The desired product eluted at around 20-30% ethyl acetate in hexane. Evaporation of the product fractions gave 0.8 g (yield, 48%) of desired product as a solid. LC-MS: m/z=231.1 (M+H).

Step 3: Preparation of 4-(5-chloro-2-hydroxyphenyl)picolinic acid)

To a solution of 4-(5-chloro-2-hydroxyphenyl)picolinonitrile (0.5 g, 2.17 mmol) in THF (20 ml) was added a solution of potassium hydroxide (4.276 g, 14 mmol) in water (10 ml) at room temperature. The resulting reaction mixture was then refluxed at 100° C. for 5 hours. After completion of the reaction, the mixture was concentrated under vacuo. Ice cold water was added in to the reaction mixture, the resulting mixture was then acidified between pH 3-6 with 1N HCl. The resulting solid precipitate was filtered and dried to afford 0.5 g (yield: 93%) of product as a solid. LC-MS: m/z=249.8 (M+H).

Step 4: Preparation of methyl 3-(4-(5-chloro-2-hydroxyphenyl)-picolinamido)propanoate)

To a solution of 4-(5-chloro-2-hydroxyphenyl)picolinic acid (0.6 g, 2.40 mmol) in THF (20 ml) was sequentially added EDC (0.69 g, 3.61 mmol) and HOBT (0.49 g, 3.61 mmol) at 0° C. The reaction mixture was stirred at 0° C. for 30 minutes. Beta-alanine methyl ester (0.40 g, 2.88 mol) was added at 0° C. The reaction mixture temperature was then allowed to rise to room temperature and stirred for 20 hours. After completion of reaction, water (50 ml) was added in to the reaction mixture. The resulting mixture was then extracted with ethyl acetate (3×25 ml). The combined organic extract was washed with water (20 ml), brine (20 ml), dried over sodium sulfate and concentrated under vacuo to get the desired crude product. The crude product was purified by column chromatography using normal phase silica gel. The desired product eluted at around 0-5% Methanol in dichloromethane. Evaporation of the product fractions gave 0.72 g (yield: 89%) of desired product. LC-MS: m/z=335.6 (M+H).

Step 5: Synthesis of methyl-3-(4-(5-chloro-2-(2-chloro-4-(N-(2,4-dimethoxybenzyl)-N-(1,2,4-thiadiazol-5-yl)sulfamoyl)-5-fluorophenoxy)phenyl)picolinamido)propanoate)

To a solution of methyl 3-(4-(5-chloro-2-hydroxyphenyl)picolinamido)propanoate) (0.72 g, 2.15 mmol) in DMF (10 ml) was added K$_2$CO$_3$ (0.59 g, 4.3 mol) in one portion under nitrogen atmosphere at room temperature. The resulting reaction mixture was then allowed to stir at room temperature for 15 minutes. To the above reaction mixture was then added calculated quantity of 5-chloro-N-(2,4-dimethoxybenzyl)-2,4-difluoro-N-(1,2,4-thiadiazol-5-yl)benzenesulfonamide (1.0 g, 2.15 mol). The resulting reaction mixture was further allowed to stir at room temperature for 3 hours. After completion of reaction, water (10 ml) was added and the resulting mixture was extracted with ethyl acetate (3×25 ml). The combined organic extract was washed with water (20 ml), brine (20 ml), dried over sodium sulfate and concentrated under vacuo. The crude product was purified by column chromatography using normal phase silica gel. The desired product eluted at around 20 to 25% ethyl acetate in hexane. Evaporation of the product fractions gave 1.0 g (yield: 60%) of desired product. LC-MS: m/z=776.3 (M+H).

Step 6: Preparation of 3-(4-(5-chloro-2-(2-chloro-4-(N-(2,4-dimethoxybenzyl)-N-(1,2,4-thiadiazol-5-yl)sulfamoyl)-5-fluorophenoxy)phenyl)picolinamido)propanoic acid)

To the solution of methyl-3-(4-(5-chloro-2-(2-chloro-4-(N-(2,4-dimethoxybenzyl)-N-(1,2,4-thiadiazol-5-yl)sulfamoyl)-5-fluorophenoxy)phenyl)picolinamido)propanoate) (1.0 g, 1.28 mmol) in THF (10 mL) was added a solution of Lithium hydroxide monohydrate (0.27 g, 6.43 mmol) in water (5 ml). The resulting reaction mixture was then allowed to stir at room temperature for 3 hours. After completion of reaction, ice cold water was added in to the reaction mixture, the resulting mixture was acidified between pH 4-6 with 1N HCl. The resulting acidic aqueous was extracted with Ethyl acetate (3×25 ml). The combined organic extract was washed with water (20 ml), brine (20 ml), dried over sodium sulphate and concentrated under vacuo. The crude product was purified by column chromatography using normal phase silica gel. The desired product eluted at around 0 to 5% methanol in dichloromethane. Evaporation of the product fractions gave 1 g (yield: 99%) of desired product. LC-MS: m/z=762.8 (M+H).

Step 7: Preparation of 3-(4-(2-(4-(N-1,2,4-thiadiazol-5-ylsulfamoyl)-2-chloro-5-fluorophenoxy)-5-chlorophenyl)picolinamido)propanoicacid To the solution of 3-(4-(5-chloro-2-(2-chloro-4-(N-(2,4-dimethoxybenzyl)-N-(1,2,4-thiadiazol-5-yl)sulfamoyl)-5-fluorophenoxy)phenyl)picolinamido)propanoic acid) (1.0 g, 1.3 mmol) in DCM (10 ml) was added drop wise 4N solution of hydrochloric acid in ethyl acetate (0.5 ml) at room temperature. The resulting reaction mixture was further stirred at room temperature for 2 hour. After completion of reaction, pentane (20 ml) was added in to the reaction mixture which resulted in precipitation of solid. The solid thus obtained was washed twice with pentane (15 ml) and dried under vacuo. The resulting crude material was further purified by Prep HPLC using 0.1% HCl in water:acetonitrile mobile phase. Evaporation of the pure Prep fractions gave 0.29 g (yield: 34%) of desired product as HCl salt. LC-MS: m/z=612.9 (M+H). 1H NMR (DMSO-d6), δ 9.03 (br, 1H), 8.71 (d, J=4.8 Hz, 1H), 8.51 (s, 1H), 8.20 (s, 1H), 7.88 (d, J=7.2 Hz, 1H), 7.80 (br, 2H), 7.60 (d, J=8.4 Hz, 1H), 7.28 (d, J=8.4 Hz, 1H), 7.22 (d, J=10.8 Hz, 1H), 4.01 (br, 2H).

The following nine compounds were synthesized according to the synthetic scheme described for Example 1.

Scheme 6
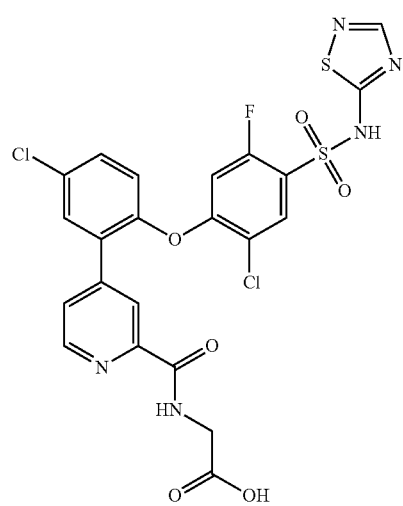
2
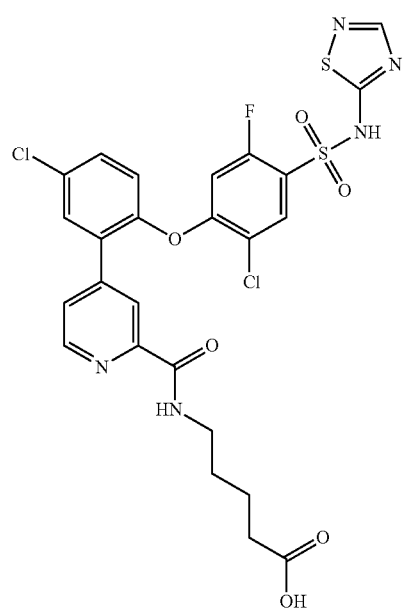
3
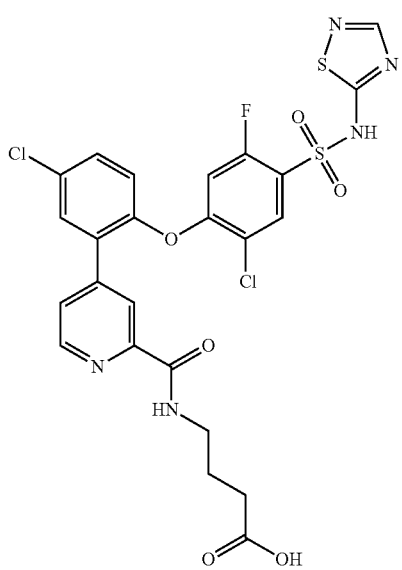
4
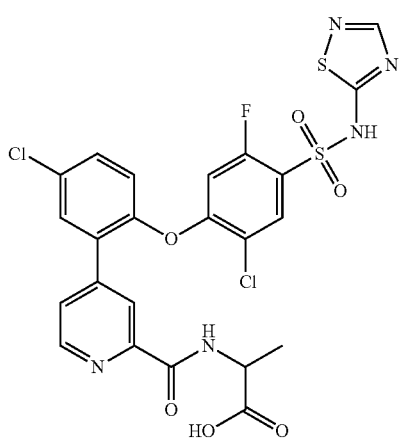
5
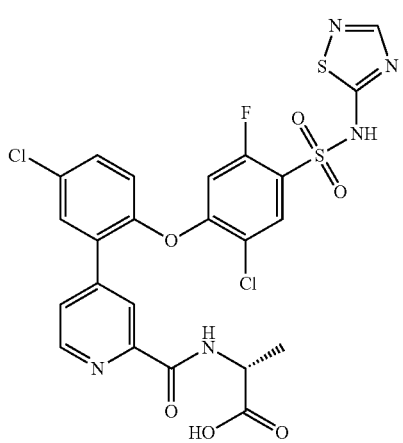
6

7

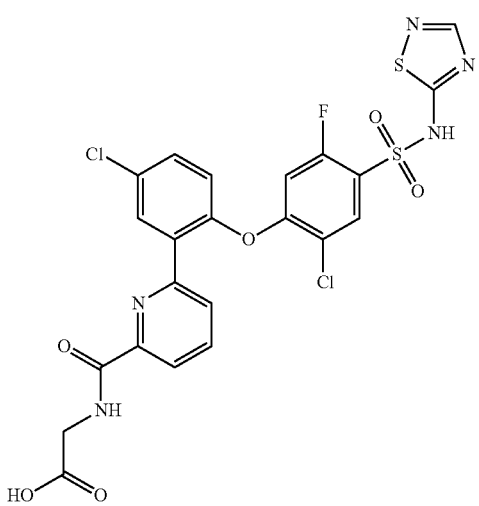

8

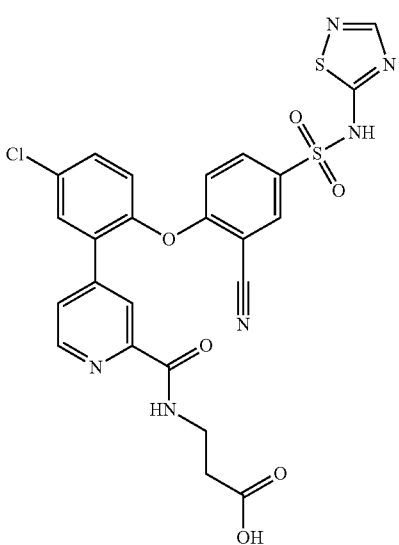

9

10

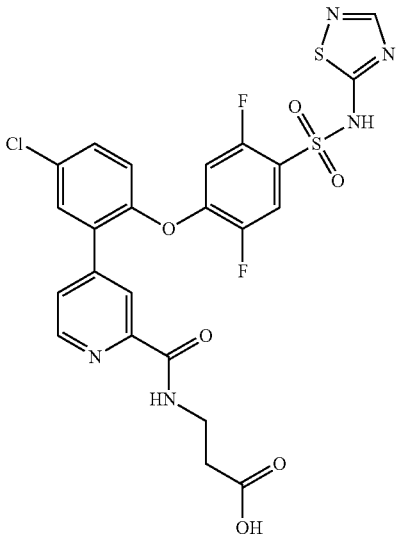

Example 2

2-(4-(2-(4-(N-(1,2,4-thiadiazol-5-yl)sulfamoyl)-2-chloro-5-fluorophenoxy)-5-chlorophenyl)picolinamido)acetic acid Compound 2 was synthesized according to the procedure described for the synthesis of example 1 by replacing beta-alanine methyl ester with glycine methyl ester hydrochloride in step 4. LC-MS: m/z=598.5 (M+H). 1H NMR (DMSO-d6), δ 9.03 (t, J=6.0 Hz, 1H), 8.71 (d, J=4.8 Hz, 1H), 8.53 (s, 1H), 8.19 (s, 1H), 7.88 (d, J=7.2 Hz, 1H), 7.78-7.81 (m, 2H), 7.60 (dd, J=2.4, 8.8 Hz, 1H), 7.29 (d, J=8.8 Hz, 1H), 7.22 (d, J=10.8 Hz, 1H), 4.00 (br, 2H).

Example 3

5-(4-(2-(4-(N-(1,2,4-thiadiazol-5-yl)sulfamoyl)-2-chloro-5-fluorophenoxy)-5-chlorophenyl)picolinamido)pentanoic acid Compound 3 was synthesized according to the procedure described for the synthesis of compound 1 by replacing beta-alanine methyl ester methyl 5-aminopentanoate in step 4. LC-MS: m/z=640.2 (M+H).

Example 4

4-(4-(2-(4-(N-(1,2,4-thiadiazol-5-yl)sulfamoyl)-2-chloro-5-fluorophenoxy)-5-chlorophenyl)picolinamido)butanoic acid Compound 4 was synthesized according to the procedure described for the synthesis of compound 1 by replacing beta-alanine methyl ester with methyl 4-aminobutanoate in step 4. LC-MS: m/z=626.6 (M+H). 1H NMR (MeOH-d4), δ 8.65 (d, J=4.8 Hz, 1H), 8.27 (s, 1H), 8.26 (s, 1H), 7.91 (d, J=6.8 Hz, 1H), 7.74 (d, J=4.4 Hz, 1H), 7.71 (d, J=2.4 Hz, 1H), 7.60 (dd, J=2.8, 8.8 Hz, 1H), 7.24 (d, J=8.8 Hz, 1H), 6.94 (s, 1H), 6.78 (d, J=10.8 Hz, 1H), 3.75 (br, 2H), 2.41 (t, J=7.2 Hz, 2H), 1.97 (t, J=7.2 Hz, 2H).

Example 5

(Rac)-2-(4-(2-(4-(N-1,2,4-thiadiazol-5-ylsulfamoyl)-2-chloro-5-fluorophenoxy)-5-chlorophenyl)picolinamido)propanoic acid Compound 5 was synthesized according to the procedure described for the synthesis of compound 1 by replacing beta-alanine methyl ester with DL-alanine methyl ester hydrochloride in step 4. LC-MS: m/z=613.8 (M+H). 1H NMR (MeOH-d4), δ 8.65 (d, J=5.6 Hz, 1H), 8.27 (s, 1H), 8.25 (s, 1H), 7.90 (d, J=6.8 Hz, 1H), 7.74 (dd, J=1.6, 4.8 Hz, 1H), 7.70 (d, J=2.4 Hz, 1H), 7.59 (dd, J=2.8, 8.8 Hz, 1H), 7.23 (d, J=8.8 Hz, 1H), 6.78 (d, J=10.8 Hz, 1H), 4.63 (q, J=7.2 Hz, 1H), 1.56 (d, J=7.6 Hz, 3H).

Example 6

(R)-2-(4-(2-(4-(N-1,2,4-thiadiazol-5-ylsulfamoyl)-2-chloro-5-fluorophenoxy)-5-chlorophenyl)picolinamido)propanoic acid Compound 6 was synthesized according to the procedure described for the synthesis of compound 1 by replacing beta-alanine methyl ester with D-alanine methyl ester hydrochloride in step 4. LC-MS: m/z=613.8 (M+H). 1H NMR (MeOH-d4), δ 8.67 (d, J=5.2 Hz, 1H), 8.27 (s, 1H), 8.25 (s, 1H), 7.91 (d, J=7.2 Hz, 1H), 7.75 (dd, J=2.0, 5.2 Hz, 1H), 7.71 (d, J=2.8 Hz, 1H), 7.60 (dd, J=2.4, 8.4 Hz, 1H), 7.24 (d, J=8.8 Hz, 1H), 6.78 (d, J=10.8 Hz, 1H), 4.63 (q, J=7.2 Hz, 1H), 1.56 (d, J=7.6 Hz, 3H).

Example 7

2-(6-(2-(4-(N-(1,2,4-thiadiazol-5-yl)sulfamoyl)-2-chloro-5-fluorophenoxy)-5-chlorophenyl)picolinamido)acetic acid Compound 7 was synthesized according to the procedure described for the synthesis of compound 1 by replacing 4-Chloropicolinonitrile with 6-chloropicolinonitrile in step 2. LC-MS: m/z=597.7 (M+H). 1H-NMR (MeOD), δ 8.19 (s, 1H), 8.00-8.07 (m, 4H), 7.9 s (d, J=6.8 Hz, 1H), 7.59 (dd, J=2.4, 8.8 Hz, 1H), 7.25 (d, J=8.8 Hz, 1H), 6.72 (d, J=10.4 Hz, 1H), 4.09 (s, 2H).

Example 8

(S)-2-(4-(2-(4-(N-1,2,4-thiadiazol-5-ylsulfamoyl)-2-chloro-5-fluorophenoxy)-5-chlorophenyl)picolinamido)propanoic acid Compound 8 was synthesized according to the procedure described for the synthesis of compound 1 by replacing beta-alanine methyl ester with L-alanine methyl ester hydrochloride in step 4. LC-MS: m/z=612.6 (M+H). 1H NMR (DMSO-d6), δ 8.85 (d, J=7.6 Hz, 1H), 8.71 (d, J=5.6 Hz, 1H), 8.52 (s, 1H), 8.19 (s, 1H), 7.88 (d, J=7.2 Hz, 1H), 7.78-7.80 (m, 2H), 7.60 (dd, J=2.4, 8.8 Hz, 1H), 7.28 (d, J=8.8 Hz, 1H), 7.22 (d, J=10.8 Hz, 1H), 4.47 (q, J=7.2 Hz, 1H), 1.42 (d, J=7.2 Hz, 3H).

Example 9

3-(4-(2-(4-(N-(1,2,4-thiadiazol-5-yl)sulfamoyl)-2-cyanophenoxy)-5-chlorophenyl)picolinamido)propanoic acid Compound 9 was synthesized according to the procedure described for the synthesis of compound 1 by replacing 5-chloro-N-(2,4-dimethoxybenzyl)-2,4-difluoro-N-(1,2,4-thiadiazol-5-yl)benzenesulfonamide with 3-cyano-N-(2,4-dimethoxybenzyl)-4-fluoro-N-(1,2,4-thiadiazol-5-yl)benzenesulfonamide in step 5. LC-MS: m/z=584.8 (M+H). 1H-NMR (MeOD), δ 8.63 (d, J=4.8 1H), 8.23 (s, 1H), 8.19 (s, 1H), 8.14 (d, J=2.0 Hz, 1H), 7.95 (dd, J=2.4, 8.8 Hz, 1H), 7.74-7.76 (m, 2H), 7.63 (dd, J=2.4, 8.8 Hz, 1H), 6.97 (d, J=10.0 Hz, 1H), 3.68 (t, J=6.8 Hz, 2H), 2.65 (t, J=6.8 Hz, 2H).

Example 10

3-(4-(2-(4-(N-(1,2,4-thiadiazol-5-yl)sulfamoyl)-2,5-difluorophenoxy)-5-chlorophenyl)picolinamido)propanoic acid Compound 10 was synthesized according to the procedure described for the synthesis of compound 1 by replacing 5-chloro-N-(2,4-dimethoxybenzyl)-2,4-difluoro-N-(1,2,4-thiadiazol-5-yl)benzenesulfonamide with N-(2,4-dimethoxybenzyl)-2,4,5-trifluoro-N-(1,2,4-thiadiazol-5-yl)benzenesulfonamide in step 5. LC-MS: m/z=595.8 (M+H). 1H-NMR (MeOD), δ 8.66 (d, J=4.8 1H), 8.28 (s, 1H), 8.26 (s, 1H), 7.69-7.77 (m, 3H), 7.56 (dd, J=2.8, 8.8 Hz, 1H), 6.94 (dd, J=6.4, 10.0 Hz, 1H), 3.70 (t, J=6.4 Hz, 2H), 2.67 (t, J=6.8 Hz, 2H).

Example 11

Preparation of 2-(3-(5-chloro-2-(2-chloro-5-fluoro-4-(N-thiazol-4-ylsulfamoyl)phenoxy)phenyl)propylamino)acetic acid

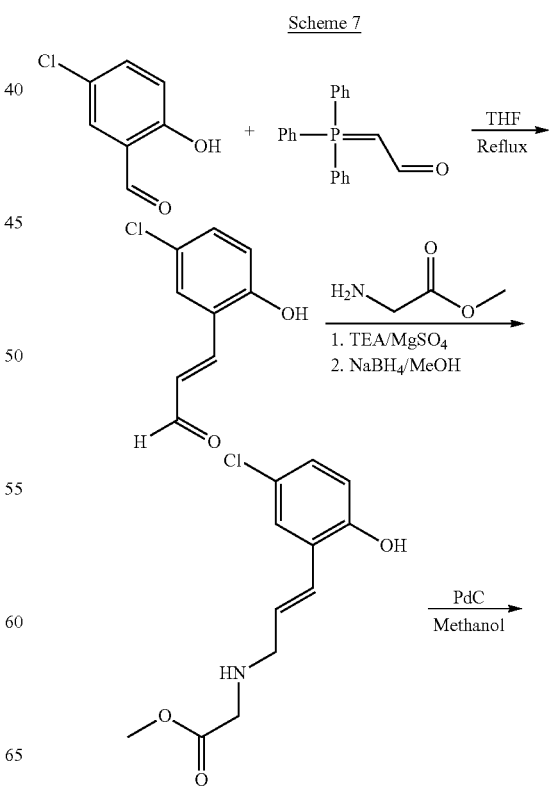

Scheme 7

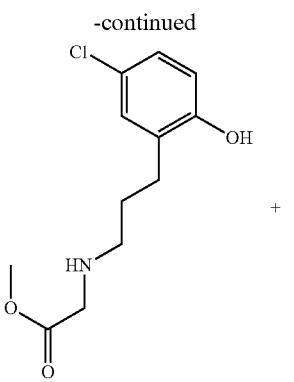

+

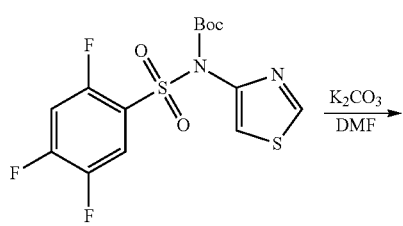

K₂CO₃ / DMF →

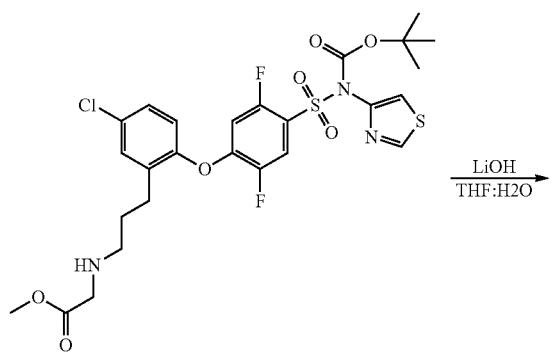

LiOH THF:H2O →

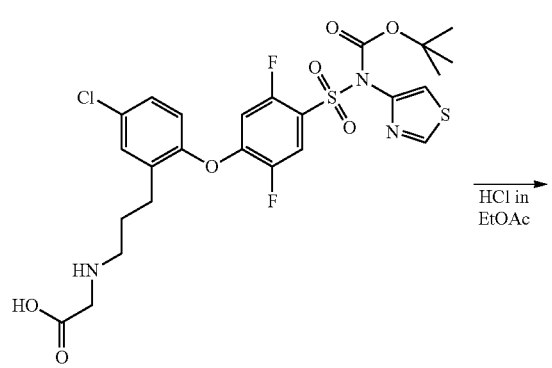

HCl in EtOAc →

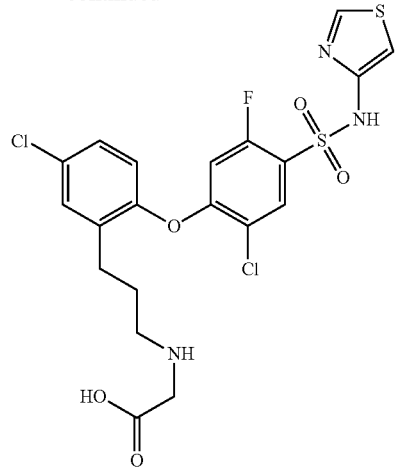

Step 1: Preparation of 3-(5-chloro-2-hydroxyphenyl)acrylaldehyde

To a solution of 5-chloro-2-hydroxybenzaldehyde (20 g, 127 mmol) in THF (300 ml) was added (formylmethylene) triphenylphosphorane (43 g, 140 mmol) at room temperature. The resulting reaction mixture was refluxed at 100° C. for 20 hours. The reaction mixture was cooled to room temperature, and extracted with water (200 ml) and ethyl acetate (3×250 ml). The combined organic phase was washed with water (200 ml), brine (200 ml), dried over sodium sulphate and concentrated under vacuo to give the desired crude product. The crude product was purified by column chromatography using normal phase silica gel. The desired product eluted at around 20-30% ethyl acetate in hexane. Evaporation of the product fractions gave 20 g (yield, 87%) of desired compound as yellow solid. LC-MS: m/z=183.4 (M+H).

Step 2: Preparation of methyl 2-(3-(5-chloro-2-hydroxyphenyl)allylamino)acetate To a solution of 3-(5-chloro-2-hydroxyphenyl)acrylaldehyde (5 g, 27 mmol) and glycine methyl ester hydrochloride (4.1 g, 32 mmol) in dichloromethane (80 ml) was added magnesium sulphate (6 g, 50 mmol) and triethylamine (12 ml, 82 mmol) at room temperature. The above reaction mixture was stirred at room temperature for 18 hours. The resulting reaction mixture was then concentrated under vacuo. The concentrated mass thus obtained was dissolved in methanol (50 ml) and cooled to a temperature between 5-10° C. To the above mixture, sodium borohydride (3.0 g, 82 mmol) was added in small portions over a period of 20 minutes; during addition temperature of the reaction mixture was maintained between 10-20° C. The reaction mixture was allowed to stir at room temperature for 2 hours and concentrated under vacuo. Water (100 ml) was added to the above crude mass and the resulting mixture was extracted with ethyl acetate (3×100 ml). The combined organic extract was washed with water (50 ml), brine (50 ml), dried over sodium sulphate and concentrated under vacuo to get the desired crude product. The crude product was purified by column chromatography using normal phase silica gel. The desired product eluted at around 1-5% methanol in dichloromethane. Evaporation of the product fractions gave 4 g (yield, 58%) of desired compound as yellow solid. LC-MS: m/z=256.43 (M+H).

Step 3: Preparation of methyl 2-(3-(5-chloro-2-hydroxyphenyl)propylamino)acetate To a solution of methyl 2-(3-(5-chloro-2-hydroxyphenyl)allylamino)acetate (3.5 g, 13.6 mmol) in methanol (80 ml) was carefully added 10% Palladium on carbon with 50% moisture (0.145 g, 1.3 mmol). Hydrogen gas was then bubbled into the reaction mixture at room temperature for a period of 30 minutes. After completion of the reaction, the reaction mixture was filtered through celite. The celite bed was carefully washed with some amount of methanol. The filtrate thus obtained was concentrated under vacuo to afford 3 g (yield, 85%) of compound as colorless liquid and used as is in the next step. LC-MS: m/z=258.5 (M+H).

Step 4: Preparation of methyl 2-(3-(2-(4-(N-(tert-butoxycarbonyl)-N-(thiazol-4-yl)sulfamoyl)-2-chloro-5-fluorophenoxy)-5-chlorophenyl)propylamino)acetate To a solution methyl 2-(3-(5-chloro-2-hydroxyphenyl)propylamino)acetate (0.7 g, 2.7 mmol) in DMF (8 ml) was added $K_2CO_3$ (1.2 g, 8.1 mmol) in one portion under nitrogen atmosphere at room temperature. The resulting reaction mixture was then stirred at room temperature for 15 minutes. To the above mixture was added tert-butyl 5-chloro-2,4-difluorophenylsulfonyl(thiazol-4-yl)carbamate (1.22 g, 2.9 mmol) at room temperature and the resulting reaction mixture was stirred at room temperature for 3 hrs. After completion of reaction, water (10 ml) was added and the resulting mixture was extracted with ethyl acetate (3×25 ml). The combined organic extract was washed with water (20 ml), brine (20 ml), dried over sodium sulphate and concentrated under vacuo. The crude product was purified by column chromatography using normal phase silica gel. The desired product eluted at around 20 to 25% Ethyl acetate in Hexane. Evaporation of the product fractions gave 0.6 g (yield, 36%) of desired compound as a solid. LC-MS: m/z=648.4 (M+H).

Step 5: Preparation of 2-(3-(2-(4-(N-(tert-butoxycarbonyl)-N-(thiazol-4-yl)sulfamoyl)-2-chloro-5-fluorophenoxy)-5-chlorophenyl)propylamino)acetic acid To the solution of methyl 2-(3-(2-(4-(N-(tert-butoxycarbonyl)-N-(thiazol-4-yl)sulfamoyl)-2-chloro-5-fluorophenoxy)-5-chlorophenyl)propylamino)acetate (0.6 g, 0.9 mmol) in THF (10 mL) was added a solution of lithium hydroxide monohydrate (0.0529, 4.6 mmol) in water (6 ml) at room temperature. The resulting reaction mixture was stirred at room temperature for 3 hours. After completion of reaction ice cold water (15 ml) was added in to the reaction mixture, the resulting mixture was then acidified between 4-6 pH with aqueous 1N hydrochloric acid. The resulting acidic aqueous was extracted with ethyl acetate (3×25 ml). The combined organic extract was washed with water (20 ml), brine (20 ml), dried over sodium sulphate and concentrated under vacuo to afford 0.5 g (yield, 85%) of compound as white solid. This material was used in the next step as is.

Step 6: Preparation of 2-(3-(5-chloro-2-(2-chloro-5-fluoro-4-(N-thiazol-4-ylsulfamoyl)phenoxy)phenyl)propylamino)acetic acid To the solution of 2-(3-(2-(4-(N-(tert-butoxycarbonyl)-N-(thiazol-4-yl)sulfamoyl)-2-chloro-5-fluorophenoxy)-5-chlorophenyl)propylamino)acetic acid (0.5 g, 0.78 mmol) in dichloromethane (15 ml) was added drop-wise a 4N solution of hydrochloric acid in ethyl acetate (0.5 ml) at room temperature. The resulting reaction mixture was stirred room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% hydrochloric acid in Water: Acetonitrile mobile phase. Evaporation of the pure product fractions obtained from Prep HPLC provided HCl salt of the desired product (0.16 g, 38% yield). LC-MS: m/z=533.9 (M+H). 1H-NMR (MeOD), δ 8.77 (d, J=2.4 Hz, 1H), 8.03 (d, J=6.8 Hz, 1H), 7.49 (d, J=2.4 Hz, 1H), 7.37 (dd, J=2.8, 8.8 Hz, 1H), 7.12 (d, J=2.4 Hz, 1H), 7.03 (d, J=8.8 Hz, 1H), 6.76 (d, J=10.8 Hz, 1H), 3.8 (s, 2H), 3.09-3.05 (m, 2H), 2.68 (t, J=7.6 Hz, 2H), 2.04-2.01 (m, 2H).

The compounds 12 to 32 were synthesized according to the synthetic scheme described for example 11.

Scheme 8

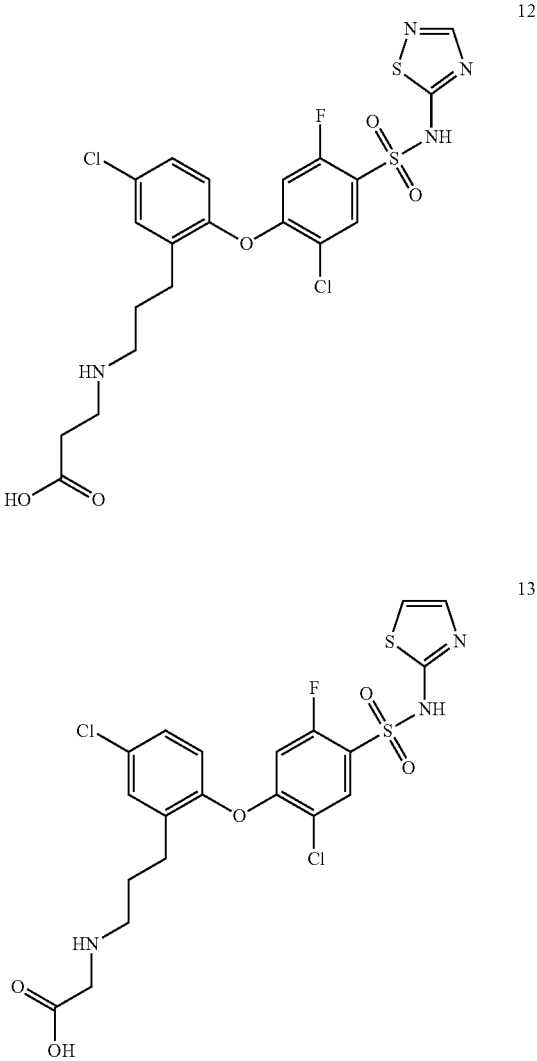

14
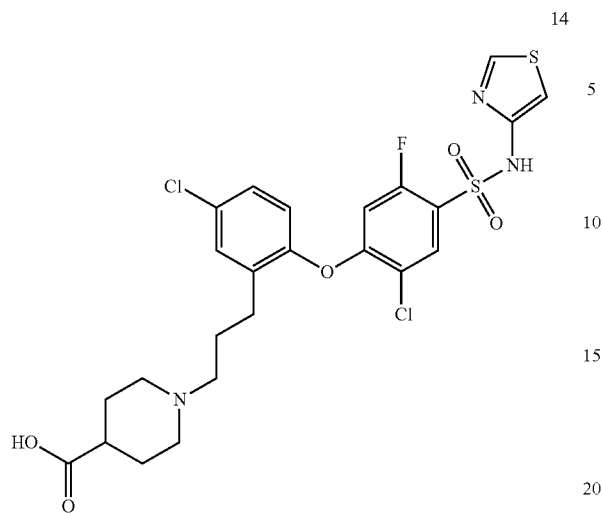
15
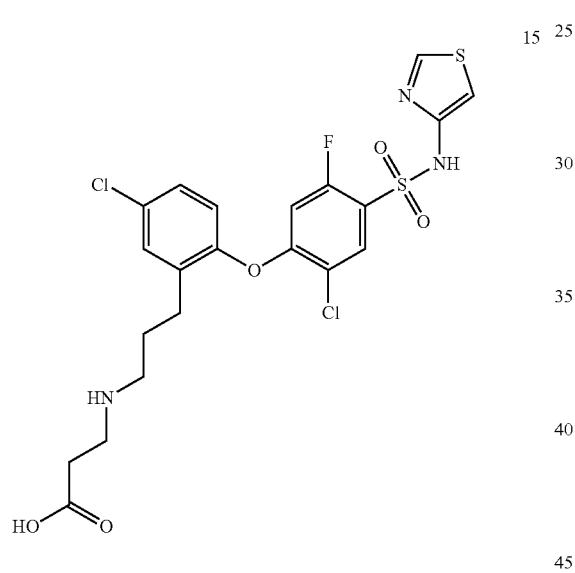
16
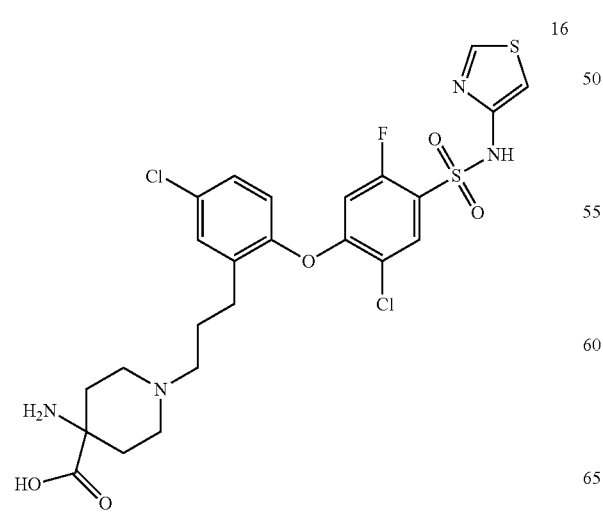
17
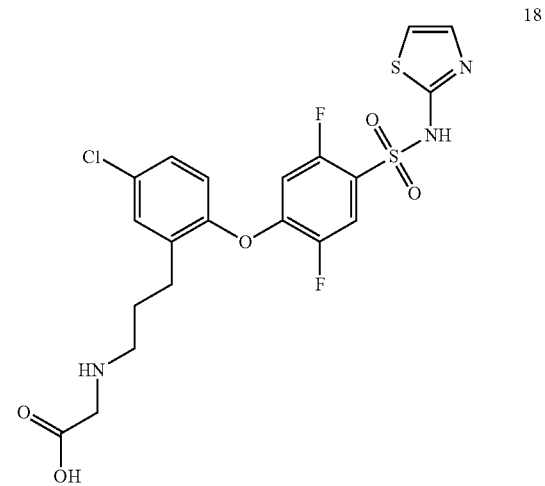
18
19
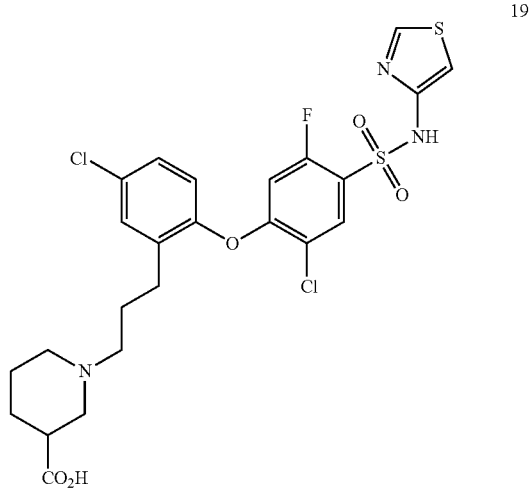

127
-continued
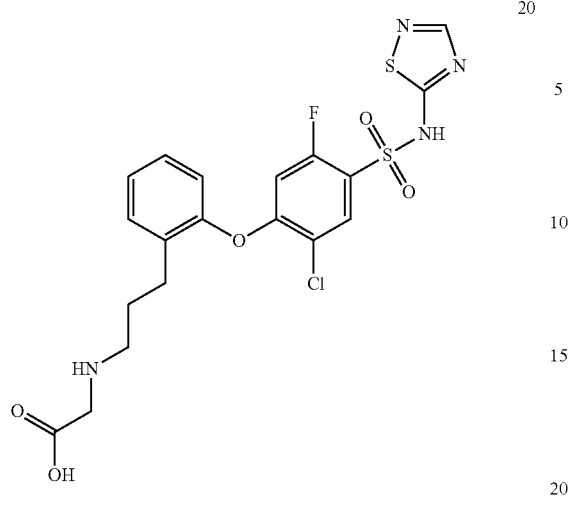
20
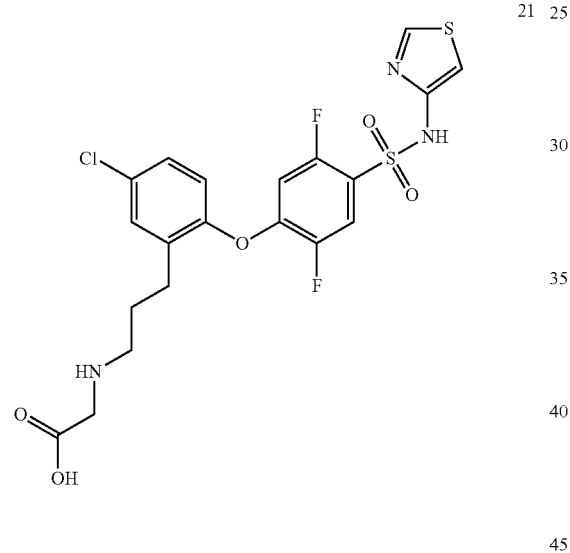
21
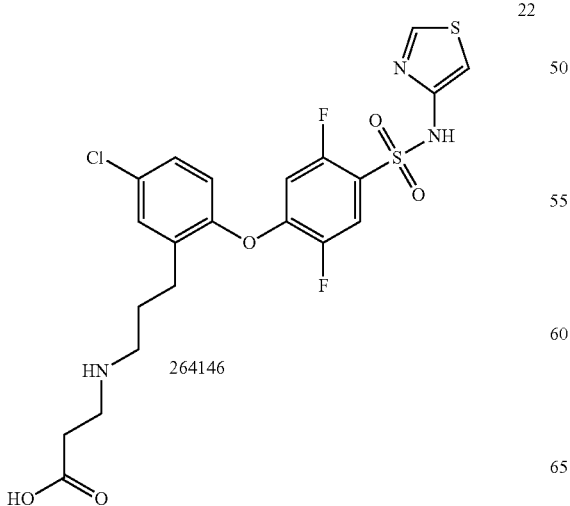
22
128
-continued
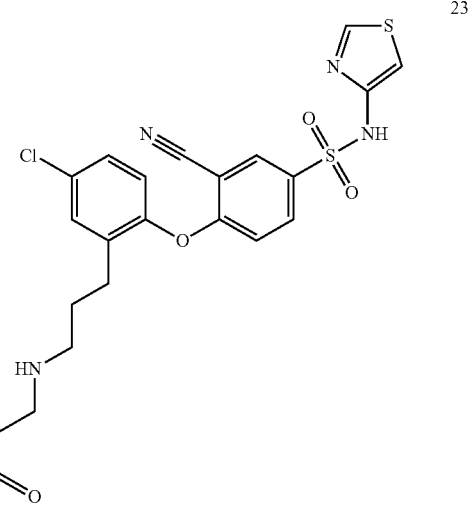
23
Scheme 9
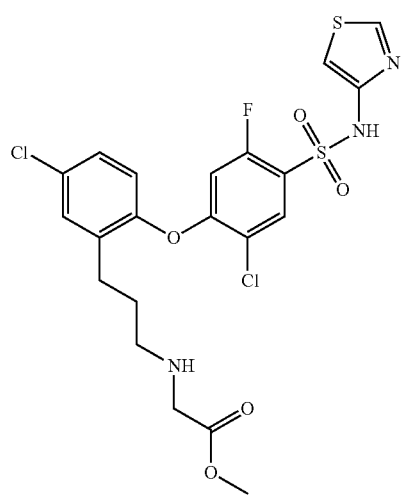
24
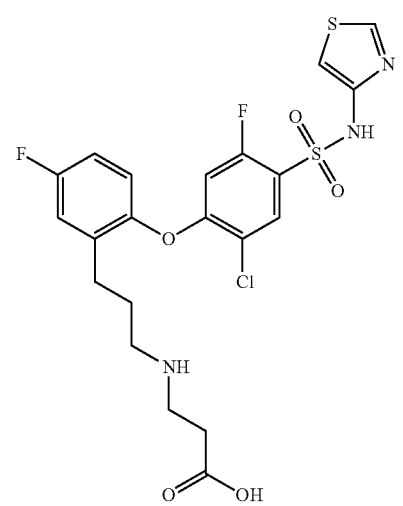
25

26
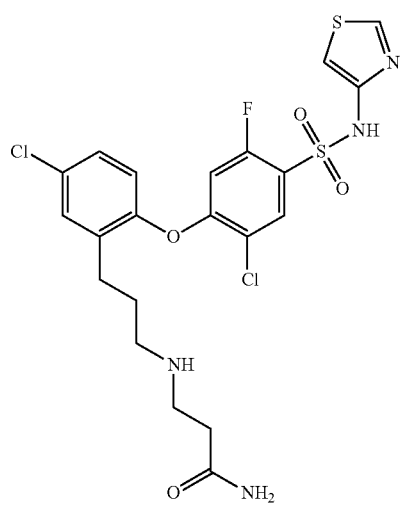
27
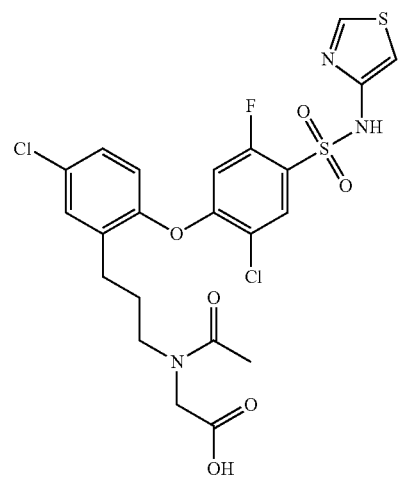
28
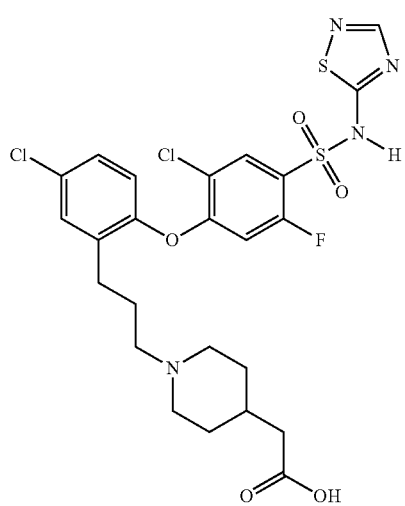
29
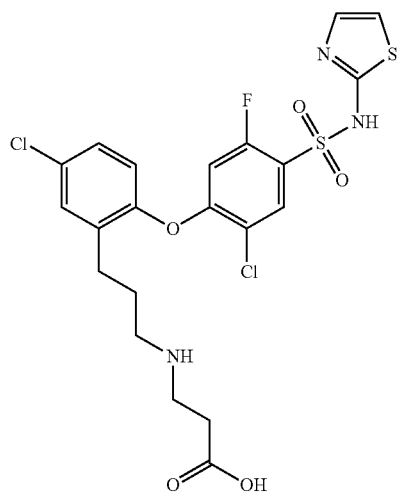
30
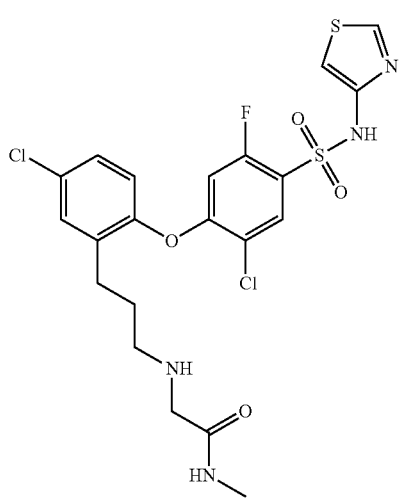
31
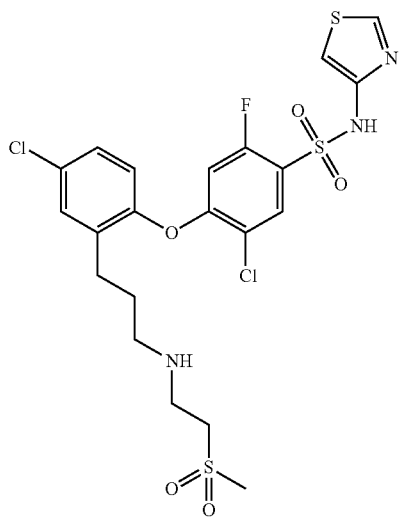

32

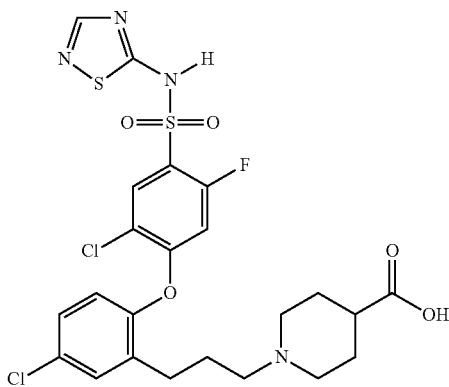

Example 12

3-((3-(2-(4-(N-(1,2,4-thiadiazol-5-yl)sulfamoyl)-2-chloro-5-fluorophenoxy)-5-chlorophenyl)propyl)amino)propanoic acid Compound 12 was synthesized according to the procedure described for the synthesis of compound 11 by replacing glycine methyl ester with beta alanine methyl ester in step 2, and replacing tert-butyl 5-chloro-2,4-difluorophenylsulfonyl(thiazol-4-yl)carbamate with 5-chloro-N-(2,4-dimethoxybenzyl)-2,4-difluoro-N-(1,2,4-thiadiazol-5-yl)benzenesulfonamide in step 4. LC-MS: m/z=549.6 (M+H). 1H-NMR (MeOD), δ 8.27 (s, 1H), 8.05 (d, J=7.2 Hz, 1H), 7.49 (d, J=2.4 Hz, 1H), 7.36 (dd, J=2.8, 8.8 Hz, 1H), 7.03 (d, J=8.8 Hz, 1H), 6.78 (d, J=6.4 Hz, 1H), 3.26 (t, J=6.4 Hz, 2H), 3.08 (t, J=7.6 Hz, 2H), 2.68-2.75 (m, 4H), 2.01-2.06 (m, 2H).

Example 13

2-((3-(5-chloro-2-(2-chloro-5-fluoro-4-(N-(thiazol-2-yl)sulfamoyl)phenoxy)phenyl)propyl)amino)acetic acid Compound 13 was synthesized according to the procedure described for the synthesis of compound 11 by replacing tert-butyl 5-chloro-2,4-difluorophenylsulfonyl(thiazol-4-yl)carbamate with 5-chloro-N-(2,4-dimethoxybenzyl)-2,4-difluoro-N-(thiazol-2-yl)benzenesulfonamide in step 4. LC-MS: m/z=533.8 (M+H). 1H-NMR (MeOD), δ 7.94 (d, J=6.8 Hz, 1H), 7.52 (d, J=5.8, 1H), 7.35-7.38 (dd, J=2.4, 8.8 Hz, 1H), 7.33 (d, J=4.4 Hz, 1H), 7.11 (d, J=8.8 Hz, 1H), 6.91-6.94 (m, 2H), 3.60 (s, 2H), 2.80 (m, 2H), 2.56 (m, 2H), 1.99 (m, 2H).

Example 14

1-(3-(5-chloro-2-(2-chloro-5-fluoro-4-(N-(thiazol-4-yl)sulfamoyl)phenoxy)phenyl)propyl)piperidine-4-carboxylic acid Compound 14 was synthesized according to the procedure described for the synthesis of compound 11 by replacing glycine methyl ester with methyl piperidine-4-carboxylate in step 2. LC-MS: m/z=589.8 (M+H).

Example 15

3-((3-(5-chloro-2-(2-chloro-5-fluoro-4-(N-(thiazol-4-yl)sulfamoyl)phenoxy)phenyl)propyl)amino)propanoic acid Compound 15 was synthesized according to the procedure described for the synthesis of compound 11 by replacing glycine methyl ester with beta alanine methyl ester in step 2. LC-MS: m/z=547.8 (M+H). 1H-NMR (MeOD), δ 8.77 (d, J=2.0 Hz, 1H), 8.03 (d, J=10.8 Hz, 1H), 7.49 (d, J=2.4 Hz, 1H), 7.35-7.38 (m, 1H), 7.12 (d, J=2.8 Hz, 1H), 7.03 (d, J=8.4 Hz, 1H), 6.76 (d, J=10.4 Hz, 1H), 3.26 (br, 2H), 3.07 (br, 2H), 2.67-2.76 (m, 4H), 2.02 (br, 2H).

Example 16

4-amino-1-(3-(5-chloro-2-(2-chloro-5-fluoro-4-(N-(thiazol-4-yl)sulfamoyl)phenoxy)phenyl)propyl)piperidine-4-carboxylic acid Compound 16 was synthesized according to the procedure described for the synthesis of compound 11 by replacing glycine methyl ester with methyl 4-((tert-butoxycarbonyl)amino)piperidine-4-carboxylate in step 2. LC-MS: m/z=602.8 (M+H). 1H-NMR (MeOD), δ 8.77 (d, J=2.0 Hz, 1H), 8.02 (d, J=7.2 Hz, 1H), 7.52 (d, J=2.8 Hz, 1H), 7.36-7.38 (dd, J=2.8, 8.8 Hz, 1H), 7.12 (d, J=2.0 Hz, 1H), 7.03 (d, J=8.4 Hz, 1H), 6.77 (d, J=10.4 Hz, 1H), 3.25-3.70 (m, 6H) 2.67-2.71 (m, 2H), 2.50 (br, 2H), 2.27 (br, 2H), 2.12 (br, 2H).

Example 17

2-amino-4-((3-(5-chloro-2-(2-chloro-5-fluoro-4-(N-(thiazol-4-yl)sulfamoyl)phenoxy)phenyl)propyl)amino)butanoic acid

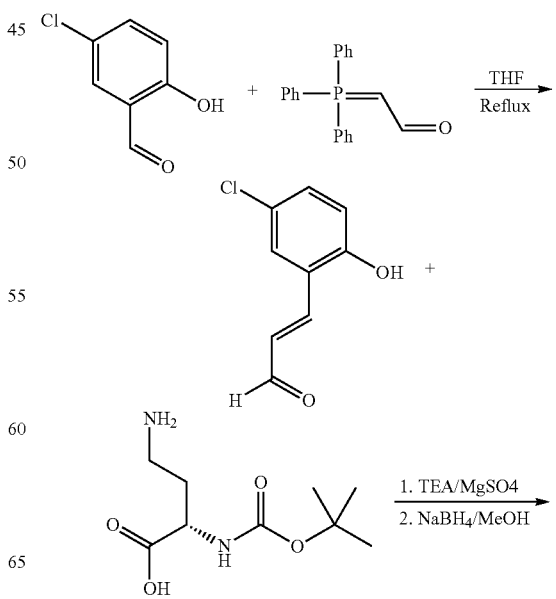

133
-continued

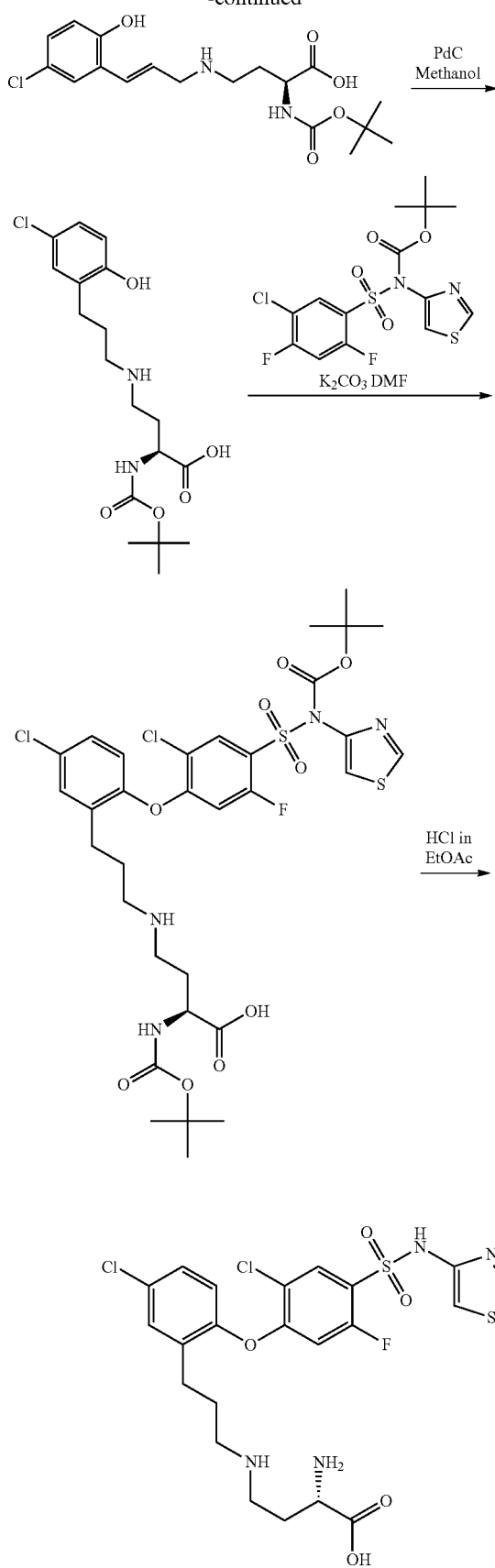

134

Step 1: Preparation of (S)-4-amino-2-(tert-butoxycarbonylamino)butanoic acid To a solution of (S)-5-amino-2-(tert-butoxycarbonylamino)-5-oxopentanoic acid (2 g, 8.1 mmol) in DMF: water (1:1, v/v, 18 ml) was added pyridine (1.3 ml, 16.2 mmol). The resulting reaction mixture was stirred at room temperature for 5-10 minutes. Iodobenzene diacetate (3.92 g, 12.1 mmol) was added and further stirred for 4 hours. After completion of reaction D.M. water (100 ml) was added and the resulting mixture was extracted with ethyl acetate (3×100 ml). The combined organic extracts was washed with D.M. water (100 ml), brine (100 ml), dried over sodium sulphate and concentrated under vacuo to get the desired crude product. The crude product was purified by triturating with diethyl ether. Evaporation of the product fractions gave 1.1 g (yield, 62%) of desired compound as brown solid. LC-MS: m/z=219.1 (M+H).

Step 2: Preparation of (E)-3-(5-chloro-2-hydroxyphenyl)acrylaldehyde

To a solution of 5-chloro-2-hydroxybenzaldehyde (20 g, 127 mmol) in THF (300 ml) was added (Formylmethylene)triphenylphosphorane (43 g, 140 mmol) at room temperature. The resulting reaction mixture was then refluxed at 100° C. for 20 hrs. After completion of reaction, the reaction mixture was allowed to cool to room temperature. D.M. water (200 ml) was added and the resulting mixture was extracted with ethyl acetate (3×250 ml). The combined organic extract was washed with D.M. water (200 ml), brine (200 ml), dried over sodium sulphate and concentrated under vacuo to get the desired crude product. The crude product was purified by column chromatography using normal phase silica gel. The desired product eluted at around 20-30% ethyl acetate in hexane. Evaporation of the product fractions gave 20 g (yield, 87%) of the desired compound as yellow solid. LC-MS: m/z=183.4 (M+H).

Step 3: (S,E)-2-(tert-butoxycarbonylamino)-4-(3-(5-chloro-2-hydroxyphenyl)allylamino)butanoic acid To a solution of 3-(5-chloro-2-hydroxyphenyl)acrylaldehyde (0.5 g, 3.2 mmol) and (S)-4-amino-2-(tert-butoxycarbonylamino)butanoic acid (0.769 g, 3.52 mmol) in dichloromethane (80 ml) was added magnesium sulphate (0.77 g, 6.4 mmol) and triethylamine (1.34 ml, 9.615 mmol) at room temperature. The above reaction mixture was stirred at room temperature for 12 hours. The resulting reaction mixture was then concentrated under vacuo. The concentrated mass thus obtained was dissolved in methanol (20 ml) and cooled to a temperature between 5-10° C. To the above mixture, sodium borohydride (0.36 g, 9.61 mmol) was added in small portions over a period of 10 minutes, during addition temperature of the reaction mixture was maintained between 10-20° C. After completion of addition, the resulting reaction mixture was allowed to stir at room temperature for 2 hours. After completion of reaction, the reaction mixture was concentrated under vacuo. D.M. water (40 ml) was added to the above crude mass and the resulting mixture was extracted with ethyl acetate (3×60 ml). The combined organic extract was washed with D.M. water (50 ml), brine (50 ml), dried over sodium sulphate and concentrated under vacuo to get the desired crude product. The crude product was purified by column chromatography using normal phase silica gel. The desired product eluted at around 1-5% methanol in dichloromethane. Evaporation of the product fractions gave 0.4 g (yield, 32.5%) of the desired compound as a brown liquid. LC-MS: m/z=385.2 (M+H).

Step 4: (S)-2-(tert-butoxycarbonylamino)-4-(3-(5-chloro-2-hydroxyphenyl)propylamino)butanoic acid To a solution of (S,E)-2-(tert-butoxycarbonylamino)-4-(3-(5-chloro-2-hydroxyphenyl)allylamino)butanoic acid (0.4 g, 13.6 mmol) in methanol (10 ml) was carefully added 10% Palladium on carbon with 50% moisture (0.120 g, 1.3 mmol). Hydrogen gas was then bubbled into the reaction mixture at room temperature for a period of 15-20 minutes. After completion of the reaction, the reaction mixture was filtered through celite hyflow. The celite bed was carefully washed with some amount of methanol. The filtrate thus obtained was concentrated under vacuo to afford 0.35 g (yield, 87.06%) of the desired compound as a colorless liquid. LC-MS: m/z=387.4 (M+H).

Note: For this particular step, we also observed occurrence of dechlorination, its proportion remained variable. This step was thus monitored cautiously and worked up soon upon completion.

Step 5: (S)-4-(3-(2-(4-(N-(tert-butoxycarbonyl)-N-(thiazol-4-yl)sulfamoyl)-2-chloro-5-fluorophenoxy)-5-chlorophenyl)propylamino)-2-(tert-butoxycarbonylamino)butanoic acid To a solution (S)-2-(tert-butoxycarbonylamino)-4-(3-(5-chloro-2-hydroxyphenyl)propylamino)butanoic acid (0.350 g, 2.7 mmol) in DMF (0.7 ml) was added $K_2CO_3$ (0.375 g, 2.7 mmol) in one portion under nitrogen atmosphere at room temperature. The resulting reaction mixture was then stirred at room temperature for 15 minutes. To the above mixture was added tert-butyl 5-chloro-2,4-difluorophenylsulfonyl (thiazol-4-yl)carbamate (0.408 g, 0.99 mmol) and the resulting reaction mixture was stirred at room temperature for 3 hours. After completion of reaction, D.M. water (20 ml) was added and the resulting mixture was extracted with ethyl acetate (3×30 ml). The combined organic extract was washed with ice cold water (100 ml), brine (50 ml), dried over sodium sulphate and concentrated under vacuo. The crude product was purified by column chromatography using normal phase silica gel. The desired product eluted at around 1 to 2% Methanol in DCM. Evaporation of the product fractions gave 0.4 g (yield, 56.8%) of the desired compound as a brown liquid. LC-MS: m/z=777.6 (M+H).

Step 6: Preparation of (S)-2-amino-4-(3-(5-chloro-2-(2-chloro-5-fluoro-4-(N-thiazol-4-ylsulfamoyl)phenoxy)phenyl)propylamino)butanoic acid To a solution of (S)-4-(3-(2-(4-(N-(tert-butoxycarbonyl)-N-(thiazol-4-yl)sulfamoyl)-2-chloro-5-fluorophenoxy)-5-chlorophenyl)propylamino)-2-(tert-butoxycarbonylamino) butanoic acid (0.4 g, 0.78 mmol) in dichloromethane (10 ml) was added drop-wise a 4N solution of hydrochloric acid in ethyl acetate (2 ml) at room temperature. The resulting reaction mixture was stirred room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% Formic acid in Water: Acetonitrile mobile phase. Evaporation of the pure product fractions obtained from Prep HPLC provided the desired product as HCl salt (0.0253 g, 8.6% yield). LC-MS: m/z=576.8 (M+H).

Example 18

2-((3-(5-chloro-2-(2,5-difluoro-4-(N-(thiazol-2-yl)sulfamoyl)phenoxy)phenyl)propyl)amino)acetic acid Compound 18 was synthesized according to the procedure described for the synthesis of compound 11 by replacing tert-butyl 5-chloro-2,4-difluorophenylsulfonyl(thiazol-4-yl) carbamate with N-(2,4-dimethoxybenzyl)-2,4,5-trifluoro-N-(thiazol-2-yl)benzenesulfonamide in step 4. LC-MS: m/z=517.8 (M+H). 1H-NMR (MeOD), δ 7.81-7.85 (dd, J=6.4, 10.4 Hz, 1H), 7.46 (d, J=6.4, 1H), 7.31-7.34 (dd, J=2.8, 8.8 Hz, 1H), 7.17 (d, J=4.8 Hz, 1H), 6.99 (d, J=8.4 Hz, 1H), 6.86-6.90 (dd, J=6.4, 10.0 Hz, 1H), 6.81 (d, J=4.8 Hz, 1H), 3.92 (s, 2H), 3.08-3.12 (m, 2H), 2.75 (t, J=8.0 Hz, 2H), 2.03-2.08 (m, 2H).

Example 19

1-(3-(5-chloro-2-(2-chloro-5-fluoro-4-(N-(thiazol-4-yl)sulfamoyl)phenoxy)phenyl)propyl)piperidine-3-carboxylic acid Compound 19 was synthesized according to the procedure described for the synthesis of compound 11 by replacing glycine methyl ester with methyl piperidine-3-carboxylate in step 2. LC-MS: m/z=589.8 (M+H).

Example 20

2-((3-(2-(4-(N-(1,2,4-thiadiazol-5-yl)sulfamoyl)-2-chloro-5-fluorophenoxy)phenyl)propyl)amino)acetic acid Compound 20 was synthesized according to the procedure described for the synthesis of compound 11 by replacing 5-chloro-2-hydroxybenzaldehyde with 2-hydroxybenzaldehyde in step 1. LC-MS: m/z=500.8 (M+H). 1H-NMR (MeOD), δ 8.90 (s, 2H), 8.51 (s, 1H), 7.97 (d, J=7.2 Hz, 1H), 7.41-7.44 (dd, J=1.6, 7.2 Hz, 1H), 7.26-7.34 (m, 2H), 7.07 (dd, J=1.2, 8.0 Hz, 1H), 6.81 (d, J=10.8 Hz, 1H), 3.89 (s, 2H), 2.93 (br, 2H), 2.57-2.61 (m, 2H), 1.92 (br, 2H).

Example 21

2-((3-(5-chloro-2-(2,5-difluoro-4-(N-(thiazol-4-yl) sulfamoyl)phenoxy)phenyl)propyl)amino)acetic acid Compound 21 was synthesized according to the procedure described for the synthesis of compound 11 by replacing tert-butyl 5-chloro-2,4-difluorophenylsulfonyl(thiazol-4-yl) carbamate with tert-butyl 2,4,5-trfluorophenylsulfonyl(thiazol-4-yl)carbamate in step 4. LC-MS: m/z=517.8 (M+H). 1H-NMR (MeOD), δ 8.77 (d, J=2.0 Hz, 1H), 7.79-7.83 (dd, J=6.4, 10.0 Hz, 1H), 7.47 (d, J=2.4 Hz, 1H), 7.32-7.35 (dd, J=2.4, 8.4 Hz, 1H), 7.11 (d, J=2.4 Hz, 1H), 7.02 (d, J=8.8 Hz, 1H), 6.85-6.89 (dd, J=6.4, 10.4 Hz, 1H), 3.92 (s, 2H), 3.09-3.16 (m, 2H), 2.73 (t, J=7.6 Hz, 2H), 1.99-2.07 (m, 2H).

Example 22

3-((3-(5-chloro-2-(2,5-difluoro-4-(N-(thiazol-4-yl)sulfamoyl)phenoxy)phenyl)propyl)amino)propanoic acid Compound 22 was synthesized according to the procedure described for the synthesis of compound 11 by replacing glycine methyl ester with beta alanine methyl ester in step 2, and replacing tert-butyl 5-chloro-2,4-difluorophenylsulfonyl(thiazol-4-yl)carbamate with tert-butyl 2,4,5-trfluorophenylsulfonyl(thiazol-4-yl)carbamate in step 4. LC-MS: m/z=531.8 (M+H). 1H-NMR (MeOD), δ 8.78 (d, J=2.4 Hz, 1H), 7.79-7.83 (dd, J=6.4, 10.4 Hz, 1H), 7.47 (d, J=2.4 Hz, 1H), 7.32-7.35 (dd, J=2.4, 8.4 Hz, 1H), 7.11 (d, J=2.4 Hz, 1H), 7.01 (d, J=8.8 Hz, 1H), 6.85-6.90 (dd, J=6.4, 10.4 Hz, 1H), 3.27 (t, J=6.8 Hz, 2H), 3.07 (t, J=8.0 Hz, 2H), 2.71-2.78 (m, 4H), 1.97-2.05 (m, 2H).

Example 23

3-((3-(5-chloro-2-(2-cyano-4-(N-(thiazol-4-yl)sulfamoyl)phenoxy)phenyl)propyl)amino)propanoic acid Compound 23 was synthesized according to the procedure described for the synthesis of compound 11 by replacing glycine methyl ester with beta alanine methyl ester in step 2, and replacing tert-butyl 5-chloro-2,4-difluorophenylsulfonyl(thiazol-4-yl)carbamate with tert-butyl (3-cyano-4-fluorophenyl)sulfonyl(thiazol-4-yl)carbamate in step 4. LC-MS: m/z=520.9 (M+H). 1H-NMR (MeOD), δ 8.77 (d, J=2.0 Hz, 1H), 8.30 (d, J=2.0 Hz, 1H), 8.03 (dd, J=2.4, 9.2 Hz, 1H), 7.52 (d, J=2.4 Hz, 1H), 7.39 (dd, J=2.8, 8.8 Hz, 1H), 7.16 (d, J=2.0 Hz, 1H), 7.14 (s, 1H), 6.96 (d, J=9.2 Hz, 1H), 3.09 (t, J=6.8 Hz, 2H), 3.09 (t, J=8.0 Hz, 2H), 2.76 (t, J=6.4 Hz, 2H), 2.69 (t, J=8.0 Hz, 2H), 1.99-2.07 (m, 2H).

Example 24 methyl 2-((3-(5-chloro-2-(2-chloro-5-fluoro-4-(N-(thiazol-4-yl)sulfamoyl)phenoxy)phenyl)propyl)amino)acetate Compound 24 was synthesized according to the procedure described for the synthesis of compound 11 without hydrolysis of methyl ester (step 5). LC-MS: m/z=548.4 (M+H). 1H-NMR (MeOD), δ 8.77 (d, J=2.4 Hz, 1H), 8.02 (d, J=6.8 Hz, 1H), 7.49 (d, J=2.4 Hz, 1H), 7.35-7.38 (dd, J=2.4, 8.4 Hz, 1H), 7.12 (d, J=2.4 Hz, 1H), 7.02 (d, J=8.8 Hz, 1H), 6.75 (d, J=10.4 Hz, 1H), 3.99 (s, 2H), 3.85 (s, 3H), 3.08-3.12 (m, 2H), 2.68 (t, J=7.6 Hz, 2H), 2.00-2.08 (m, 2H).

Example 25

3-((3-(2-(2-chloro-5-fluoro-4-(N-(thiazol-4-yl)sulfamoyl)phenoxy)-5-fluorophenyl)propyl)amino)propanoic acid Compound 25 was synthesized according to the procedure described for the synthesis of compound 11 by replacing 5-chloro-2-hydroxybenzaldehyde with 5-fluoro-2-hydroxybenzaldehyde in step 1, and replacing glycine methyl ester with beta alanine methyl ester in step 2. LC-MS: m/z=531.9 (M+H). 1H-NMR (MeOD), δ 8.77 (d, J=2.4 Hz, 1H), 8.01 (d, J=6.8 Hz, 1H), 7.23 (dd, J=2.4, 8.8 Hz, 1H), 7.11-7.13 (m, 3H), 6.65 (d, J=10.8 Hz, 1H), 3.25 (t, J=6.8 Hz, 2H), 3.06 (t, J=8.0 Hz, 2H), 2.73 (t, J=6.4 Hz, 2H), 2.66 (t, J=7.6 Hz, 2H), 1.99-2.03 (m, 2H).

Example 26

3-((3-(5-chloro-2-(2-chloro-5-fluoro-4-(N-(thiazol-4-yl)sulfamoyl)phenoxy)phenyl)propyl)amino)propanamide

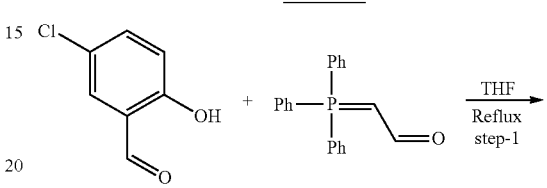

Scheme 11

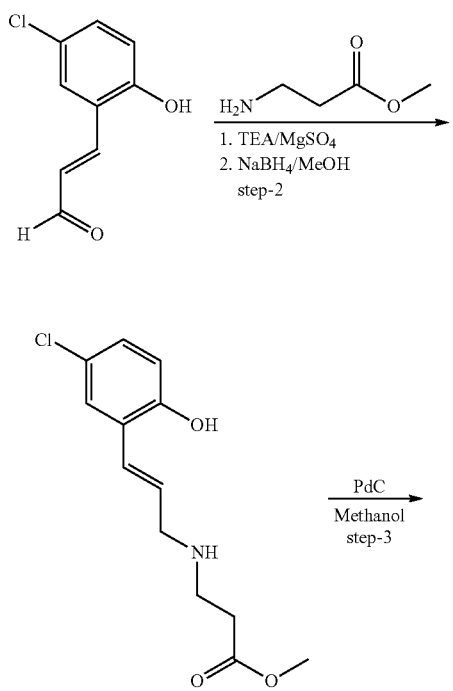

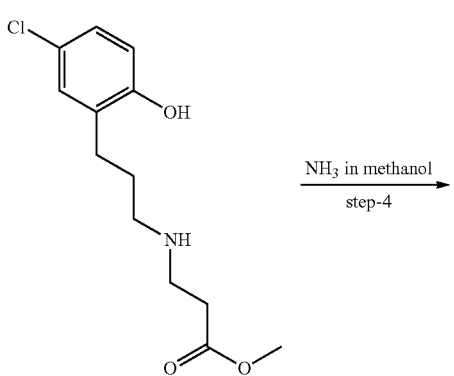

-continued

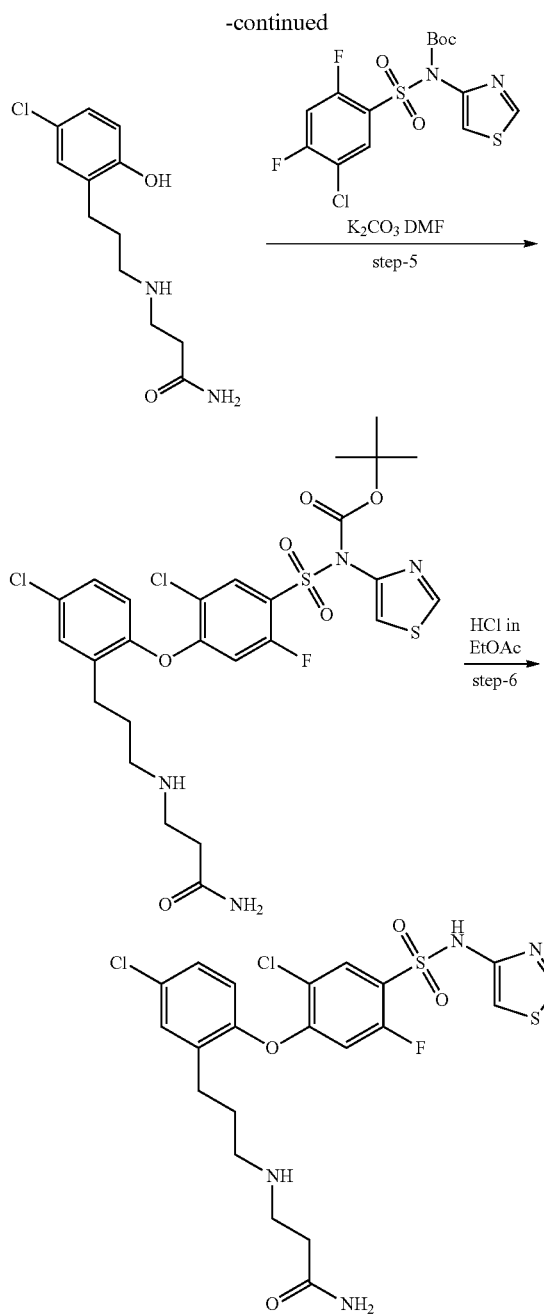

Step 1: Preparation of
3-(5-chloro-2-hydroxyphenyl)acrylaldehyde

To a solution of 5-chloro-2-hydroxybenzaldehyde (20 g, 127 mmol) in THF (300 ml) was added (formylmethylene) triphenylphosphorane (43 g, 140 mmol) at room temperature. The resulting reaction mixture was then refluxed at 100° C. for 20 hrs. After completion of reaction, the reaction mixture was allowed to cool to room temperature. Water (200 ml) was added and the resulting mixture was extracted with ethyl acetate (3×250 ml). The combined organic extract was washed with water (200 ml), brine (200 ml), dried over sodium sulphate and concentrated under vacuo to get the desired crude product. The crude product was purified by column chromatography using normal phase silica gel. The desired product eluted at around 20-30% ethyl acetate in hexane. Evaporation of the product fractions gave 20 g (yield, 87%) of desired compound as yellow solid. LC-MS: m/z=181.34 (M−H).

Step 2: Preparation of methyl 3-[3-(5-chloro-2-hydroxyphenyl)allylamino]propanoate)

To a solution of 3-(5-chloro-2-hydroxyphenyl)acrylaldehyde (1.0 g, 5.47 mmol) and β-Alanine methyl ester hydrochloride (0.917 g, 6.57 mmol) in DCM (20 ml) was added magnesium sulphate (1.317 g, 1.09 mmol) and TEA (2.3 ml, 16.41 mmol) at room temperature and the resulting reaction mixture was stirred at room temperature for 12 hours. The reaction mixture was then concentrated under vacuo. The concentrated mass thus obtained was dissolved in methanol (20 ml) and cooled to 5-10° C. To this cold reaction mixture, sodium borohydrate (0.620 g, 16.41 mmol) was then added in small portions over a period of 10-20 mins, during addition the temperature was maintained in between 10-20° C. After completion of addition the resulting reaction mixture was allowed to stir at room temperature for 2 hours. After completion of the reaction, it was concentrated under vacuo. To the resulting crude mass water (50 ml) was added and the mixture was extracted with EtOAc (3×25 ml). The combined organic extract was washed with water (20 ml), brine (20 ml), dried over sodium sulphate and concentrated under vacuo to get the desired crude product. The crude product was purified by column chromatography using normal phase silica gel. The desired product eluted at around 1-5% Methanol in DCM. Evaporation of the product fractions gave 0.9 g (yield, 61%) of desired compound as white solid. LC-MS: m/z=270.6 (M+H).

Step 3: Preparation of methyl 3-[3-(5-chloro-2-hydroxyphenyl)propylamino]propanoate)

To a solution of 3-[3-(5-chloro-2-hydroxyphenyl)allylamino]propanoate) (0.35 g, 1.3 mmol) in methanol (20 ml) was carefully added 10% Palladium on carbon with 50% moisture (0.104 g, 0.065 mmol). Hydrogen gas was then bubbled into the reaction mixture at room temperature for a period of 30 mins. The reaction mixture was monitored on TLC using ethyl acetate as mobile phase. After completion of the reaction, the reaction mixture was filtered through celite. The celite bed was carefully washed with some amount of methanol. The filtrate thus obtained was concentrated under vacuo to afford 0.3 g (yield, 85%) of desired compound colorless liquid. m/z=272.6 (M+H).

Step 4: Preparation of 3-[3-(5-chloro-2-hydroxyphenyl)propylamino]propanamide)

A solution of methyl 3-[3-(5-chloro-2-hydroxyphenyl)propylamino]propanoate) (0.3 g, 1.08 mmol) in methanolic ammonia (10 mL) was heated at 100° C. in sealed tube (35 mL) for a time period of 12 hours. After completion of reaction methanol was evaporated under vacuo. The crude product was purified by column chromatography using normal phase silica gel. The desired product eluted at around 30-40% ethyl acetate in hexane. Evaporation of the product fractions gave 0.16 g (yield, 33.9%) of the desired compound as a colorless liquid. m/z=257.2 (M+H).

Step 5: Preparation of methyl 3-(3-(2-(4-(N-(tert-butoxycarbonyl)-N-(thiazol-4-yl)sulfamoyl)-2-chloro-5-fluorophenoxy)-5-chlorophenyl)propylamino)propanoate To a solution 3-[3-(5-chloro-2-hydroxyphenyl)propylamino]propanoate) (0.09 g, 0.35 mmol) in DMF (2 ml) was added K₂CO₃ (0.145, 1.05 mmol) in one portion under nitrogen atmosphere at room temperature. The resulting reaction mixture was stirred at room temperature for 15 minutes. To the above mixture was added tert-butyl 5-chloro-2,4-difluorophenylsulfonyl(thiazol-4-yl)carbamate (0.143 g, 0.35 mmol) and the resulting mixture was stirred at room temperature for 3 hours. After completion of reaction, water (10 ml) was added and the resulting mixture was extracted with ethyl acetate (3×25 ml). The combined organic extract was washed with water (20 ml), brine (20 ml), dried over sodium sulphate and concentrated under vacuo. The crude product was purified by column chromatography using normal phase silica gel. The desired product eluted at around 20 to 25% ethyl acetate in hexane. Evaporation of the product fractions gave 0.15 g (yield, 66.2%) of desired compound as a solid. This material was used for the next step without any further purification and analysis. The material was used directly for the next step.

Step 6: Preparation of 3-(3-(5-chloro-2(2-chloro-5-fluoro-4-(N-thiazol-4-ylsulfamoyl)phenoxy)phenyl) propylamino)propanamide fluorophenyl sulfonyl (thiazol-4-yl)carbamate To a solution of 3-(3-(2-(4-(N-(tert-butoxycarbonyl)-N-(thiazol-4-yl)sulfamoyl)-2-chloro-5-fluorophenoxy)-5-chlorophenyl)propylamino)propanoate (0.15 g, 0.23 mmol) in dichloromethane (5 ml) was added drop-wise a 4N solution of hydrochloric acid in ethyl acetate (0.5 ml) at room temperature. The resulting reaction mixture was stirred room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% Formic acid in Water:Acetonitrile mobile phase. Evaporation of the pure product fractions obtained from Prep HPLC provided the desired product as HCl salt. (0.009 g, 7.1% yield). LC-MS: m/z=548.8 (M+H). 1H-NMR (MeOD), δ 8.75 (d, J=2.4 Hz, 1H), 8.01 (d, J=7.2 Hz, 1H), 7.48 (d, J=2.4 Hz, 1H), 7.34-7.37 (dd, J=2.4, 8.8 Hz, 1H), 7.06 (d, J=2.4 Hz, 1H), 7.01 (d, J=8.4 Hz, 1H), 6.73 (d, J=10.4 Hz, 1H), 3.22 (t, J=6.4 Hz, 2H), 3.02-3.06 (m, 2H), 2.62-2.70 (m, 4H), 1.99-2.03 (m, 2H).

Example 27

2-(N-(3-(5-chloro-2-(2-chloro-5-fluoro-4-(N-(thiazol-4-yl)sulfamoyl)phenoxy)phenyl)propyl)acetamido)acetic acid Scheme 12

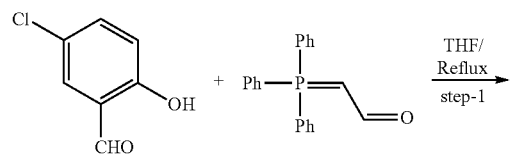

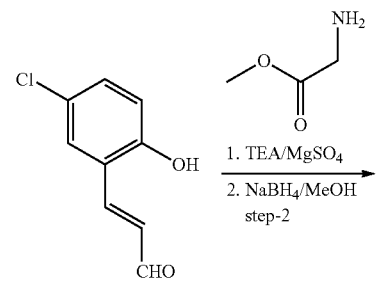

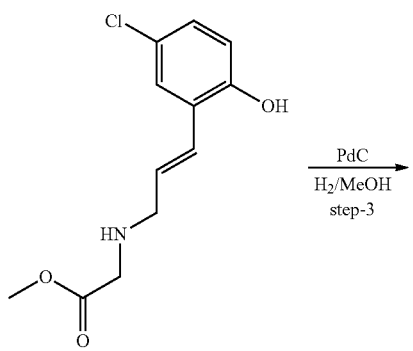

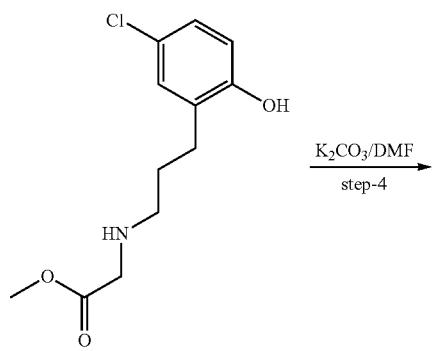

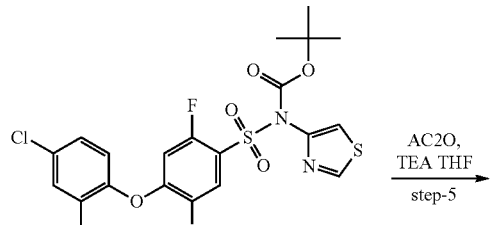

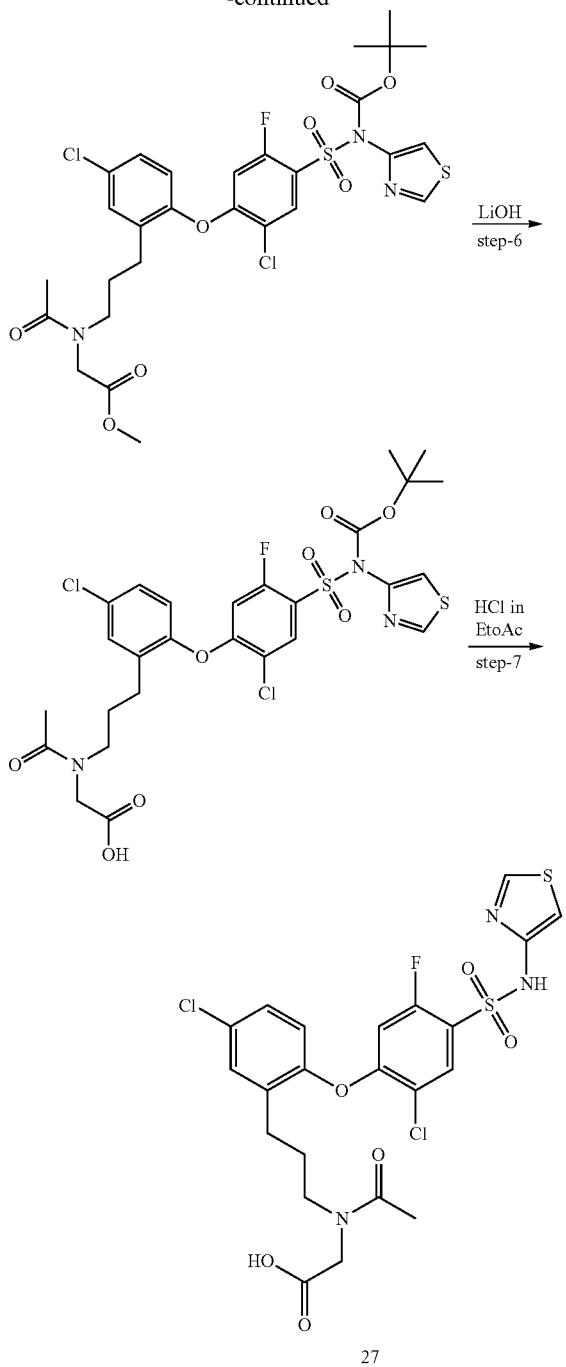

27

Step 1: Preparation of
(E)-3-(5-chloro-2-hydroxyphenyl)acrylaldehyde

To a solution of 5-chloro-2-hydroxybenzaldehyde (20 g, 127 mmol) in THF (300 ml) was added (formylmethylene) triphenylphosphorane (43 g, 140 mmol) at room temperature. The resulting reaction mixture was then refluxed at 100° C. for 20 hrs. After completion of reaction, the reaction mixture was allowed to cool to room temperature. Water (200 ml) was added and the resulting mixture was extracted with ethyl acetate (3×250 ml). The combined organic extract was washed with water (200 ml), brine (200 ml), dried over sodium sulphate and concentrated under vacuo to get the desired crude product. The crude product was purified by column chromatography using normal phase silica gel. The desired product eluted at around 20-30% ethyl acetate in hexane. Evaporation of the product fractions gave 20 g (yield, 87%) of the desired compound as a yellow solid LC-MS: m/z=183.4 (M+H).

Step 2: Preparation of (E)-methyl 2-(3-(5-chloro-2-hydroxyphenyl)allylamino)acetate To a solution of (E)-3-(5-chloro-2-hydroxyphenyl)acrylaldehyde (1.0 g, 5.4 mmol) and glycine methyl ester hydrochloride (0.590 g, 6.55 mmol) in dichloromethane (20 ml) was added magnesium sulphate (1.5 g, 10.9 mmol) and triethylamine (2.28 ml, 16.38 mmol) at room temperature. The above reaction mixture was stirred at room temperature for 12 hours. The resulting reaction mixture was then concentrated under vacuo. The concentrated mass thus obtained was dissolved in methanol (20 ml) and cooled to a temperature between 5-10° C. To the above mixture, sodium borohydride (0.606 g, 16.38 mmol) was added in small portions over a period of 10 minutes; during addition temperature of the reaction mixture was maintained between 10-20° C. After completion of addition, the resulting reaction mixture was allowed to stir at room temperature for 2 hours. After completion of reaction, the reaction mixture was concentrated under vacuo. Water (40 ml) was added to the above crude mass and the resulting mixture was extracted with ethyl acetate (3×60 ml). The combined organic extract was washed with water (50 ml), brine (50 ml), dried over sodium sulphate and concentrated under vacuo to get the desired crude product. The crude product was purified by column chromatography using normal phase silica gel. The desired product eluted at around 2-3% methanol in dichloromethane. Evaporation of the product fractions gave 0.8 g (yield, 57.4%) of the desired compound as a brown liquid. LC-MS: m/z=256.07 (M+H).

Step 3: Preparation of methyl 2-(3-(5-chloro-2-hydroxyphenyl)propylamino)acetate To a solution of (E)-methyl 2-(3-(5-chloro-2-hydroxyphenyl)allylamino)acetate (0.8 g, 3.13 mmol) in methanol (50 ml) was carefully added Palladium hydroxide (0.199 g, 0.09 mmol). Hydrogen gas was then bubbled into the reaction mixture at room temperature for a period of 30 minutes. After completion of the reaction, the reaction mixture was filtered through celite. The celite bed was carefully washed with some amount of methanol. The filtrate thus obtained was concentrated under vacuo to afford 0.7 g (yield, 86.81%) of compound as colorless liquid. LC-MS: m/z=258.07 (M+H).

Step 4: Preparation of methyl 2-(3-(2-(4-(N-(tert-butoxycarbonyl)-N-(thiazol-4-yl)sulfamoyl)-2-chloro-5-fluorophenoxy)-5-chlorophenyl)propylamino)acetate To a solution of methyl 2-(3-(5-chloro-2-hydroxyphenyl) propylamino)acetate (0.7 g, 2.72 mmol) in DMF (7 ml) was added K$_2$CO$_3$ (1.12 g, 8.17 mmol) in one portion under nitrogen atmosphere at room temperature. The resulting reaction mixture was then stirred at room temperature for 15 minutes. To the above mixture was added tert-butyl 5-chloro-2,4-difluorophenylsulfonyl(thiazol-4-yl)carbamate (1.22 g, 2.996 mmol) and the resulting reaction mixture was stirred at room temperature for 3 hours. After completion of reaction, water (20 ml) was added and the resulting mixture was extracted with ethyl acetate (3×50 ml). The combined organic extract was washed with water (20 ml), brine (20 ml), dried over sodium sulphate and concentrated under vacuo to afford 0.54 g (yield, 30.64%) of the compound as a white solid. LC-MS: m/z=646.20 (M−H).

Step 5: Preparation of methyl 2-(N-(3-(2-(4-(N-(tert-butoxycarbonyl)-N-(thiazol-4-yl)sulfamoyl)-2-chloro-5-fluorophenoxy)-5-chlorophenyl)propyl)acetamido)acetate To a solution of methyl 2-(3-(2-(4-(N-(tert-butoxycarbonyl)-N-(thiazol-4-yl)sulfamoyl)-2-chloro-5-fluorophenoxy)-5-chlorophenyl)propylamino)acetate (0.35 g, 0.54 mmol) in THF (5 mL) was added triethyl amine (0.22 ml, 1.62 mmol). The resulting reaction mixture was stirred at 0° C. for 5-10 minutes. Acetic anhydride (0.102 ml, 1.08 mmol) was added at 0° C. The resulting reaction mixture was then refluxed at 80° C. for 12 hours. To the reaction mixture water (30 ml) was added and the resulting mixture was extracted with ethyl acetate (3×50 ml). The combined organic extracts was washed with water (30 ml), brine (30 ml), dried over sodium sulphate and concentrated under vacuo to get the desired crude product. The crude product was purified by triturating with diethyl ether. Evaporation of the product fractions gave 0.35 g (yield, 94.01%) of the desired compound as a brown solid. LC-MS: m/z=690.5 (M+H).

Step 6: Preparation of 2-(N-(3-(2-(4-(N-(tert-butoxycarbonyl)-N-(thiazol-4-yl)sulfamoyl)-2-chloro-5-fluorophenoxy)-5-chlorophenyl)propyl)acetamido)acetic acid To the solution of methyl 2-(N-(3-(2-(4-(N-(tert-butoxycarbonyl)-N-(thiazol-4-yl)sulfamoyl)-2-chloro-5-fluorophenoxy)-5-chlorophenyl)propyl)acetamido)acetate (0.35 g, 0.50 mmol) in THF (5 ml) was added a solution of lithium hydroxide monohydrate (0.212 g, 5.07 mmol) in water (0.5 ml) at room temperature. The resulting reaction mixture was stirred at room temperature for 3 hours. After completion of reaction ice cold water (15 ml) was added in to the reaction mixture, the resulting mixture was then acidified between 4-6 pH with aqueous 1N hydrochloric acid. The resulting acidic aqueous was extracted with ethyl acetate (3×25 ml). The combined organic extract was washed with water (20 ml), brine (20 ml), dried over sodium sulphate and concentrated under vacuo to afford 0.3 g (yield, 87.49%) of the compound as a white solid. This material was directly used for next step without any further purification and analysis. LC-MS: m/z=676.41 (M+H).

Step 7: Preparation of 2-(N-(3-(5-chloro-2-(2-chloro-5-fluoro-4-(N-thiazol-4-ylsulfamoyl)phenoxy)phenyl)propyl)acetamido)acetic acid To the solution of 2-(N-(3-(2-(4-(N-(tert-butoxycarbonyl)-N-(thiazol-4-yl)sulfamoyl)-2-chloro-5-fluorophenoxy)-5-chlorophenyl)propyl)acetamido)acetic acid (0.3 g, 0.44 mmol) in dichloromethane (4 ml) was added drop-wise a 4N solution of hydrochloric acid in ethyl acetate (1 ml) at room temperature. The resulting reaction mixture was stirred room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% Hydrochloric acid in water: acetonitrile mobile phase. Evaporation of the pure product fractions obtained from Prep HPLC provided the desired product as HCl salt (0.060 g, 23.47% yield). LC-MS: m/z=575.92 (M+H).

Example 28

2-(1-(3-(2-(4-(N-(1,2,4-thiadiazol-5-yl)sulfamoyl)-2-chloro-5-fluorophenoxy)-5-chlorophenyl)propyl)piperidin-4-yl)acetic acid Compound 28 was synthesized according to the procedure described for the synthesis of compound 11 by replacing glycine methyl ester with methyl 2-(piperidin-4-yl)acetate in step 2, and replacing tert-butyl 5-chloro-2,4-difluorophenylsulfonyl(thiazol-4-yl)carbamate with 5-chloro-N-(2,4-dimethoxybenzyl)-2,4-difluoro-N-(1,2,4-thiadiazol-5-yl)benzenesulfonamide in step 4. LC-MS: m/z=601.2 (M+H).

Example 29

3-((3-(5-chloro-2-(2-chloro-5-fluoro-4-(N-(thiazol-2-yl)sulfamoyl)phenoxy)phenyl)propyl)amino)propanoic acid Compound 29 was synthesized according to the procedure described for the synthesis of compound 11 by replacing glycine methyl ester with beta alanine methyl ester in step 2, and replacing tert-butyl 5-chloro-2,4-difluorophenylsulfonyl(thiazol-4-yl)carbamate with 5-chloro-N-(2,4-dimethoxybenzyl)-2,4-difluoro-N-(thiazol-2-yl)benzenesulfonamide in step 4. LC-MS: m/z=547.9 (M+H). 1H-NMR (MeOD), δ 8.05 (d, J=6.8 Hz, 1H), 7.49 (d, J=2.8 Hz, 1H), 7.34 (dd, J=2.4, 8.4 Hz, 1H), 7.17 (d, J=4.4 Hz, 1H), 7.02 (d, J=8.4 Hz, 1H), 6.80 (d, J=4.4 Hz, 1H), 6.75 (d, J=10.4 Hz, 1H), 3.14 (t, J=6.4 Hz, 2H), 3.04 (t, J=8.0 Hz, 2H), 2.71 (t, J=8.0 Hz, 2H), 2.49 (t, J=6.4 Hz, 2H), 2.00-2.03 (m, 2H).

Example 30

2-((3-(5-chloro-2-(2-chloro-5-fluoro-4-(N-(thiazol-4-yl)sulfamoyl)phenoxy)phenyl)propyl)amino)-N-methylacetamide Compound 30 was synthesized according to the procedure described for the synthesis of compound 11 by replacing glycine methyl ester with 2-amino-N-methylacetamide in step 2. LC-MS: m/z=547.1 (M+H). 1H-NMR (MeOD), δ 8.77 (d, J=2.4 Hz, 1H), 8.01 (d, J=7.2 Hz, 1H), 7.48 (d, J=2.4 Hz, 1H), 7.35 (dd, J=2.4, 8.4 Hz, 1H), 7.10 (d, J=2.0 Hz, 1H), 7.02 (d, J=8.8 Hz, 1H), 6.73 (d, J=10.4 Hz, 1H), 3.70 (s, 2H), 2.97-3.02 (m, 2H), 2.80 (s, 3H), 2.65-2.69 (m, 2H), 1.96-2.06 (m, 2H).

Example 31

5-chloro-4-(4-chloro-2-(3-((2-(methylsulfonyl)ethyl)amino)propyl)phenoxy)-2-fluoro-N-(thiazol-4-yl)benzenesulfonamide Compound 31 was synthesized according to the procedure described for the synthesis of compound 11 by replacing glycine methyl ester with 2-(methylsulfonyl)ethanamine in step 2. LC-MS: m/z=581.8 (M+H). 1H-NMR (MeOD), δ 8.77 (d, J=2.4 Hz, 1H), 8.02 (d, J=6.8 Hz, 1H), 7.48 (d, J=2.4

Hz, 1H), 7.36 (dd, J=2.8, 8.8 Hz, 1H), 7.10 (d, J=2.4 Hz, 1H), 7.02 (d, J=8.4 Hz, 1H), 6.73 (d, J=10.4 Hz, 1H), 3.33-3.50 (m, 4H), 3.03 (s, 3H), 2.99-3.01 (m, 2H), 2.65-2.68 (m, 2H), 1.95-2.03 (m, 2H).

Example 32

1-(3-(2-(4-(N-(1,2,4-thiadiazol-5-yl)sulfamoyl)-2-chloro-5-fluorophenoxy)-5-chlorophenyl)propyl)piperidine-4-carboxylic acid Compound 32 was synthesized according to the procedure described for the synthesis of compound 11 by replacing glycine methyl ester with methyl piperidine-4-carboxylate in step 2, and replacing tert-butyl 5-chloro-2,4-difluorophenylsulfonyl(thiazol-4-yl)carbamate with 5-chloro-N-(2,4-dimethoxybenzyl)-2,4-difluoro-N-(1,2,4-thiadiazol-5-yl)benzenesulfonamide in step 4. LC-MS: m/z=589.6 (M+H).

Example 33

5-chloro-4-(4-chloro-2-(4,5,6,7-tetrahydropyrazolo[1,5-a]pyrimidin-3-yl)phenoxy)-2-fluoro-N-(thiazol-4-yl)benzenesulfonamide Scheme 13

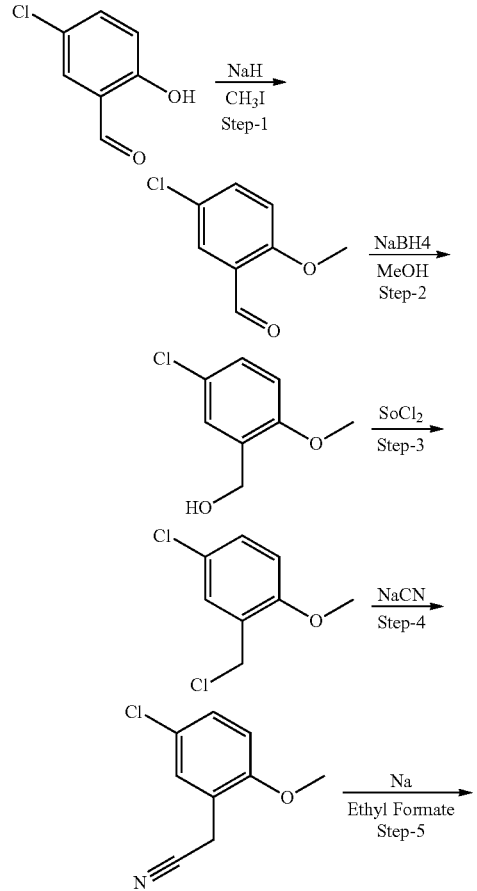

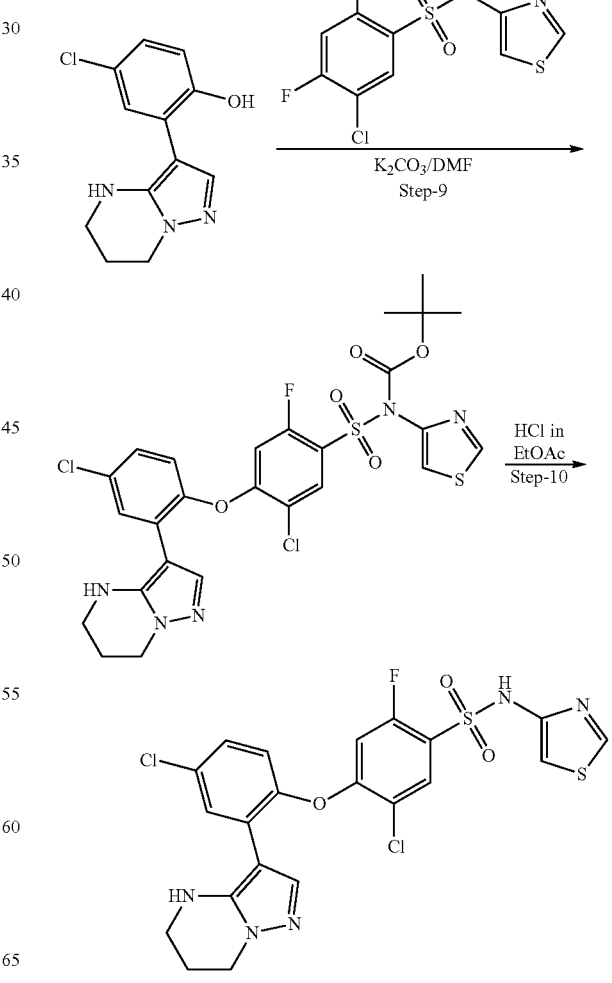

Step 1: Preparation of 5-chloro-2-methoxybenzaldehyde

A solution of 5-chloro-2-hydroxybenzaldehyde (20 g, 128 mmol) in DMF (70 mL) was cooled to a temperature between 5-10° C. Sodium hydride (7.69 g, 192 mmol) was added to the above solution in small portions over a period of 20 minutes. Methyl iodide (23.8 ml, 384 mmol) was then added drop wise to the above reaction mixture whilst maintaining its temperature below 15° C. After completion of addition the reaction mixture was stirred at room temperature for 2 hours. Thereafter the reaction mixture was poured in to cold saturated ammonium chloride solution (250 mL) to get white precipitates. The precipitates thus formed were filtered off and dried under vacuo. The resulting solid was triturated with 100 ml of pentane:diethyl ether (4:1) to afford 18 g (yield, 82.58%) of the desired compound as a white solid. LC-MS: m/z=170.1 (M+H).

Step 2: Preparation of (5-chloro-2-methoxyphenyl)methanol

A solution of 5-chloro-2-methoxybenzaldehyde (18 g, 105.8 mmol) in methanol (100 mL) was cooled to temperature in between 5-10° C. To the above solution sodium borohydride (11.8 g, 317 mmol) was added in portion over a period of 30 mins. After completion of addition the resulting reaction mixture was allowed to stir at room temperature for next ~2 hours. The reaction was monitored on TLC using ethyl acetate:hexane (1:1) as mobile phase. After completion of it, it was concentrated under vacuo. To the resulting crude mass, cold water (200 ml) was added to get white precipitate. The precipitate thus formed was filtered and dried to afford 16 g (yield, 87.8%) of desired compound as white solid. The material was used directly for the next step.

Step 3: Preparation of 4-chloro-2-(chloromethyl)-1-methoxybenzene

A solution of 5-chloro-2-methoxyphenyl)methanol (16 g, 94 mmol) in DCM (100 ml) was cooled to a temperature between 5-10° C. To the above solution thionyl chloride (11 ml, 140 mmol) was added drop wise over a period of 30 minutes. After completion of addition the resulting reaction mixture was allowed to stir at room temperature for 4 hours. After completion of the reaction, it was concentrated under vacuo. To the resulting crude mass, cold water (150 ml) was added to get white precipitates. The precipitate thus formed was filtered off and dried under vacuo to afford 12 g (yield, 67.9%) of the desired compound as a white solid. The material was used directly for the next step.

Step 4: Preparation of 2-(5-chloro-2-methoxyphenyl)acetonitrile

To a solution of 4-chloro-2-(chloromethyl)-1-methoxybenzene (12 g, 63.15 mmol) in DMSO (60 mL) was carefully added sodium cyanide (4.4 g, 95.6 mmol) at room temperature. Above reaction mixture was then heated at 100° C. for 3 hours. After cooling to room temperature, the reaction mixture was poured in to cold water (200 mL) to get precipitate. The precipitate thus formed was filtered off and dried under vacuo to afford 10 g (yield, 87.46%) of the desired compound as an off white solid. The material was used directly for the next step.

Step 5: Preparation of 2-(5-chloro-2-methoxyphenyl)-3-oxopropanenitrile

To a solution of 2-(5-chloro-2-methoxyphenyl)acetonitrile (10 g, 47.84 mmol) in ethyl formate (50 mL) was added sodium metal (4.4 g, 95.6 mmol) at room temperature. The resulting reaction mixture was heated at 100° C. for 3 hours. After completion of the reaction, it was cooled to room temperature, water (100 ml) and dichloromethane (100 ml) were added to the reaction mixture and the solution was adjusted to pH-3 with the help of concentrated hydrochloric acid. The layers were separated and the aqueous layer was extracted with dichloromethane (2×100 ml). The combined organics were washed with saturated aqueous sodium chloride solution (150 ml), dried over sodium sulphate, filtered and evaporated under vacuo. The crude product was purified by column chromatography using normal phase silica gel. The desired product eluted at around 0.7 to 0.9% methanol in dichloromethane. Evaporation of the product fractions gave 9 g (yield, 77.94%) of the desired compound as a white solid. LC-MS: m/z=208.0 (M−H).

Step 6: Preparation of 4-(5-chloro-2-methoxyphenyl)-1H-pyrazol-5-amine

To a solution of 2-(5-chloro-2-methoxyphenyl)-3-oxopropanenitrile (9 g, 43 mmol) in ethanol (90 mL) was added hydrazine hydrate (4.3 g, 86.12 mmol) and glacial acetic acid (2.7 mL, 51.6 mmol) at room temperature. The reaction mixture was then heated under reflux for 3 hours. After completion of the reaction, the reaction mixture was cooled to room temperature and quenched with aqueous sodium bicarbonate (150 ml). The resulting mixture was extracted with dichloromethane (3×100 ml). The combined organic layers were washed with brine, dried over sodium sulphate and concentrated under vacuo. The crude product was purified by column chromatography using normal phase silica gel. The desired product eluted at around 0.9 to 1.1% methanol in dichloromethane. Evaporation of the product fractions gave 7 g (yield, 72.8%) of the desired compound as a white solid. LC-MS: m/z=224.1 (M+H).

Step 7: Preparation of 3-(5-chloro-2-methoxyphenyl)-4,5,6,7-tetrahydropyrazolo[1,5-a]pyrimidine A solution of 4-(5-chloro-2-methoxyphenyl)-1H-pyrazol-5-amine (3 g, 13.45 mmol) in dry DMF (15 mL) was cooled to a temperature in between 5-10° C. Sodium hydride (0.806 g, 20.17 mmol) was added to the above solution in small portions over a period of 30 minutes. The resulting reaction mixture was stirred for 30 minutes at 5-10° C., thereafter 1,3-dibromopropane (1.78 ml, 17.48 mmol) was added drop wise to the above mixture. The resulting reaction mixture was heated at 100° C. for a period of 4 hrs. After completion of reaction, the solution was diluted with cold water (100 mL) and the product was extracted with ethyl acetate (3×100). The combined organic layers were washed with brine, dried over sodium sulphate and concentrated under vacuo. The crude product was purified by column chromatography using normal phase silica gel. The desired product eluted at around 1.2 to 1.5% methanol in dichloromethane. Evaporation of the product fractions gave 0.65 g (yield, 18.36%) of the desired compound as a semisolid. LC-MS: m/z=264.2 (M+H).

Step 8: Preparation of 4-chloro-2-(4,5,6,7-tetrahydropyrazolo[1,5-a]pyrimidin-3-yl)phenol A solution of 3-(5-chloro-2-methoxyphenyl)-4,5,6,7-tetrahydropyrazolo[1,5-a]pyrimidine (0.65 g, 1.9 mmol) in dichloromethane (30 mL) was cooled to a temperature between 5-10° C. To the above solution, boron tribromide in dichloromethane (4.7 mL, 4.75 mmol) was added drop wise over a period of 30 minutes. After completion of addition, the resulting reaction mixture was stirred at room temperature for 4 hours. After completion of reaction, the solution was diluted with cold water (40 mL) and the product was extracted with ethyl acetate (3×30 mL). The combined organic layers were washed with brine, dried over sodium sulphate and concentrated under vacuo to afford 0.65 g (yield, 81.24%) of desired compound as white solid. LC-MS: m/z=250.2 (M+H).

Step 9: Preparation of tert-butyl 5-chloro-4-(4-chloro-2-(4,5,6,7-tetrahydropyrazolo[1,5-a]pyrimidin-3-yl)phenoxy)-2-fluorophenylsulfonyl(thiazol-4-yl)carbamate To a solution 4-chloro-2-(4,5,6,7-tetrahydropyrazolo[1,5-a]pyrimidin-3-yl)phenol (0.5 g, 2.008 mmol) in DMF (8 ml) was added K₂CO₃ (0.556 g, 4.016 mmol) in one portion under nitrogen atmosphere at room temperature. The resulting reaction mixture was stirred at room temperature for 15 minutes. To the above mixture was added tert-butyl 5-chloro-2,4-difluorophenylsulfonyl(thiazol-4-yl)carbamate (0.989 g, 2.409 mmol) and the resulting reaction mixture was stirred at room temperature for 3 hours. After completion of reaction, water (10 ml) was added and the resulting mixture was extracted with ethyl acetate (3×25 ml). The combined organic extract was washed with water (20 ml), brine (20 ml), dried over sodium sulphate and concentrated under vacuo. The crude product was purified by column chromatography using normal phase silica gel. The desired product eluted at around 40 to 50% ethyl acetate in hexane. Evaporation of the product fractions gave 0.4 g (yield, 31.18%) of the desired compound as a white solid. LC-MS: m/z=640.1 (M+H).

Step 10: Preparation of 5-chloro-4-(4-chloro-2-(4,5,6,7-tetrahydropyrazolo[1,5-a]pyrimidin-3-yl)phenoxy)-2-fluoro-N-(thiazol-4-yl)benzenesulfonamide To a solution of tert-butyl 5-chloro-4-(4-chloro-2-(4,5,6,7-tetrahydropyrazolo[1,5-a]pyrimidin-3-yl)phenoxy)-2-fluorophenyl sulfonyl(thiazol-4-yl)carbamate (0.4 g, 0.626 mmol) in dichloromethane (15 ml) was added drop-wise a 4N solution of hydrochloric acid in ethyl acetate (0.8 ml) at room temperature. The resulting reaction mixture was stirred at room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% Hydrochloric acid in Water:Acetonitrile mobile phase. Evaporation of the pure product fractions obtained from Prep HPLC provided the desired product as HCl salt (0.130 g, 38.6% yield). LC-MS: m/z=539.78 (M+H). 1H NMR (400 MHz, Methanol-d4) δ 8.76 (d, J=2.4 Hz, 1H), 8.02 (s, 1H), 7.95 (d, J=7.2 Hz, 1H), 7.61 (d, J=2.4 Hz, 1H), 7.54 (dd, J=2.4, 8.4 Hz, 1H), 7.27 (d, J=8.4 Hz, 1H), 7.09 (d, J=2.0 Hz, 1H), 6.62 (d, J=10.8 Hz, 1H), 4.14 (t, J=6.0 Hz, 2H), 3.40 (t, J=5.6 Hz, 2H), 2.14 (p, J=6.0 Hz, 2H).

Example 34

2-((3-(5-chloro-2-(2-chloro-5-fluoro-4-(N-(thiazol-2-yl)sulfamoyl)phenoxy)phenyl)propyl)(ethoxycarbonyl)amino)acetic acid

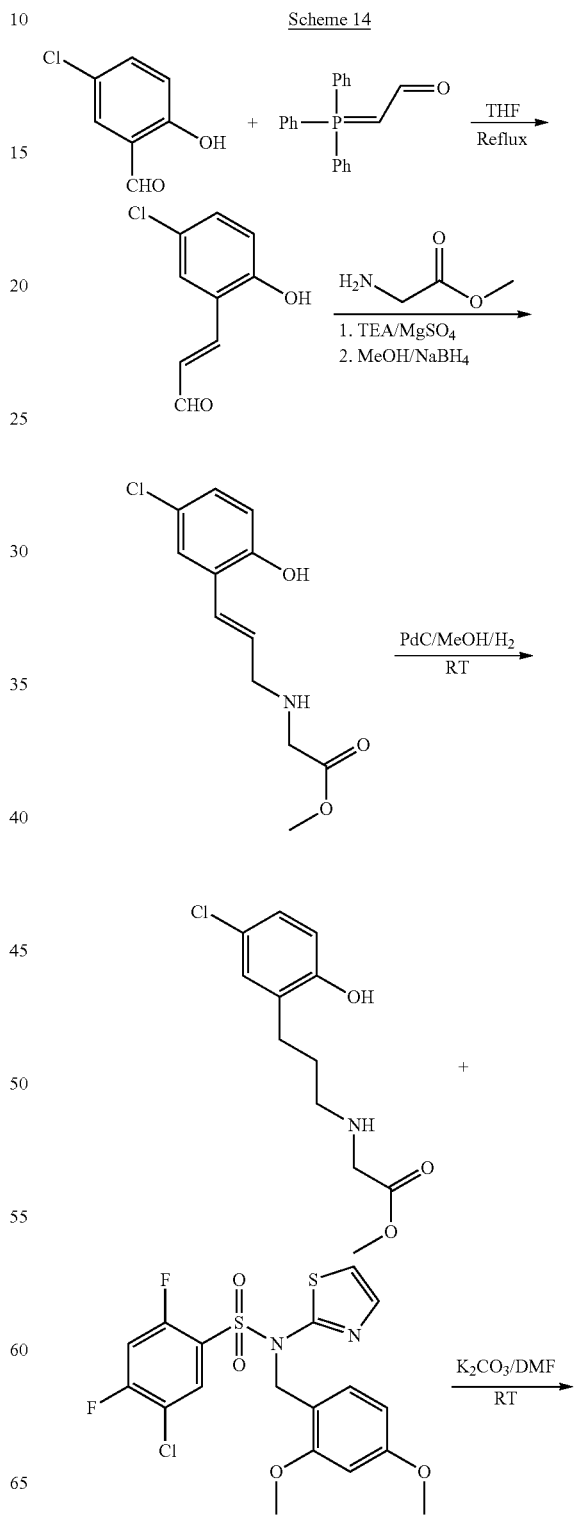

Scheme 14

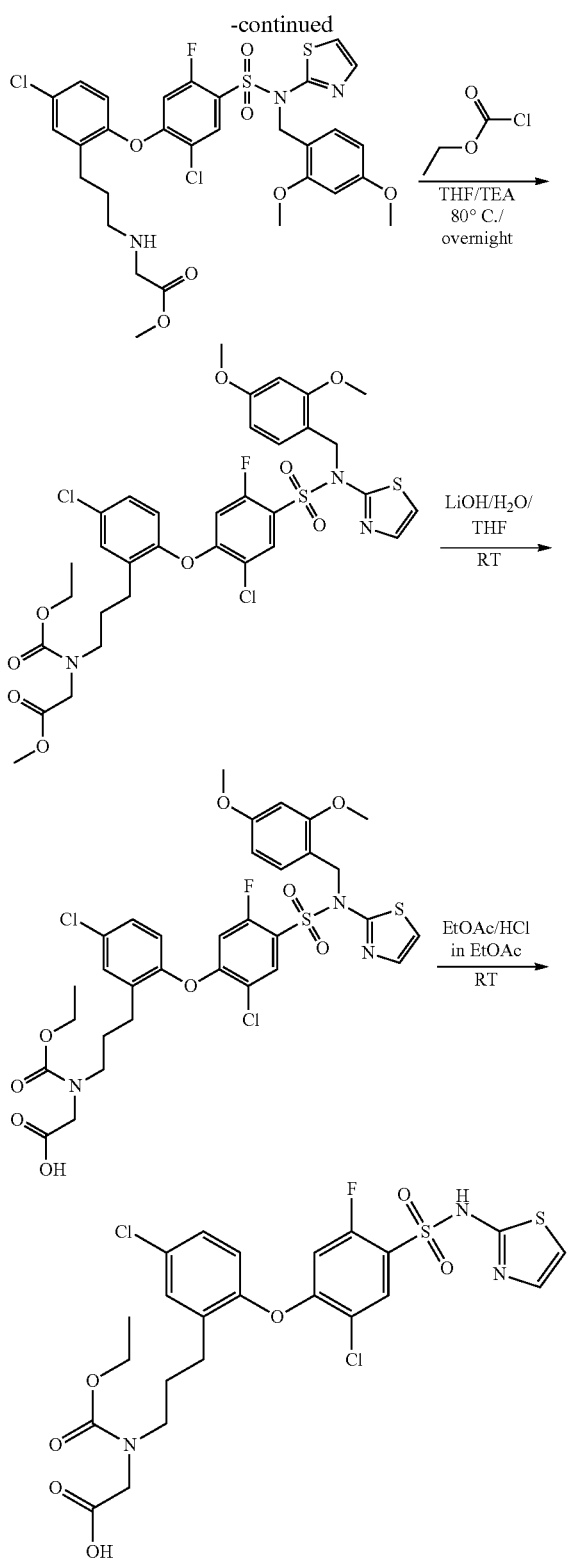

34

Step 1: Preparation of 3-(5-chloro-2-hydroxyphenyl)acrylaldehyde

To a solution of 5-chloro-2-hydroxybenzaldehyde (20 g, 127 mmol) in THF (300 ml) was added (formylmethylene) triphenylphosphorane (43 g, 140 mmol) at room temperature. The resulting reaction mixture was refluxed at 100° C. for 20 hours. The reaction mixture was cooled to room temperature, and extracted with water (200 ml) and ethyl acetate (3×250 ml). The combined organic phase was washed with water (200 ml), brine (200 ml), dried over sodium sulphate and concentrated under vacuo to give the desired crude product. The crude product was purified by column chromatography using normal phase silica gel. The desired product eluted at around 20-30% ethyl acetate in hexane. Evaporation of the product fractions gave 20 g (yield, 87%) of desired compound as yellow solid. LC-MS: m/z=183.4 (M+H).

Step 2: Preparation of methyl 2-(3-(5-chloro-2-hydroxyphenyl)allylamino)acetate To a solution of 3-(5-chloro-2-hydroxyphenyl)acrylaldehyde (5 g, 27 mmol) and glycine methyl ester hydrochloride (4.1 g, 32 mmol) in dichloromethane (80 ml) was added magnesium sulphate (6 g, 50 mmol) and triethylamine (12 ml, 82 mmol) at room temperature. The above reaction mixture was stirred at room temperature for 18 hours. The resulting reaction mixture was then concentrated under vacuo. The concentrated mass thus obtained was dissolved in methanol (50 ml) and cooled to a temperature between 5-10° C. To the above mixture, sodium borohydride (3.0 g, 82 mmol) was added in small portions over a period of 20 minutes; during addition temperature of the reaction mixture was maintained between 10-20° C. The reaction mixture was allowed to stir at room temperature for 2 hours and concentrated under vacuo. Water (100 ml) was added to the above crude mass and the resulting mixture was extracted with ethyl acetate (3×100 ml). The combined organic extract was washed with water (50 ml), brine (50 ml), dried over sodium sulphate and concentrated under vacuo to get the desired crude product. The crude product was purified by column chromatography using normal phase silica gel. The desired product eluted at around 1-5% methanol in dichloromethane. Evaporation of the product fractions gave 4 g (yield, 58%) of desired compound as yellow solid. LC-MS: m/z=256.43 (M+H).

Step-3: Preparation of methyl 2-(3-(5-chloro-2-hydroxyphenyl)propylamino)acetate To a solution of methyl 2-(3-(5-chloro-2-hydroxyphenyl)allylamino)acetate (3.5 g, 13.6 mmol) in methanol (80 ml) was carefully added 10% Palladium on carbon with 50% moisture (0.145 g, 1.3 mmol). Hydrogen gas was then bubbled into the reaction mixture at room temperature for a period of 30 minutes. After completion of the reaction, the reaction mixture was filtered through celite. The celite bed was carefully washed with some amount of methanol. The filtrate thus obtained was concentrated under vacuo to afford 3 g (yield, 85%) of compound as colorless liquid and used as is in the next step. LC-MS: m/z=258.5 (M+H).

Step-4: Preparation of methyl (3-(5-chloro-2-(2-chloro-4-(N-(2,4-dimethoxybenzyl)-N-(thiazol-2-yl)sulfamoyl)-5-fluorophenoxy)phenyl)propyl)glycinate To a solution methyl 2-(3-(5-chloro-2-hydroxyphenyl)propylamino)acetate (1.1 g, 4.28 mmol) in DMF (12 ml) was added $K_2CO_3$ (1.77 g, 12.8 mmol) in one portion under nitrogen atmosphere at room temperature. The resulting reaction mixture was stirred at room temperature for 15 minutes. To the above mixture was added 5-chloro-N-(2,4-dimethoxybenzyl)-2,4-difluoro-N-(thiazol-2-yl)benzenesulfonamide (1.96 g, 4.28 mmol) and the resulting mixture was stirred at room temperature for 4 hours. After completion of reaction, D.M. water (100 ml) was added and the resulting mixture was extracted with ethyl acetate (3×50 ml). The combined organic extract was washed with D.M. water (50 ml), brine (50 ml) and concentrated under vacuo to afford 1.5 g (yield, 50.2%) of desired compound. The material was used directly for next step. LC-MS: m/z=698.5 (M+H).

Step-5: Preparation of methyl N-(3-(5-chloro-2-(2-chloro-4-(N-(2,4-dimethoxybenzyl)-N-(thiazol-2-yl)sulfamoyl)-5-fluorophenoxy)phenyl)propyl)-N-(ethoxycarbonyl)glycinate To a solution of methyl (3-(5-chloro-2-(2-chloro-4-(N-(2,4-dimethoxybenzyl)-N-(thiazol-2-yl)sulfamoyl)-5-fluorophenoxy)phenyl)propyl)glycinate (1.0 g, 1.43 mmol) in dichloromethane (50 mL) was added triethyl amine (0.596 ml, 4.29 mmol) at room temperature. The resulting reaction mixture was stirred at the same temperature for 10 minutes. Ethylchloroformate (0.407 ml, 4.29 mmol) was added to the reaction mixture at room temperature. The resulting reaction mixture was then refluxed at 80° C. for 12 hours. After completion of the reaction, the reaction mixture was cooled to room temperature and dumped in to D.M. water (50 ml). The resulting mixture was extracted with dichloromethane (3×50 ml). The combined organic extract was washed with D.M. water (50 ml), brine (50 ml), dried over sodium sulphate and concentrated under vacuo to get the desired crude product. The crude product was purified by triturating with diethyl ether which gave 0.860 g (yield, 78.09%) of the desired compound as a brown solid. The material was directly used for the next step. LC-MS: m/z=770.2 (M+H).

Step-6: Preparation of N-(3-(5-chloro-2-(2-chloro-4-(N-(2,4-dimethoxybenzyl)-N-(thiazol-2-yl)sulfamoyl)-5-fluorophenoxy)phenyl)propyl)-N-(ethoxycarbonyl)glycine To the solution of methyl N-(3-(5-chloro-2-(2-chloro-4-(N-(2,4-dimethoxybenzyl)-N-(thiazol-2-yl)sulfamoyl)-5-fluorophenoxy)phenyl)propyl)-N-(ethoxycarbonyl)glycinate (0.85 g, 1.10 mmol) in THF (10 ml) was added a solution of lithium hydroxide monohydrate (0.135 g, 5.62 mmol) in D.M. water (10 ml) at room temperature. The resulting reaction mixture was stirred at room temperature for 3 hours. After completion of reaction ice cold water (20 ml) was added in to the reaction mixture, the resulting mixture was then acidified between 4-6 pH with aqueous 1N hydrochloric acid. The resulting acidic aqueous was extracted with ethyl acetate (3×30 ml). The combined organic extract was washed with D.M. water (20 ml), brine (20 ml), dried over sodium sulphate and concentrated under vacuo to afford 0.55 g (yield, 66.13%) of the compound as a white solid. This material was directly used for next step.

Step-7: Preparation of N-(3-(5-chloro-2-(2-chloro-5-fluoro-4-(N-(thiazol-2-yl)sulfamoyl)phenoxy)phenyl)propyl)-N-(ethoxycarbonyl)glycine To a solution of N-(3-(5-chloro-2-(2-chloro-4-(N-(2,4-dimethoxybenzyl)-N-(thiazol-2-yl)sulfamoyl)-5-fluorophenoxy)phenyl)propyl)-N-(ethoxycarbonyl)glycine (0.5 g, 0.66 mmol) in dichloromethane (10 ml) was added drop-wise a 4N solution of hydrochloric acid in ethyl acetate (5 ml) at room temperature. The resulting reaction mixture was stirred room temperature for 4 hours. After completion of reaction, pentane (15 ml) was added in to the reaction mixture which resulted in precipitation of solid. The solvent layer was decanted off; the solid thus obtained was washed twice with pentane (10 ml) and dried under vacuo. The resulting crude material was further purified by Prep HPLC using 0.1% HCl in Water: Acetonitrile mobile phase (PREP HPLC Method A). Evaporation of the pure product fractions obtained from Prep HPLC provided the desired product (0.04 g, 10% yield). LC-MS: m/z=606.16 (M+H). 1H-NMR (MeOD), δ 8.00-8.06 (m, 1H), 7.45 (s, 1H), 7.28-7.35 (m, 1H), 7.16 (d, J=4.6 Hz, 1H), 6.97-7.06 (m, 1H), 6.80 (d, J=4.7 Hz, 1H), 6.61-6.71 (m, 1H), 4.01-4.12 (m, 1H), 3.95 (d, J=10.6 Hz, 2H), 2.52-2.63 (m, 2H), 1.79-1.90 (m, 2H), 1.14-1.25 (m, 3H).

Example 35 ethyl 2-((3-(5-chloro-2-(2-chloro-5-fluoro-4-(N-(thiazol-2-yl)sulfamoyl)phenoxy)phenyl)propyl)amino)acetate

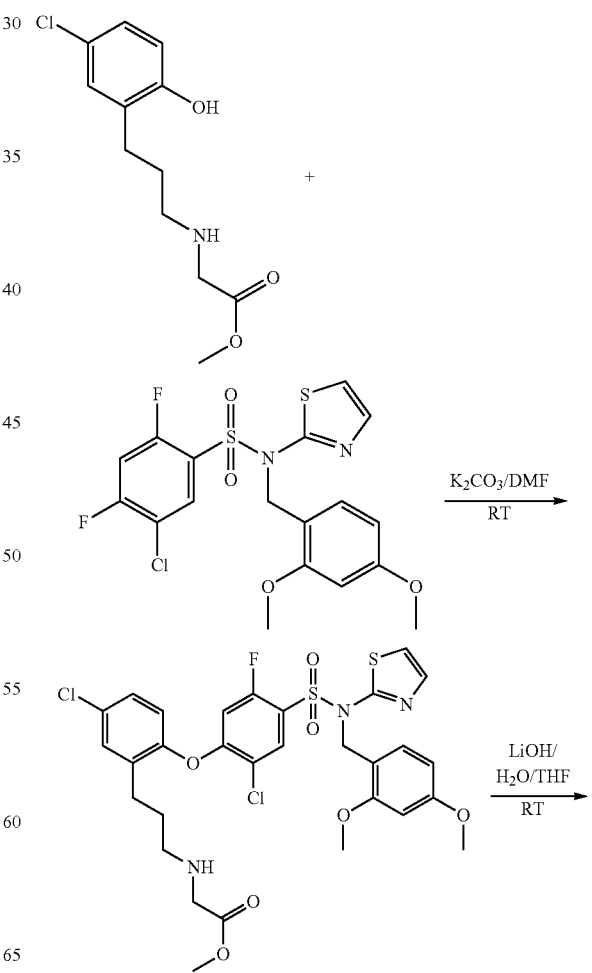

Scheme 15

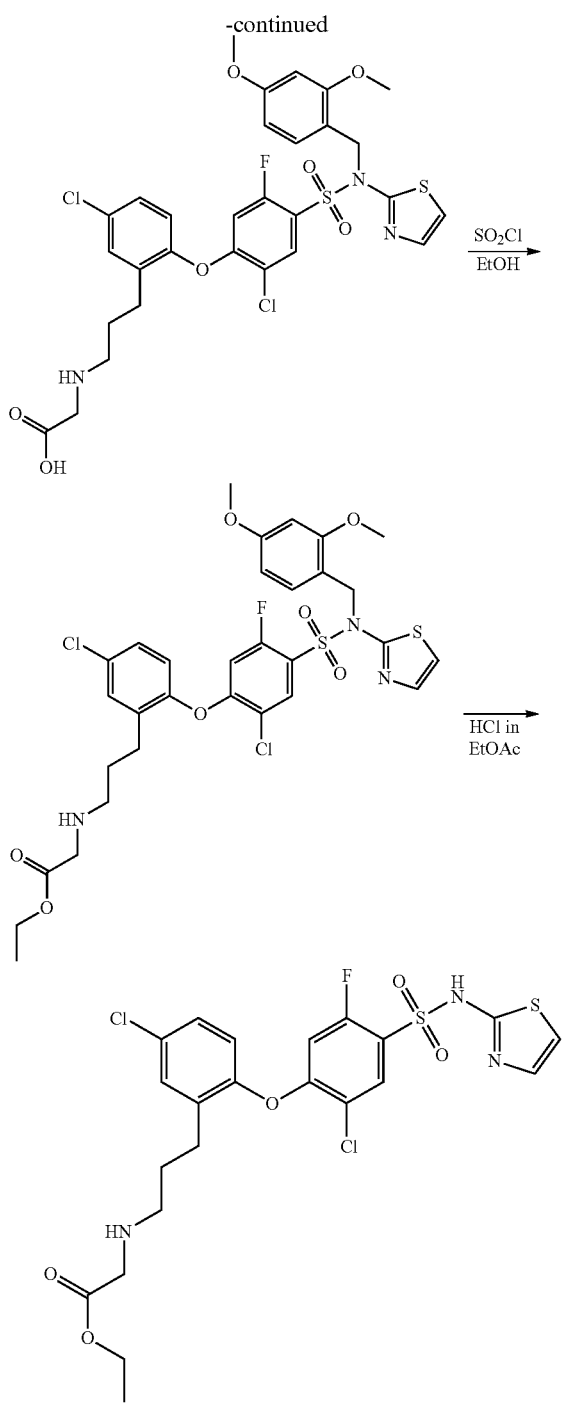

5-chloro-N-(2,4-dimethoxybenzyl)-2,4-difluoro-N-(thiazol-2-yl)benzenesulfonamide (3.14 g, 6.8 mmol) and the resulting mixture was stirred at room temperature for 4 hours. After completion of reaction, D.M. water (100 ml) was added and the resulting mixture was extracted with ethyl acetate (3×50 ml). The combined organic extract was washed with D.M. water (50 ml), brine (50 ml) and concentrated under vacuo to afford 1.0 g (yield, 23.2%) of desired compound as a solid. The material was used directly for next step.

Step-2: Preparation of (3-(5-chloro-2-(2-chloro-4-(N-(2,4-dimethoxybenzyl)-N-(thiazol-2-yl)sulfamoyl)-5-fluorophenoxy)phenyl)propyl)glycine To the solution of methyl (3-(5-chloro-2-(2-chloro-4-(N-(2,4-dimethoxybenzyl)-N-(thiazol-2-yl)sulfamoyl)-5-fluorophenoxy)phenyl)propyl)glycinate (1 g, 1.43 mmol) in THF (15 ml) was added a solution of lithium hydroxide monohydrate (0.3 g, 7.16 mmol) in D.M. water (15 ml) at room temperature. The resulting reaction mixture was stirred at room temperature for 3 hours. After completion of reaction ice cold water (20 ml) was added in to the reaction mixture, the resulting mixture was then acidified between 4-6 pH with aqueous 1N hydrochloric acid. The resulting acidic aqueous was extracted with ethyl acetate (3×30 ml). The combined organic extract was washed with D.M. water (20 ml), brine (20 ml), dried over sodium sulphate and concentrated under vacuo to afford 0.7 g (yield, 71.55%) of the compound as a white solid. This material was directly used for next step without any further purification and analysis. LC-MS: m/z=684.15 (M+H).

Step-3: Preparation of ethyl (3-(5-chloro-2-(2-chloro-4-(N-(2,4-dimethoxybenzyl)-N-(thiazol-2-yl)sulfamoyl)-5-fluorophenoxy)phenyl)propyl)glycinate To a solution of (3-(5-chloro-2-(2-chloro-4-(N-(2,4-dimethoxybenzyl)-N-(thiazol-2-yl)sulfamoyl)-5-fluorophenoxy)phenyl)propyl)glycine (0.5 g, 0.73 mmol) in ethanol (10 ml) was added thionyl chloride (0.53 ml, 7.3 mmol) at 0° C. The resulting reaction mixture was then refluxed for 12 hours. After completion of reaction the reaction mixture was evaporated under vacuo and D.M. water (30 ml) was added to the resulting residue. The resulting mixture was extracted with ethyl acetate (3×50 ml). The combined organic extracts was washed with D.M. water (20 ml), brine (20 ml), dried over sodium sulphate and concentrated under vacuo to get the desired crude product. The crude product was purified by triturating with diethyl ether which gave 0.4 g (yield, 76.9%) of the desired compound. The material was used directly for next step. LC-MS: m/z=712.4 (M+H).

Step-4: Preparation of ethyl (3-(5-chloro-2-(2-chloro-5-fluoro-4-(N-(thiazol-2-yl)sulfamoyl)phenoxy)phenyl)propyl)glycinate To a solution of ethyl (3-(5-chloro-2-(2-chloro-4-(N-(2,4-dimethoxybenzyl)-N-(thiazol-2-yl)sulfamoyl)-5-fluorophenoxy)phenyl)propyl)glycinate (0.35 g, 0.49 mmol) in dichloromethane (10 ml) was added drop-wise a 4N solution of hydrochloric acid in ethyl acetate (5 ml) at room temperature. The resulting reaction mixture was stirred room temperature for 4 hours. After completion of reaction, pentane (15 ml) was added in to the reaction mixture which resulted in precipitation of solid. The solvent layer was decanted off; the solid thus obtained was washed twice with

35

Step-1: Preparation of methyl (3-(5-chloro-2-(2-chloro-4-(N-(2,4-dimethoxybenzyl)-N-(thiazol-2-yl)sulfamoyl)-5-fluorophenoxy)phenyl)propyl)glycinate To a solution methyl 2-(3-(5-chloro-2-hydroxyphenyl)propylamino)acetate (1.6 g, 6.22 mmol), which was synthesized according to the procedure described for compound 11, in DMF (12 ml) was added $K_2CO_3$ (2.5 g, 18.6 mmol) in one portion under nitrogen atmosphere at room temperature. The resulting reaction mixture was stirred at room temperature for 15 minutes. To the above mixture was added pentane (10 ml) and dried under vacuo. The resulting crude material was further purified by Prep HPLC using 0.1% HCl in water: acetonitrile mobile phase (PREP HPLC Method A). Evaporation of the pure product fractions obtained from Prep HPLC provided the desired product (0.045 g, 16.32% yield). LC-MS: m/z=562.04 (M+H). $^1$H-NMR (MeOD), δ 8.03-8.08 (m, 1H) 7.46-7.49 (m, 1H) 7.33-7.38 (m, 1H) 7.15-7.19 (m, 1H) 7.00-7.04 (m, 1H) 6.81-6.85 (m, 1H) 6.75-6.79 (m, 1H) 4.29-4.36 (m, 2H) 3.97 (s, 2H) 3.07-3.13 (m, 2H) 2.67-2.74 (m, 2H) 2.00-2.08 (m, 2H) 1.29-1.37 (m, 3H).

Example 42

4-(2-(3-((1H-pyrazol-4-yl)amino)propyl)-4-chloro-phenoxy)-5-chloro-2-fluoro-N-(thiazol-2-yl)benzenesulfonamide Compound 42 was synthesized according to the procedure described for the synthesis of compound 11 by replacing glycine methyl ester with 1H-pyrazol-4-amine in step 2, and omitting step 5. LC-MS: m/z=541.82 (M+H). 1H-NMR (MeOD), δ 8.78 (d, J=2.1 Hz, 1H), 8.02 (d, J=7.1 Hz, 1H), 7.89 (s, 2H), 7.48 (d, J=2.4 Hz, 1H), 7.32-7.40 (m, 1H), 7.12 (d, J=2.1 Hz, 1H), 7.01 (d, J=8.7 Hz, 1H), 6.74 (d, J=10.7 Hz, 1H), 3.36-3.44 (m, 2H), 2.70 (t, J=7.7 Hz, 2H), 2.06 (s, 2H).

Example 43

3-((3-(5-chloro-2-(2,5-difluoro-4-(N-(thiazol-2-yl)sulfamoyl)phenoxy)phenyl)propyl)amino)propanoic acid Compound 43 was synthesized according to the procedure described for the synthesis of compound 11 by replacing glycine methyl ester with beta alanine methyl ester in step 2, and replacing tert-butyl 5-chloro-2,4-difluorophenylsulfonyl(thiazol-4-yl)carbamate with N-(2,4-dimethoxybenzyl)-2,4,5-trifluoro-N-(thiazol-2-yl)benzenesulfonamide in step 4. LC-MS: m/z=532.14 (M+H). 1H-NMR (MeOD), δ 7.78-7.85 (m, 1H) 7.44-7.51 (m, 1H) 7.27-7.36 (m, 1H) 7.13-7.19 (m, 1H) 6.96-7.03 (m, 1H) 6.83-6.91 (m, 1H) 6.79 (s, 1H) 3.11-3.18 (m, 2H) 3.01-3.08 (m, 2H) 2.71-2.80 (m, 2H) 2.43-2.52 (m, 2H) 1.97-2.08 (m, 2H).

Example 44

5-chloro-4-(4-chloro-2-(3-((2-(methylsulfonyl)ethyl)amino)propyl)phenoxy)-2-fluoro-N-(thiazol-4-yl)benzenesulfonamide Compound 44 was synthesized according to the procedure described for the synthesis of compound 11 by replacing glycine methyl ester with 2-(methylsulfonyl)ethanamine in step 2, and omitting step 5. LC-MS: m/z=581.83 (M+H). 1H-NMR (MeOD), δ 8.77 (d, J=2.2 Hz, 1H), 7.99-8.07 (m, 1H), 7.46-7.53 (m, 1H), 7.31-7.41 (m, 1H), 7.10 (d, J=2.2 Hz, 1H), 7.04 (s, 1H), 6.69-6.77 (m, 1H), 3.46-3.52 (m, 2H), 3.39-3.45 (m, 2H), 3.09 (s, 3H), 2.97-3.04 (m, 2H), 2.63-2.71 (m, 2H), 1.94-2.04 (m, 2H).

Example 45

4-(2-(3-((1H-pyrazol-3-yl)amino)propyl)-4-chloro-phenoxy)-5-chloro-2-fluoro-N-(thiazol-4-yl)benzenesulfonamide Compound 45 was synthesized according to the procedure described for the synthesis of compound 11 by replacing glycine methyl ester with 1H-pyrazol-3-amine in step 2, and omitting step 5. LC-MS: m/z=541.99 (M+H). 1H-NMR (MeOD), δ 8.76 (d, J=2.2 Hz, 1H), 7.95 (d, J=7.2 Hz, 1H), 7.76-7.82 (m, 1H), 7.45 (d, J=2.6 Hz, 1H), 7.33 (dd, J=8.6, 2.6 Hz, 1H), 7.10 (d, J=2.2 Hz, 1H), 7.02 (d, J=8.7 Hz, 1H), 6.63 (d, J=10.8 Hz, 1H), 5.74 (d, J=2.9 Hz, 1H), 3.19 (t, J=6.7 Hz, 2H), 2.62-2.71 (m, 2H), 1.82-1.98 (m, 2H).

Example 46

2-((3-(5-chloro-2-(2-chloro-5-fluoro-4-(N-(thiazol-4-yl)sulfamoyl)phenoxy)phenyl)propyl)amino)-N-methylacetamide Compound 46 was synthesized according to the procedure described for the synthesis of compound 11 by replacing glycine methyl ester with 2-amino-N-methylacetamide in step 2, and omitting step 5. LC-MS: m/z=546.88 (M+H). 1H-NMR (MeOD), δ 8.74-8.81 (m, 1H), 7.97-8.07 (m, 1H), 7.46-7.51 (m, 1H), 7.32-7.40 (m, 1H), 7.09-7.15 (m, 1H), 6.97-7.06 (m, 1H), 6.68-6.82 (m, 1H), 3.76 (s, 2H), 3.01-3.09 (m, 2H), 2.80 (s, 3H), 2.63-2.72 (m, 2H), 1.97-2.07 (m, 2H).

Example 47

2-((3-(5-chloro-2-(2-chloro-5-fluoro-4-(N-(thiazol-4-yl)sulfamoyl)phenoxy)phenyl)propyl)(methyl)amino)acetic acid Compound 47 was synthesized according to the procedure described for the synthesis of compound 11 by replacing glycine methyl ester with sarcosine methyl ester in step 2. LC-MS: m/z=548.04 (M+H). 1H-NMR (MeOD), δ 8.73 (d, J=2.1 Hz, 1H), 8.01 (d, J=7.1 Hz, 1H), 7.49 (d, J=2.5 Hz, 1H), 7.34 (dd, J=8.7, 2.6 Hz, 1H), 6.99 (d, J=8.7 Hz, 1H), 6.94 (d, J=2.1 Hz, 1H), 6.74 (d, J=10.6 Hz, 1H), 3.61 (s, 2H), 3.09-3.19 (m, 2H), 2.84 (s, 3H), 2.67 (t, J=7.7 Hz, 2H), 2.06 (t, J=8.0 Hz, 2H).

Example 48

5-chloro-4-(4-chloro-2-(3-(6,7-dihydro-1H-pyrazolo[4,3-c]pyridin-5(4H)-yl)propyl)phenoxy)-2-fluoro-N-(thiazol-4-yl)benzenesulfonamide Compound 48 was synthesized according to the procedure described for the synthesis of compound 11 by replacing glycine methyl ester with 4,5,6,7-tetrahydro-1H-pyrazolo[4,3-c]pyridine in step 2, and omitting step 5. LC-MS: m/z=581.90 (M+H). 1H-NMR (MeOD), δ 8.76 (br. s, 1H), 8.02 (br. s, 1H), 7.67 (br. s, 1H), 7.54 (br. s, 1H), 7.35 (br. s, 1H), 7.13 (br. s, 1H), 7.03 (d, J=6.7 Hz, 1H), 6.73-6.79 (m, 1H), 4.55-4.57 (m, 1H), 4.19-4.21 (m, 1H), 3.81 (br. s, 1H), 3.66 (br. s, 1H), 3.50 (br. s, 1H), 3.29 (s, 1H), 3.15 (br. s, 3H), 2.68-2.72 (m, 3H), 2.15 (br. s, 2H).

Example 49

2-((3-(5-chloro-2-(2-chloro-5-fluoro-4-(N-(thiazol-4-yl)sulfamoyl)phenoxy)phenyl)propyl)amino)acetamide Preparation of 2-((3-(5-chloro-2-hydroxyphenyl)propyl)amino)acetamide Methyl (3-(5-chloro-2-hydroxyphenyl)propyl)glycinate was synthesized as described in the procedure for compound 11. A solution of methyl (3-(5-chloro-2-hydroxyphenyl)propyl)glycinate (6.0 g, 23.25 mmol) in methanol (200 ml) was cooled to −78° C. using acetone/dry ice bath. Ammonia gas was then purged in this cold reaction mixture for 1-3 hours. The reaction assembly was then tightly closed and the reaction mixture was allowed to warm to room temperature whereby it further stirred for next 18 hours. The reaction mixture was monitored on TLC using pure ethyl acetate as mobile phase. After completion of reaction, the reaction mixtures was mixed and evaporated under vacuo to get a crude material which was further co-evaporated two times with diethyl ether. This crude material was triturated with Diethyl ether (2×50 ml) and pentane (50 ml), the resulting solid filtered off under vacuo and was directly used for the next step without any further purification. LC-MS: m/z=243.08 (M+H).

Preparation of 2-((3-(5-chloro-2-(2-chloro-5-fluoro-4-(N-(thiazol-4-yl)sulfamoyl)phenoxy)phenyl)propyl)amino)acetamide (49)

Compound 49 was synthesized according to the procedure described for the synthesis of compound 11 by replacing methyl 2-(3-(5-chloro-2-hydroxyphenyl)propylamino)acetate with 2-((3-(5-chloro-2-hydroxyphenyl)propyl)amino) acetamide in step 4, and omitting step 5. LC-MS: m/z=533. (M+H). 1H-NMR (MeOD), δ 8.77 (s, 1H), 8.03 (d, J=6.4 Hz, 1H), 7.49 (s, 1H), 7.37 (d, J=8.8 Hz, 1H), 7.12 (s, 1H), 7.03 (d, J=8.8 Hz, 1H), 6.76 (d, J=10.4 Hz, 1H), 3.80 (s, 2H), 3.06 (t, J=8 Hz, 2H), 2.68 (t, J=7.6 Hz, 2H), 2.03 (t, J=8 Hz, 2H).

Example 50 isopentyl 2-((3-(5-chloro-2-(2-chloro-5-fluoro-4-(N-(thiazol-2-yl)sulfamoyl)phenoxy)phenyl)propyl) amino)acetate Compound 50 was synthesized according to the procedure described for the synthesis of compound 35 by replacing ethanol with 3-methylbutan-1-ol in step 3. LC-MS: m/z=604.14 (M+H). 1H-NMR (DMSO), δ 7.91-8.00 (m, 1H), 7.50-7.56 (m, 1H), 7.32-7.40 (m, 2H), 7.06-7.14 (m, 1H), 6.90-6.99 (m, 2H), 4.16-4.25 (m, 2H), 3.98-4.04 (m, 2H), 2.90-2.97 (m, 2H), 2.57-2.64 (m, 2H), 1.87-1.96 (m, 2H), 1.61-1.72 (m, 1H), 1.45-1.55 (m, 2H), 0.90 (d, J=6.6 Hz, 6H).

Example 51 isopropyl 2-((3-(5-chloro-2-(2-chloro-5-fluoro-4-(N-(thiazol-2-yl)sulfamoyl)phenoxy)phenyl)propyl) amino)acetate Compound 51 was synthesized according to the procedure described for the synthesis of compound 35 by replacing ethanol with isopropanol in step 3. LC-MS: m/z=575.92 (M+H). 1H-NMR (MeOD), δ 1.31 (s, 3H) 1.32 (s, 3H) 2.01-2.09 (m, 2H) 2.71 (t, J=7.63 Hz, 2H) 3.07-3.15 (m, 2H) 3.95 (s, 2H) 5.11-5.19 (m, 1H) 6.76 (d, J 10.45 Hz, 1H) 6.82 (d, J=4.65 Hz, 1H) 7.01 (d, J=8.70 Hz, 1H) 7.18 (d, J=4.65 Hz, 1H) 7.35 (dd, J=8.70, 2.59 Hz, 1H) 7.49 (d, J=2.52 Hz, 1H) 8.05 (d, J=7.10 Hz, 1H).

Example 52 methyl 2-((3-(5-chloro-2-(2-chloro-5-fluoro-4-(N-(thiazol-4-yl)sulfamoyl)phenoxy)phenyl)propyl) (methyl)amino)acetate Compound 52 was synthesized according to the procedure described for the synthesis of compound 11 by replacing glycine methyl ester with sarcosine methyl ester in step 2, and omitting step 5. LC-MS: m/z=562.14 (M+H). 1H-NMR (MeOD), δ 8.76 (d, J=2.2 Hz, 1H), 8.00 (d, J=7.2 Hz, 1H), 7.45 (d, J=2.6 Hz, 1H), 7.29-7.36 (m, 1H), 6.97-7.10 (m, 2H), 6.66 (d, J=10.8 Hz, 1H), 3.68 (s, 3H), 3.24 (s, 2H), 2.56 (s, 2H), 2.48 (d, J=7.6 Hz, 2H), 2.28 (s, 3H), 1.71-1.81 (m, 2H).

Example 53

2-((3-(5-chloro-2-(2-chloro-5-fluoro-4-(N-(thiazol-2-yl)sulfamoyl)phenoxy)phenyl)propyl)((pentyloxy) carbonyl)amino)acetic acid Scheme 16

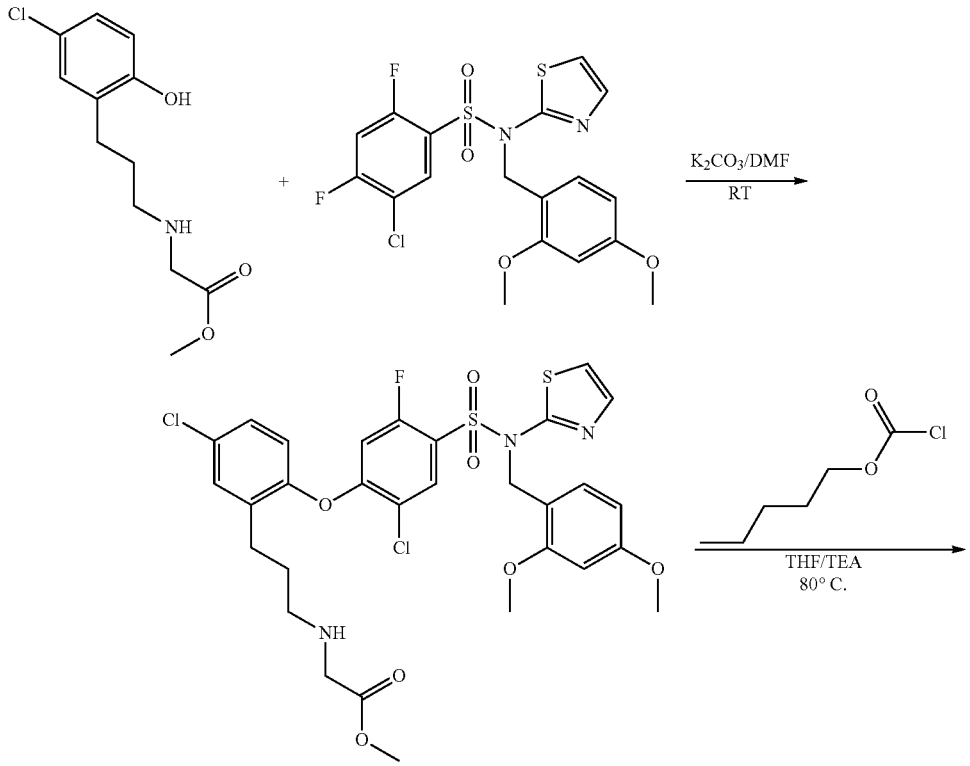

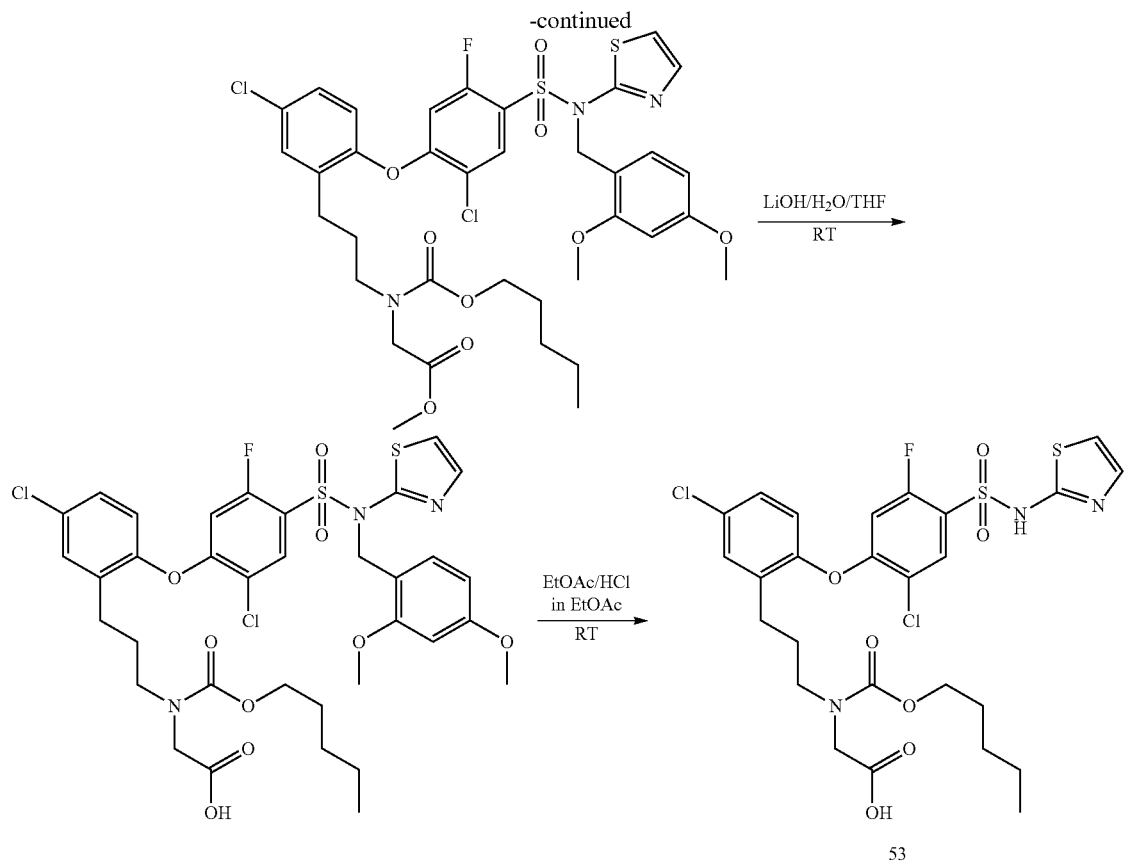

Step-1: Preparation of methyl (3-(5-chloro-2-(2-chloro-4-(N-(2,4-dimethoxybenzyl)-N-(thiazol-2-yl)sulfamoyl)-5-fluorophenoxy)phenyl)propyl)glycinate To a solution methyl 2-(3-(5-chloro-2-hydroxyphenyl)propylamino)acetate (0.6 g, 2.3 mmol), which was synthesized according to the procedure described for compound 11, in DMF (10 ml) was added K$_2$CO$_3$ (0.96 g, 6.9 mmol) in one portion under nitrogen atmosphere at room temperature. The resulting reaction mixture was stirred at room temperature for 15 minutes. To the above mixture was added 5-chloro-N-(2,4-dimethoxybenzyl)-2,4-difluoro-N-(thiazol-2-yl)benzenesulfonamide (1.17 g, 2.5 mmol) and the resulting mixture was stirred at room temperature for 4 hours. After completion of reaction, D.M. water (100 ml) was added and the resulting mixture was extracted with ethyl acetate (3×50 ml). The combined organic extract was washed with D.M. water (50 ml), brine (50 ml). The combined organic layers were washed with brine, dried over sodium sulphate and concentrated under vacuo to afford 0.6 g (yield, 37.36%) of the desired compound. The material was used directly for next step. LC-MS: m/z=698.1 (M+H).

Step-2: Preparation of methyl N-(3-(5-chloro-2-(2-chloro-4-(N-(2,4-dimethoxybenzyl)-N-(thiazol-2-yl)sulfamoyl)-5-fluorophenoxy)phenyl)propyl)-N-((pentyloxy)carbonyl)glycinate To a solution of methyl (3-(5-chloro-2-(2-chloro-4-(N-(2,4-dimethoxybenzyl)-N-(thiazol-2-yl)sulfamoyl)-5-fluorophenoxy)phenyl)propyl)glycinate (0.6 g, 0.85 mmol) in dichloromethane (30 ml) was added triethyl amine (0.36 ml, 2.57 mmol) at room temperature. The resulting reaction mixture was stirred at the same temperature for 10 minutes. Pentyl chloroformate (0.38 ml, 2.57 mmol) was added to the reaction mixture at room temperature. The resulting reaction mixture was then refluxed at 80° C. for 12 hours. After completion of the reaction, the reaction mixture was cooled to room temperature and dumped in to D.M. water (50 ml). The resulting mixture was extracted with dichloromethane (3×50 ml). The combined organic extract was washed with D.M. water (50 ml), brine (50 ml), dried over sodium sulphate and concentrated under vacuo to get the desired crude product. The crude product was purified by triturating with diethyl ether which gave 0.6 g (yield, 86.9%) of the desired compound as a brown solid. MS: m/z=812.21 (M+H).

Step-3: Preparation of N-(3-(5-chloro-2-(2-chloro-4-(N-(2,4-dimethoxybenzyl)-N-(thiazol-2-yl)sulfamoyl)-5-fluorophenoxy)phenyl)propyl)-N-((pentyloxy)carbonyl)glycine To the solution of methyl N-(3-(5-chloro-2-(2-chloro-4-(N-(2,4-dimethoxybenzyl)-N-(thiazol-2-yl)sulfamoyl)-5-fluorophenoxy)phenyl)propyl)-N-((pentyloxy)carbonyl) glycinate (0.6 g, 0.738 mmol) in THF (20 ml) was added a solution of lithium hydroxide monohydrate (0.1 g, 4.43 mmol) in D.M. water (10 ml) at room temperature. The resulting reaction mixture was stirred at room temperature for 3 hours. After completion of reaction ice cold water (20 ml) was added in to the reaction mixture, the resulting mixture was then acidified between 4-6 pH with aqueous 1N hydrochloric acid. The resulting acidic aqueous was extracted with ethyl acetate (3×30 ml). The combined organic extract was washed with D.M. water (20 ml), brine (20 ml), dried over sodium sulphate and concentrated under vacuo to afford 0.5 g (yield, 84.89%) of the compound as a white solid. This material was directly used for next step.

Step-4: Preparation of N-(3-(5-chloro-2-(2-chloro-5-fluoro-4-(N-(thiazol-2-yl)sulfamoyl)phenoxy)phenyl)propyl)-N-((pentyloxy)carbonyl)glycine To a solution of N-(3-(5-chloro-2-(2-chloro-4-(N-(2,4-dimethoxybenzyl)-N-(thiazol-2-yl)sulfamoyl)-5-fluorophenoxy)phenyl)propyl)-N-((pentyloxy)carbonyl)glycine (0.5 g, 0.626 mmol) in dichloromethane (15 ml) was added drop-wise a 4N solution of hydrochloric acid in ethyl acetate (5 ml) at room temperature. The resulting reaction mixture was stirred room temperature for 4 hours. After completion of reaction, pentane (10 ml) was added in to the reaction mixture which resulted in precipitation of solid. The solvent layer was decanted off; the solid thus obtained was washed twice with pentane (10 ml) and dried under vacuo. The resulting crude material was further purified by Prep HPLC using 0.1% HCl in water: acetonitrile mobile phase (PREP HPLC Method A). Evaporation of the pure product fractions obtained from Prep HPLC provided the desired product (0.05 g, 12.3% yield). LC-MS: m/z=648.14 (M+H). 1H-NMR (DMSO), δ 13.02 (br. s, 1H), 12.63 (br. s, 1H), 7.89-7.96 (m, 1H), 7.44-7.51 (m, 1H), 7.30-7.36 (m, 2H), 7.05-7.13 (m, 1H), 6.80-6.94 (m, 2H), 3.83-3.93 (m, 4H), 3.16-3.28 (m, 2H), 1.66-1.81 (m, 2H), 1.39-1.51 (m, 2H), 1.12-1.28 (m, 4H), 0.74-0.88 (m, 3H).

Example 54

2-((3-(5-chloro-2-(2-chloro-5-fluoro-4-(N-(thiazol-2-yl)sulfamoyl)phenoxy)phenyl)propyl)(prop-2-yn-1-yl)amino)acetic acid

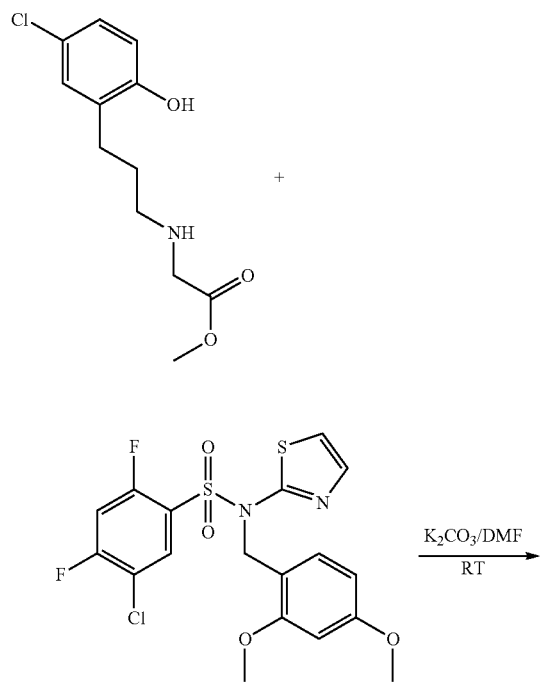

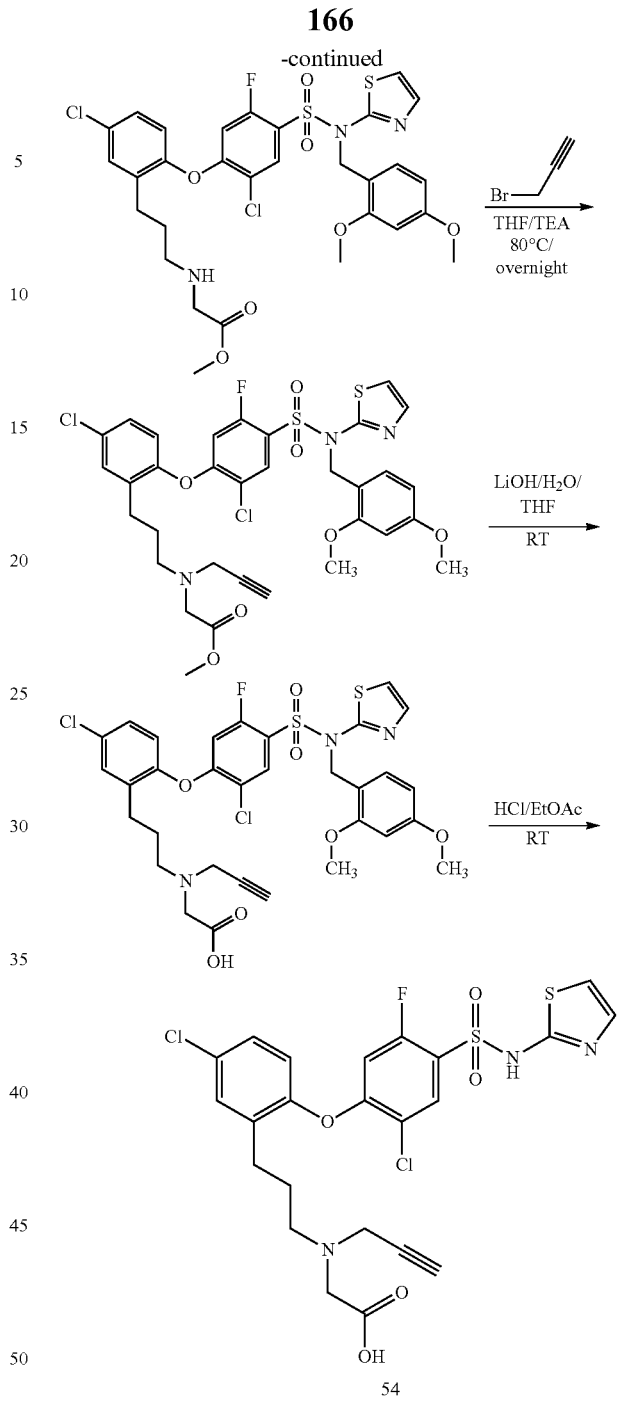

Step-1: Preparation of methyl (3-(5-chloro-2-(2-chloro-4-(N-(2,4-dimethoxybenzyl)-N-(thiazol-2-yl)sulfamoyl)-5-fluorophenoxy)phenyl)propyl)glycinate To a solution methyl 2-(3-(5-chloro-2-hydroxyphenyl)propylamino)acetate (1.1 g, 4.28 mmol) in DMF (12 ml) was added $K_2CO_3$ (1.77 g, 12.8 mmol) in one portion under nitrogen atmosphere at room temperature. The resulting reaction mixture was stirred at room temperature for 15 minutes. To the above mixture was added 5-chloro-N-(2,4-dimethoxybenzyl)-2,4-difluoro-N-(thiazol-2-yl)benzenesulfonamide (1.96 g, 4.28 mmol) and the resulting mixture was stirred at room temperature for 4 hours. After completion of reaction, D.M. water (100 ml) was added and the resulting mixture was extracted with ethyl acetate (3×50 ml). The combined organic extract was washed with D.M. water (50 ml), brine (50 ml). The combined organic layers were washed with brine, dried over sodium sulphate and concentrated under vacuo to afford 1.5 g (yield, 50.2%) of desired compound as a solid. The material was used directly for next step. LC-MS: m/z=698.5 (M+H).

Step-2: Preparation of methyl N-(3-(5-chloro-2-(2-chloro-4-(N-(2,4-dimethoxybenzyl)-N-(thiazol-2-yl)sulfamoyl)-5-fluorophenoxy)phenyl)propyl)-N-(prop-2-yn-1-yl)glycinate To a solution of methyl (3-(5-chloro-2-(2-chloro-4-(N-(2,4-dimethoxybenzyl)-N-(thiazol-2-yl)sulfamoyl)-5-fluorophenoxy)phenyl)propyl)glycinate (0.9 g, 1.28 mmol) in dichloromethane (30 mL) was added triethyl amine (0.54 ml, 3.86 mmol) at room temperature. The resulting reaction mixture was stirred at the same temperature for 10 minutes. 3-Bromoprop-1-yne (0.346 ml, 3.86 mmol) was added to the reaction mixture at room temperature. The resulting reaction mixture was then refluxed at 80° C. for 12 hours. After completion of the reaction, the reaction mixture was cooled to room temperature and dumped in to D.M. water (50 ml). The resulting mixture was extracted with dichloromethane (3×50 ml). The combined organic extract was washed with D.M. water (50 ml), brine (50 ml), dried over sodium sulphate and concentrated under vacuo to get the desired crude product. The crude product was purified by triturating with diethyl ether which gave 0.780 g (yield, 77.8%) of the desired compound as a brown solid. LC-MS: m/z=736.15 (M+H).

Step-3: Preparation of N-(3-(5-chloro-2-(2-chloro-4-(N-(2,4-dimethoxybenzyl)-N-(thiazol-2-yl)sulfamoyl)-5-fluorophenoxy)phenyl)propyl)-N-(prop-2-yn-1-yl)glycine To the solution of methyl N-(3-(5-chloro-2-(2-chloro-4-(N-(2,4-dimethoxybenzyl)-N-(thiazol-2-yl)sulfamoyl)-5-fluorophenoxy)phenyl)propyl)-N-(prop-2-yn-1-yl)glycinate (0.7 g, 0.95 mmol) in THF (30 ml) was added a solution of lithium hydroxide monohydrate (0.2 g, 4.75 mmol) in D.M. water (10 ml) at room temperature. The resulting reaction mixture was stirred at room temperature for 3 hours. After completion of reaction ice cold water (20 ml) was added in to the reaction mixture, the resulting mixture was then acidified between 4-6 pH with aqueous 1N hydrochloric acid. The resulting acidic aqueous was extracted with ethyl acetate (3×30 ml). The combined organic extract was washed with D.M. water (20 ml), brine (20 ml), dried over sodium sulphate and concentrated under vacuo to afford 0.43 g (yield, 62.68%) of the compound as a white solid. This material was directly used for next step.

Step-4: Preparation of N-(3-(5-chloro-2-(2-chloro-5-fluoro-4-(N-(thiazol-2-yl)sulfamoyl)phenoxy)phenyl)propyl)-N-(prop-2-yn-1-yl)glycine To a solution of N-(3-(5-chloro-2-(2-chloro-4-(N-(2,4-dimethoxybenzyl)-N-(thiazol-2-yl)sulfamoyl)-5-fluorophenoxy)phenyl)propyl)-N-(prop-2-yn-1-yl)glycine (0.4 g, 0.554 mmol) in ethyl acetate (10 ml) was added drop-wise a 4N solution of hydrochloric acid in ethyl acetate (5 ml) at room temperature. The resulting reaction mixture was stirred room temperature for 4 hours. After completion of reaction, pentane (10 ml) was added in to the reaction mixture which resulted in precipitation of solid. The solvent layer was decanted off; the solid thus obtained was washed twice with pentane (10 ml) and dried under vacuo. The resulting crude material was further purified by Prep HPLC using 0.1% HCl in Water: Acetonitrile mobile phase (PREP HPLC Method A). Evaporation of the pure product fractions obtained from Prep HPLC provided the desired product (0.045 g (yield, 14.12%). LC-MS: m/z=572.09 (M+H). 1H-NMR (MeOD), δ 8.05 (d, J=7.1 Hz, 1H), 7.49 (d, J=2.6 Hz, 1H), 7.30-7.39 (m, 1H), 7.17 (d, J=4.7 Hz, 1H), 7.01 (d, J=8.7 Hz, 1H), 6.81 (d, J=4.7 Hz, 1H), 6.75 (d, J=10.5 Hz, 1H), 4.07 (d, J=2.3 Hz, 2H), 3.87 (s, 2H), 3.17-3.25 (m, 3H), 2.64-2.73 (m, 2H), 1.99-2.10 (m, 2H).

Example 55

5-chloro-4-(4-chloro-2-(3-(5,6-dihydroimidazo[1,2-a]pyrazin-7(8H)-yl)propyl)phenoxy)-2-fluoro-N-(thiazol-4-yl)benzenesulfonamide Compound 55 was synthesized according to the procedure described for the synthesis of compound 11 by replacing glycine methyl ester with 5,6,7,8-tetrahydroimidazo[1,2-a]pyrazine in step 2, and omitting step 5. LC-MS: m/z=583 (M+H). 1H-NMR (MeOD), δ 8.72 (d, J=2.2 Hz, 1H), 7.93-8.03 (m, 1H), 7.45-7.52 (m, 1H), 7.29-7.42 (m, 1H), 7.00-7.10 (m, 2H), 6.95 (d, J=1.4 Hz, 1H), 6.61-6.69 (m, 1H), 3.94-4.05 (m, 2H), 3.63 (s, 2H), 2.82-2.87 (m, 2H), 2.72-2.77 (m, 2H), 2.53-2.65 (m, 4H), 1.79-1.92 (m, 2H).

Example 56

5-chloro-2-fluoro-4-(2-(4,5,6,7-tetrahydropyrazolo[1,5-a]pyrimidin-3-yl)phenoxy)-N-(thiazol-2-yl)benzenesulfonamide Compound 56 was synthesized according to the procedure described for the synthesis of compound 33 by replacing 2-(5-chloro-2-methoxyphenyl)acetonitrile with 2-(2-methoxyphenyl)acetonitrile in step 5, and omitting steps 1 to 4. LC-MS: m/z=506.33 (M+H). 1H-NMR (DMSO), δ 7.86 (d, J=7.2 Hz, 1H), 7.55 (d, J=7.6 Hz, 1H), 7.22-7.36 (m, 4H), 7.14-7.19 (m, 1H), 6.85 (d, J=4.3 Hz, 1H), 6.44 (d, J=10.9 Hz, 1H), 6.03 (br. s, 1H), 3.91 (t, J=5.6 Hz, 2H), 3.16 (br. s, 2H), 1.93 (br. s, 2H).

Example 57

5-chloro-4-(4-chloro-2-(4,5,6,7-tetrahydropyrazolo[1,5-a]pyrimidin-3-yl)phenoxy)-2-fluoro-N-(thiazol-2-yl)benzenesulfonamide Compound 57 was synthesized according to the procedure described for the synthesis of compound 33 by replacing tert-butyl 5-chloro-2,4-difluorophenylsulfonyl(thiazol-4-yl)carbamate with 5-chloro-N-(2,4-dimethoxybenzyl)-2,4-difluoro-N-(thiazol-2-yl)benzenesulfonamide in step 9. LC-MS: m/z=539.82 (M+H). 1H-NMR (DMSO), δ 7.89 (s, 1H), 7.56 (d, J=2.5 Hz, 1H), 7.48 (s, 1H), 7.32 (br. s, 1H), 7.22 (s, 1H), 6.88-6.94 (m, 1H), 6.65-6.70 (m, 1H), 3.95 (t, J=5.6 Hz, 2H), 3.18 (t, J=4.8 Hz, 2H), 1.90-2.00 (m, 2H).

Example 58

5-chloro-2-fluoro-4-(2-(4,5,6,7-tetrahydropyrazolo[1,5-a]pyrimidin-3-yl)phenoxy)-N-(thiazol-4-yl)benzenesulfonamide Compound 58 was synthesized according to the procedure described for the synthesis of compound 33 by omitting steps 1 to 4, replacing 2-(5-chloro-2-methoxyphenyl)acetonitrile with 2-(2-methoxyphenyl)acetonitrile in step 5, and replacing tert-butyl 5-chloro-2,4-difluorophenylsulfonyl(thiazol-4-yl)carbamate with tert-butyl ((5-chloro-2,4-difluorophenyl)sulfonyl)(thiazol-4-yl)carbamate in step 9. LC-MS: m/z=505.87 (M+H). 1H-NMR (MeOD), δ 8.76 (d, J=2.2 Hz, 1H), 7.91-7.97 (m, 2H), 7.51-7.62 (m, 2H), 7.43-7.50 (m, 1H), 7.25-7.32 (m, 1H), 7.08 (d, J=2.2 Hz, 1H), 6.49 (d, J=10.8 Hz, 1H), 4.12 (s, 2H), 3.35-3.43 (m, 2H), 2.08-2.20 (m, 2H), 1.32 (s, 2H).

Example 59

5-chloro-4-(4-chloro-2-(3-((2-(methylsulfonyl)ethyl)amino)propyl)phenoxy)-2-fluoro-N-(thiazol-2-yl)benzenesulfonamide Compound 59 was synthesized according to the procedure described for the synthesis of compound 11 by omitting step 5, replacing glycine methyl ester with 2-(methylsulfonyl)ethanamine in step 2 and replacing tert-butyl 5-chloro-2,4-difluorophenylsulfonyl(thiazol-4-yl)carbamate with 5-chloro-N-(2,4-dimethoxybenzyl)-2,4-difluoro-N-(thiazol-2-yl)benzenesulfonamide in step 4. LC-MS: m/z=584.44 (M+H). 1H-NMR (MeOD), δ 8.05 (d, J=7.1 Hz, 1H), 7.49 (d, J=2.5 Hz, 1H), 7.35 (dd, J=8.7, 2.6 Hz, 1H), 7.18 (d, J=4.7 Hz, 1H), 7.01 (d, J=8.7 Hz, 1H), 6.71-6.86 (m, 2H), 3.49-3.61 (m, 4H), 3.09-3.18 (m, 5H), 2.72 (t, J=7.7 Hz, 2H), 2.05 (d, J=1.8 Hz, 2H).

Example 60

2-((3-(2-(2-chloro-5-fluoro-4-(N-(thiazol-4-yl)sulfamoyl)phenoxy)phenyl)propyl)amino)acetamide Scheme 18

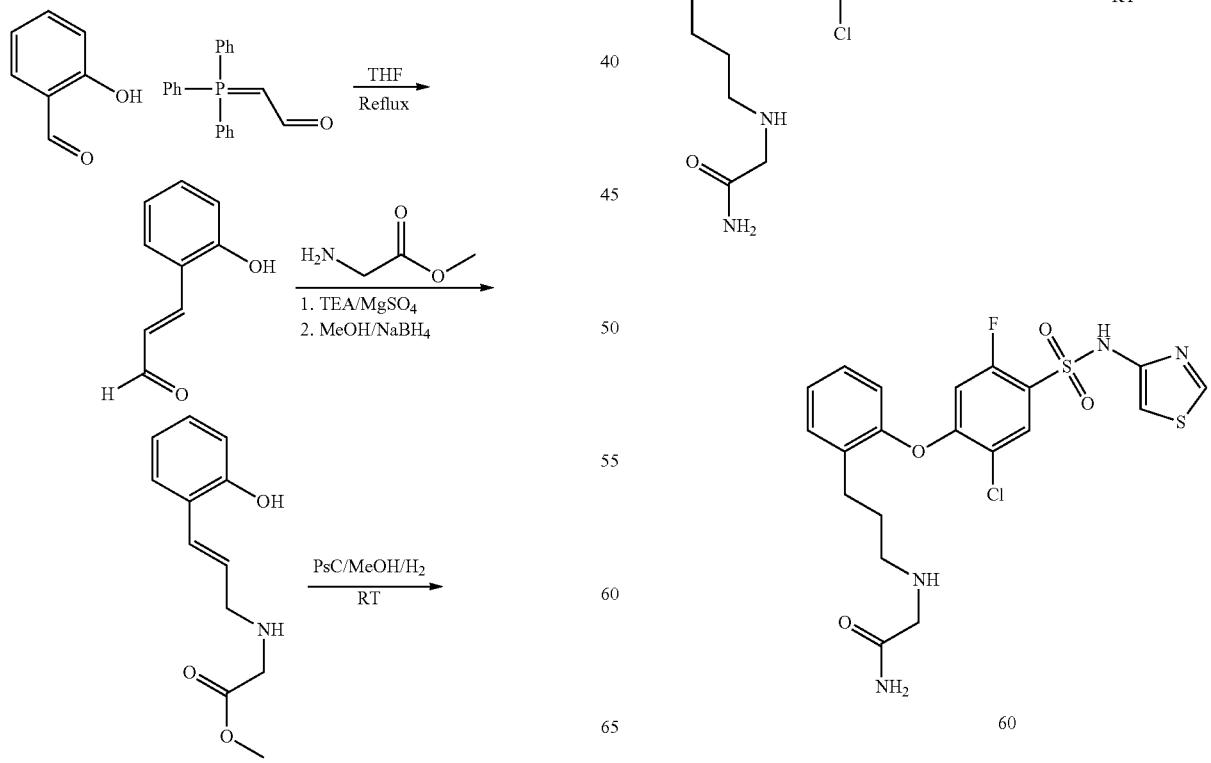

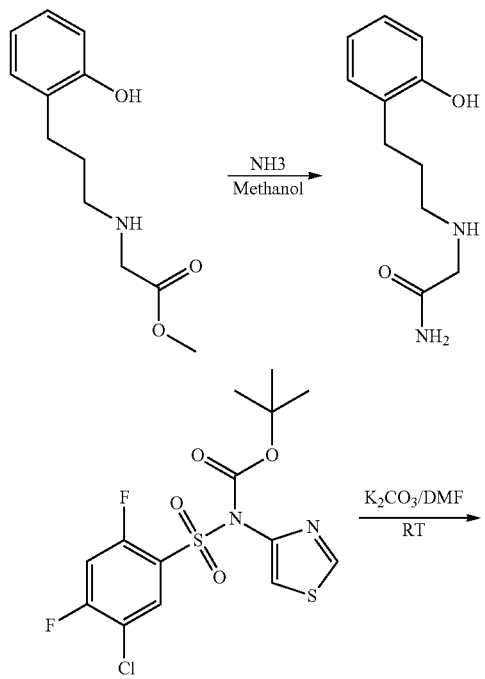

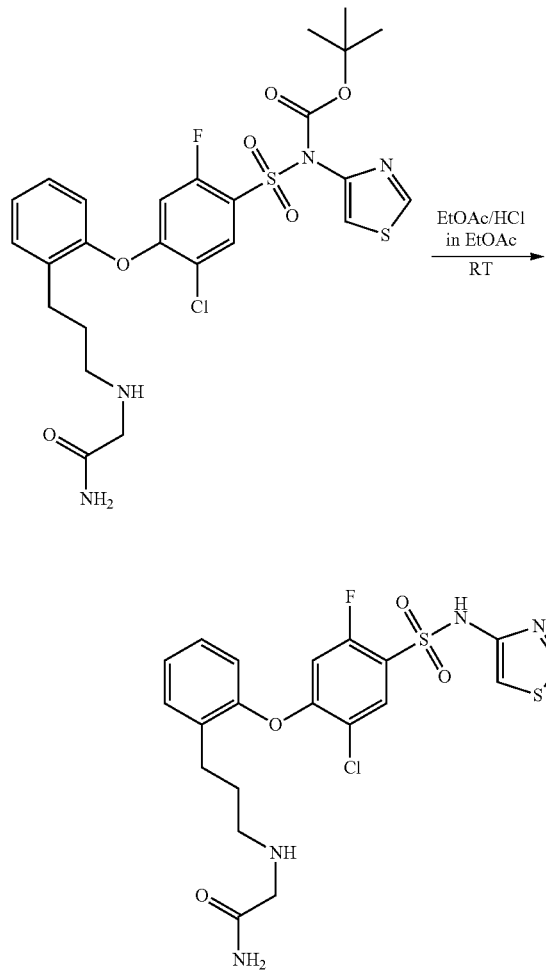

Step 1: Preparation of 3-(2-hydroxyphenyl)acrylaldehyde

To a solution of 2-hydroxybenzaldehyde (10 g, 81.8 mmol) in THF (150 ml) was added (formylmethylene) triphenylphosphorane (24.89 g, 81.8 mmol) at room temperature. The resulting reaction mixture was refluxed at 100° C. for 20 hours. The reaction mixture was cooled to room temperature, and extracted with water (200 ml) and ethyl acetate (3×150 ml). The combined organic phase was washed with water (150 ml), brine (150 ml), dried over sodium sulphate and concentrated under vacuo to give the desired crude product. The crude product was purified by column chromatography using normal phase silica gel. The desired product eluted at around 20-30% ethyl acetate in hexane. Evaporation of the product fractions gave 8.7 g (yield, 71.86%) of desired compound as yellow solid. LC-MS: m/z=149.42 (M+H).

Step 2: Preparation of methyl (3-(2-hydroxyphenyl)allyl)glycinate

To a solution of 3-(2-hydroxyphenyl)acrylaldehyde (8 g, 56.7 mmol) and glycine methyl ester hydrochloride (7.8 g, 62.4 mmol) in dichloromethane (100 ml) was added magnesium sulphate (10.21 g, 85.1 mmol) and triethylamine (16 ml, 113.4 mmol) at room temperature. The above reaction mixture was stirred at room temperature for 18 hours. The resulting reaction mixture was then concentrated under vacuo. The concentrated mass thus obtained was dissolved in methanol (50 ml) and cooled to a temperature between 5-10° C. To the above mixture, sodium borohydride (6.4 g, 170.2 mmol) was added in small portions over a period of 20 minutes; during addition temperature of the reaction mixture was maintained between 10-20° C. The reaction mixture was allowed to stir at room temperature for 2 hours and concentrated under vacuo. Water (100 ml) was added to the above crude mass and the resulting mixture was extracted with ethyl acetate (3×100 ml). The combined organic extract was washed with water (50 ml), brine (50 ml), dried over sodium sulphate and concentrated under vacuo to get the desired crude product. The crude product was purified by column chromatography using normal phase silica gel. The desired product eluted at around 1-5% methanol in dichloromethane. Evaporation of the product fractions gave 8 g (yield, 64.64%) of desired compound as yellow solid. LC-MS: m/z=222.33 (M+H).

Step-3: Preparation of methyl (3-(2-hydroxyphenyl)propyl)glycinate

To a solution of methyl (3-(2-hydroxyphenyl)allyl)glycinate (7.0 g, 31.6 mmol) in methanol (70 ml) was carefully added 10% Palladium on carbon with 50% moisture (0.335 g, 3.1 mmol). Hydrogen gas was then bubbled into the reaction mixture at room temperature for a period of 30 minutes. After completion of the reaction, the reaction mixture was filtered through celite. The celite bed was carefully washed with some amount of methanol. The filtrate thus obtained was concentrated under vacuo to afford 6 g (yield, 85.14%) of compound as colorless liquid and used as is in the next step. LC-MS: m/z=224.33 (M+H).

Step-4: Preparation of 2-((3-(2-hydroxyphenyl)propyl)amino)acetamide

A solution of methyl (3-(2-hydroxyphenyl)propyl)glycinate (2 g, 8.96 mmol) in methanol (60 ml) was cooled to −78° C. using acetone/dry ice bath. Ammonia gas was then purged in this cold reaction mixture for 1-2 hours. The reaction assembly was then tightly closed and the reaction mixture was allowed to warm to room temperature whereby it further stirred for next 18 hours. The reaction mixture was monitored on TLC using pure ethyl acetate as mobile phase. After completion of reaction, the reaction mixture is evaporated under vacuo and the obtained crude material is further co-evaporated two times with diethyl ether. This final crude material was directly used for the next step without purification. The above process gave 1.8 g (yield, 96.58%) of the desired compound. LC-MS: m/z=208.83 (M+H).

Step-5: Preparation of tert-butyl 44-(2-(3-((2-amino-2-oxoethyl)amino)propyl)phenoxy)-5-chloro-2-fluorophenyl)sulfonyl)(thiazol-4-yl)carbamate To a solution 2-((3-(2-hydroxyphenyl)propyl)amino)acetamide (0.1 g, 0.48 mmol) in DMF (3 ml) was added $K_2CO_3$ (0.13 g, 0.96 mmol) in one portion under nitrogen atmosphere at room temperature. The resulting reaction mixture was stirred at room temperature for 15 minutes. To the above reaction mixture was added tert-butyl ((5-chloro-2,4-difluorophenyl)sulfonyl)(thiazol-4-yl)carbamate (0.23 g, 0.576 mmol) and the resulting mixture was stirred at room temperature for 4-8 hours. After completion of reaction, D.M. water (20 ml) was added and the resulting mixture was extracted with ethyl acetate (2×30 ml). The combined organic extract was washed with D.M. water (20 ml), brine (20 ml), dried over sodium sulphate and concentrated under vacuo. The crude product was purified by column chromatography using normal phase silica gel. The desired product eluted at around 20 to 25% ethyl acetate in hexane. Evaporation of the product fractions gave 0.15 g (yield, 52.16%) of desired compound as a solid LC-MS: m/z=599.69 (M+H).

Step-6: Preparation of 2-((3-(2-(2-chloro-5-fluoro-4-(N-(thiazol-4-yl)sulfamoyl)phenoxy)phenyl)propyl)amino)acetamide To a solution of tert-butyl ((4-(2-(3-(2-amino-2-oxoethyl)amino)propyl)phenoxy)-5-chloro-2-fluorophenyl)sulfonyl)(thiazol-4-yl)carbamate (0.15 g, 0.25 mmol) in dichloromethane (10 ml) was added drop-wise a 4N solution of hydrochloric acid in ethyl acetate (5 ml) at room temperature. The resulting reaction mixture was stirred at room temperature for 4 hours. After completion of reaction, pentane (15 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% Formic acid in Water: Acetonitrile mobile phase (PREP HPLC Method B). Evaporation of the pure product fractions obtained from Prep HPLC provided the desired product (0.025 g, 20.04% yield). LC-MS: m/z=499.23 (M+H). 1H-NMR (MeOD), δ 8.71-8.88 (m, 1H), 7.96-8.08 (m, 1H), 7.42-7.53 (m, 1H), 7.25-7.40 (m, 2H), 7.09-7.13 (m, 1H), 7.00-7.07 (m, 1H), 6.48-6.68 (m, 1H), 3.73 (s, 2H), 2.95-3.05 (m, 2H), 2.62-2.72 (m, 2H), 1.93-2.06 (m, 2H).

Example 61

2-((3-(5-chloro-2-(2-chloro-5-fluoro-4-(N-(thiazol-4-yl)sulfamoyl)phenoxy)phenyl)propyl)(prop-2-yn-1-yl)amino)acetic acid Compound 61 was synthesized according to the procedure described for the synthesis of compound 54 by replacing 5-chloro-N-(2,4-dimethoxybenzyl)-2,4-difluoro-N-(thiazol-2-yl)benzenesulfonamide with tert-butyl 5-chloro-2,4-difluorophenylsulfonyl(thiazol-4-yl)carbamate in step 1. LC-MS: m/z=572.20 (M+H). 1H-NMR (MeOD), δ 8.77 (d, J=2.1 Hz, 1H), 8.01 (d, J=7.1 Hz, 1H), 7.49 (d, J=2.4 Hz, 1H), 7.34 (dd, J=8.7, 2.5 Hz, 1H), 7.11 (d, J=2.2 Hz, 1H), 7.02 (d, J=8.7 Hz, 1H), 6.73 (d, J=10.8 Hz, 1H), 3.91 (br. s, 2H), 3.59 (br. s, 2H), 2.98-3.07 (m, 3H), 2.60-2.67 (m, 2H), 1.92-2.02 (m, 2H).

Example 62

2-(allyl(3-(5-chloro-2-(2-chloro-5-fluoro-4-(N-(thiazol-2-yl)sulfamoyl)phenoxy)phenyl)propyl)amino)acetic acid Compound 62 was synthesized according to the procedure described for the synthesis of compound 54 by replacing 3-bromoprop-1-yne with allyl bromide in step 2. LC-MS: m/z=573.86 (M+H). 1H-NMR (DMSO), δ 12.66 (s, 1H), 7.93 (d, J=7.2 Hz, 1H), 7.50 (br. s, 1H), 7.32 (br. s, 2H), 7.09 (d, J=8.4 Hz, 1H), 6.82-6.93 (m, 2H), 5.66-5.78 (m, 1H), 5.04-5.19 (m, 2H), 3.22 (br. s, 4H), 2.60 (br. s, 2H), 2.52-2.57 (m, 2H), 1.63-1.75 (m, 2H).

Example 63

2-((3-(5-chloro-2-(2-chloro-5-fluoro-4-(N-(thiazol-2-yl)sulfamoyl)phenoxy)phenyl)propyl)amino)acetamide Compound 63 was synthesized according to the procedure described for the synthesis of compound 60 by replacing 2-hydroxybenzaldehyde with 5-chloro-2-hydroxybenzaldehyde in step 1, and replacing tert-butyl 5-chloro-2,4-difluorophenylsulfonyl(thiazol-4-yl)carbamate with 5-chloro-N-(2,4-dimethoxybenzyl)-2,4-difluoro-N-(thiazol-2-yl)benzenesulfonamide in step 5. LC-MS: m/z=532.92 (M+H). 1H-NMR (MeOD), δ 7.97-8.10 (m, 1H), 7.44-7.51 (m, 1H), 7.29-7.41 (m, 1H), 7.13-7.22 (m, 1H), 6.98-7.08 (m, 1H), 6.78-6.84 (m, 1H), 6.71-6.77 (m, 1H), 3.73 (s, 2H), 2.95-3.08 (m, 2H), 2.64-2.78 (m, 2H), 1.92-2.10 (m, 2H).

Example 64

2-(but-2-yn-1-yl(3-(5-chloro-2-(2-chloro-5-fluoro-4-(N-(thiazol-2-yl)sulfamoyl)phenoxy)phenyl)propyl)amino)acetic acid Compound 64 was synthesized according to the procedure described for the synthesis of compound 54 by replacing 3-bromoprop-1-yne with 1-bromo-2-butyne in step 2. LC-MS: m/z=585.95 (M+H). 1H-NMR (MeOD), δ 7.98-8.11 (m, 1H), 7.46-7.54 (m, 1H), 7.32-7.43 (m, 1H), 7.13-7.25 (m, 1H), 6.98-7.05 (m, 1H), 6.72-6.85 (m, 2H), 3.86-4.09 (m, 2H), 3.68-3.80 (m, 2H), 3.17-3.28 (m, 2H), 2.60-2.75 (m, 2H), 1.99-2.12 (m, 2H), 1.87 (s, 3H).

Example 65

2-((3-(5-chloro-2-(2-chloro-5-fluoro-4-(N-(thiazol-2-yl)sulfamoyl)phenoxy)phenyl)propyl)(propyl)amino)acetic acid Compound 65 was synthesized according to the procedure described for the synthesis of compound 54 by replacing 3-bromoprop-1-yne with 1-bromopropane in step 2. LC-MS: m/z=575.90 (M+H). 1H-NMR (MeOD), δ 8.03-8.08 (m, 1H), 7.48-7.52 (m, 1H), 7.30-7.37 (m, 1H), 7.17 (d, J=4.7 Hz, 1H), 7.02 (d, J=8.8 Hz, 1H), 6.81 (d, J=4.6 Hz, 2H), 3.65 (s, 2H), 3.16-3.23 (m, 2H), 3.05-3.13 (m, 2H), 2.63-2.71 (m, 2H), 2.01-2.11 (m, 2H), 1.66-1.78 (m, 2H), 0.98 (t, J=7.4 Hz, 3H).

Example 66

3-((3-(5-chloro-2-(2-chloro-5-fluoro-4-(N-(thiazol-2-yl)sulfamoyl)phenoxy)phenyl)propyl)(prop-2-yn-1-yl)amino)propanoic acid Compound 66 was synthesized according to the procedure described for the synthesis of compound 54 by replacing methyl 2-(3-(5-chloro-2-hydroxyphenyl)propylamino)acetate with methyl 3-[3-(5-chloro-2-hydroxyphenyl)propylamino]propanoate in step 1. LC-MS: m/z=585.88 (M+H). 1H-NMR (DMSO), δ 12.26-12.67 (m, 1H), 7.93 (d, J=7.2 Hz, 1H), 7.50 (d, J=2.6 Hz, 1H), 7.29-7.36 (m, 2H), 7.09 (d, J=8.7 Hz, 1H), 6.85-6.93 (m, 2H), 3.05 (s, 1H), 2.61-2.68 (m, 2H), 2.38-2.44 (m, 2H), 2.27-2.36 (m, 2H), 1.58-1.71 (m, 2H).

Example 67

2-((3-(5-chloro-2-(2,5-difluoro-4-(N-(thiazol-2-yl)sulfamoyl)phenoxy)phenyl)propyl)(prop-2-yn-1-yl)amino)acetic acid Compound 67 was synthesized according to the procedure described for the synthesis of compound 54 by replacing 5-chloro-N-(2,4-dimethoxybenzyl)-2,4-difluoro-N-(thiazol-2-yl)benzenesulfonamide with N-(2,4-dimethoxybenzyl)-2,4,5-trifluoro-N-(thiazol-2-yl)benzenesulfonamide step 1. LC-MS: m/z=555.93 (M+H). 1H-NMR (MeOD), δ 7.77-7.86 (m, 1H), 7.46 (d, J=2.6 Hz, 1H), 7.27-7.34 (m, 1H), 7.17 (d, J=4.7 Hz, 1H), 6.99 (d, J=8.7 Hz, 1H), 6.78-6.89 (m, 2H), 3.93 (s, 2H), 3.59 (s, 2H), 2.99-3.10 (m, 3H), 2.66-2.76 (m, 2H), 1.92-2.03 (m, 2H).

Example 68 ethyl 2-((3-(5-chloro-2-(2-chloro-5-fluoro-4-(N-(thiazol-2-yl)sulfamoyl)phenoxy)phenyl)propyl)(methyl)amino)acetate Compound 68 was synthesized according to the procedure described for the synthesis of compound 11 by replacing glycine methyl ester with sarcosine ethyl ester in step 2, and replacing tert-butyl 5-chloro-2,4-difluorophenylsulfonyl(thiazol-4-yl)carbamate with N-(2,4-dimethoxybenzyl)-2,4,5-trifluoro-N-(thiazol-2-yl)benzenesulfonamide in step 4, and omitting step 5. LC-MS: m/z=575.85 (M+H). 1H-NMR (MeOD), δ 8.05 (d, J=7.0 Hz, 1H), 7.50 (d, J=2.5 Hz, 1H), 7.33-7.39 (m, 1H), 7.18 (d, J=4.7 Hz, 1H), 7.01 (d, J=8.6 Hz, 1H), 6.81 (d, J=4.7 Hz, 1H), 6.77 (d, J=10.5 Hz, 1H), 4.32 (d, J=7.2 Hz, 2H), 4.07-4.22 (m, 2H), 3.14-3.24 (m, 2H), 2.96 (s, 3H), 2.70 (s, 2H), 2.05-2.15 (m, 2H), 1.32 (t, J=7.1 Hz, 3H).

Example 69

2-((3-(5-chloro-2-(2,5-difluoro-4-(N-(thiazol-4-yl)sulfamoyl)phenoxy)phenyl)propyl)amino)acetamide Compound 69 was synthesized according to the procedure described for the synthesis of compound 49 by replacing tert-butyl 5-chloro-2,4-difluorophenylsulfonyl(thiazol-4-yl)carbamate with tert-butyl thiazol-4-yl((2,4,5-trifluorophenyl)sulfonyl)carbamate in step 4. LC-MS: m/z=516.8 (M+H). 1H-NMR (DMSO-d6), d 8.94 (d, J=2.0 Hz, 1H), 8.90 (br, 2H), 7.84-7.88 (m, 2H), 7.58 (s, 1H), 7.50 (d, J=2.4 Hz, 1H), 7.33-7.37 (dd, J=2.8, 8.8 Hz, 1H), 7.09-7.13 (m, 3H), 3.66 (s, 2H), 2.90 (br, 2H), 2.62 (t, J=7.6 Hz, 2H), 1.88-1.92 (m, 2H).

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following embodiments.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

What is claimed is:

1. A compound selected from the group consisting of: 2-((3-(5-chloro-2-(2-chloro-5-fluoro-4-(N-(thiazol-2-yl)sulfamoyl)phenoxy)phenyl)propyl)(propyl)amino)acetic acid, 2-(allyl(3-(5-chloro-2-(2-chloro-5-fluoro-4-(N-(thiazol-2-yl)sulfamoyl)phenoxy)phenyl) propyl)amino)acetic acid, 3-((3-(5-chloro-2-(2-chloro-5-fluoro-4-(N-(thiazol-2-yl)sulfamoyl)phenoxy)phenyl)propyl)(prop-2-yn-1-yl)amino) propanoic acid, and 2-((3-( 5-chloro-2-(2-chloro-5-fluoro-4-(N-(thiazol-4-yl)sulfamoyl)phenoxy)phenyl)propyl) amino) acetamide; or a pharmaceutically acceptable salt, or a tautomeric form thereof.

2. The compound of claim 1, wherein the compound is 2-((3-(5-chloro-2-(2-chloro-5-fluoro-4-(N-(thiazol-2-yl)sulfamoyl)phenoxy)phenyl)propyl)(propyl)amino) acetic acid; or a pharmaceutically acceptable salt, or a tautomeric form thereof.

3. The compound of claim 1, wherein the compound is 2-(allyl(3-(5-chloro-2-(2-chloro-5-fluoro-4-(N-(thiazol-2-yl)sulfamoyl)phenoxy)phenyl)propyl)amino)acetic acid; or a pharmaceutically acceptable salt, or a tautomeric form thereof.

4. The compound of claim 1, wherein the compound is 3-((3-(5-chloro-2-(2-chloro-5-fluoro-4-(N-(thiazol-2-yl)sulfamoyl)phenoxy)phenyl)propyl)(prop-2-yn-1-yl)amino) propanoic acid; or a pharmaceutically acceptable salt, or a tautomeric form thereof.

5. The compound of claim 1, wherein the compound is 2-((3-(5-chloro-2-(2-chloro-5-fluoro-4-(N-(thiazol-4-yl)sulfamoyl)phenoxy)phenyl)propyl)amino)acetamide; or a pharmaceutically acceptable salt, or a tautomeric form thereof.

6. A pharmaceutical composition comprising a compound selected from the group consisting of 2-((3-(5-chloro-2-(2-chloro-5-fluoro-4-(N-(thiazol-2-yl)sulfamoyl)phenoxy)phenyl)propyl)(propyl)amino)acetic acid, 2-(allyl(3-(5-chloro-2-(2-chloro-5-fluoro-4-(N-(thiazol-2-yl)sulfamoyl)phenoxy)phenyl) propyl)amino)acetic acid, 3-((3-(5-chloro-2-(2-chloro-5-fluoro-4-(N-(thiazol-2-yl)sulfamoyl)phenoxy)phenyl)propyl)(prop-2-yn-1-yl)amino)propanoic acid, and 2-((3-(5-chloro-2-(2-chloro-5-fluoro-4-(N-(thiazol-4-yl)sulfamoyl)phenoxy)phenyl)propyl)amino) acetamide, or a pharmaceutically acceptable salt, or a tautomeric form thereof, and a pharmaceutically acceptable carrier.

7. The composition of claim 6, wherein the composition is suitable for topical, oral, subcutaneous, or intravenous administration.

8. A method for treatment of pain in a subject, wherein the method comprises administering to the subject in need of such prevention or treatment a therapeutically effective amount of a compound selected from the group consisting of 2-((3-(5-chloro-2-(2-chloro-5-fluoro-4-(N-(thiazol-2-yl)sulfamoyl)phenoxy)phenyl) propyl)(propyl)amino)acetic acid, 2-(allyl(3-(5-chloro-2-(2-chloro-5-fluoro-4-(N-(thiazol-2-yl)sulfamoyl)phenoxy)phenyl) propyl)amino)acetic acid, 3-((3-(5-chloro-2-(2-chloro-5-fluoro-4-(N-(thiazol-2-yl)sulfamoyl)phenoxy)phenyl)propyl)(prop-2-yn-1-yl)amino) propanoic acid, and 2-((3-(5-chloro-2-(2-chloro-5-fluoro-4-(N-(thiazol-4-yl)sulfamoyl)phenoxy)phenyl)propyl)amino) acetamide; or a pharmaceutically acceptable salt, or a tautomeric form thereof.

9. The method of claim 8, wherein the compound is 2-((3-(5-chloro-2-(2-chloro-5-fluoro-4-(N-(thiazol-2-yl)sulfamoyl)phenoxy) phenyl) propyl)(propyl)amino)acetic acid; or a pharmaceutically acceptable salt, or a tautomeric form thereof.

10. The method of claim 8, wherein the compound is 2-(allyl(3-(5-chloro-2-(2-chloro-5-fluoro-4-(N-(thiazol-2-yl)sulfamoyl)phenoxy)phenyl) propyl)amino)acetic acid; or a pharmaceutically acceptable salt, or a tautomeric form thereof.

11. The method of claim 8, wherein the compound is 3-((3-(5-chloro-2-(2-chloro-5-fluoro-4-(N-(thiazol-2-yl)sulfamoyl)phenoxy)phenyl)propyl)(prop-2-yn-1-yl)amino) propanoic acid; or a pharmaceutically acceptable salt, or a tautomeric form thereof.

12. The method of claim 8, wherein the compound is 2-((3-(5-chloro-2-(2-chloro-5-fluoro-4-(N-(thiazol-4-yl) sulfamoyl)phenoxy)phenyl)propyl)amino) acetamide; or a pharmaceutically acceptable salt, or a tautomeric form thereof.

13. The method of claim 8 wherein the therapeutically effective amount of a compound selected from the group consisting of 2-((3-(5-chloro-2-(2-chloro-5-fluoro-4-(N-(thiazol-2-yl)sulfamoyl)phenoxy)phenyl) propyl)(propyl)amino)acetic acid, 2-(allyl(3-(5-chloro-2-(2-chloro-5-fluoro-4-(N-(thiazol-2-yl)sulfamoyl)phenoxy)phenyl) propyl)amino)acetic acid, 3-((3-(5-chloro-2-(2-chloro-5-fluoro-4-(N-(thiazol-2-yl)sulfamoyl)phenoxy)phenyl)propyl)(prop-2-yn-1-yl)amino)propanoic acid, and 2-((3-(5-chloro-2-(2-chloro-5-fluoro-4-(N-(thiazol-4-yl)sulfamoyl)phenoxy)phenyl)propyl) amino) acetamide, or a pharmaceutically acceptable salt, or a tautomeric form thereof, is effective in inhibiting voltage-gated sodium channel NaV1.7.

14. The method of claim 8, wherein the pain is neuropathic, nociceptive or inflammatory pain.

15. The method of claim 8, wherein the therapeutically effective amount is effective to alleviate pain in a subject, wherein a compound selected from the group consisting of 2-((3-(5-chloro-2-(2-chloro-5-fluoro-4-(N-(thiazol-2-yl)sulfamoyl)phenoxy) phenyl) propyl)(propyl)amino)acetic acid, 2-(allyl(3-(5-chloro-2-(2-chloro-5-fluoro-4-(N-(thiazol-2-yl)sulfamoyl)phenoxy)phenyl) propyl)amino)acetic acid, 3-((3-(5-chloro-2-(2-chloro-5-fluoro-4-(N-(thiazol-2-yl)sulfamoyl)phenoxy)phenyl)propyl)(prop-2-yn-1-yl)amino) propanoic acid, and 2-((3-(5-chloro-2-(2-chloro-5-fluoro-4-(N-(thiazol-4-yl)sulfamoyl)phenoxy)phenyl)propyl)amino) acetamide, or a pharmaceutically acceptable salt, or a tautomeric form thereof, shows a reduction in pain response in the Formalin Assay in phase 1 or phase 2, or both, at a dose between 0.1 mg/kg and 1,000 mg/kg, at a dose between 0.5 mg/kg and 100 mg/kg, or at a dose between 1 mg/kg to 50 mg/kg.

16. The method of claim 8, wherein the pain is nociceptive pain, such as that resulting from physical trauma (e.g., a cut or contusion of the skin; or a chemical or thermal burn), osteoarthritis, rheumatoid arthritis or tendonitis; myofascial pain; neuropathic pain, such as that associated with stroke, diabetic neuropathy, luetic neuropathy, postherpetic neuralgia, trigeminal neuralgia, fibromyalgia, or painful neuropathy induced iatrogenically by drugs; or mixed pain (i.e., pain with both nociceptive and neuropathic components); visceral pain; headache pain (e.g., migraine headache pain); CRPS; CRPS type I; CRPS type II; RSD; reflex neurovascular dystrophy; reflex dystrophy; sympathetically maintained pain syndrome; causalgia; Sudeck atrophy of bone; algoneurodystrophy; shoulder hand syndrome; post-traumatic dystrophy; autonomic dysfunction; autoimmune-related pain; inflammation-related pain; cancer-related pain;

phantom limb pain; chronic fatigue syndrome; post-operative pain; spinal cord injury pain; central post-stroke pain; radiculopathy; sensitivity to temperature, light touch or color change to the skin (allodynia); pain from hyperthermic or hypothermic conditions; and other painful conditions (e.g., diabetic neuropathy, luetic neuropathy, postherpetic neuralgia, trigeminal neuralgia); chronic pain; acute pain; pain from neuromas, pain or itch associated with channelopathies (e.g., small fiber neuralgia, IEM or Raynodes); or itch from various origins (e.g., allergic itch).

17. The method of claim 8, wherein the pain is neuropathic pain.

18. A method for treating prediabetes or diabetes comprising administering to a subject in need thereof a therapeutically effective amount of a compound selected from the group consisting of 2-((3-(5-chloro-2-(2-chloro-5-fluoro-4-(N-(thiazol-2-yl)sulfamoyl)phenoxy)phenyl) propyl)(propyl)amino) acetic acid, 2-(allyl(3-(5-chloro-2-(2-chloro-5-fluoro-4-(N-(thiazol-2-yl)sulfamoyl)phenoxy)phenyl) propyl)amino)acetic acid, 3-((3-(5-chloro-2-(2-chloro-5-fluoro-4-(N-(thiazol-2-yl)sulfamoyl)phenoxy)phenyl)propyl)(prop-2-yn-1-yl)amino)propanoic acid, and 2-((3-(5-chloro-2-(2-chloro-5-fluoro-4-(N-(thiazol-4-yl)sulfamoyl) phenoxy)phenyl)propyl) amino)acetamide; or a pharmaceutically acceptable salt, or a tautomeric form thereof.

* * * * *

UNITED STATES PATENT AND TRADEMARK OFFICE
CERTIFICATE OF CORRECTION

PATENT NO. : 9,458,118 B2
APPLICATION NO. : 14/994846
DATED : October 4, 2016
INVENTOR(S) : Babich et al.

It is certified that error appears in the above-identified patent and that said Letters Patent is hereby corrected as shown below:

In the Claims

Column 175 Lines 57-67 and Column 176 Lines 1-3 should be corrected to read:

8. A method for treatment of pain in a subject, wherein the method comprises administering to the subject in need of such treatment a therapeutically effective amount of a compound selected from the group consisting of 2-((3-(5-chloro-2-(2-chloro-5-fluoro-4-(N-(thiazol-2-yl)sulfamoyl)phenoxy-)phenyl) propyl)(propyl)amino)acetic acid, 2-(allyl(3-(5-chloro-2-(2-chloro-5-fluoro-4-(N-(thiazol-2-yl)sulfamoyl)ph- enoxy)phenyl) propyl)amino)acetic acid, 3-((3-(5-chloro-2-(2-chloro-5-fluoro-4-(N-(thiazol-2-yl)sulfamoyl)phenoxy- )phenyl)propyl)(prop-2-yn-1-yl) amino)propanoic acid, and 2-((3-(5-chloro-2-(2-chloro-5-fluoro-4-(N-(thiazol-4-yl)sulfamoyl)phenoxy- )phenyl) propyl)amino) acetamide; or a pharmaceutically acceptable salt, or a tautomeric form thereof.

Signed and Sealed this
Twenty-sixth Day of June, 2018

Andrei Iancu
*Director of the United States Patent and Trademark Office*